US008178651B2

(12) United States Patent
Culler et al.

(10) Patent No.: US 8,178,651 B2
(45) Date of Patent: May 15, 2012

(54) SOMATOSTATIN-DOPAMINE CHIMERIC ANALOGS

(75) Inventors: Michael D. Culler, Hopkinton, MA (US); Zheng Xin Dong, Holliston, MA (US); Sun H. Kim, Needham, MA (US); Jacques-Pierre Moreau, Upton, MA (US)

(73) Assignee: IPSEN Pharma, S.A.S., Boulogne (FR)

( * ) Notice: Subject to any disclaimer, the term of this patent is extended or adjusted under 35 U.S.C. 154(b) by 116 days.

(21) Appl. No.: 12/456,715

(22) Filed: Jun. 22, 2009

(65) Prior Publication Data

US 2009/0275501 A1    Nov. 5, 2009

Related U.S. Application Data

(63) Continuation of application No. 11/434,273, filed on May 15, 2006, now Pat. No. 7,572,883, which is a continuation of application No. 10/479,771, filed as application No. PCT/US02/17859 on Jun. 7, 2002, now Pat. No. 7,579,435.

(60) Provisional application No. 60/297,059, filed on Jun. 8, 2001.

(51) Int. Cl.
*C07K 7/00* (2006.01)
(52) U.S. Cl. ........ 530/328; 530/327; 530/329; 530/311; 530/345
(58) Field of Classification Search ................. 530/328, 530/327, 329, 311, 345
See application file for complete search history.

(56) References Cited

U.S. PATENT DOCUMENTS

| | | | |
|---|---|---|---|
| 2,589,978 | A | 3/1952 | Stoll et al. |
| 2,619,488 | A | 11/1952 | Stoll et al. |
| 3,966,941 | A | 6/1976 | Semonsky et al. |
| 4,108,855 | A | 8/1978 | Mago nee Karacsony et al. |
| 4,526,892 | A | 7/1985 | Salvati et al. |
| 4,871,717 | A | 10/1989 | Coy et al. |
| 4,904,642 | A | 2/1990 | Coy et al. |
| 5,043,341 | A | 8/1991 | Cohen et al. |
| 5,145,837 | A | 9/1992 | Feyen et al. |
| 5,411,966 | A | 5/1995 | Sauer et al. |
| 5,621,133 | A | 4/1997 | DeNinno et al. |
| 5,753,618 | A | 5/1998 | Cavanak et al. |
| 5,925,618 | A | 7/1999 | Baumbach et al. |
| 6,025,193 | A | 2/2000 | Weiss |
| 6,066,616 | A | 5/2000 | Cavanak et al. |
| 6,117,427 | A | 9/2000 | Hill et al. |
| 6,221,870 | B1 | 4/2001 | Pfaeffli et al. |
| 6,468,767 | B1 | 10/2002 | Weinshank et al. |

FOREIGN PATENT DOCUMENTS

| | | |
|---|---|---|
| BE | 618 187 | 5/1962 |
| EP | 0 126 968 | 12/1988 |
| GB | 959261 | 5/1964 |
| GB | 1004310 | 9/1965 |
| GB | 2 103 603 | 2/1983 |
| GB | 2 112 382 | 7/1983 |
| NL | 6408237 | 1/1965 |
| WO | 91/11447 | 8/1991 |
| WO | 94/14860 | 7/1994 |
| WO | 94/17104 | 8/1994 |
| WO | 00/04018 | 1/2000 |

OTHER PUBLICATIONS

Abstract of JP 02-042026, published Feb. 13, 1990.
Abstract of JP 07-048272, published Feb. 21, 1995.
Colao, A. et al., "Growth hormone and prolactin excess," The Lancet, 1998, 352:1455-1461.
Figueroa, F. E. et al., "Bromocriptine induces immunological changes related to disease parameters in rheumatoid arthritis", Br. J. Rheum., 1997, 36:1022-1023.
Freda, P. et al., "Clinical Review 110: Diagnosis and treatment of pituitary tumors," J. Clin. Endo. Metab., 1999, 84(11):3859-3866.
Gabor, F. et al., "Drug-protein conjugates: haptenation of 1-methyl-10a-methozydihydrolysergol and 5-bromonicotinic acid to albumin for the production of epitope-specific monoclonal antibodies against nicergoline", J. Pharm. Sci., 1995, 84:1120-1125.
Hoffman, A.J. et al., "Synthesis and LSD-like Discriminative Stimulus Properties in a Series of N(6)-Alkyl Norlysergic Acid N,N-Diethylamide Derivatives," J. Med. Chem., 1985, 28(9):1252-1255.
Jaquet, P. et al., "Quantitative and functional expression of somatostatin receptor subtypes in human prolactinomas," J. Clin. Endo. Metab., 1999, 84(9):3268-3276.
Krepelka, J. et al., "Some esters of N-(D-6-methyl-8-ergolin-1-ylmethyl)-carbamic acid," Collection Czechoslov. Chem. Commun., 1977, 42:1886-1889.
Losse, G. et al., "Synthese von lysergyl-enkephalin-derivaten," Eur. J. Med. Chem., 1979, 14:325-328.
Maheshwari, H. et al., "Long-acting peptidomimergic control of gigantism caused by pituitary acidophilic stem cell adenoma," J. Clin. Endo. Metab., 2000, 85(9):3409-3416.
Mantegani, S. et al., "Synthesis and antihypertensive activity of 2,4-dioxoimidazolidin-1-yl and perhydro-2,4-dioxopyrimidin-1-yl ergoline derivatives," Il Farmaco, 1998, 53:293-304.
Miyagi, M. et al., "Dopamine receptor affinities in vitro and stereotypic activities in vivo of cabergoline in rats," Biol. Pharm. Bull., 1996, 19:1210-1213.
Rocheville, M. et al., "Receptors for Dopamine and Somatostatin: Formulation of Hetero-Oligomers with Enhanced Functional Activity," Science, 2000, 288(5643):154-157.
Saveanu, A. et al., "A chimeric somatostatin-dopamine molecule, BIM-23A387 has enhanced potency in suppressing GH and PRL secretion in acromegaly," ENEA 2002 Conference, Munich, Germany, Sep. 12-14, 2002, OC-2.4, p40, Abstract (XP-002306950).
Saveanu, A. et al., "Demonstration of enhanced potency of a chimeric somatostatin-dopamine molecule, BIM-23A387, in suppressing growth hormone and prolactin secretion from human pituitary somatotroph adenoma cells," J. Clin. Endo. & Metabl., 2002, 87:5545-5552.
Stoll, A. et al., "Synthesis of 6-Methyl-8-oxyisoergoline (I) and Attempts to Dehydrogenate Same to 6-Methyl-ergolin-8-one," 28th Report on Ergot Alkaloids, Helvetica Chimica Acta., 1952, 35(152-153):1249-1258.
Temperilli, A. et al., "Anti-hypertensive activity of ergolinyl-ureido and thioureido derivatives", Eur. J. Med. Chem., 1988, 23:77-81.
Walzel, B. et al., "Mehcanism of alkaloid cyclopeptide synthesis in the ergot fungus *Claviceps purpurea*," Chemistry and Biology, 1997, 4:223-230.

*Primary Examiner* — David Lukton
(74) *Attorney, Agent, or Firm* — Yankwich & Associates; Tony K. Uhm; Pamela C. Ball

(57) ABSTRACT

Disclosed is a series of somatostatin-dopamine chimeric analogs which retain both somatostatin and dopamine activity in vivo. An example is: 6-n-propyl-8β-ergolinglmethylthio-acetyl-D-Phe-c(Cys-Tyr-D-Trp-Lys-Abu-Cys)-Thr-NH₂.

14 Claims, No Drawings

US 8,178,651 B2

SOMATOSTATIN-DOPAMINE CHIMERIC ANALOGS

This application is a continuation of U.S. Ser. No. 11/434,273, filed May 15, 2006, now U.S. Pat. No. 7,572,883, which is a continuation of U.S. Ser. No. 10/479,771, filed May 17, 2004 now U.S. Pat. No. 7,579,435, which is a United States national filing under 35 U.S.C. §371 of international (PCT) application No. PCT/US2002/017859, filed Jun. 7, 2002, designating the United States, and claiming priority to U.S. provisional application No. 60/297,059, filed Jun. 8, 2001.

BACKGROUND OF THE INVENTION

The present invention is drawn to somatostatin-dopamine chimeric analogs.

Dopamine is a catecholamine neurotransmitter that has been implicated in the pathogenesis of both Parkinson disease and schizophrenia. Graybiel, et al., *Adv. Neurol.* 53, 17-29 (1990); Goldstein, et al., *FASEB J.* 6, 2413-2421 (1992); Olanow, et al., *Annu. Rev. Neurosci.* 22, 123-144 (1999). Egan, et al., *Curr. Opin. Neurobiol.* 7, 701-707 (1997). Dopamine and related molecules have been shown to inhibit the growth of several types of malignant tumors in mice, and this activity has been variously attributed to inhibition of tumor-cell proliferation, stimulation of tumor immunity or effects on melanin metabolism in malignant melanomas. Wick, M. M., *J. Invest. Dermatol.* 71, 163-164 (1978); Wick, M. M., *J. Natl. Cancer Inst.* 63, 1465-1467 (1979); Wick, M. M., *Cancer Treat. Rep.* 63, 991-997 (1979); Wick, M. M., *Cancer Res.* 40, 1414-1418 (1980); Wick, M. M., *Cancer Treat. Rep.* 65, 861-867 (1981); Wick, M. M. & Mui, *J. Natl. Cancer Inst.* 66, 351-354 (1981); Dasgupta, et al., *J. Cancer Res. Clin. Oncol.* 113, 363-368 (1987); Basu, et al., *Endocrine* 12, 237-241 (2000); Basu, et al., *J. Neuroimmunol.* 102, 113-124 (2000). Recent studies demonstrated the presence of D2 dopamine receptors on endothelial cells. Ricci, et al., *J. Auton. Pharmacol.*, 14, 61-68 (1994); Bacic, et al., *J. Neurochem.* 57, 1774-1780 (1991). Dopamine has recently been reported to strongly and selectively inhibit at non-toxic levels the vascular permeabilizing and angiogenic activities of VPF/VEGF. Basu et al., Nat. Med. 7 (5), 569-574 (2001).

Somatostatin (SS), a tetradecapeptide discovered by Brazeau et al., has been shown to have potent inhibitory effects on various secretory processes in tissues such as pituitary, pancreas and gastrointestinal tract. SS also acts as a neuromodulator in the central nervous system. These biological effects of SS, all inhibitory in nature, are elicited through a series of G protein coupled receptors, of which five different subtypes have been characterized (SSTR1-SSTR5) (Reubi J C, et al., Cancer Res 47: 551-558, Reisine T, et al., Endocrine Review 16: 427-442, Lamberts S W, et al., Endocr Rev 12: 450-482, 4 Patel Y C, 1999 Front Neuroendocrinology 20: 157-198). These five subtypes have similar affinities for the endogenous SS ligands but have differing distribution in various tissues. Somatostatin binds to the five distinct receptor (SSTR) subtypes with relatively high and equal affinity for each subtype.

There is evidence that SS regulates cell proliferation by arresting cell growth via SSTR1, 2, 4, and 5 subtypes (Buscail L, et al., 1995 Proc Natl Acad Sci USA 92: 1580-1584; Buscail L, et al., 1994 Proc Natl Acad Sci USA 91: 2315-2319; Florio T, et al., 1999 Mol Endocrinol 13: 24-37; Sharma K, et al., 1999 Mol Endocrinol 13: 82-90), or by inducing apoptosis via SSTR3 subtype (Sharma K, et al., 1996 Mol Endocrinol 10: 1688-1696). SS and various analogues have been shown to inhibit normal and neoplastic cell proliferation in vitro and vivo (Lamberts S W, et al., Endocr Rev 12: 450-482) via specific SS receptors (SSTR's) (Patel Y C, 1999 Front Neuroendocrinology 20: 157-198) and possibly different postreceptor actions (Weckbecker G, et al., Pharmacol Ther 60: 245-264; Bell G I, Reisine T 1993 Trends Neurosci 16: 34-38; Patel Y C, et al., Biochem Biophys Res Commun 198: 605-612; Law S F, et al., Cell Signal 7:1-8). In addition, there is evidence that distinct SSTR subtypes are expressed in normal and neoplastic human tissues (9), conferring different tissue affinities for various SS analogues and variable clinical response to their therapeutic effects.

Binding to the different types of somatostatin receptor subtypes have been associated with the treatment of various conditions and/or diseases. ("SSTR2") (Raynor, et al., Molecular Pharmacol. 43:838 (1993); Lloyd, et al., Am. J. Physiol. 268:G102 (1995)) while the inhibition of insulin has been attributed to the somatostatin type-5 receptor ("SSTR5") (Coy, et al. 197:366-371 (1993)). Activation of types 2 and 5 have been associated with growth hormone suppression and more particularly GH secreting adenomas (Acromegaly) and TSH secreting adenomas. Activation of type 2 but not type 5 has been associated with treating prolactin secreting adenomas. Other indications associated with activation of the somatostatin receptor subtypes include inhibition of insulin and/or glucagon for treating diabetes mellitus, angiopathy, proliferative retinopathy, dawn phenomenon and nephropathy; inhibition of gastric acid secretion and more particularly peptic ulcers, enterocutaneous and pancreaticocutaneous fistula, irritable bowel syndrome, Dumping syndrome, watery diarrhea syndrome, AIDS related diarrhea, chemotherapy-induced diarrhea, acute or chronic pancreatitis and gastrointestinal hormone secreting tumors; treatment of cancer such as hepatoma; inhibition of angiogenesis; treatment of inflammatory disorders such as arthritis; retinopathy; chronic allograft rejection; angioplasty; preventing graft vessel and gastrointestinal bleeding. It is preferred to have an analog which is selective for the specific somatostatin receptor subtype or subtypes responsible for the desired biological response, thus, reducing interaction with other receptor subtypes which could lead to undesirable side effects.

Somatostatin (SS) and its receptors (SSTR1 to SSTR5) are expressed in normal human parafollicular C cells and medullary thyroid carcinoma (MTC). MTC is a tumor originating from thyroid parafollicular C cells that produces calcitonin (CT), somatostatin, as well as several other peptides (Moreau J P, et al., Metabolism 45 (8 Suppl 1): 24-26). Recently, Mato et al. showed that SS and SSTR's are expressed in human MTC (Mato E, et al., J Clin Endocrinol Metab 83: 2417-2420). It has been documented that SS and its analogues induce a decrease in plasma CT levels and a symptomatic improvement in MTC patients. However, until now the antiproliferative activity of SS analogues on tumor cells had not been clearly demonstrated (Mahler C, et al., Clin Endocrinol 33: 261-9; Lupoli G, et al., Cancer 78: 1114-8; Smid W M, et al., Neth J Med 40: 240-243). Thus, development and assessment of SSTR subtype analogues selective on MTC cell growth provides a useful tool for clinical application. Until now, no data concerning specific SSTR subtype involvement in MTC cell growth regulation have been reported.

SUMMARY OF THE INVENTION

The present invention is concerned with the discovery of a series of somatostatin-dopamine chimeric analogs that retain both somatostatin and dopamine activity in vivo, including several of which display enhanced biological activity over the native somatostatin and dopamine analogs alone, and the therapeutic uses thereof.

In one aspect the invention features a dopamine-somatostatin chimer of formula (I),

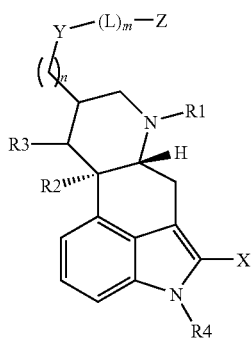
(I)

wherein:
X is H, Cl, Br, I, F, —CN, or $C_{1-5}$ alkyl;
R1 is H, $C_{1-4}$ alkyl, allyl, alkenyl or —CN;
R2 and R3, each are, independently H or absent, provided that when R2 and R3 are absent a double bond is present between the carbon atoms to which they are attached;
R4 is H or —$CH_3$;
Y is —O—, —C(O)—, —S—, —S—($CH_2$)s-C(O)—, —S(O)—, —S(O)$_2$—, —SC(O)—, —OC(O)—, —N(R5)-C(O)—, or —N(R6)-;
R5, R6, R7 and R8 each is, independently, H or $C_{1-5}$ alkyl;
R6 is H or $C_{1-5}$ alkyl;
m is 0 or 1;
n is 0-10;
L is —($CH_2$)p-C(O)—, when Y is —S—, —S(O)—, —S(O)$_2$—, —O— or —N(R6)-;
L is —C(O)—(CR7R8)q-C(O)—, when Y is —N(R6)-, —O—, or —S—;
L is -(Doc)t-, when Y is —C(O)—, SC(O)—, —OC(O)—, —S—($CH_2$)s-C(O)—, or —N(R5)-C(O)—;
p is 1-10;
q is 2-4;
s is 1-10;
t is 1-10; and
Z is somatostatin analog,
or a pharmaceutically acceptable salt thereof.

In another aspect the invention features a dopamine-somatostatin chimer of formula (II),

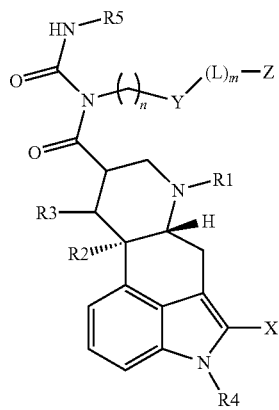
(II)

wherein:
X is H, Cl, Br, I, F, —CN, or $C_{1-5}$ alkyl;
R1 is $C_{1-4}$ alkyl, H, allyl, alkenyl or —CN;
R2 and R3, each are, independently H or absent, provided that when R2 and R3 are absent a double bond is present between the carbon atoms to which they are attached;
R4 is H or —$CH_3$;
R5 is C1-5 alkyl group, or a group of the formula of —($CH_2$)rN($CH_3$)q;
Y is —O—, —C(O)—, —S—, —SC(O)—, —OC(O)—, —N(R6)-C(O)—, —N(R7)-, or —N(R8)-($CH_2$)s-C(O)—;
R6, R7, R8, R9 and R10 each is, independently, H or $C_{1-5}$ alkyl;
L is —($CH_2$)p-C(O)—, when Y is —S—, —O— or —N(R7)-;
L is —C(O)—(CR9R10)q-C(O)—, when Y is —N(R7)-, —O—, or —S—;
L is -(Doc)t-, when Y is —C(O)—, SC(O)—, —OC(O)—, —N(R8)-($CH_2$)s-C(O)—, or —N(R6)-C(O)—;
m is 0 or 1;
n is 2-10;
r is 1-8;
q is 2-4;
p is 1-10;
s is 1-10;
t is 1-10; and
Z is somatostatin analog
or a pharmaceutically acceptable salt thereof.

In one embodiment the invention features a compound according to the formula:

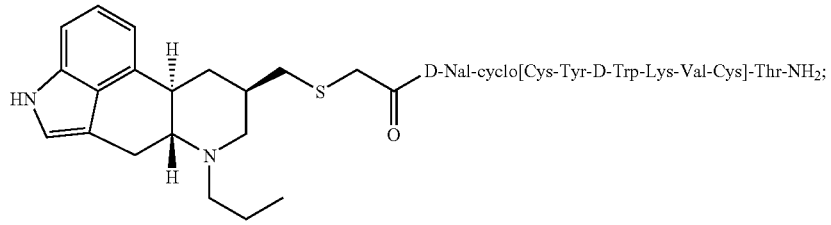
D-Nal-cyclo[Cys-Tyr-D-Trp-Lys-Val-Cys]-Thr-$NH_2$;

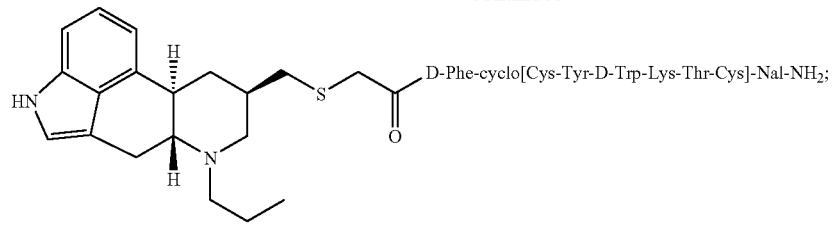 D-Phe-cyclo[Cys-Tyr-D-Trp-Lys-Thr-Cys]-Nal-NH$_2$;
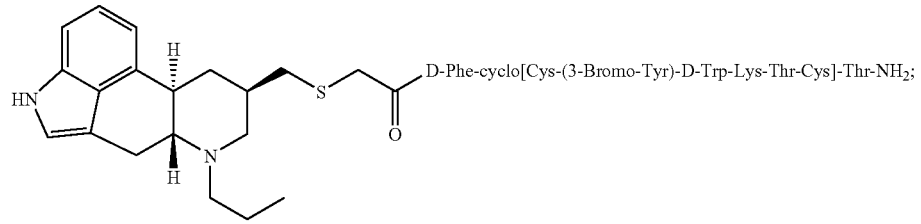 D-Phe-cyclo[Cys-(3-Bromo-Tyr)-D-Trp-Lys-Thr-Cys]-Thr-NH$_2$;
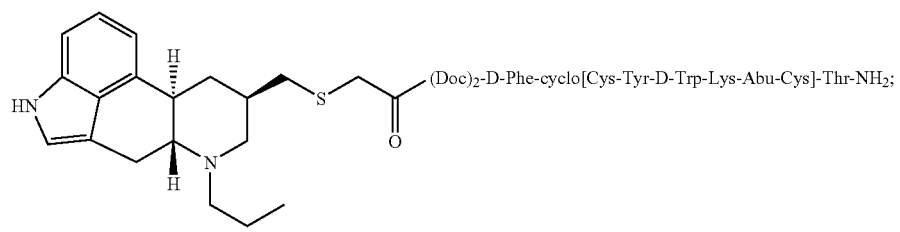 (Doc)$_2$-D-Phe-cyclo[Cys-Tyr-D-Trp-Lys-Abu-Cys]-Thr-NH$_2$;
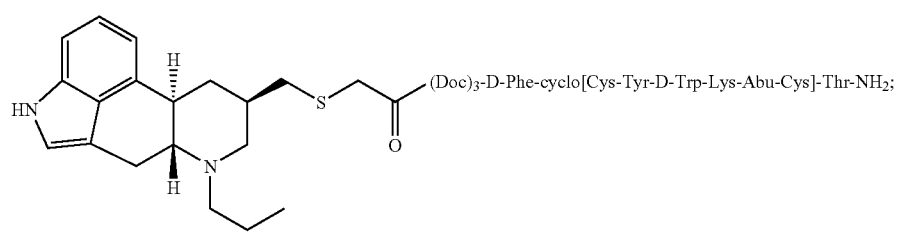 (Doc)$_3$-D-Phe-cyclo[Cys-Tyr-D-Trp-Lys-Abu-Cys]-Thr-NH$_2$;
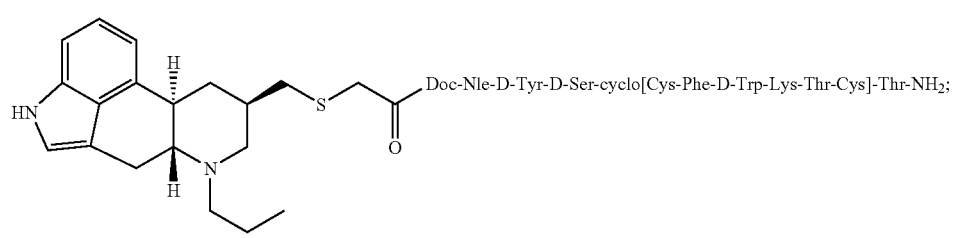 Doc-Nle-D-Tyr-D-Ser-cyclo[Cys-Phe-D-Trp-Lys-Thr-Cys]-Thr-NH$_2$;
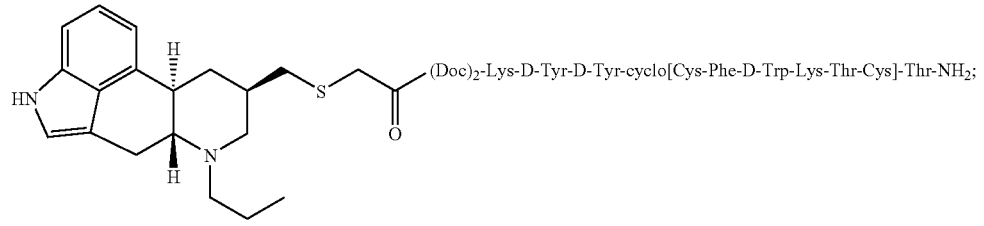 (Doc)$_2$-Lys-D-Tyr-D-Tyr-cyclo[Cys-Phe-D-Trp-Lys-Thr-Cys]-Thr-NH$_2$;
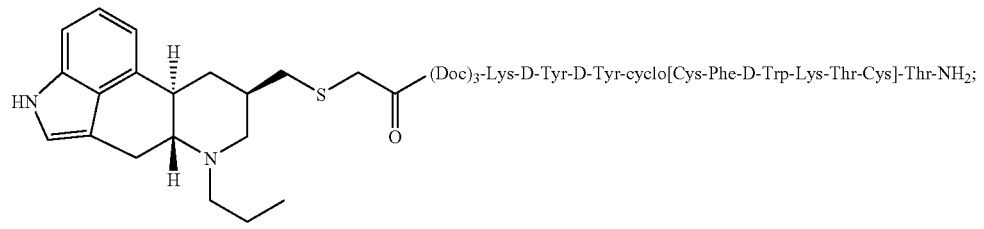 (Doc)$_3$-Lys-D-Tyr-D-Tyr-cyclo[Cys-Phe-D-Trp-Lys-Thr-Cys]-Thr-NH$_2$;

-continued
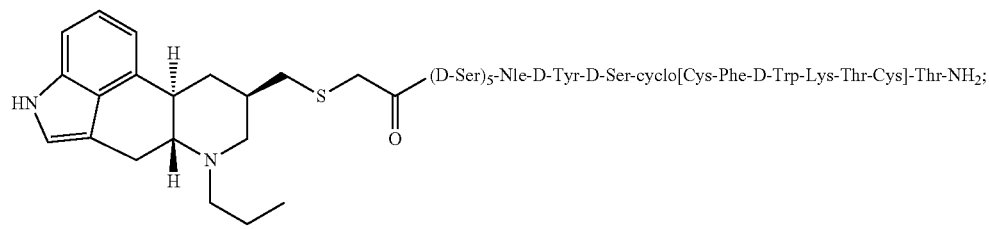
(D-Ser)₅-Nle-D-Tyr-D-Ser-cyclo[Cys-Phe-D-Trp-Lys-Thr-Cys]-Thr-NH₂;
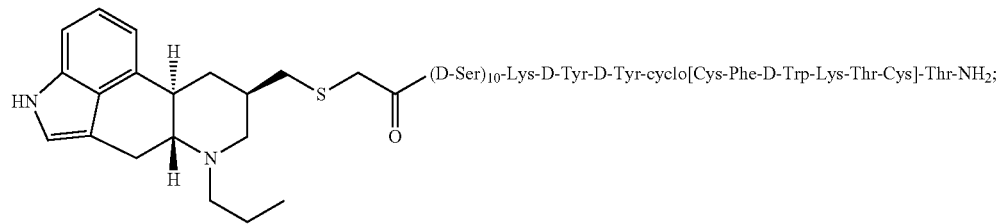
(D-Ser)₁₀-Lys-D-Tyr-D-Tyr-cyclo[Cys-Phe-D-Trp-Lys-Thr-Cys]-Thr-NH₂;
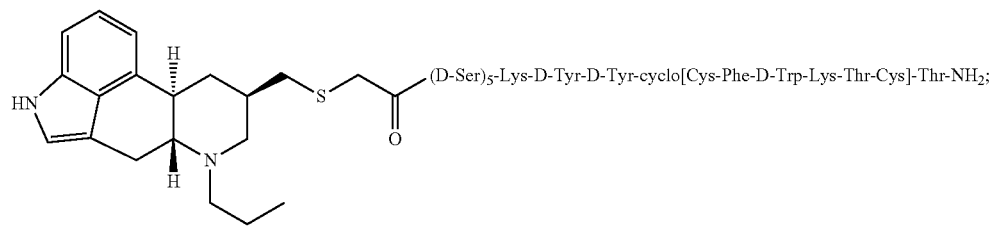
(D-Ser)₅-Lys-D-Tyr-D-Tyr-cyclo[Cys-Phe-D-Trp-Lys-Thr-Cys]-Thr-NH₂;
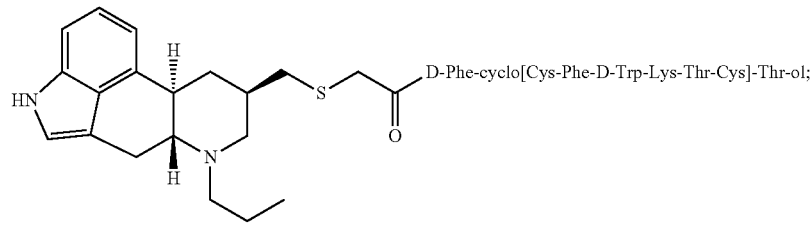
D-Phe-cyclo[Cys-Phe-D-Trp-Lys-Thr-Cys]-Thr-ol;
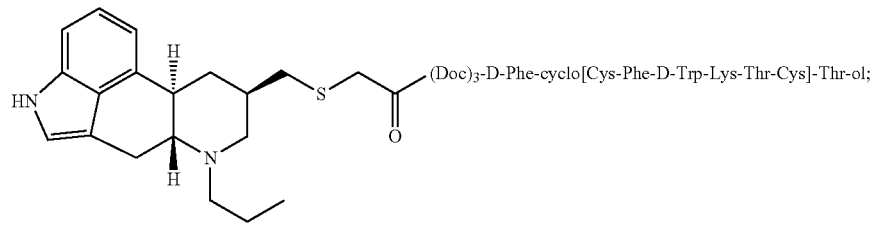
(Doc)₃-D-Phe-cyclo[Cys-Phe-D-Trp-Lys-Thr-Cys]-Thr-ol;
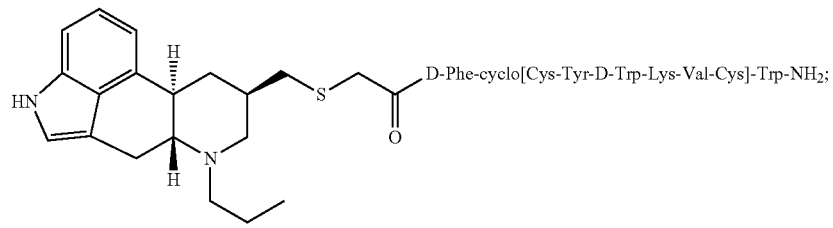
D-Phe-cyclo[Cys-Tyr-D-Trp-Lys-Val-Cys]-Trp-NH₂;
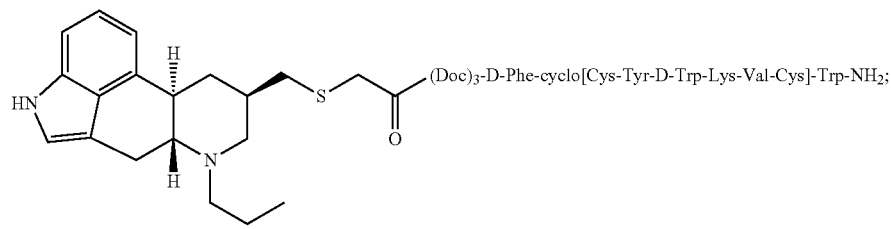
(Doc)₃-D-Phe-cyclo[Cys-Tyr-D-Trp-Lys-Val-Cys]-Trp-NH₂;

-continued

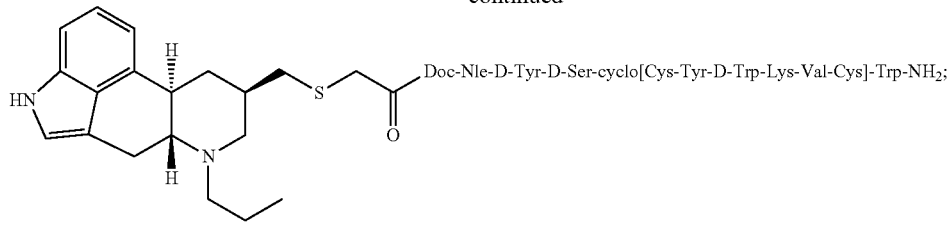
Doc-Nle-D-Tyr-D-Ser-cyclo[Cys-Tyr-D-Trp-Lys-Val-Cys]-Trp-NH$_2$;

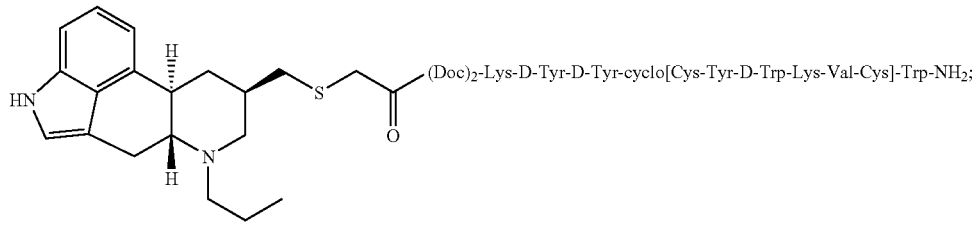
(Doc)$_2$-Lys-D-Tyr-D-Tyr-cyclo[Cys-Tyr-D-Trp-Lys-Val-Cys]-Trp-NH$_2$;

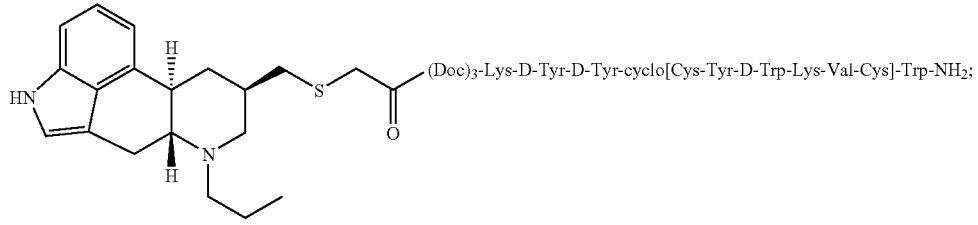
(Doc)$_3$-Lys-D-Tyr-D-Tyr-cyclo[Cys-Tyr-D-Trp-Lys-Val-Cys]-Trp-NH$_2$;

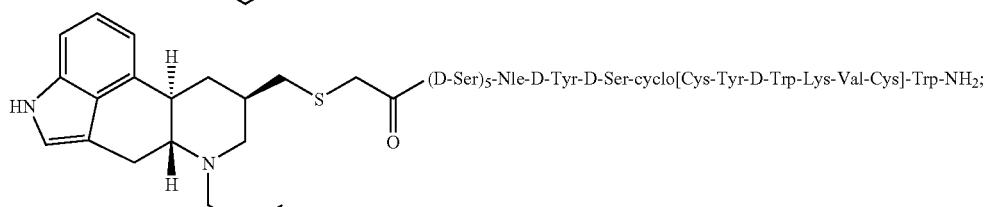
(D-Ser)$_5$-Nle-D-Tyr-D-Ser-cyclo[Cys-Tyr-D-Trp-Lys-Val-Cys]-Trp-NH$_2$;

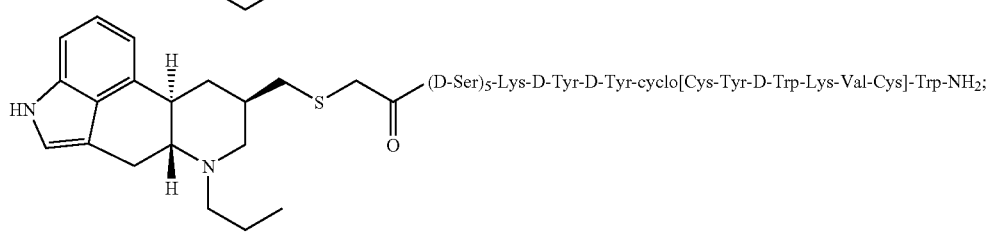
(D-Ser)$_5$-Lys-D-Tyr-D-Tyr-cyclo[Cys-Tyr-D-Trp-Lys-Val-Cys]-Trp-NH$_2$;

Caeg=N-(2-aminoethyl)-N-(2-cytosinyl-1-oxo-ethyl)-glycine

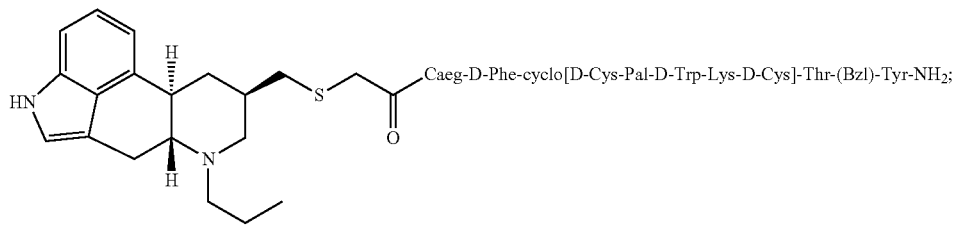
Caeg-D-Phe-cyclo[D-Cys-Pal-D-Trp-Lys-D-Cys]-Thr-(Bzl)-Tyr-NH$_2$;

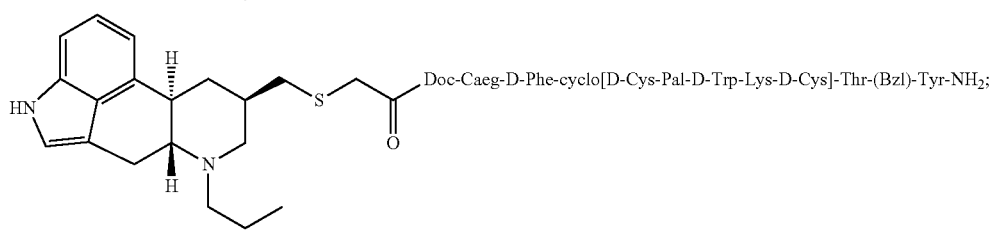
Doc-Caeg-D-Phe-cyclo[D-Cys-Pal-D-Trp-Lys-D-Cys]-Thr-(Bzl)-Tyr-NH$_2$;

-continued

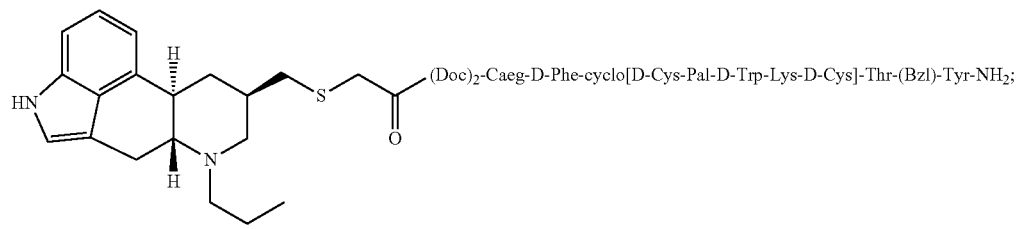
(Doc)$_2$-Caeg-D-Phe-cyclo[D-Cys-Pal-D-Trp-Lys-D-Cys]-Thr-(Bzl)-Tyr-NH$_2$;

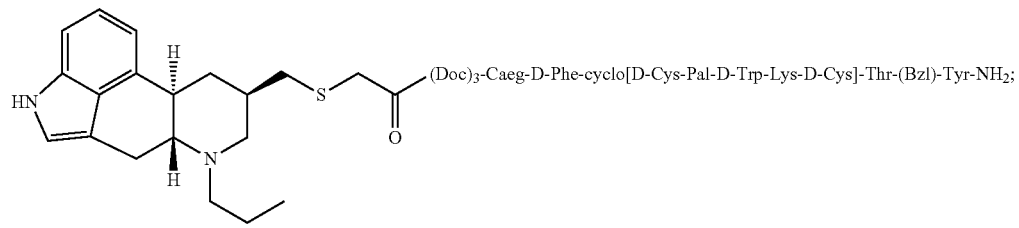
(Doc)$_3$-Caeg-D-Phe-cyclo[D-Cys-Pal-D-Trp-Lys-D-Cys]-Thr-(Bzl)-Tyr-NH$_2$;

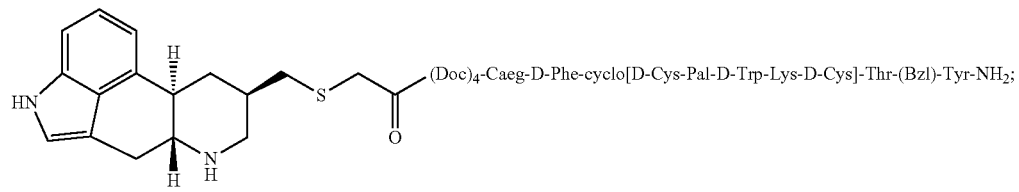
(Doc)$_4$-Caeg-D-Phe-cyclo[D-Cys-Pal-D-Trp-Lys-D-Cys]-Thr-(Bzl)-Tyr-NH$_2$;

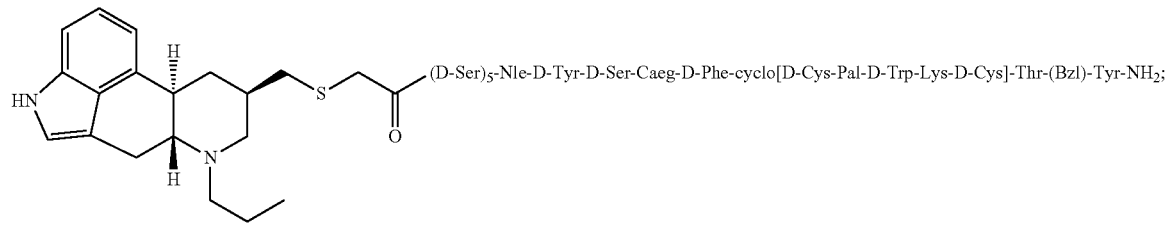
(D-Ser)$_5$-Nle-D-Tyr-D-Ser-Caeg-D-Phe-cyclo[D-Cys-Pal-D-Trp-Lys-D-Cys]-Thr-(Bzl)-Tyr-NH$_2$;

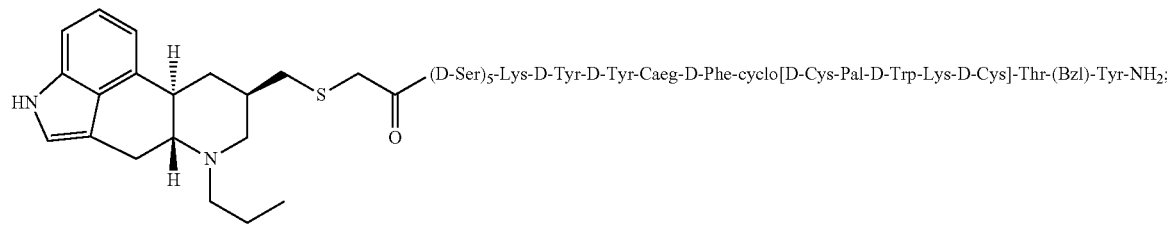
(D-Ser)$_5$-Lys-D-Tyr-D-Tyr-Caeg-D-Phe-cyclo[D-Cys-Pal-D-Trp-Lys-D-Cys]-Thr-(Bzl)-Tyr-NH$_2$;

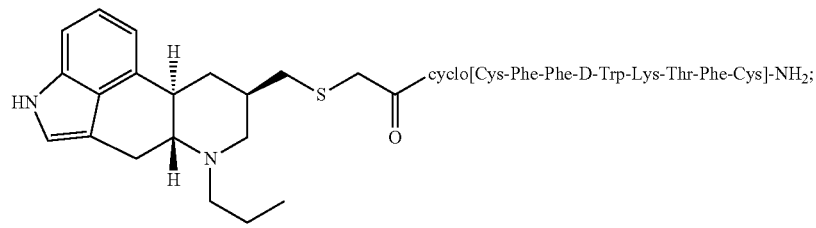
cyclo[Cys-Phe-Phe-D-Trp-Lys-Thr-Phe-Cys]-NH$_2$;

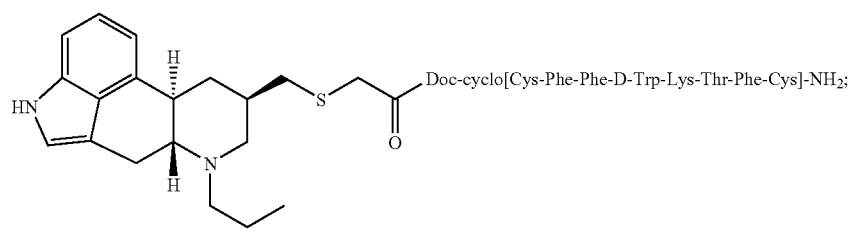
Doc-cyclo[Cys-Phe-Phe-D-Trp-Lys-Thr-Phe-Cys]-NH$_2$;

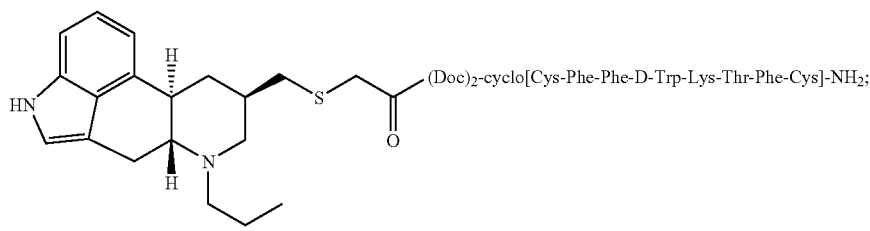 (Doc)₂-cyclo[Cys-Phe-Phe-D-Trp-Lys-Thr-Phe-Cys]-NH₂;
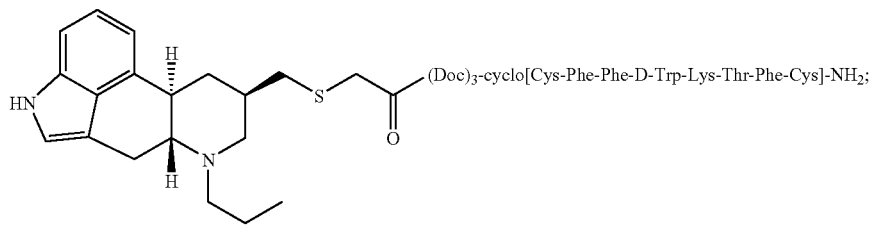 (Doc)₃-cyclo[Cys-Phe-Phe-D-Trp-Lys-Thr-Phe-Cys]-NH₂;
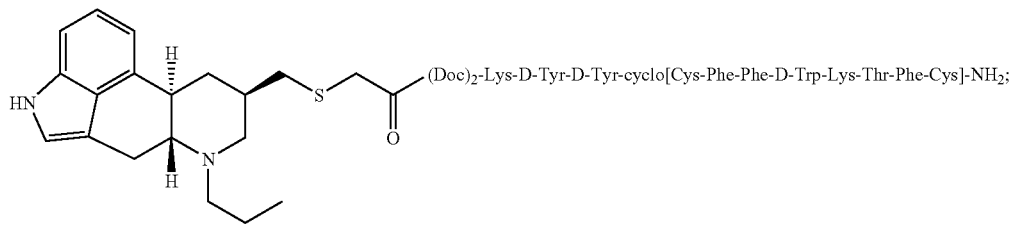 (Doc)₂-Lys-D-Tyr-D-Tyr-cyclo[Cys-Phe-Phe-D-Trp-Lys-Thr-Phe-Cys]-NH₂;
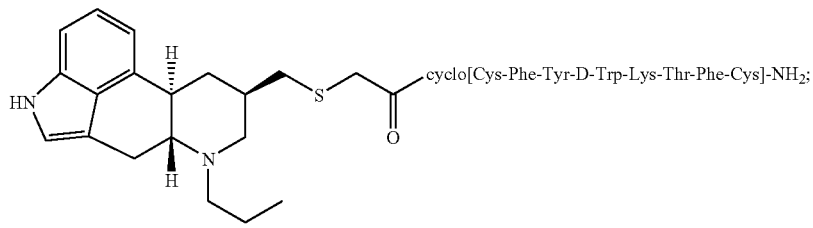 cyclo[Cys-Phe-Tyr-D-Trp-Lys-Thr-Phe-Cys]-NH₂;
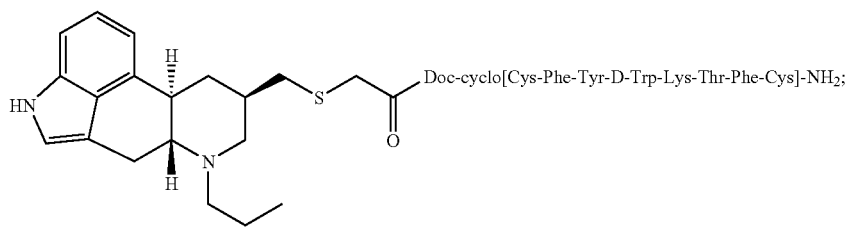 Doc-cyclo[Cys-Phe-Tyr-D-Trp-Lys-Thr-Phe-Cys]-NH₂;
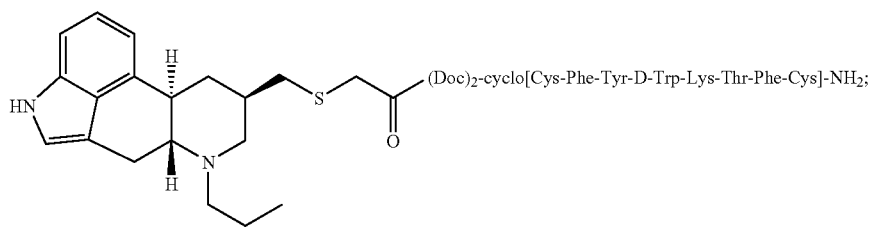 (Doc)₂-cyclo[Cys-Phe-Tyr-D-Trp-Lys-Thr-Phe-Cys]-NH₂;
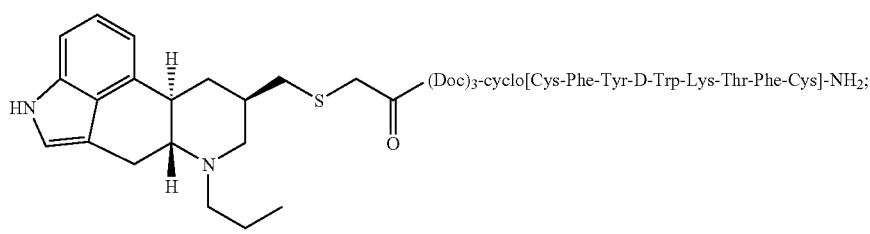 (Doc)₃-cyclo[Cys-Phe-Tyr-D-Trp-Lys-Thr-Phe-Cys]-NH₂;

-continued
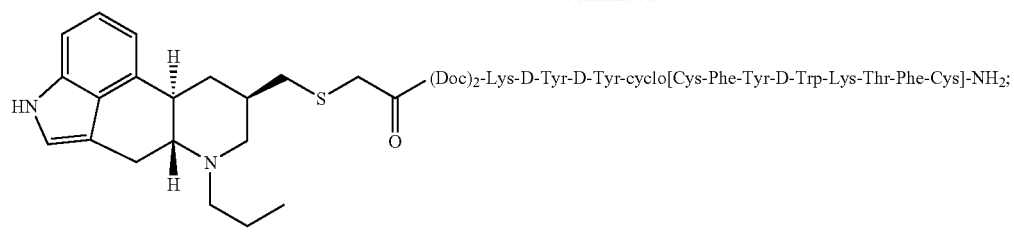
(Doc)$_2$-Lys-D-Tyr-D-Tyr-cyclo[Cys-Phe-Tyr-D-Trp-Lys-Thr-Phe-Cys]-NH$_2$;
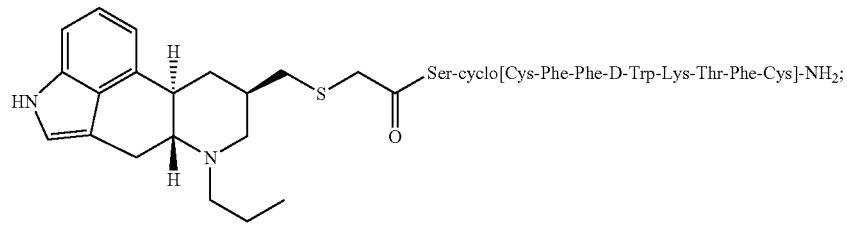
Ser-cyclo[Cys-Phe-Phe-D-Trp-Lys-Thr-Phe-Cys]-NH$_2$;
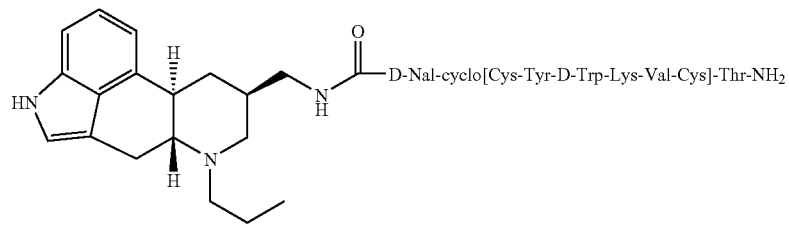
D-Nal-cyclo[Cys-Tyr-D-Trp-Lys-Val-Cys]-Thr-NH$_2$
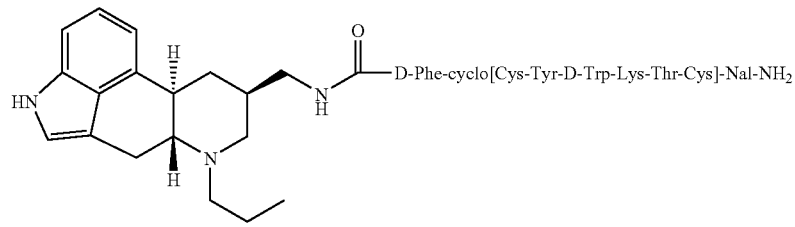
D-Phe-cyclo[Cys-Tyr-D-Trp-Lys-Thr-Cys]-Nal-NH$_2$
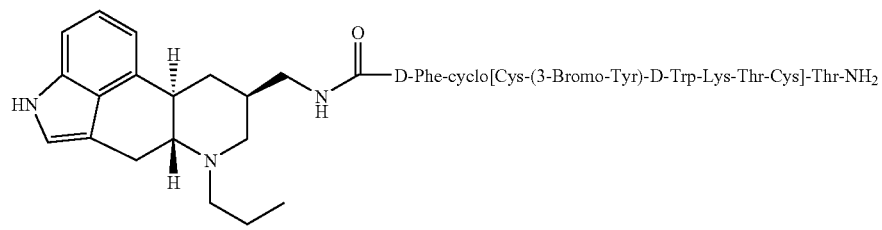
D-Phe-cyclo[Cys-(3-Bromo-Tyr)-D-Trp-Lys-Thr-Cys]-Thr-NH$_2$
Compound B
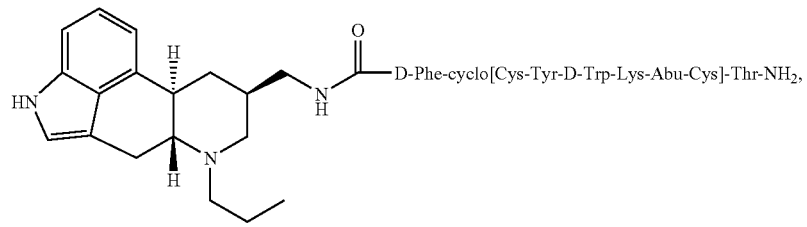
D-Phe-cyclo[Cys-Tyr-D-Trp-Lys-Abu-Cys]-Thr-NH$_2$,
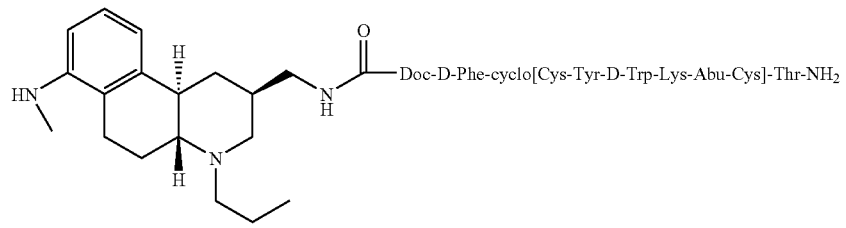
Doc-D-Phe-cyclo[Cys-Tyr-D-Trp-Lys-Abu-Cys]-Thr-NH$_2$ -continued

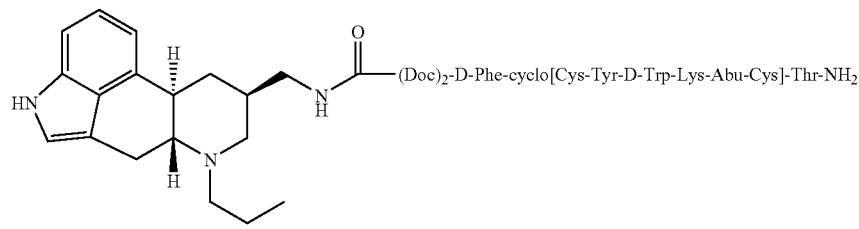
(Doc)$_2$-D-Phe-cyclo[Cys-Tyr-D-Trp-Lys-Abu-Cys]-Thr-NH$_2$

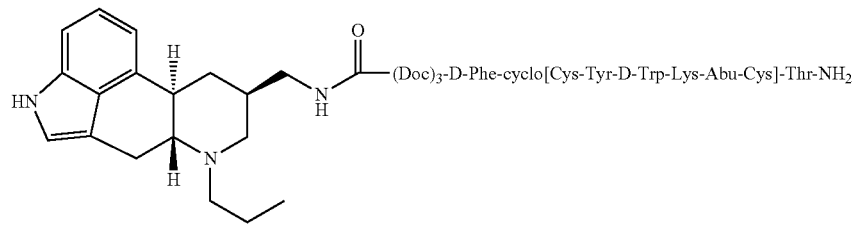
(Doc)$_3$-D-Phe-cyclo[Cys-Tyr-D-Trp-Lys-Abu-Cys]-Thr-NH$_2$

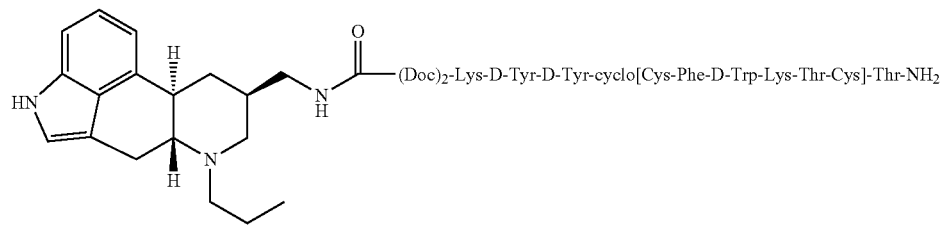
(Doc)$_2$-Lys-D-Tyr-D-Tyr-cyclo[Cys-Phe-D-Trp-Lys-Thr-Cys]-Thr-NH$_2$

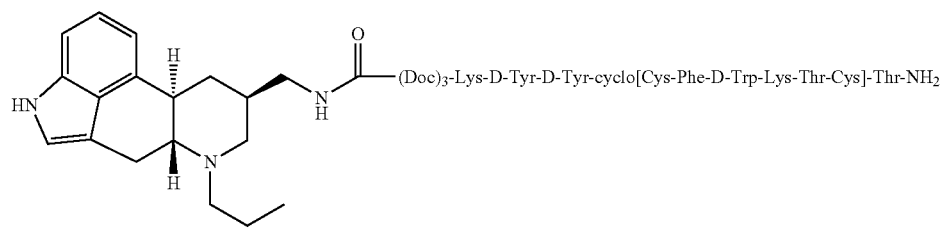
(Doc)$_3$-Lys-D-Tyr-D-Tyr-cyclo[Cys-Phe-D-Trp-Lys-Thr-Cys]-Thr-NH$_2$

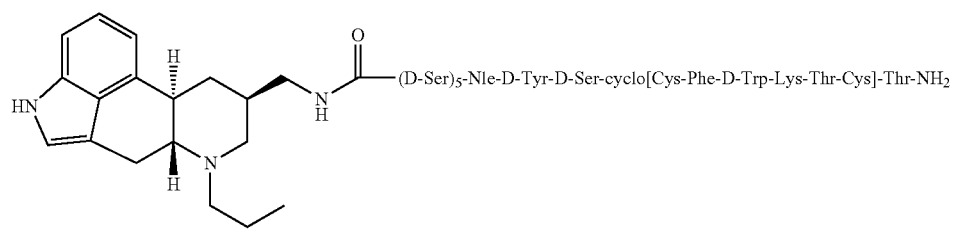
(D-Ser)$_5$-Nle-D-Tyr-D-Ser-cyclo[Cys-Phe-D-Trp-Lys-Thr-Cys]-Thr-NH$_2$

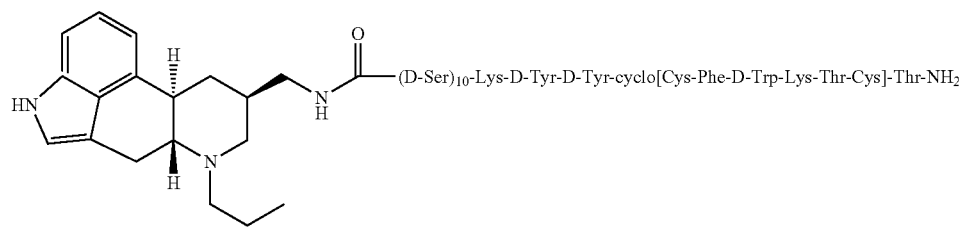
(D-Ser)$_{10}$-Lys-D-Tyr-D-Tyr-cyclo[Cys-Phe-D-Trp-Lys-Thr-Cys]-Thr-NH$_2$

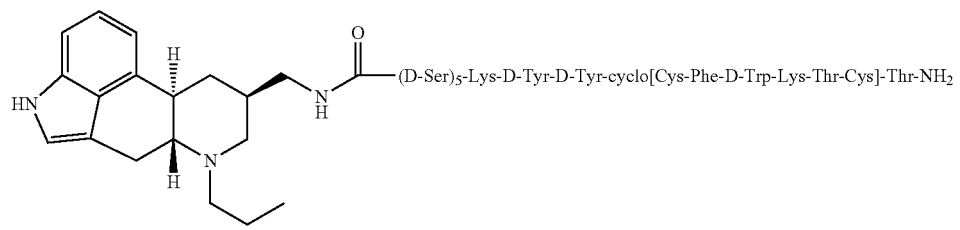
(D-Ser)$_5$-Lys-D-Tyr-D-Tyr-cyclo[Cys-Phe-D-Trp-Lys-Thr-Cys]-Thr-NH$_2$ -continued
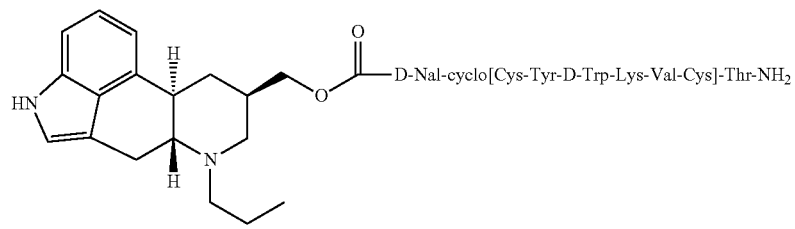
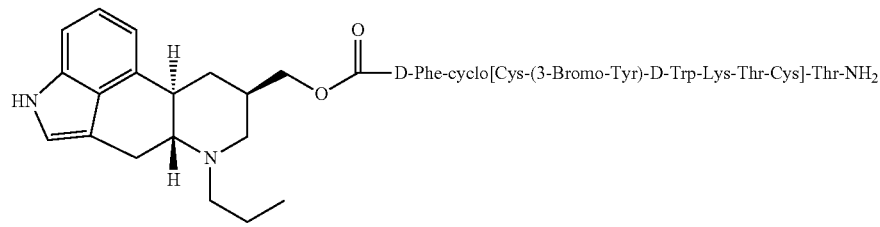
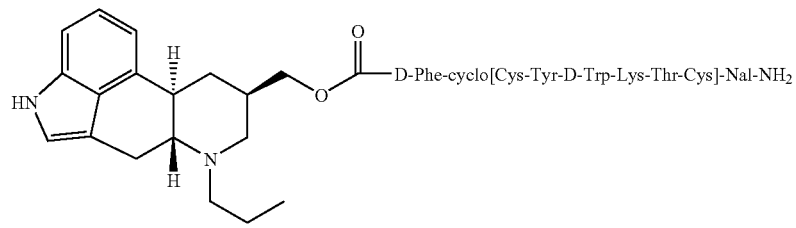
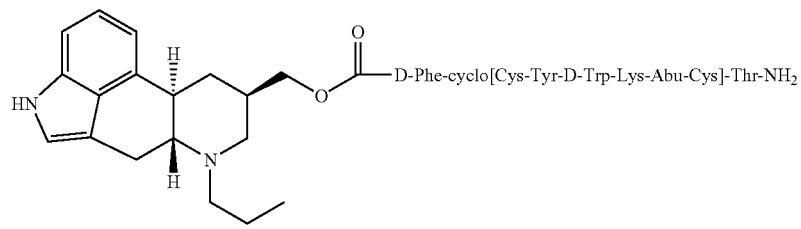
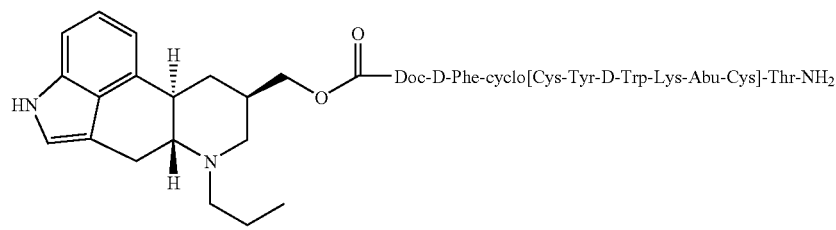
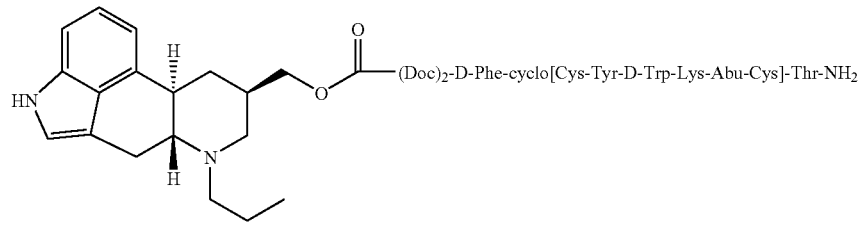

-continued
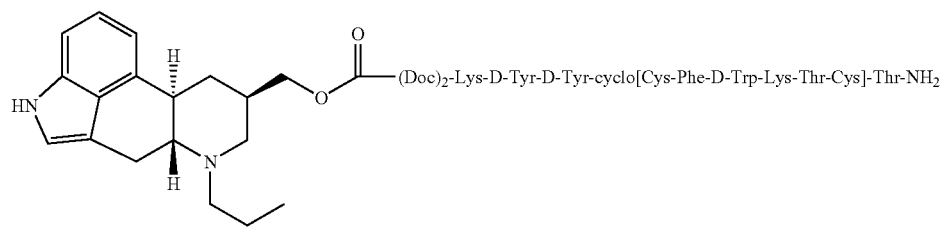
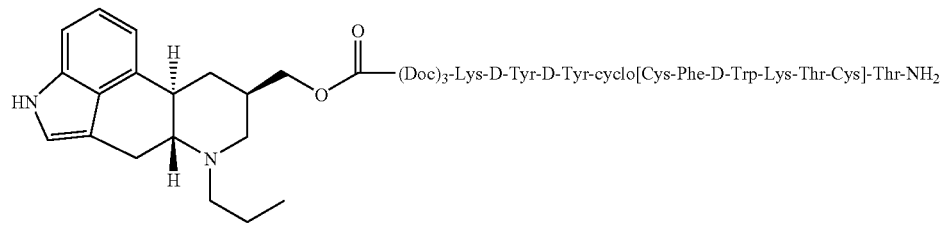
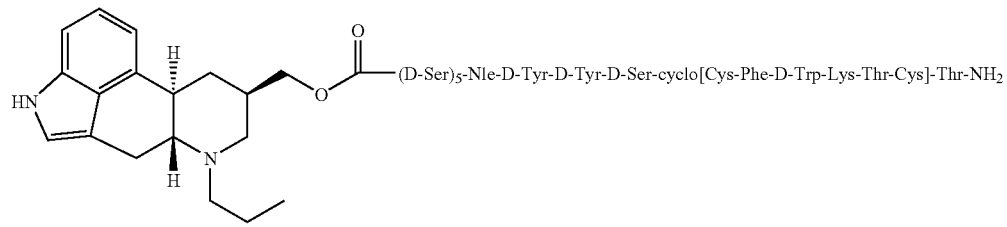
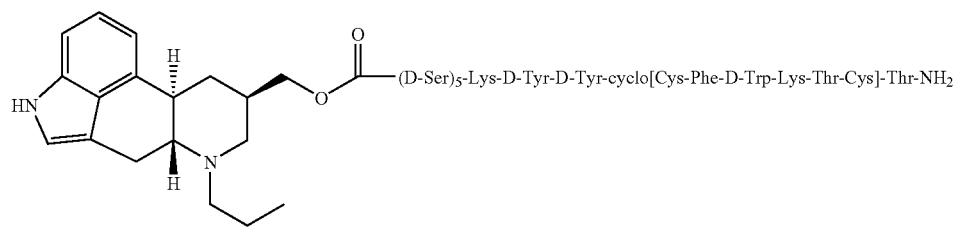
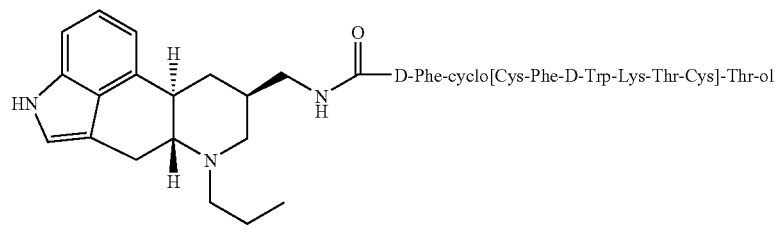
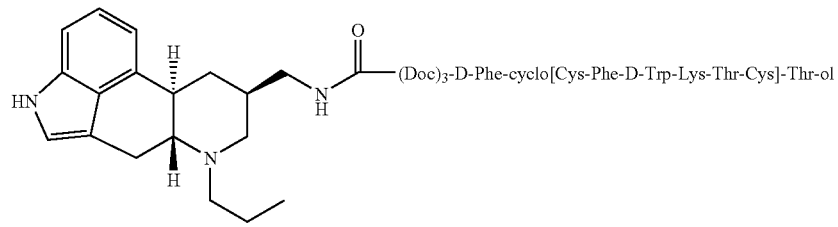
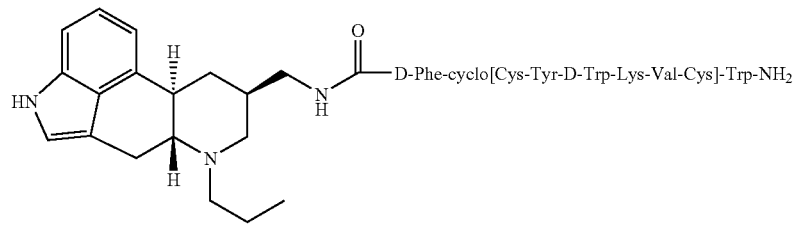

-continued

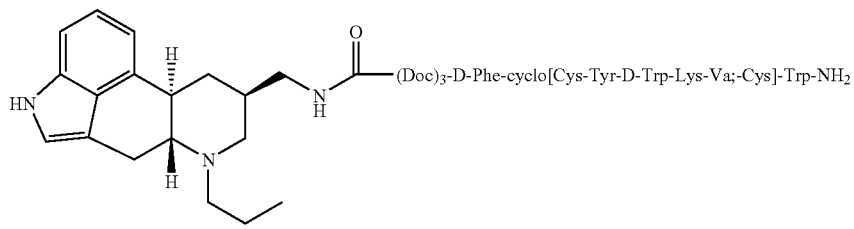
(Doc)₃-D-Phe-cyclo[Cys-Tyr-D-Trp-Lys-Va;-Cys]-Trp-NH₂

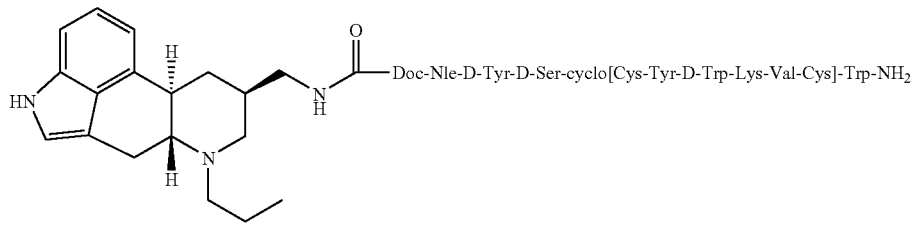
Doc-Nle-D-Tyr-D-Ser-cyclo[Cys-Tyr-D-Trp-Lys-Val-Cys]-Trp-NH₂

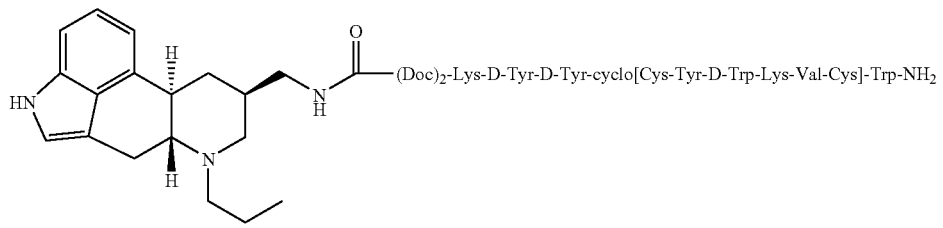
(Doc)₂-Lys-D-Tyr-D-Tyr-cyclo[Cys-Tyr-D-Trp-Lys-Val-Cys]-Trp-NH₂

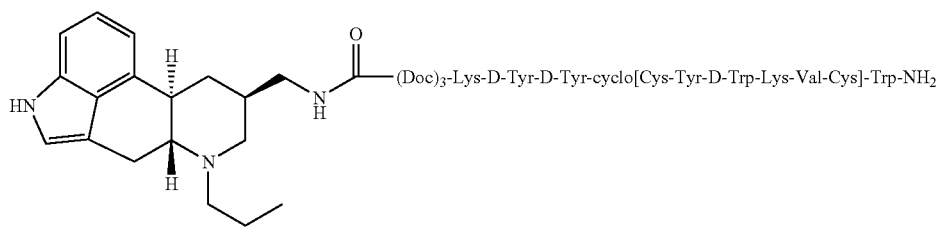
(Doc)₃-Lys-D-Tyr-D-Tyr-cyclo[Cys-Tyr-D-Trp-Lys-Val-Cys]-Trp-NH₂

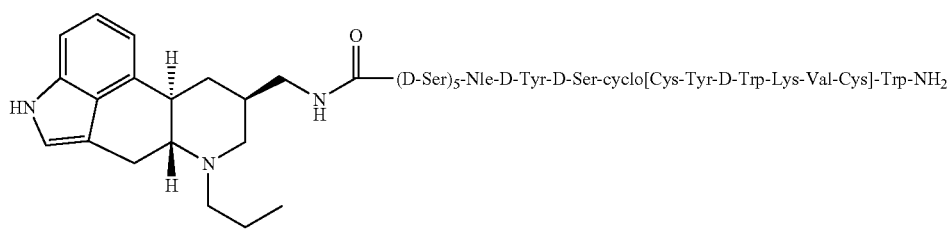
(D-Ser)₅-Nle-D-Tyr-D-Ser-cyclo[Cys-Tyr-D-Trp-Lys-Val-Cys]-Trp-NH₂

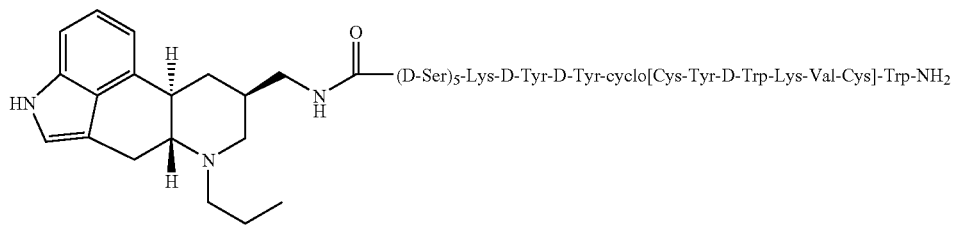
(D-Ser)₅-Lys-D-Tyr-D-Tyr-cyclo[Cys-Tyr-D-Trp-Lys-Val-Cys]-Trp-NH₂

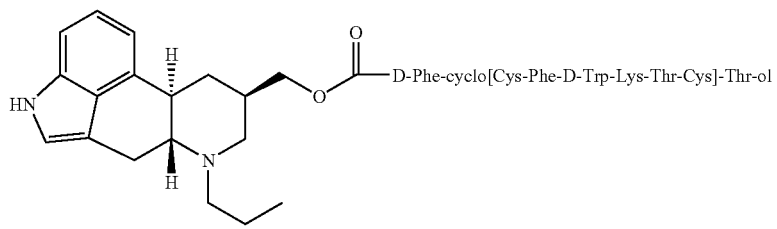
D-Phe-cyclo[Cys-Phe-D-Trp-Lys-Thr-Cys]-Thr-ol

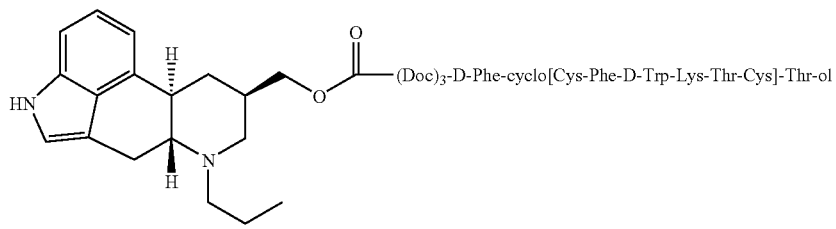
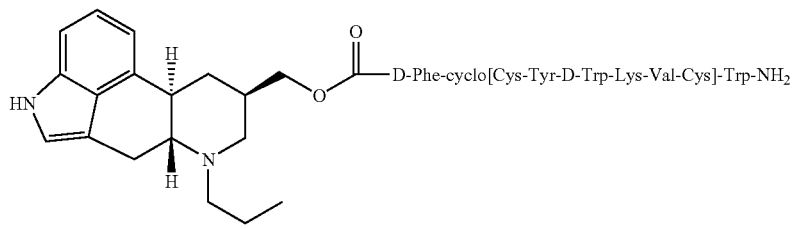
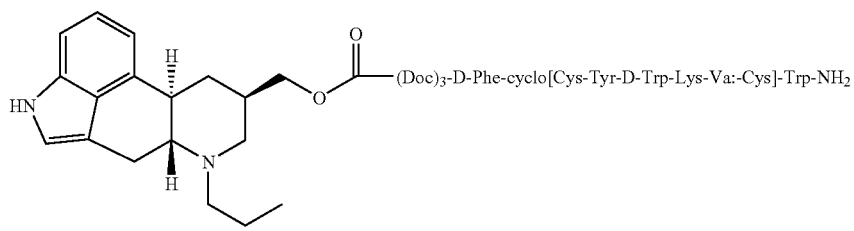
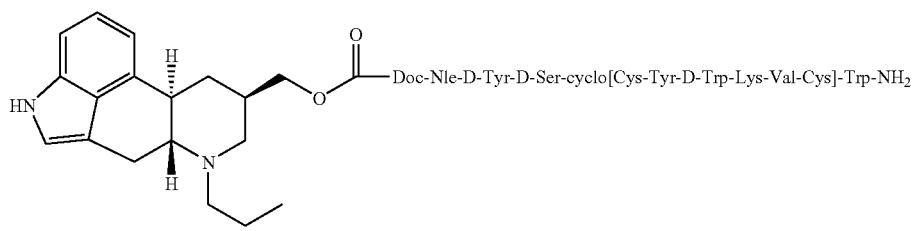
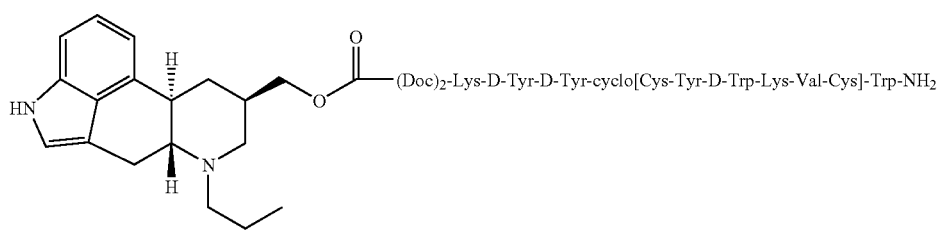
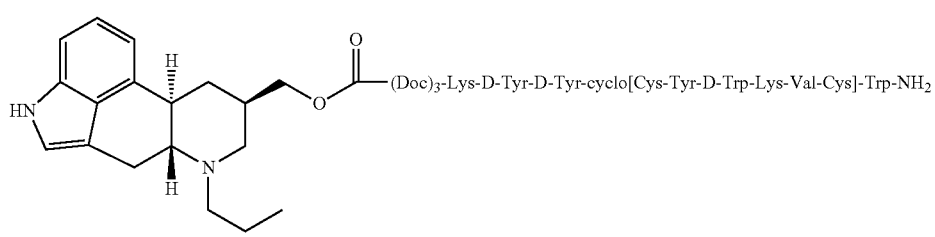
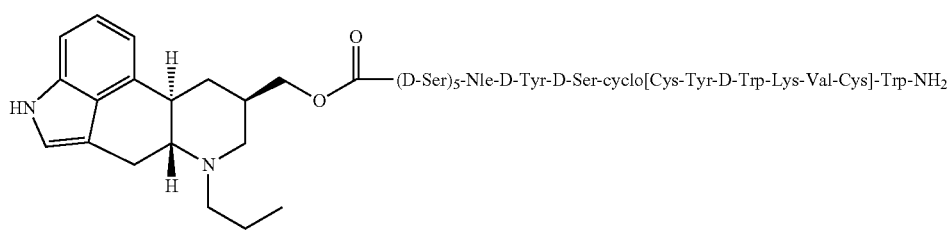

-continued
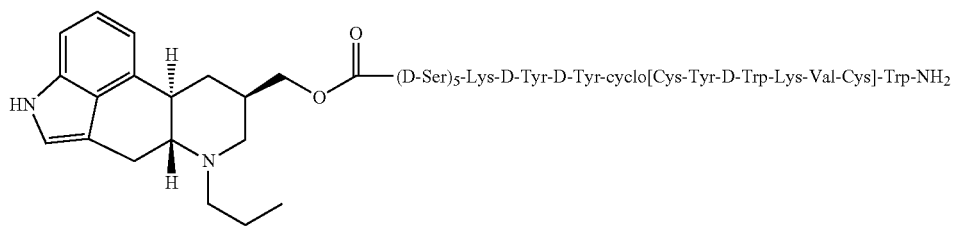
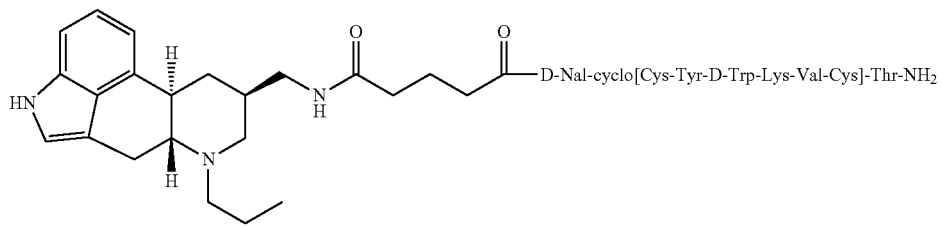
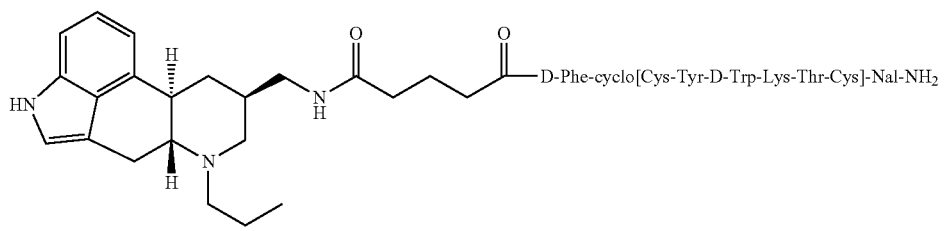
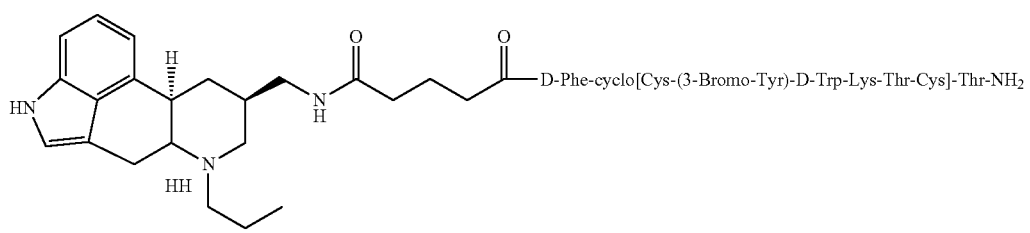
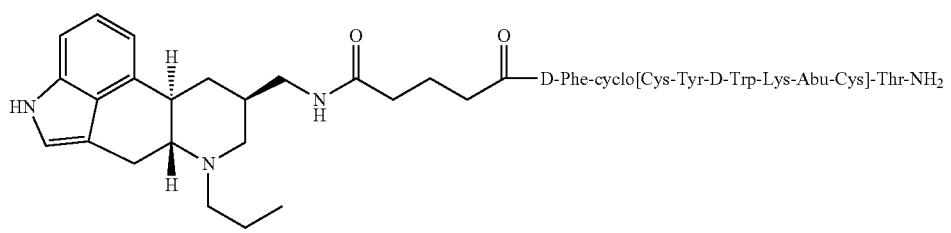
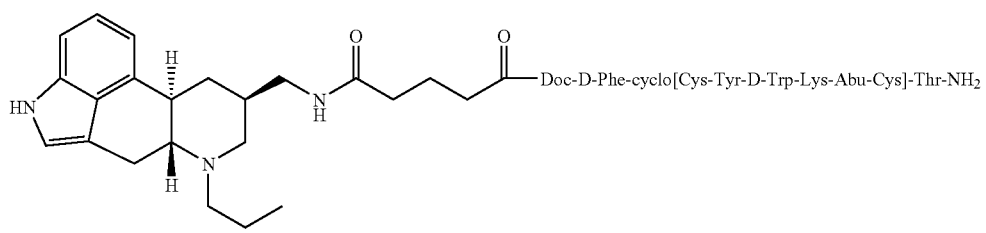
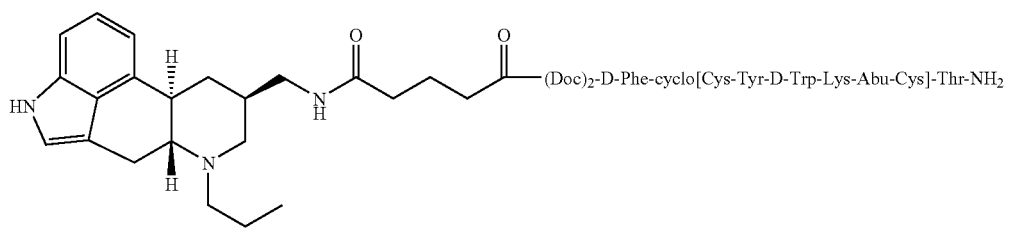

-continued

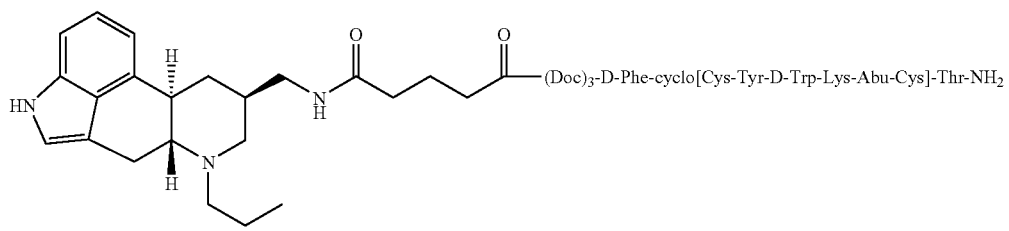
(Doc)₃-D-Phe-cyclo[Cys-Tyr-D-Trp-Lys-Abu-Cys]-Thr-NH₂

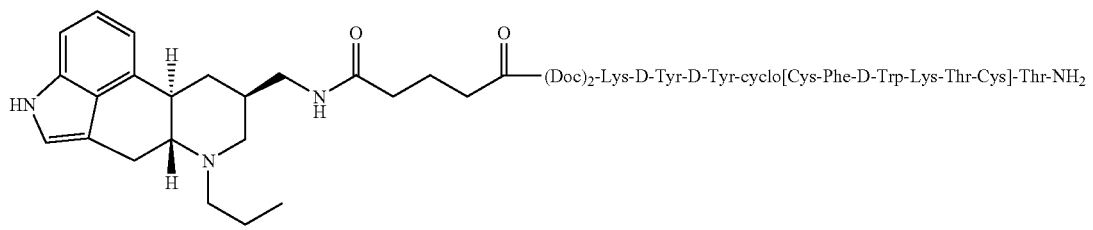
(Doc)₂-Lys-D-Tyr-D-Tyr-cyclo[Cys-Phe-D-Trp-Lys-Thr-Cys]-Thr-NH₂

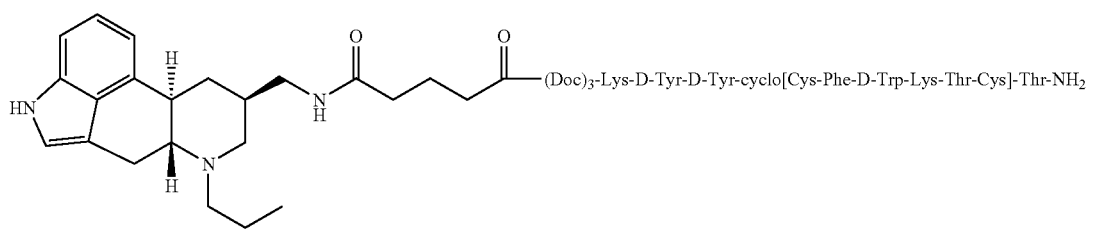
(Doc)₃-Lys-D-Tyr-D-Tyr-cyclo[Cys-Phe-D-Trp-Lys-Thr-Cys]-Thr-NH₂

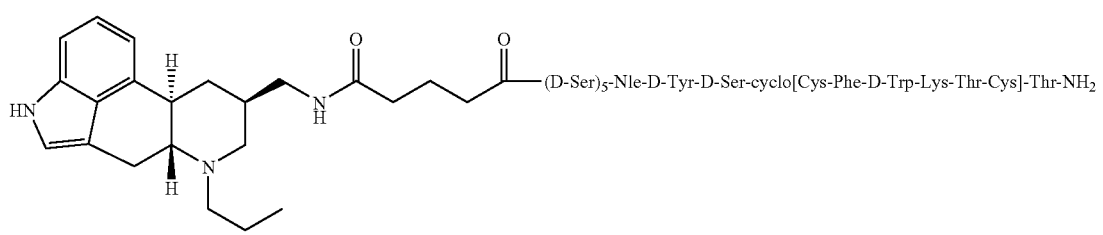
(D-Ser)₅-Nle-D-Tyr-D-Ser-cyclo[Cys-Phe-D-Trp-Lys-Thr-Cys]-Thr-NH₂

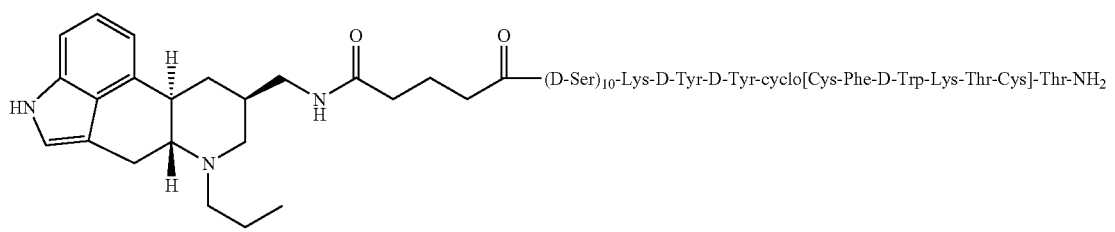
(D-Ser)₁₀-Lys-D-Tyr-D-Tyr-cyclo[Cys-Phe-D-Trp-Lys-Thr-Cys]-Thr-NH₂

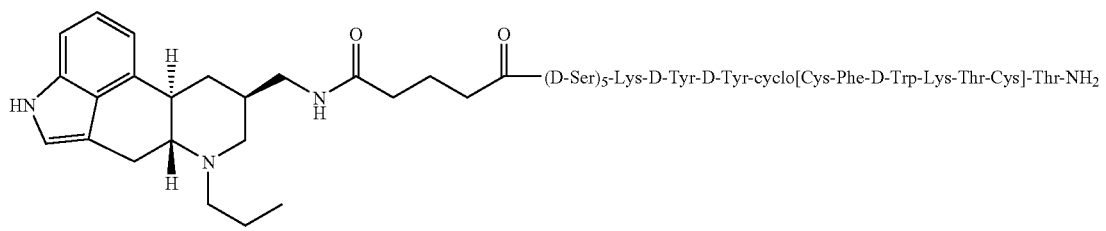
(D-Ser)₅-Lys-D-Tyr-D-Tyr-cyclo[Cys-Phe-D-Trp-Lys-Thr-Cys]-Thr-NH₂

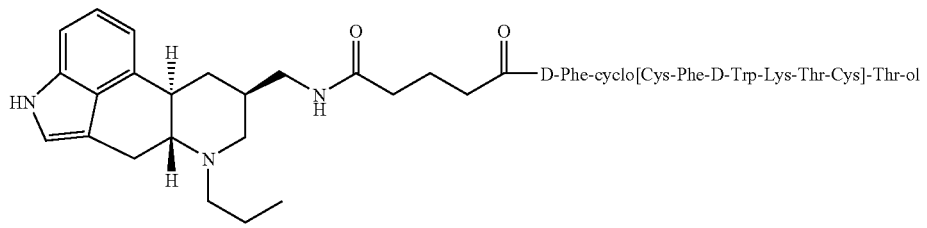
D-Phe-cyclo[Cys-Phe-D-Trp-Lys-Thr-Cys]-Thr-ol

-continued
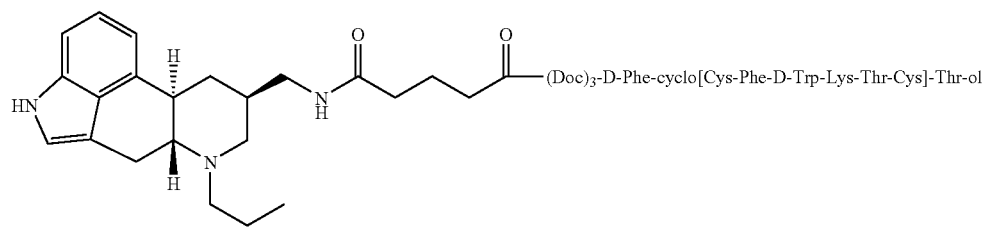
(Doc)₃-D-Phe-cyclo[Cys-Phe-D-Trp-Lys-Thr-Cys]-Thr-ol
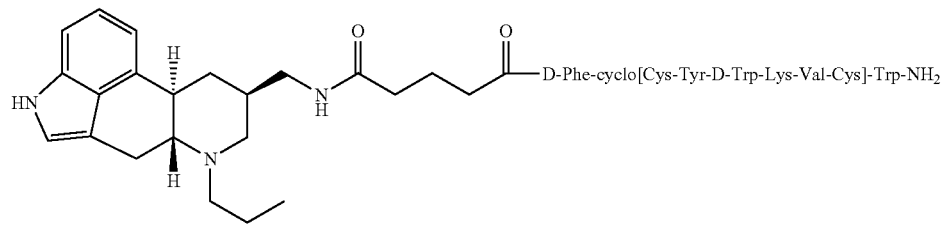
D-Phe-cyclo[Cys-Tyr-D-Trp-Lys-Val-Cys]-Trp-NH₂
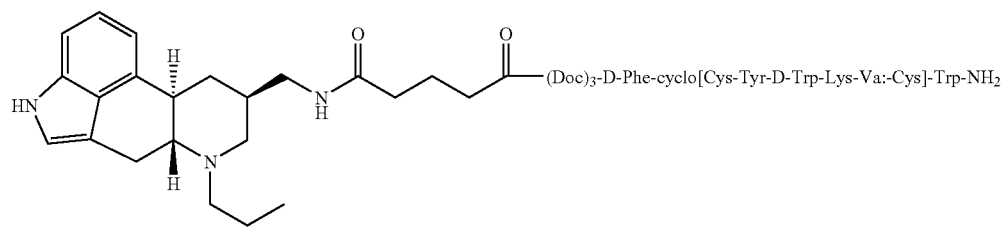
(Doc)₃-D-Phe-cyclo[Cys-Tyr-D-Trp-Lys-Val-Cys]-Trp-NH₂
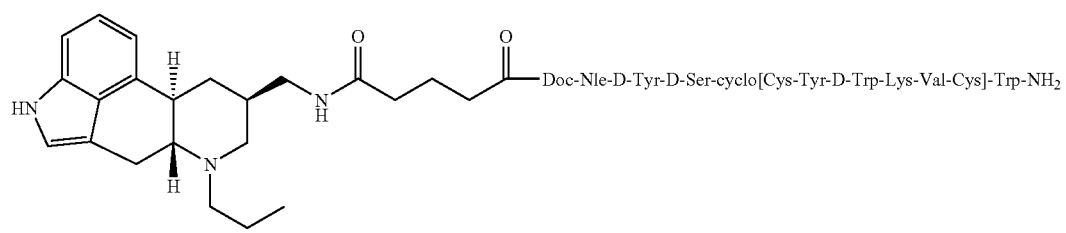
Doc-Nle-D-Tyr-D-Ser-cyclo[Cys-Tyr-D-Trp-Lys-Val-Cys]-Trp-NH₂
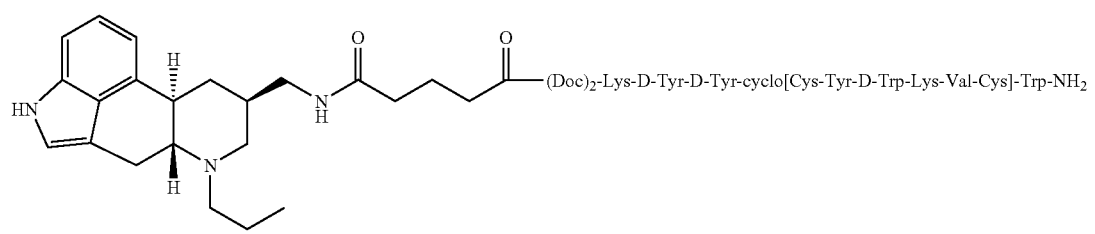
(Doc)₂-Lys-D-Tyr-D-Tyr-cyclo[Cys-Tyr-D-Trp-Lys-Val-Cys]-Trp-NH₂
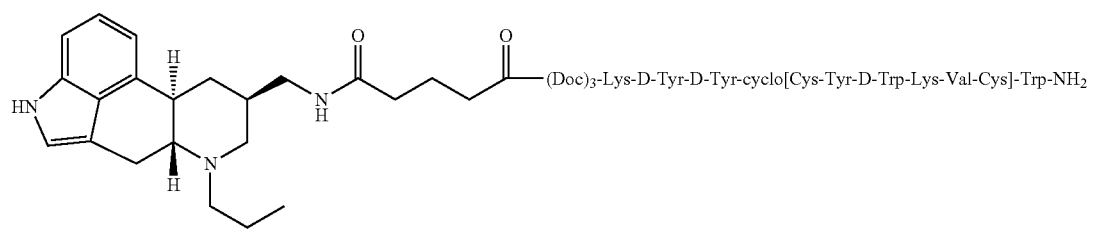
(Doc)₃-Lys-D-Tyr-D-Tyr-cyclo[Cys-Tyr-D-Trp-Lys-Val-Cys]-Trp-NH₂
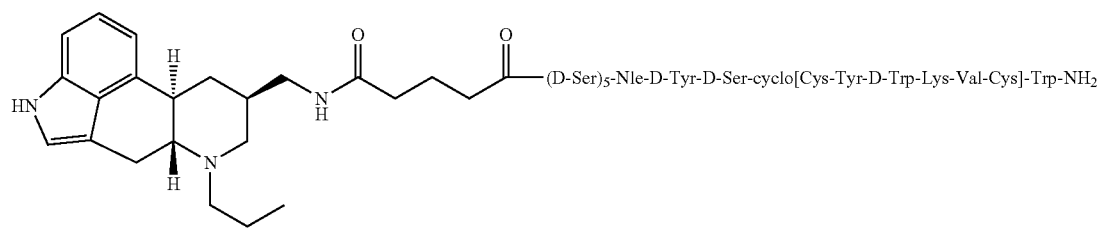
(D-Ser)₅-Nle-D-Tyr-D-Ser-cyclo[Cys-Tyr-D-Trp-Lys-Val-Cys]-Trp-NH₂

-continued
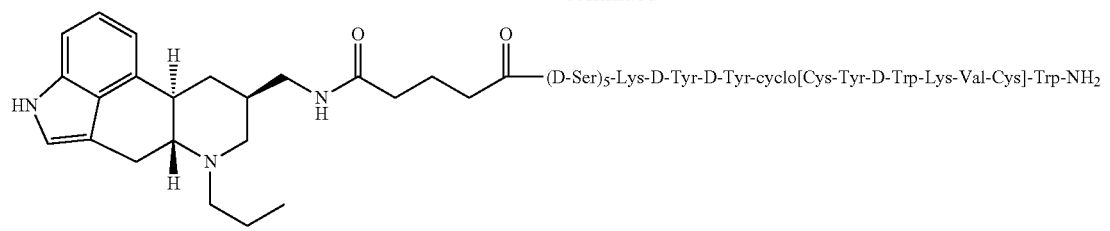
Compound E
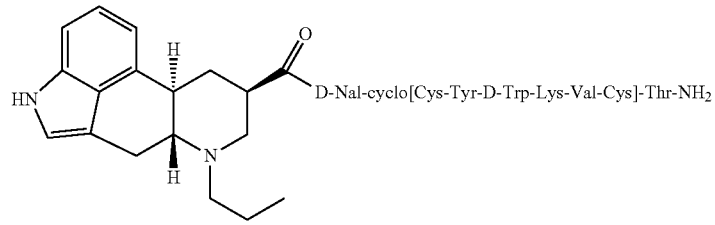
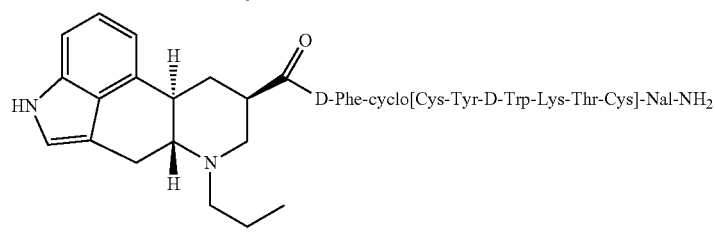
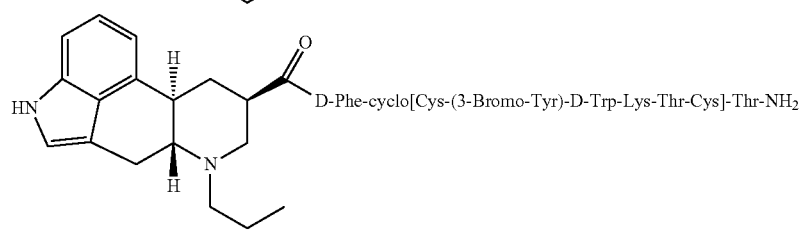
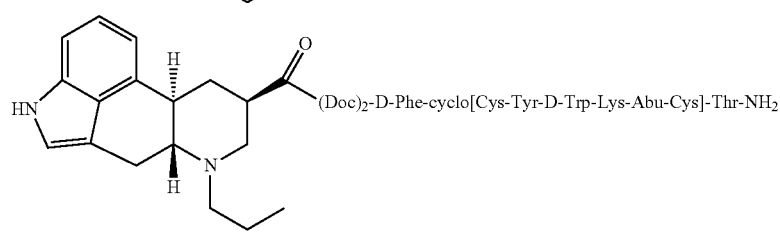
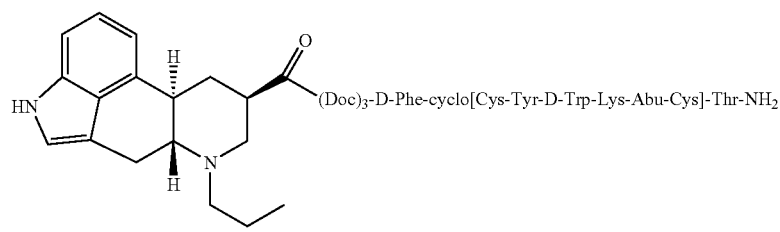
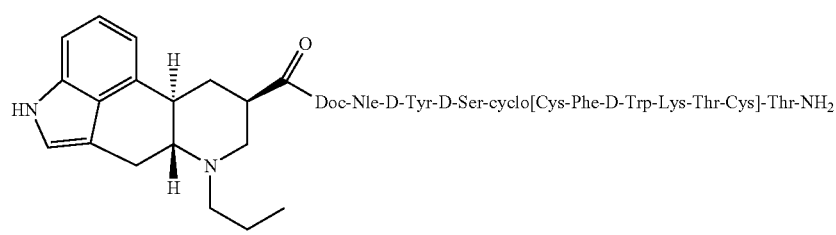

-continued

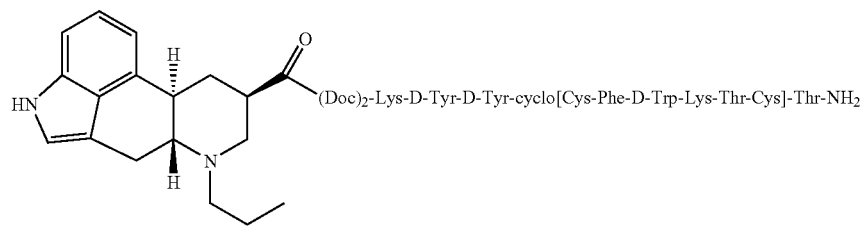
(Doc)$_2$-Lys-D-Tyr-D-Tyr-cyclo[Cys-Phe-D-Trp-Lys-Thr-Cys]-Thr-NH$_2$

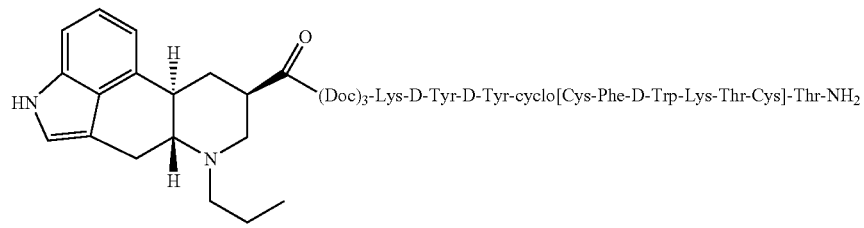
(Doc)$_3$-Lys-D-Tyr-D-Tyr-cyclo[Cys-Phe-D-Trp-Lys-Thr-Cys]-Thr-NH$_2$

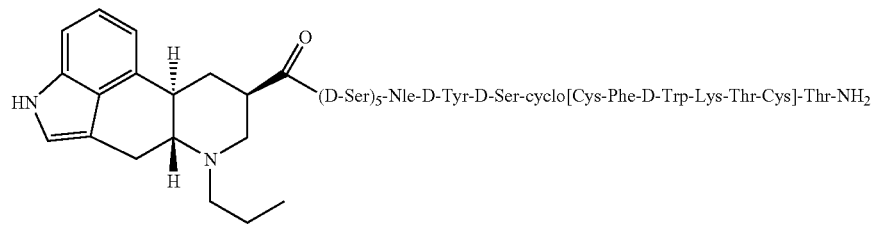
(D-Ser)$_5$-Nle-D-Tyr-D-Ser-cyclo[Cys-Phe-D-Trp-Lys-Thr-Cys]-Thr-NH$_2$

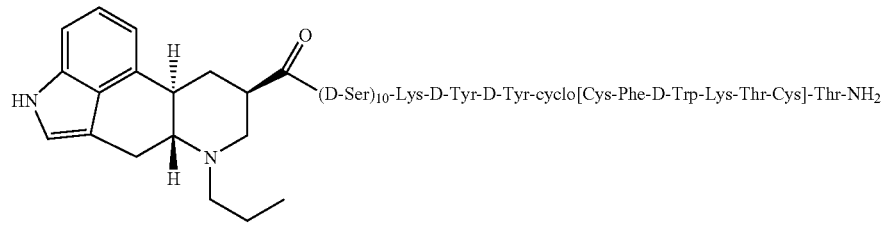
(D-Ser)$_{10}$-Lys-D-Tyr-D-Tyr-cyclo[Cys-Phe-D-Trp-Lys-Thr-Cys]-Thr-NH$_2$

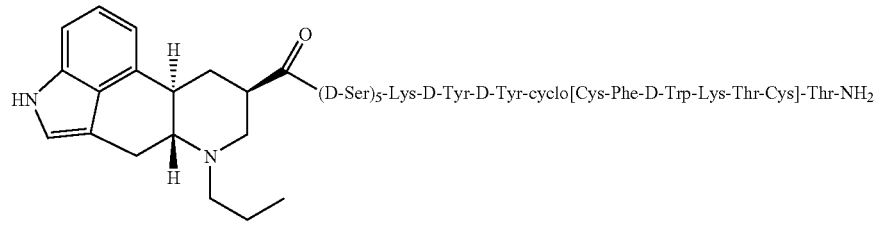
(D-Ser)$_5$-Lys-D-Tyr-D-Tyr-cyclo[Cys-Phe-D-Trp-Lys-Thr-Cys]-Thr-NH$_2$

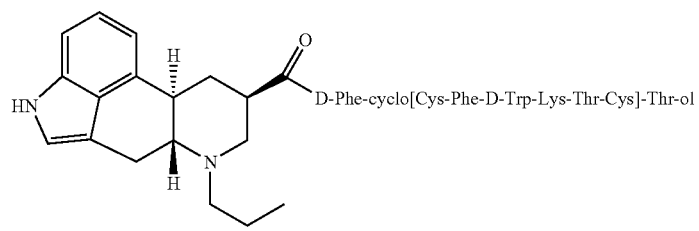
D-Phe-cyclo[Cys-Phe-D-Trp-Lys-Thr-Cys]-Thr-ol

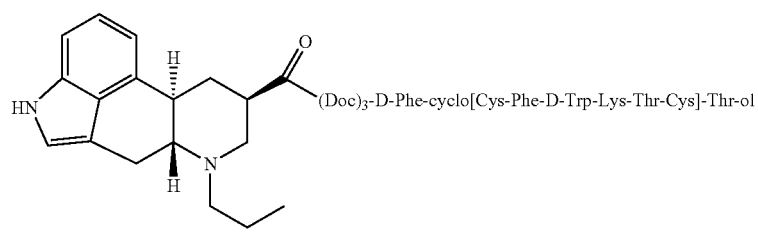
(Doc)$_3$-D-Phe-cyclo[Cys-Phe-D-Trp-Lys-Thr-Cys]-Thr-ol

-continued
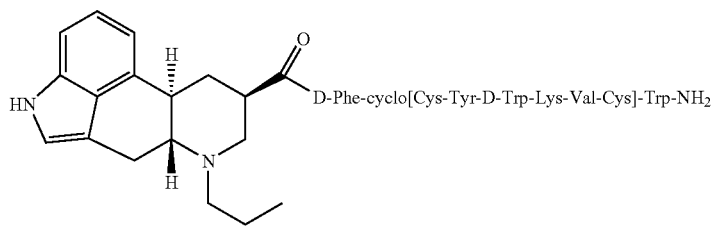
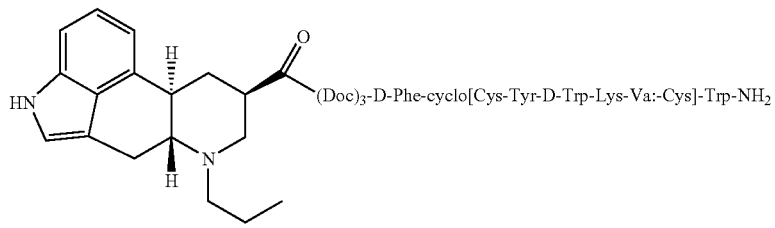
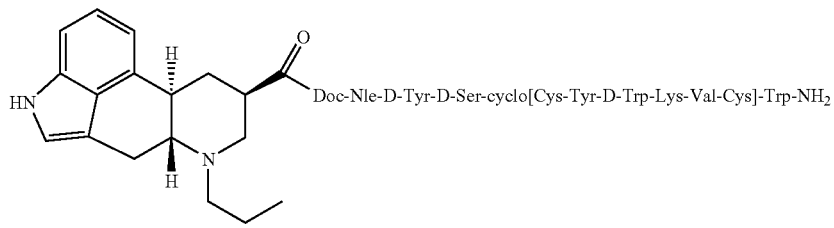
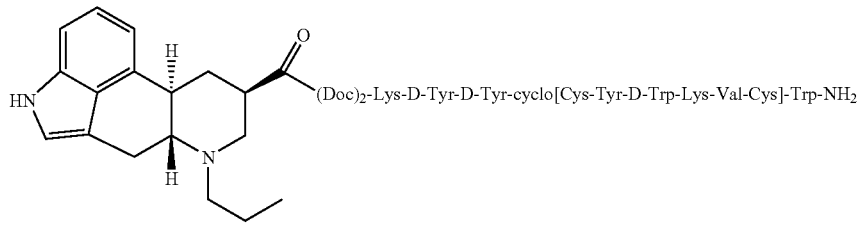
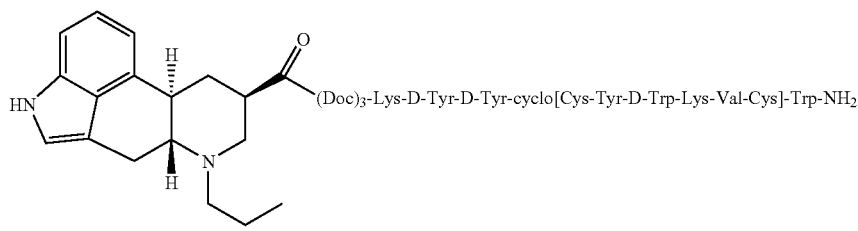
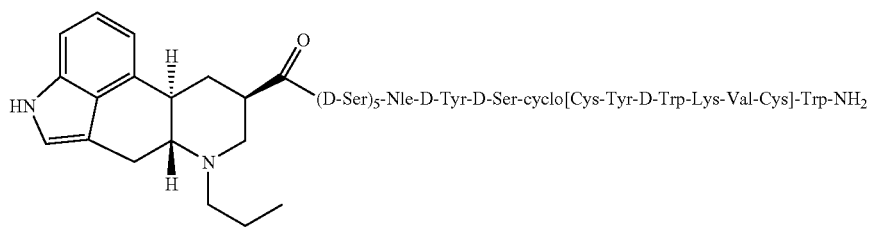
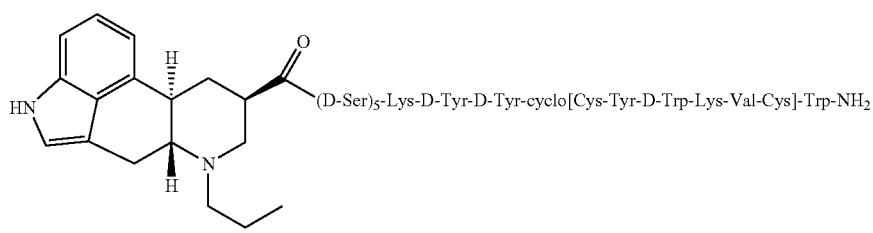

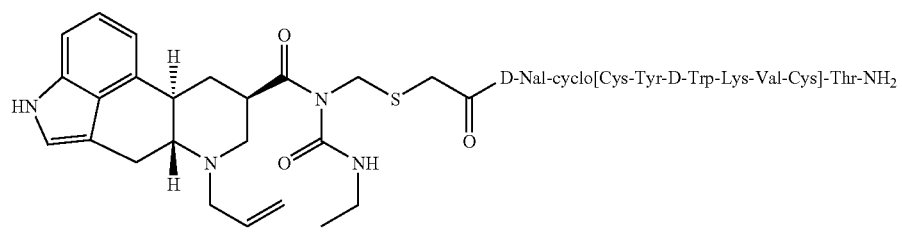
D-Nal-cyclo[Cys-Tyr-D-Trp-Lys-Val-Cys]-Thr-NH$_2$
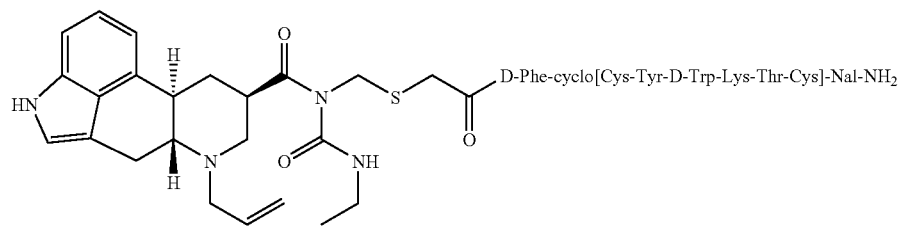
D-Phe-cyclo[Cys-Tyr-D-Trp-Lys-Thr-Cys]-Nal-NH$_2$
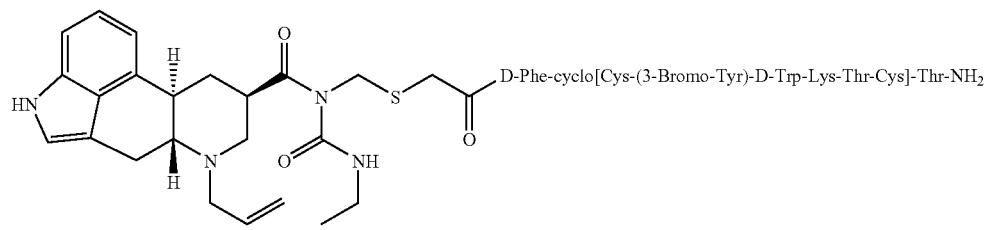
D-Phe-cyclo[Cys-(3-Bromo-Tyr)-D-Trp-Lys-Thr-Cys]-Thr-NH$_2$
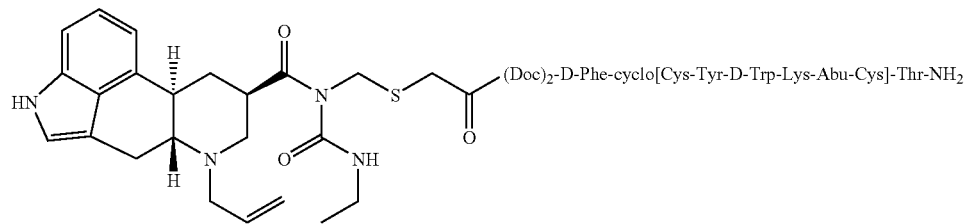
(Doc)$_2$-D-Phe-cyclo[Cys-Tyr-D-Trp-Lys-Abu-Cys]-Thr-NH$_2$
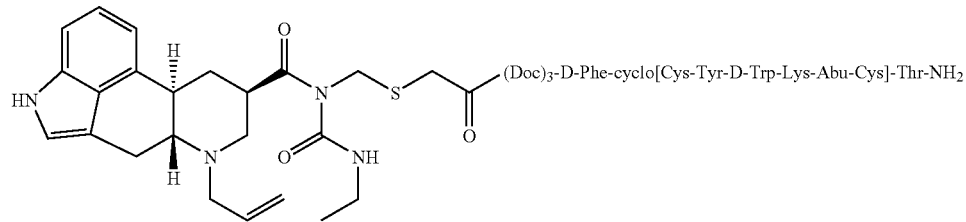
(Doc)$_3$-D-Phe-cyclo[Cys-Tyr-D-Trp-Lys-Abu-Cys]-Thr-NH$_2$
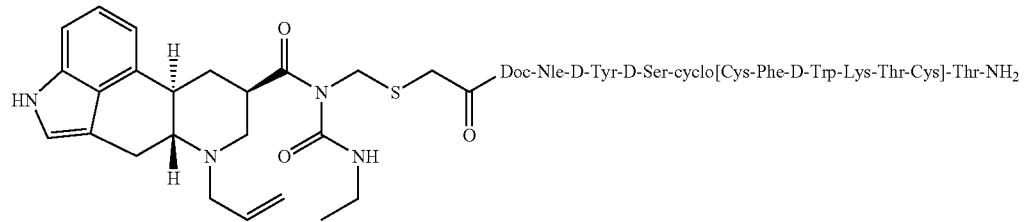
Doc-Nle-D-Tyr-D-Ser-cyclo[Cys-Phe-D-Trp-Lys-Thr-Cys]-Thr-NH$_2$
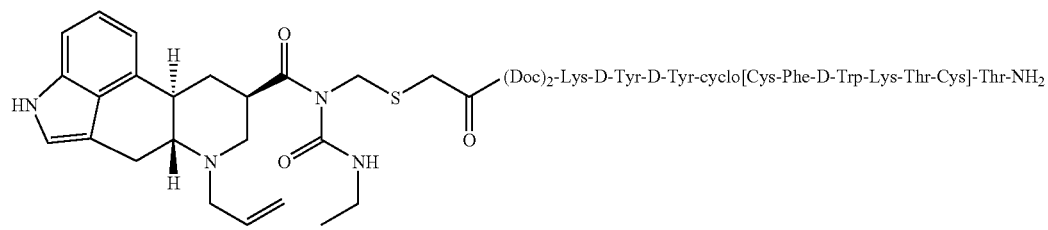
(Doc)$_2$-Lys-D-Tyr-D-Tyr-cyclo[Cys-Phe-D-Trp-Lys-Thr-Cys]-Thr-NH$_2$ -continued
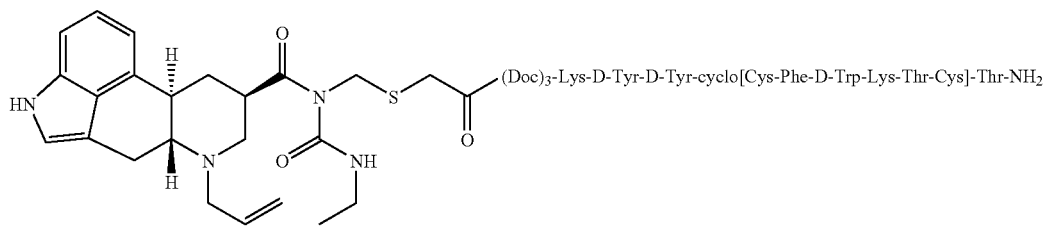
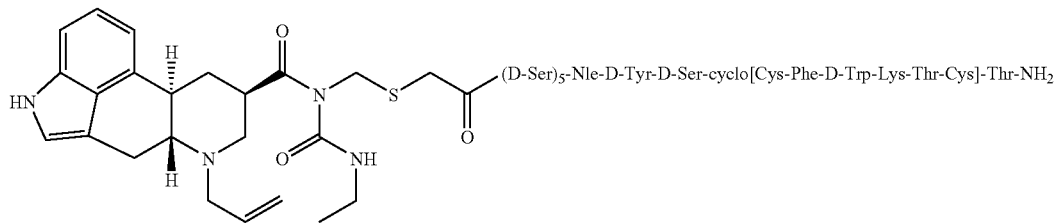
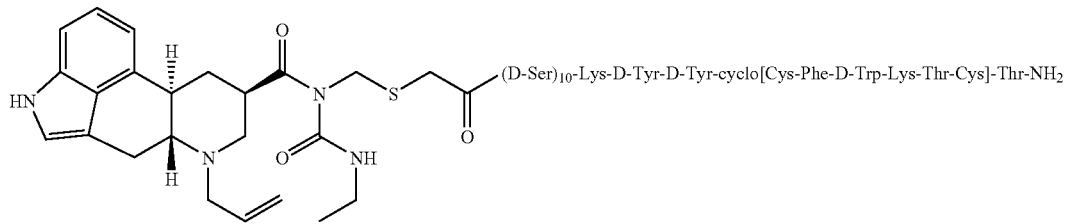
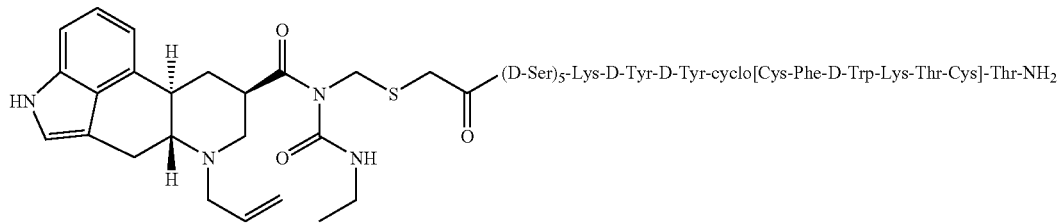
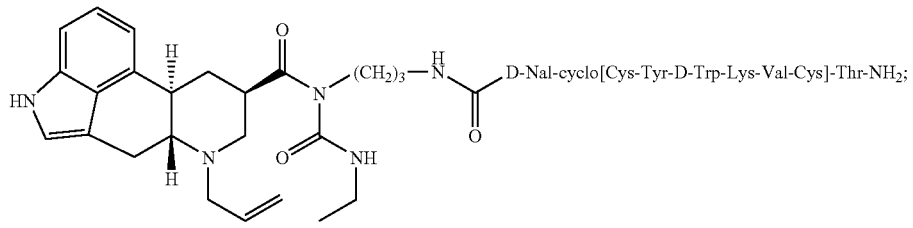
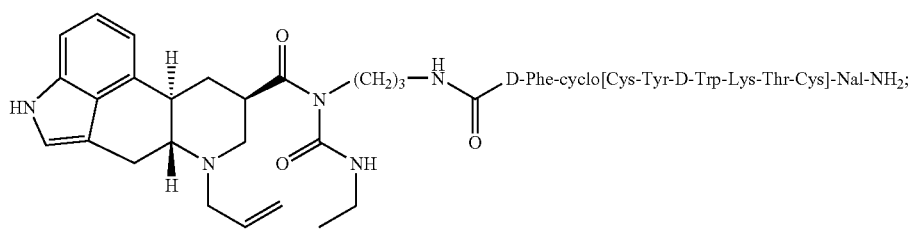
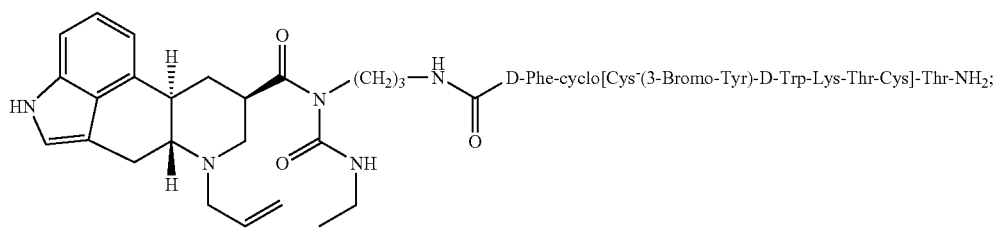

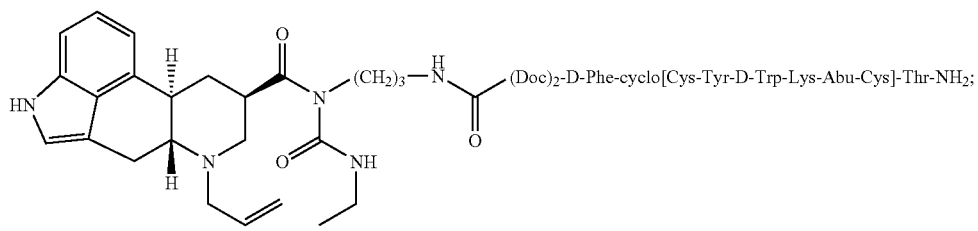
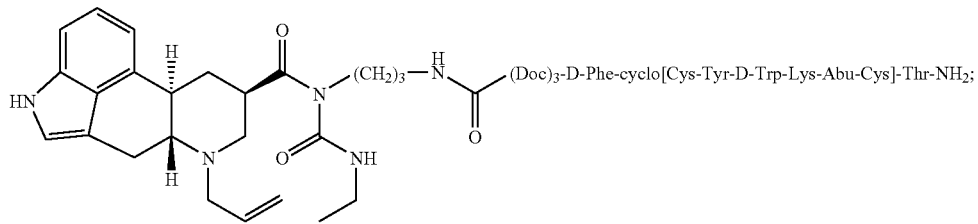
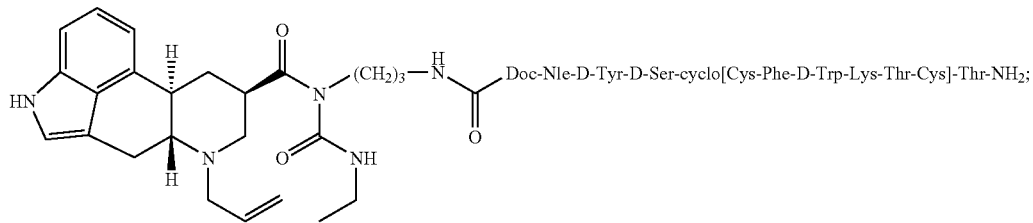
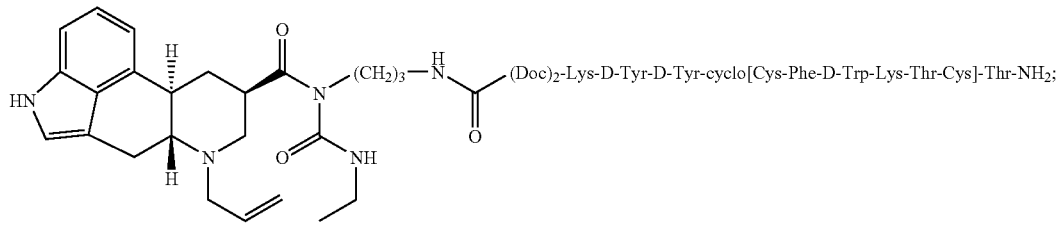
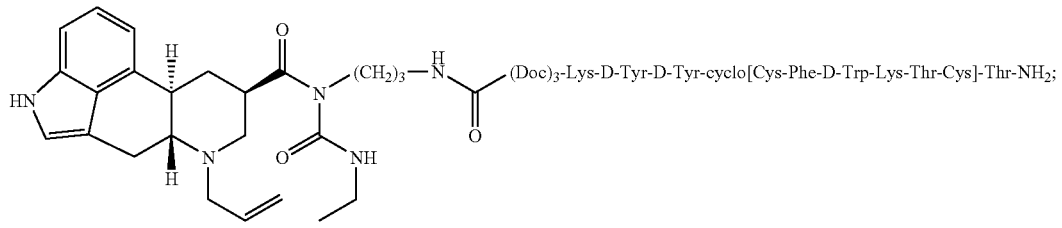
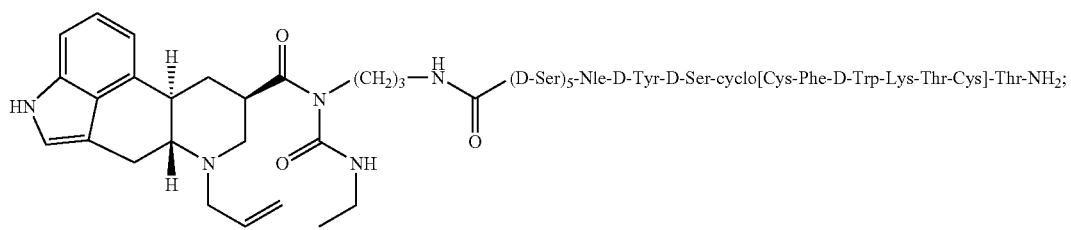
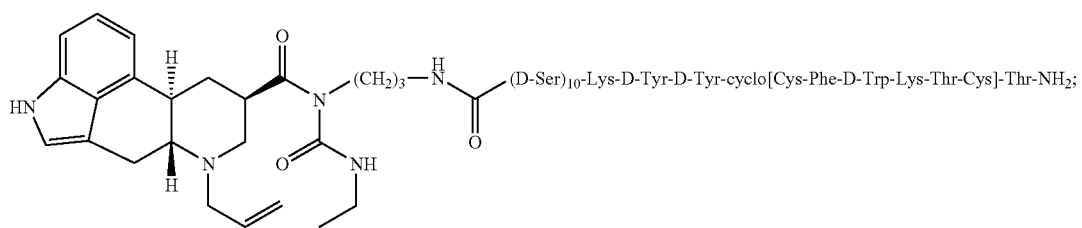

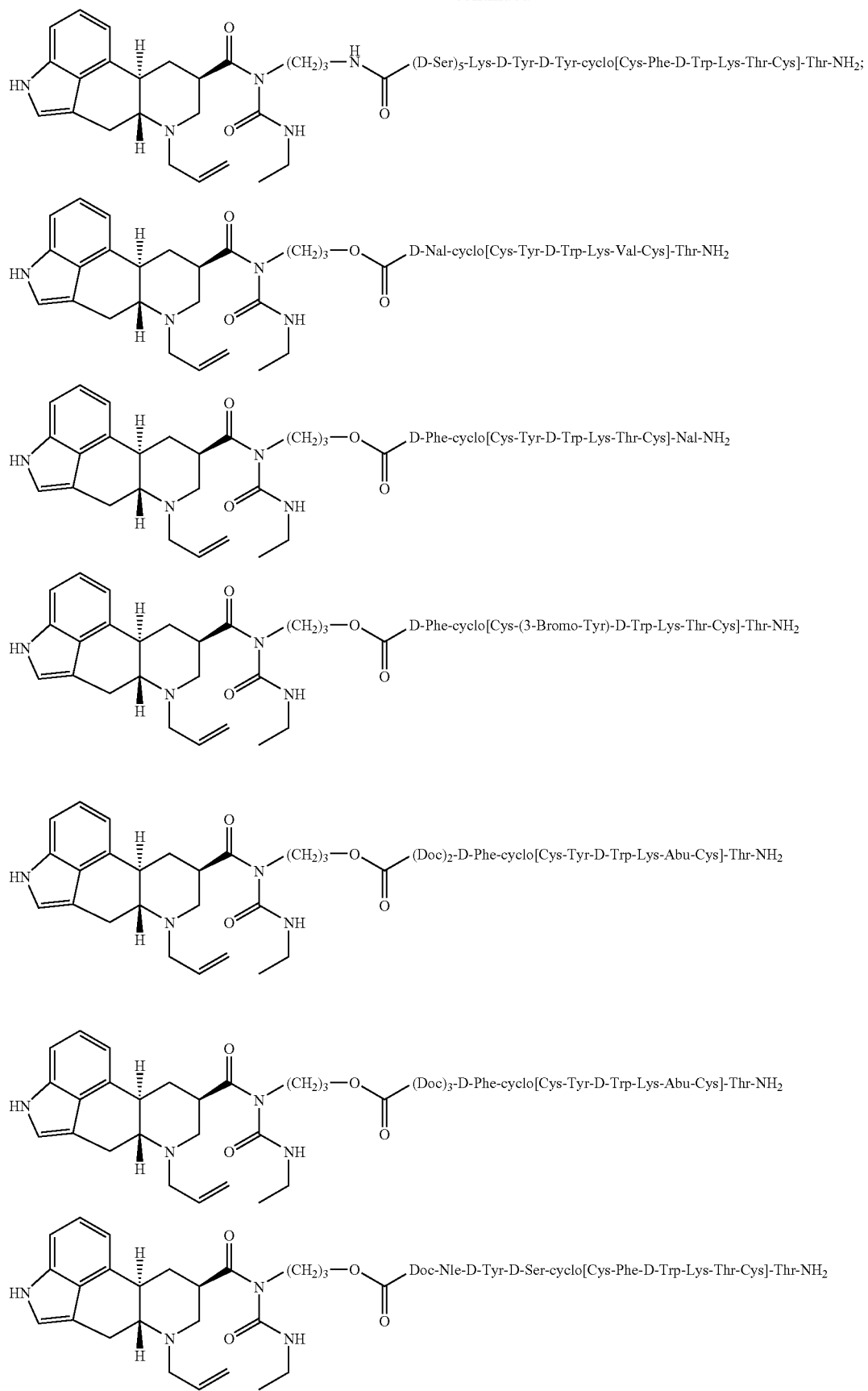

-continued
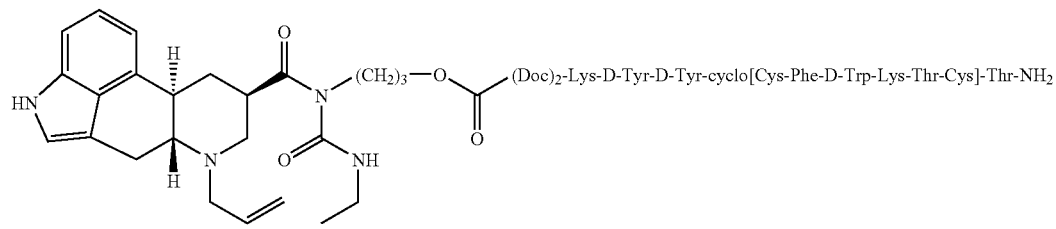
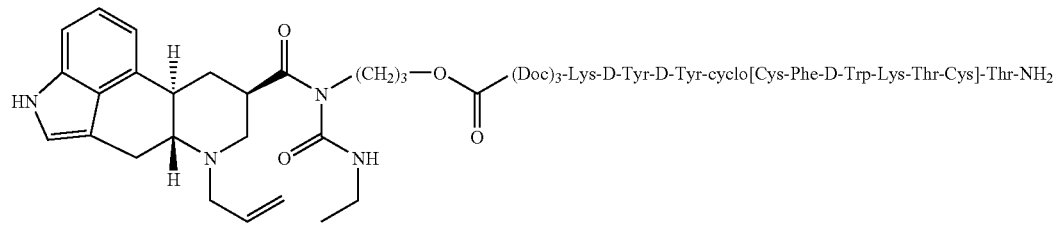
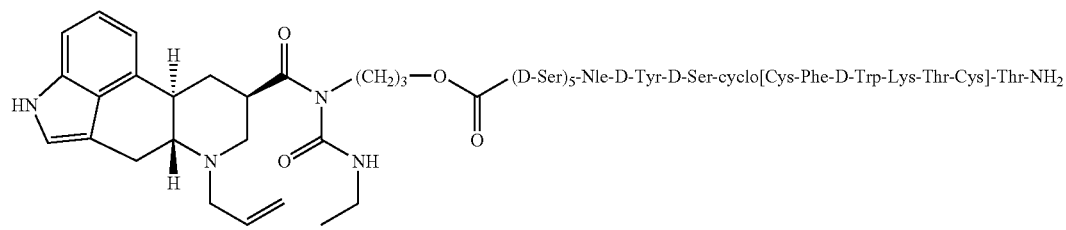
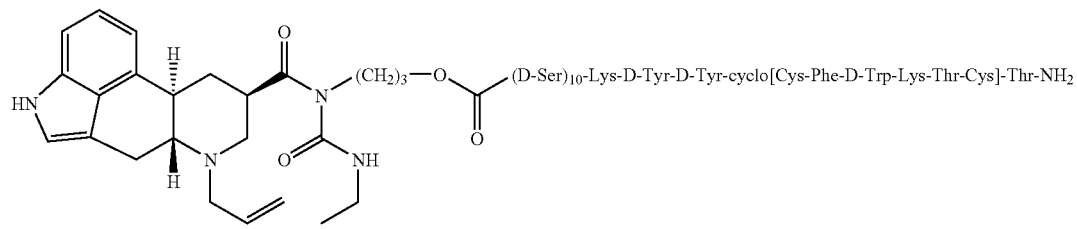
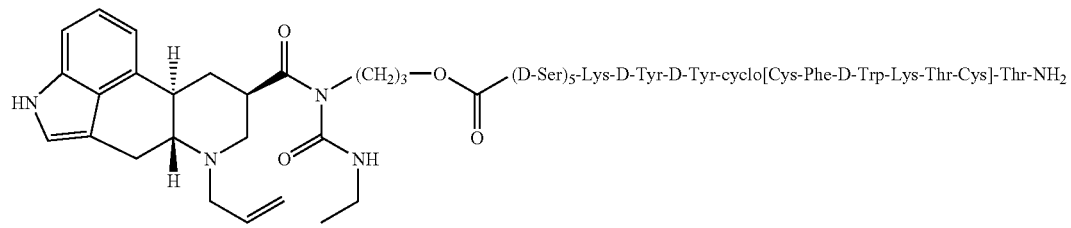
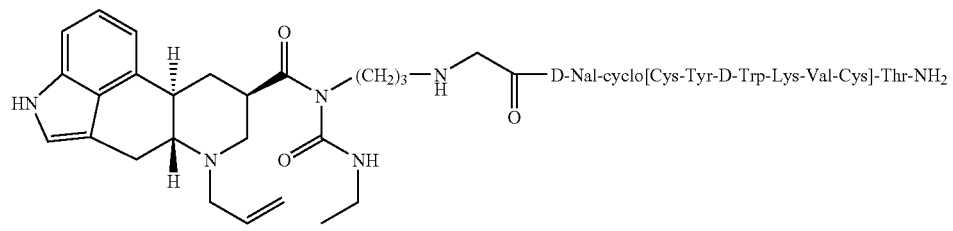
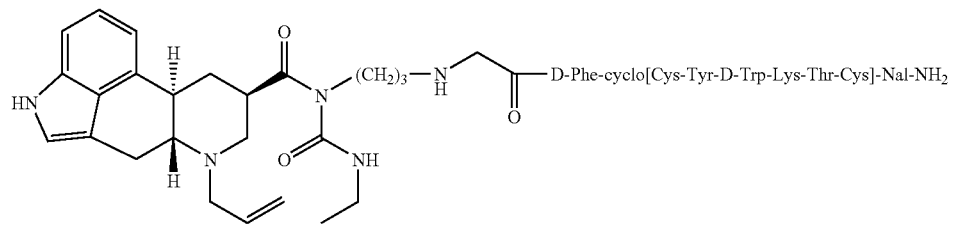

-continued
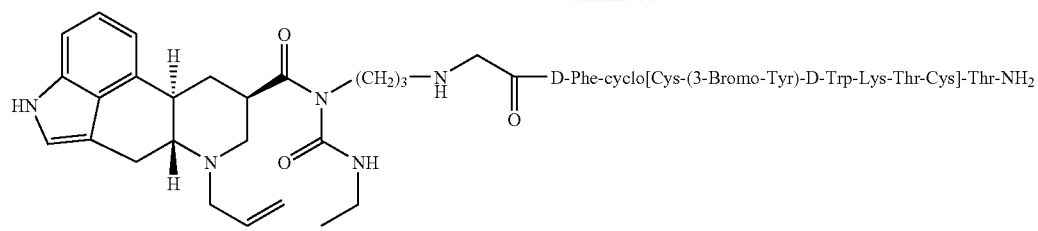
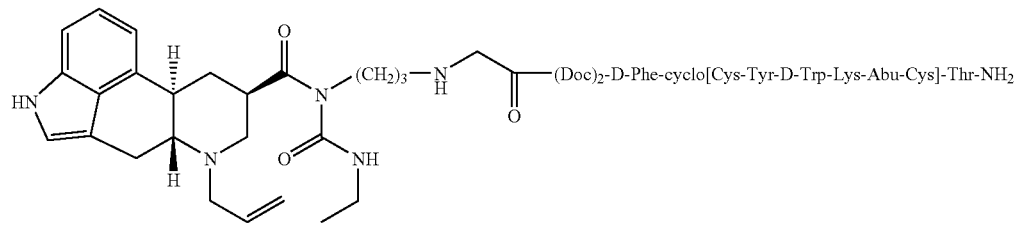
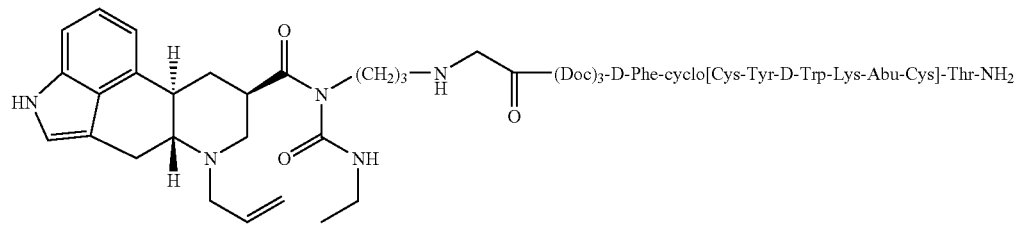
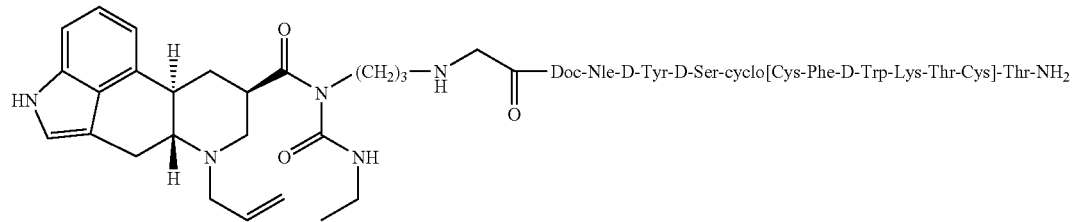
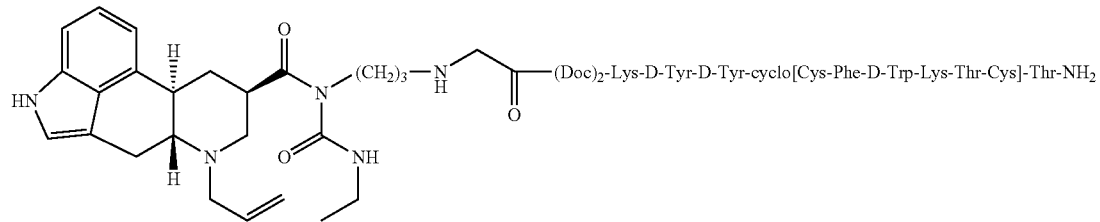
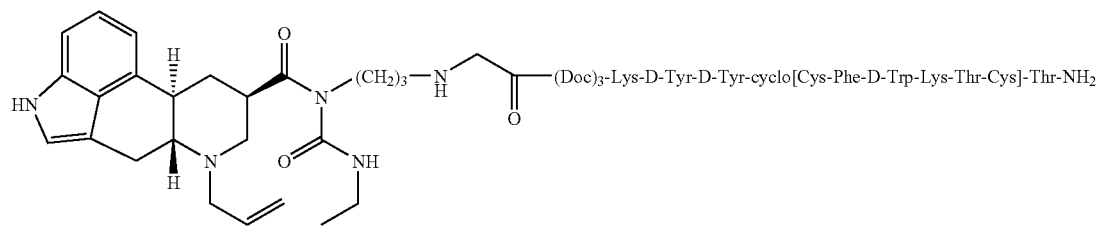
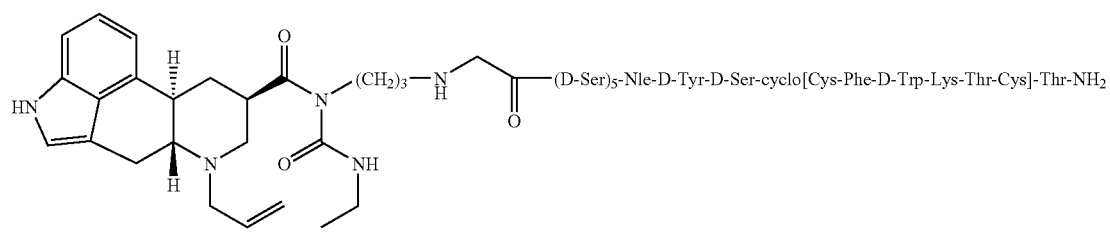

-continued
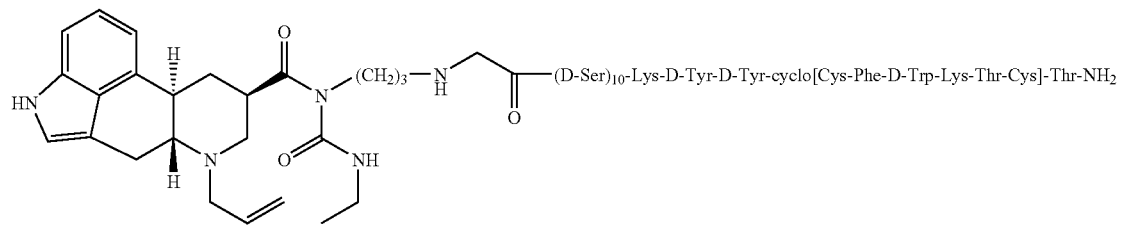
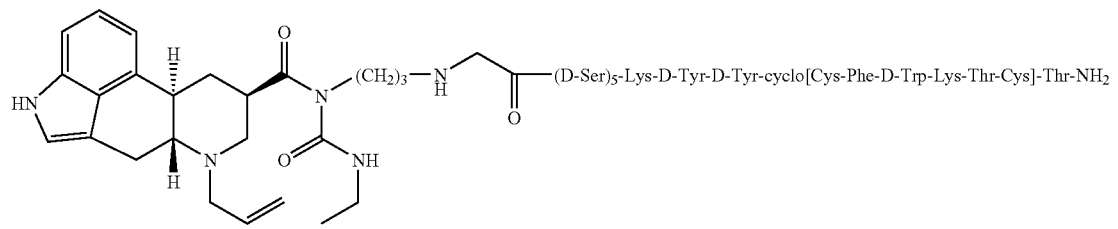
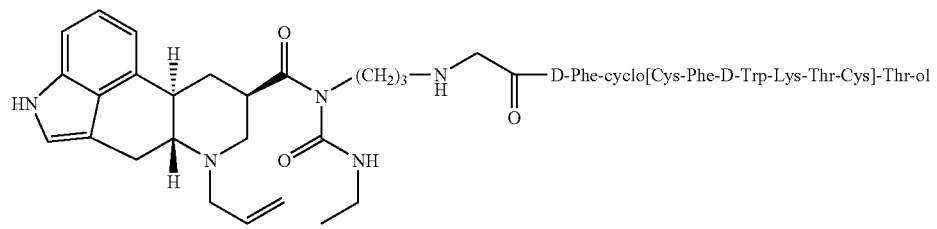
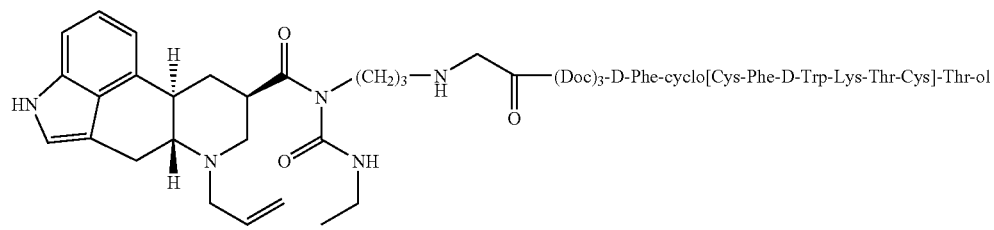
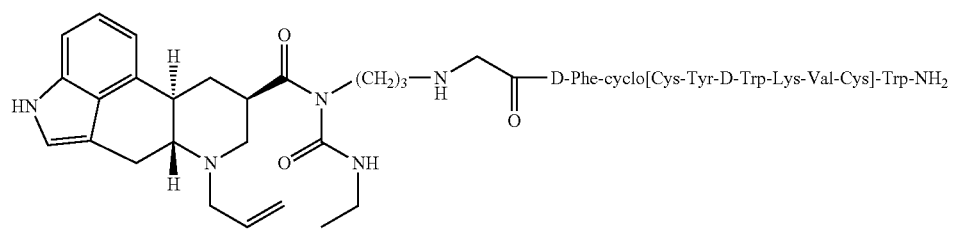
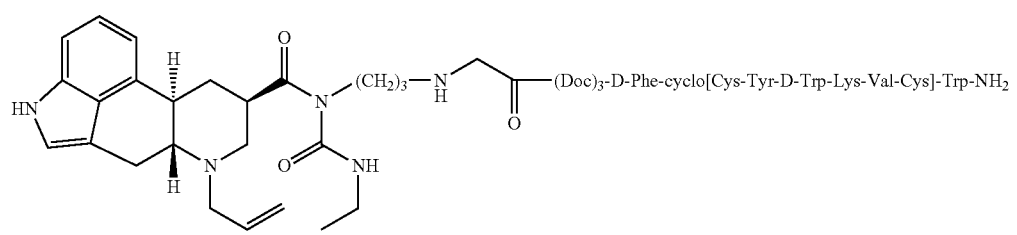
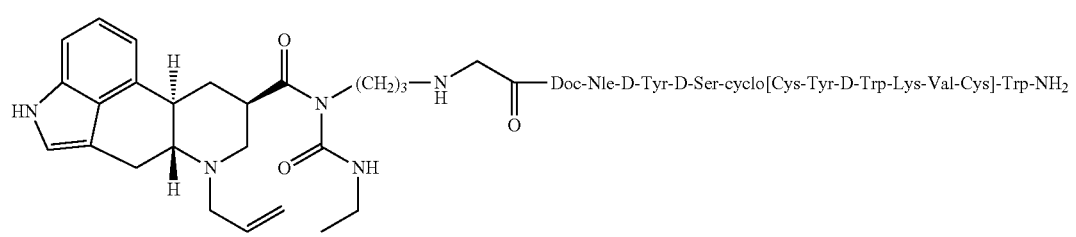

-continued
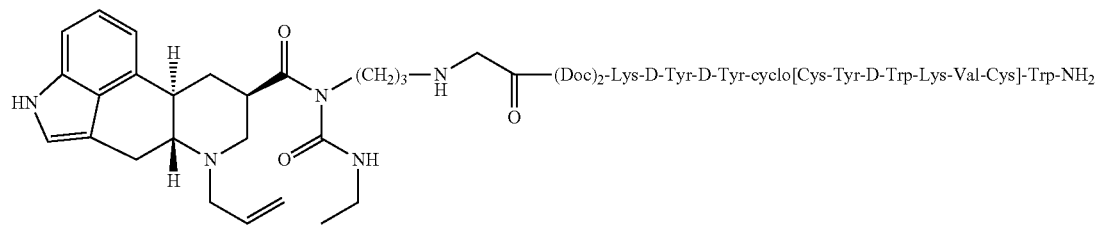
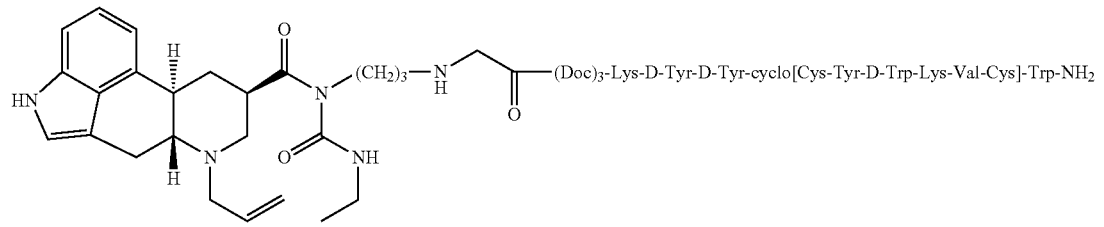
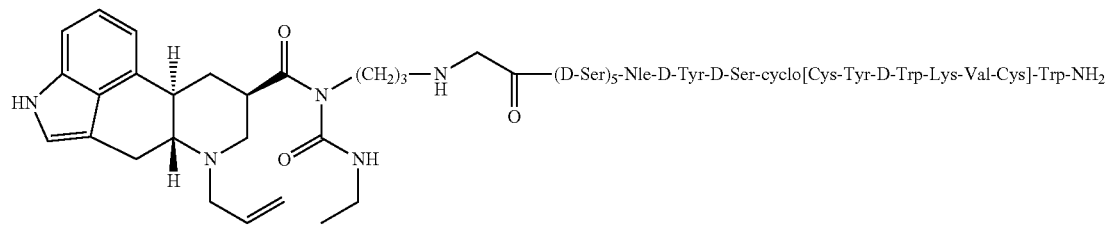
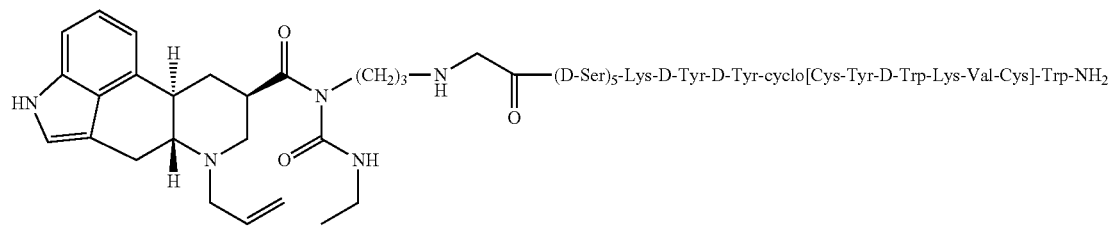
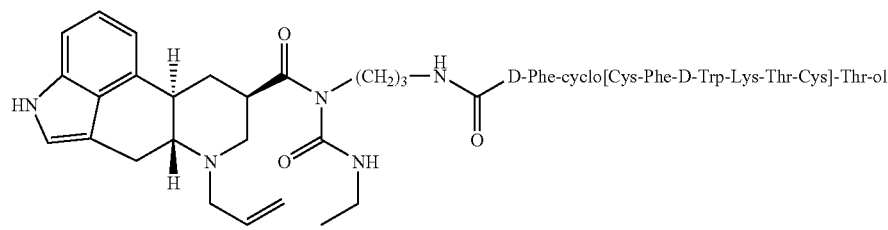
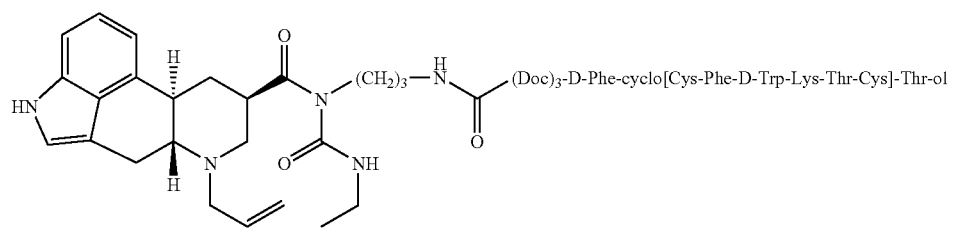
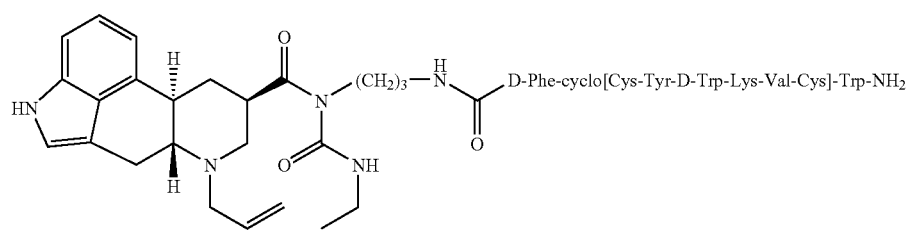

-continued
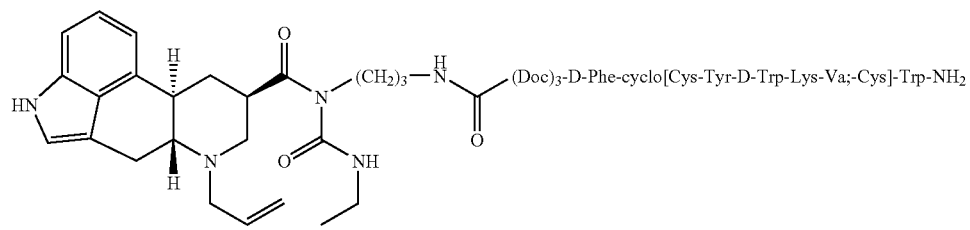
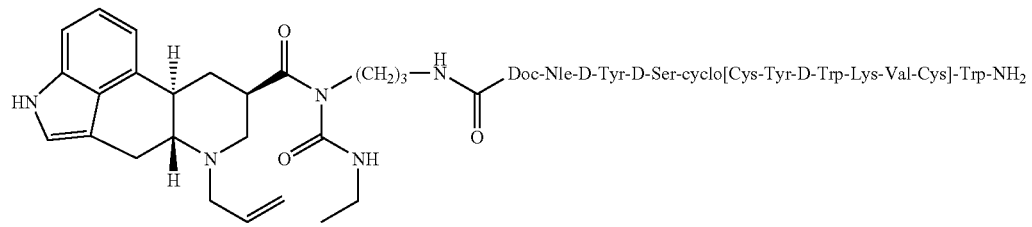
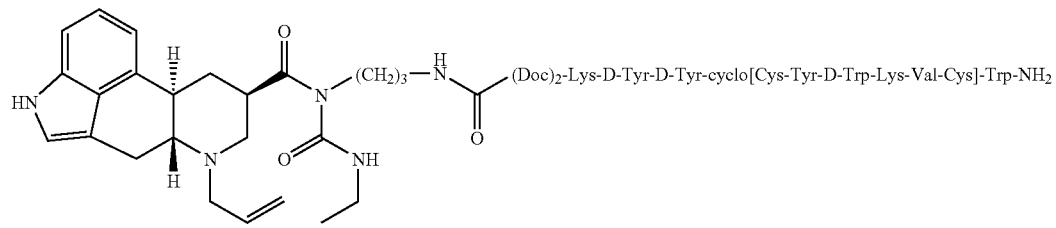
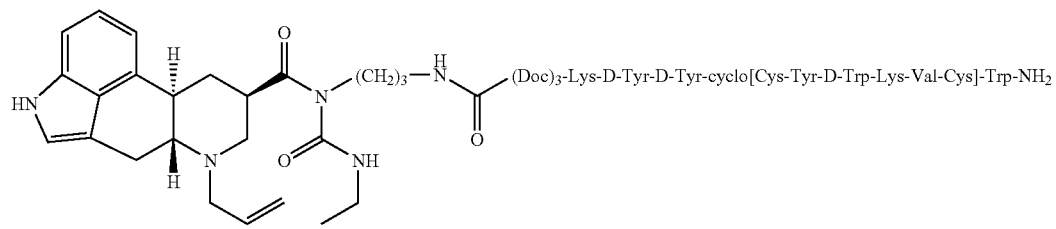
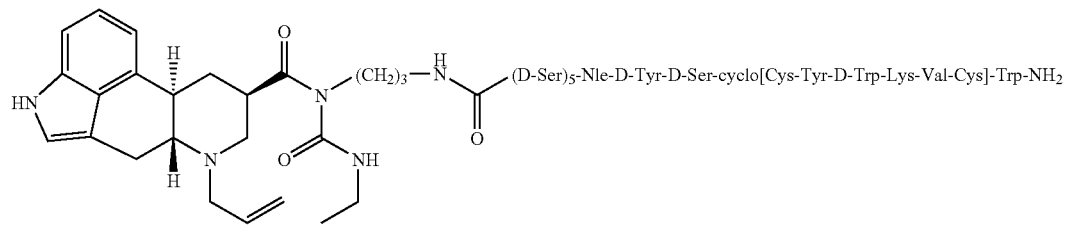
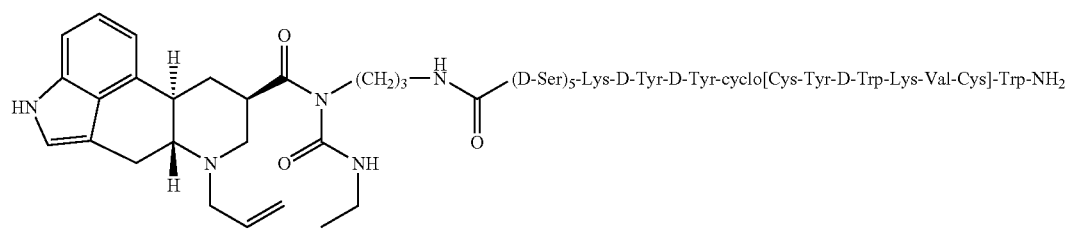
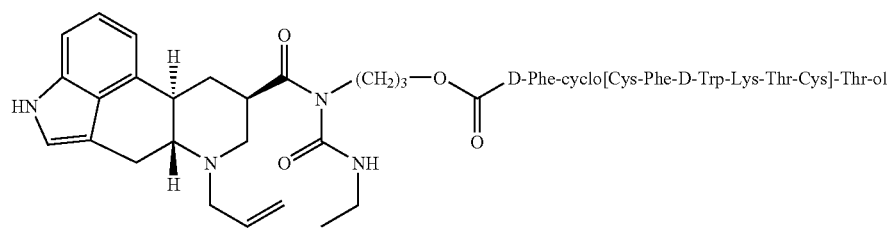

-continued
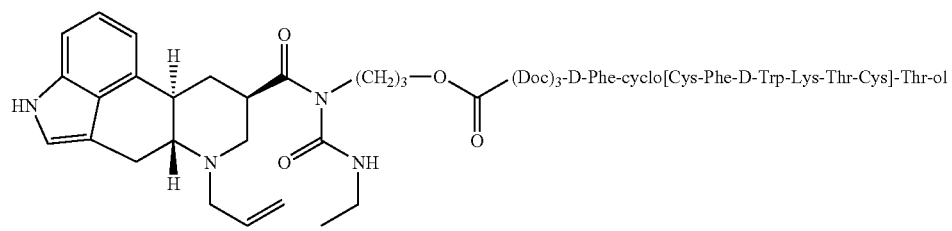
(Doc)₃-D-Phe-cyclo[Cys-Phe-D-Trp-Lys-Thr-Cys]-Thr-ol
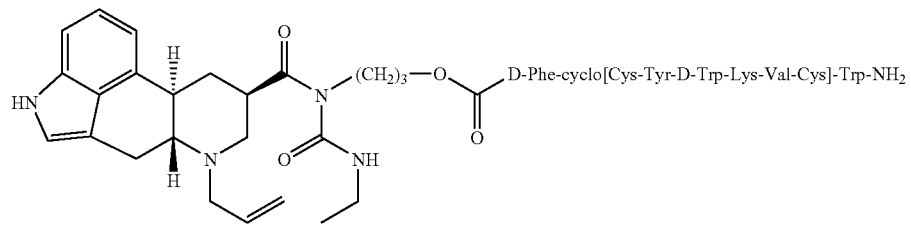
D-Phe-cyclo[Cys-Tyr-D-Trp-Lys-Val-Cys]-Trp-NH₂
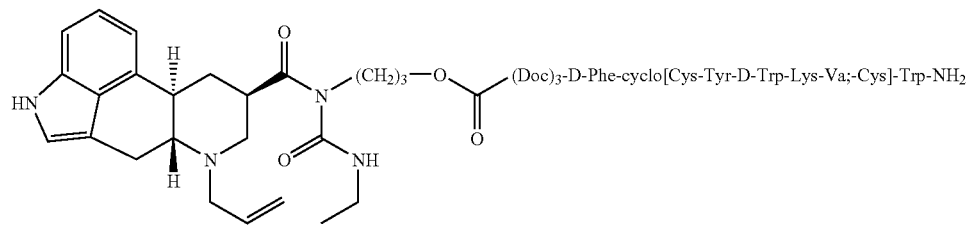
(Doc)₃-D-Phe-cyclo[Cys-Tyr-D-Trp-Lys-Va;-Cys]-Trp-NH₂
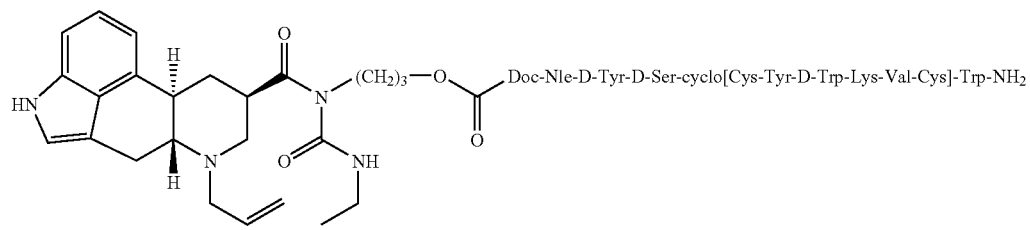
Doc-Nle-D-Tyr-D-Ser-cyclo[Cys-Tyr-D-Trp-Lys-Val-Cys]-Trp-NH₂
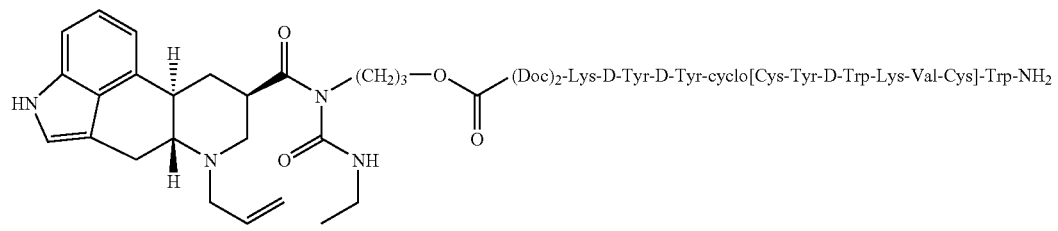
(Doc)₂-Lys-D-Tyr-D-Tyr-cyclo[Cys-Tyr-D-Trp-Lys-Val-Cys]-Trp-NH₂
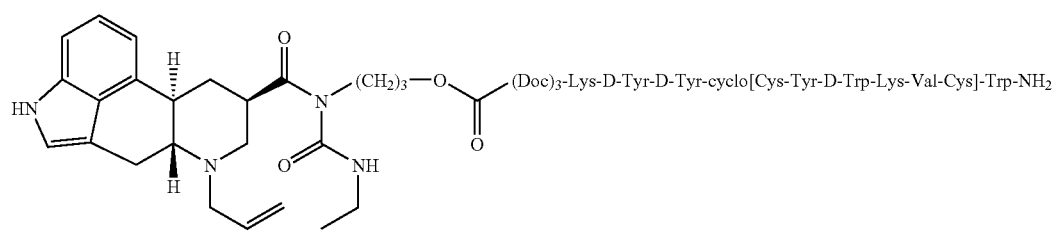
(Doc)₃-Lys-D-Tyr-D-Tyr-cyclo[Cys-Tyr-D-Trp-Lys-Val-Cys]-Trp-NH₂
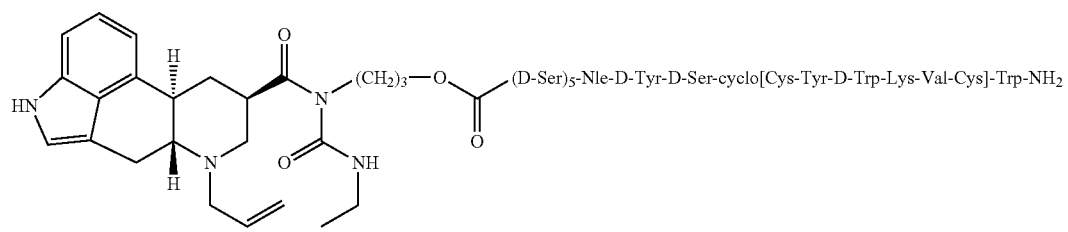
(D-Ser)₅-Nle-D-Tyr-D-Ser-cyclo[Cys-Tyr-D-Trp-Lys-Val-Cys]-Trp-NH₂

-continued
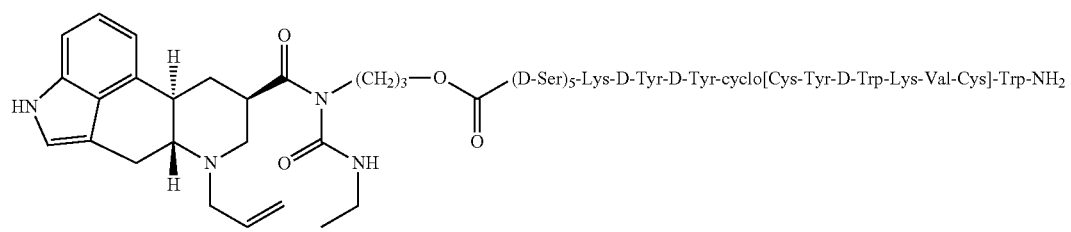(D-Ser)₅-Lys-D-Tyr-D-Tyr-cyclo[Cys-Tyr-D-Trp-Lys-Val-Cys]-Trp-NH₂
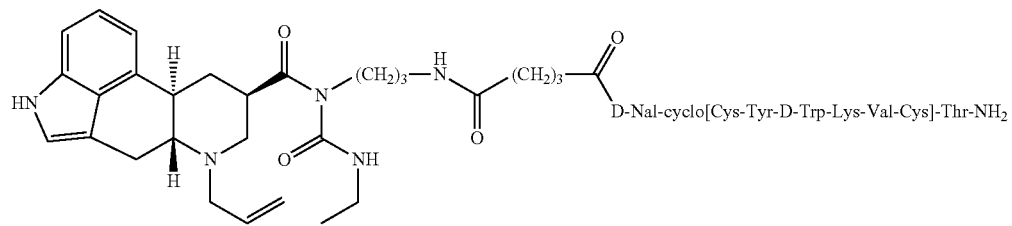D-Nal-cyclo[Cys-Tyr-D-Trp-Lys-Val-Cys]-Thr-NH₂
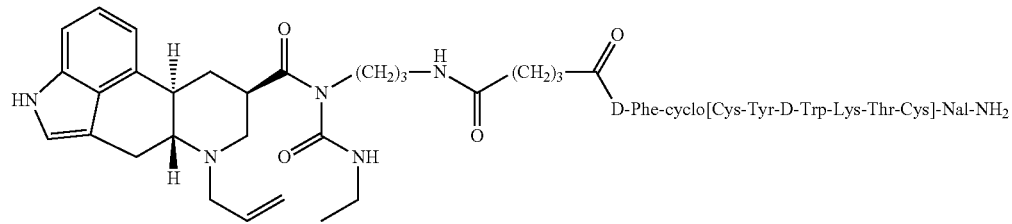D-Phe-cyclo[Cys-Tyr-D-Trp-Lys-Thr-Cys]-Nal-NH₂
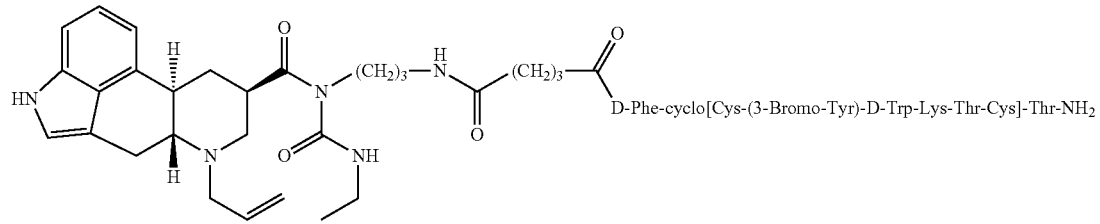D-Phe-cyclo[Cys-(3-Bromo-Tyr)-D-Trp-Lys-Thr-Cys]-Thr-NH₂
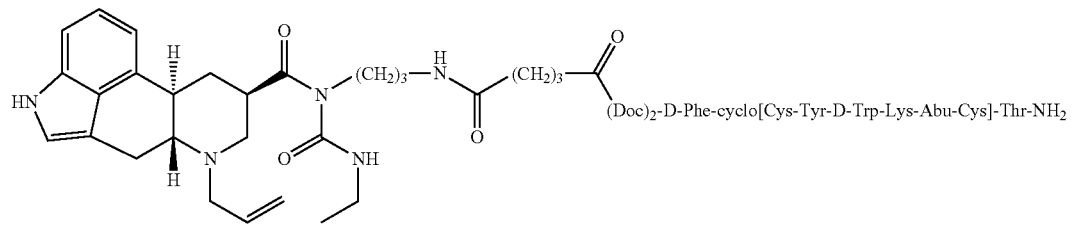(Doc)₂-D-Phe-cyclo[Cys-Tyr-D-Trp-Lys-Abu-Cys]-Thr-NH₂
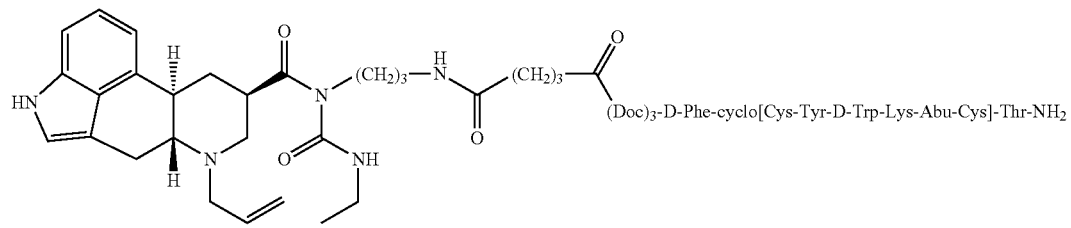(Doc)₃-D-Phe-cyclo[Cys-Tyr-D-Trp-Lys-Abu-Cys]-Thr-NH₂
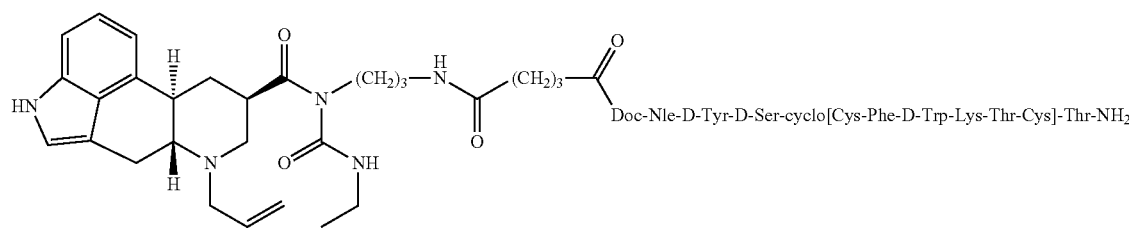Doc-Nle-D-Tyr-D-Ser-cyclo[Cys-Phe-D-Trp-Lys-Thr-Cys]-Thr-NH₂

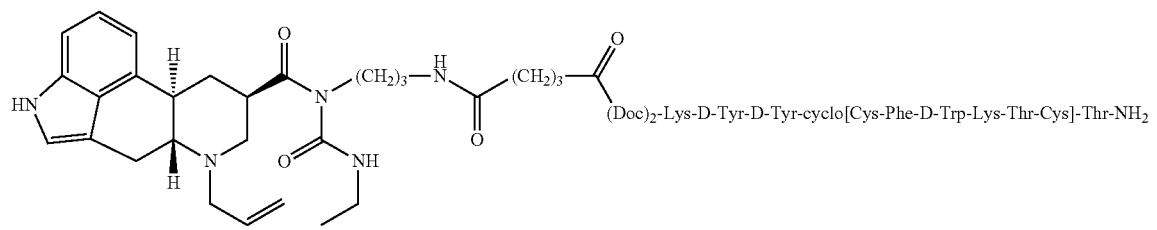
(Doc)₂-Lys-D-Tyr-D-Tyr-cyclo[Cys-Phe-D-Trp-Lys-Thr-Cys]-Thr-NH₂
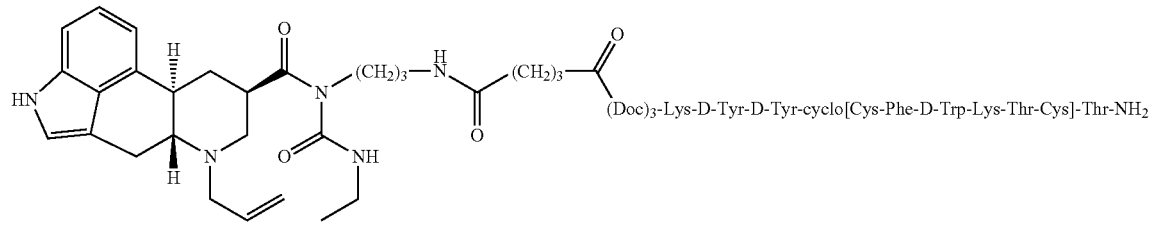
(Doc)₃-Lys-D-Tyr-D-Tyr-cyclo[Cys-Phe-D-Trp-Lys-Thr-Cys]-Thr-NH₂
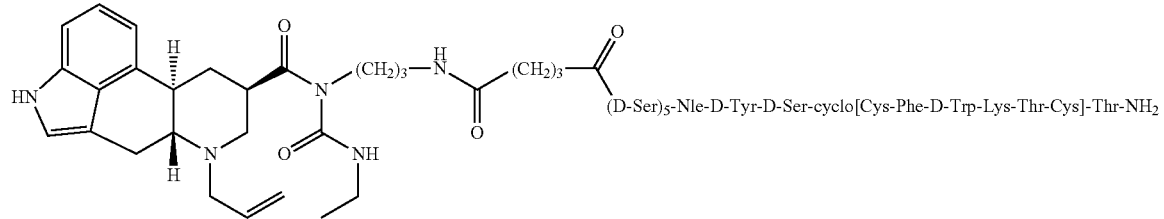
(D-Ser)₅-Nle-D-Tyr-D-Ser-cyclo[Cys-Phe-D-Trp-Lys-Thr-Cys]-Thr-NH₂
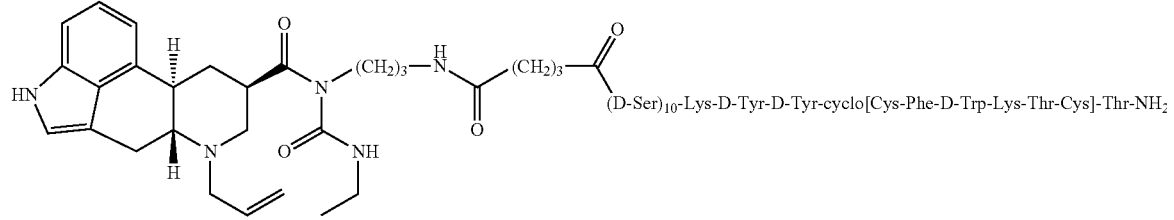
(D-Ser)₁₀-Lys-D-Tyr-D-Tyr-cyclo[Cys-Phe-D-Trp-Lys-Thr-Cys]-Thr-NH₂
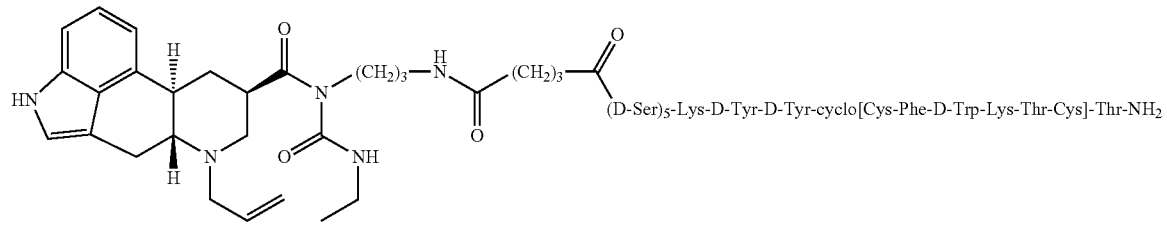
(D-Ser)₅-Lys-D-Tyr-D-Tyr-cyclo[Cys-Phe-D-Trp-Lys-Thr-Cys]-Thr-NH₂
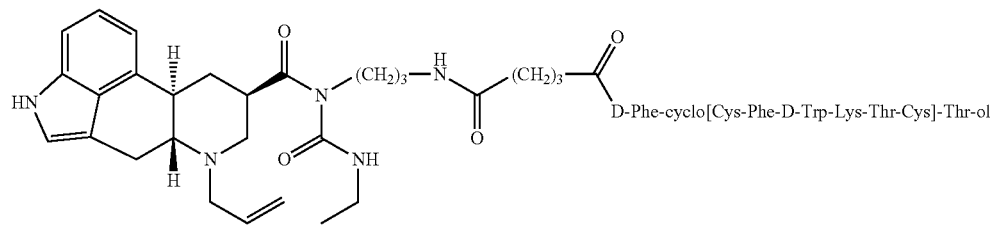
D-Phe-cyclo[Cys-Phe-D-Trp-Lys-Thr-Cys]-Thr-ol
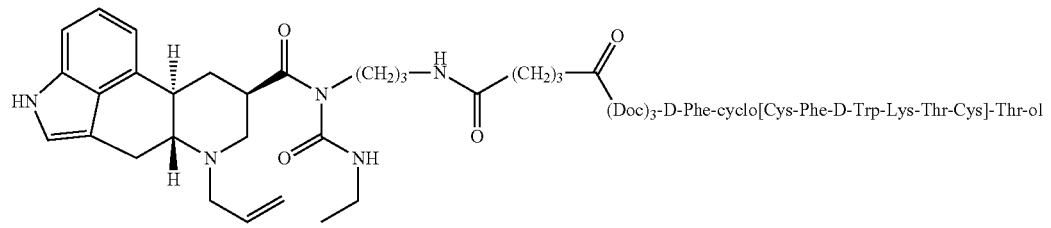
(Doc)₃-D-Phe-cyclo[Cys-Phe-D-Trp-Lys-Thr-Cys]-Thr-ol -continued

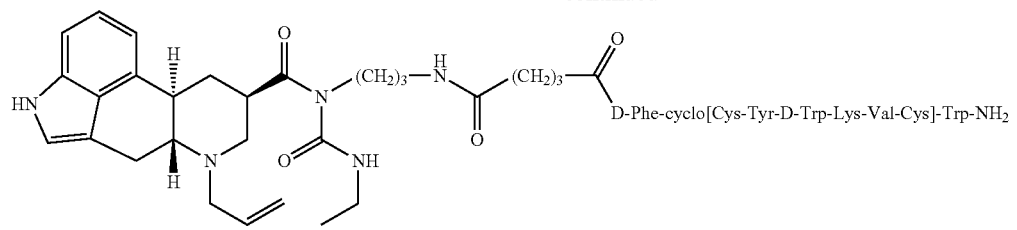
D-Phe-cyclo[Cys-Tyr-D-Trp-Lys-Val-Cys]-Trp-NH$_2$

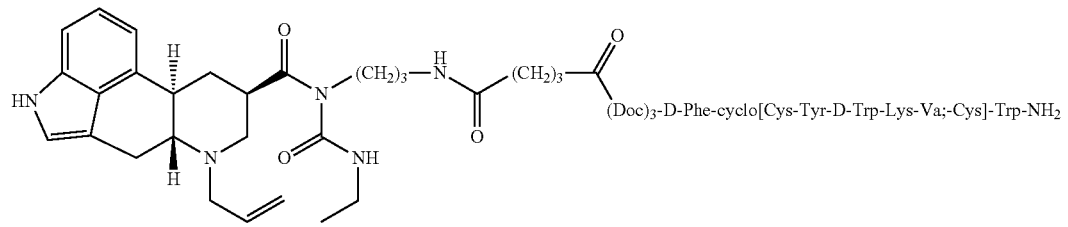
(Doc)$_3$-D-Phe-cyclo[Cys-Tyr-D-Trp-Lys-Va;-Cys]-Trp-NH$_2$

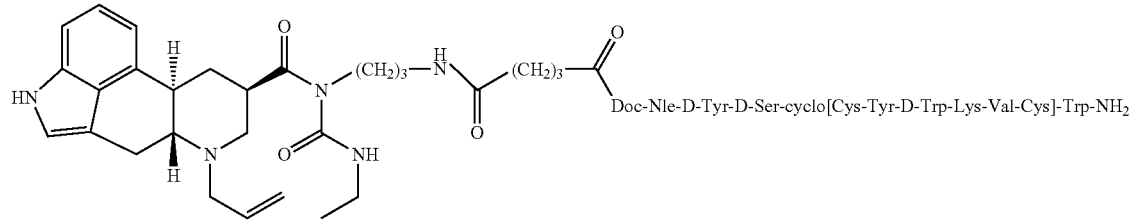
Doc-Nle-D-Tyr-D-Ser-cyclo[Cys-Tyr-D-Trp-Lys-Val-Cys]-Trp-NH$_2$

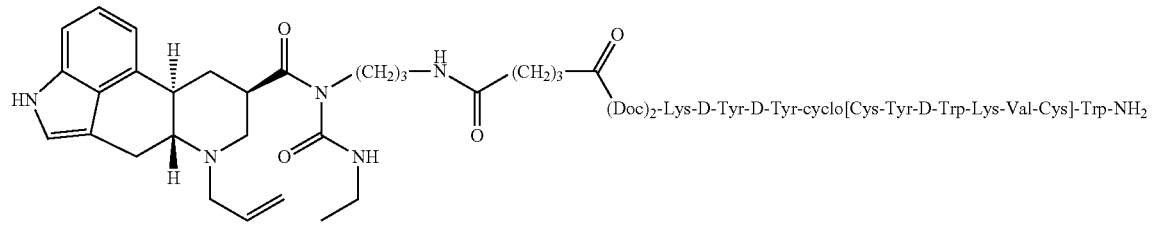
(Doc)$_2$-Lys-D-Tyr-D-Tyr-cyclo[Cys-Tyr-D-Trp-Lys-Val-Cys]-Trp-NH$_2$

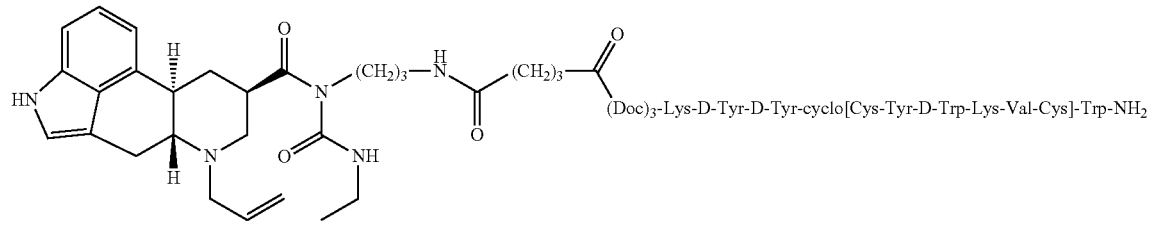
(Doc)$_3$-Lys-D-Tyr-D-Tyr-cyclo[Cys-Tyr-D-Trp-Lys-Val-Cys]-Trp-NH$_2$

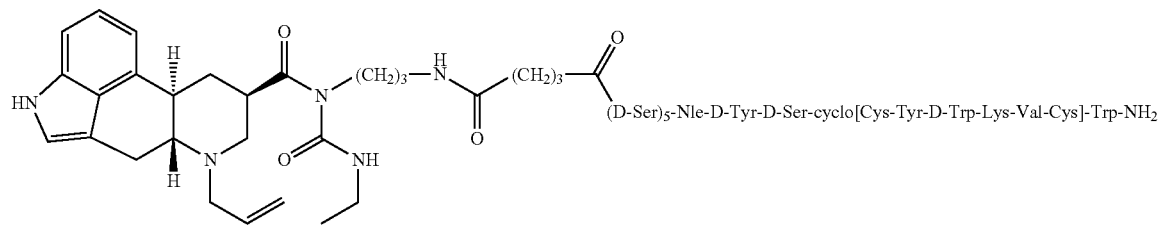
(D-Ser)$_5$-Nle-D-Tyr-D-Ser-cyclo[Cys-Tyr-D-Trp-Lys-Val-Cys]-Trp-NH$_2$

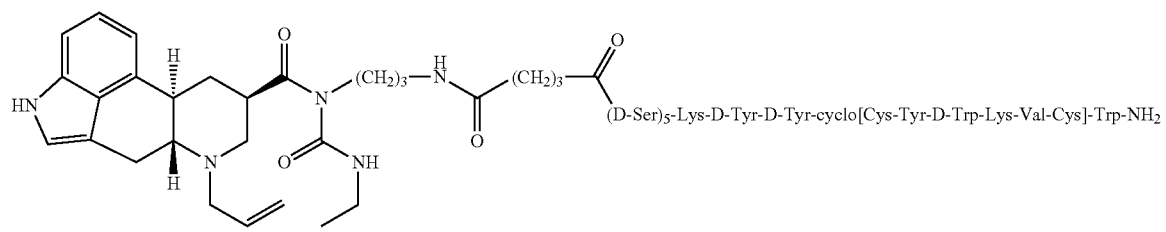
(D-Ser)$_5$-Lys-D-Tyr-D-Tyr-cyclo[Cys-Tyr-D-Trp-Lys-Val-Cys]-Trp-NH$_2$ -continued

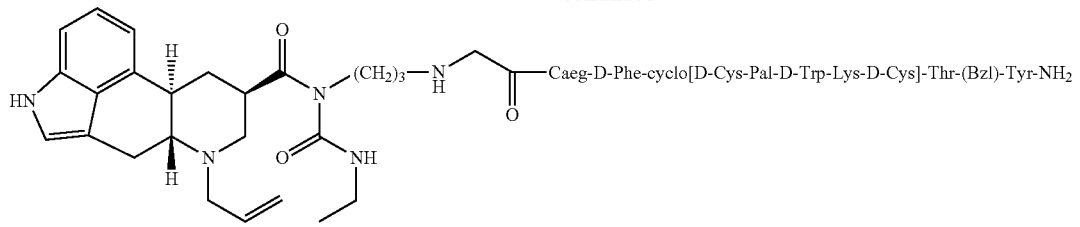
Caeg-D-Phe-cyclo[D-Cys-Pal-D-Trp-Lys-D-Cys]-Thr-(Bzl)-Tyr-NH₂

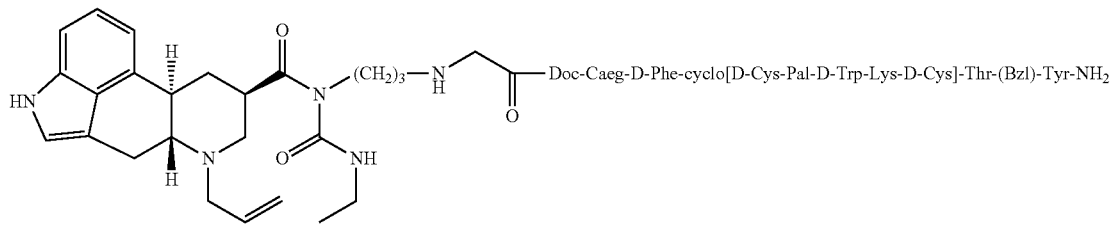
Doc-Caeg-D-Phe-cyclo[D-Cys-Pal-D-Trp-Lys-D-Cys]-Thr-(Bzl)-Tyr-NH₂

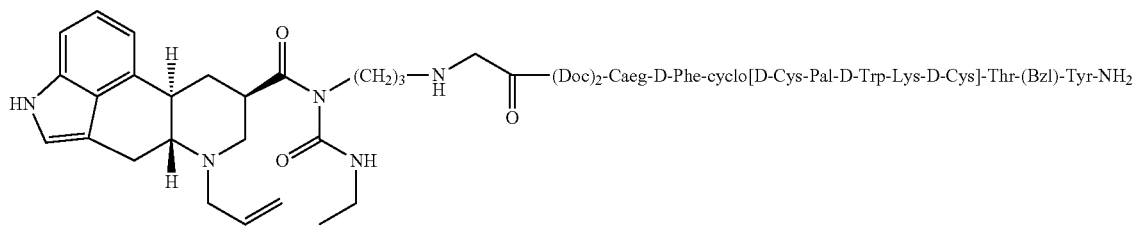
(Doc)₂-Caeg-D-Phe-cyclo[D-Cys-Pal-D-Trp-Lys-D-Cys]-Thr-(Bzl)-Tyr-NH₂

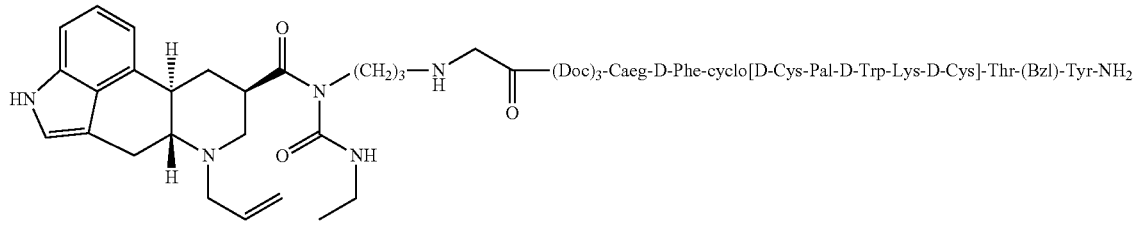
(Doc)₃-Caeg-D-Phe-cyclo[D-Cys-Pal-D-Trp-Lys-D-Cys]-Thr-(Bzl)-Tyr-NH₂

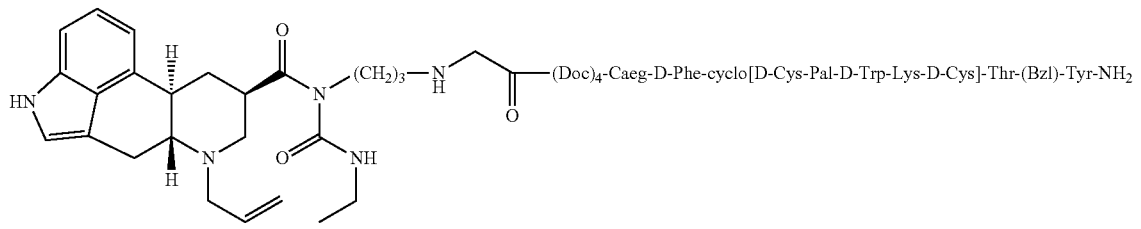
(Doc)₄-Caeg-D-Phe-cyclo[D-Cys-Pal-D-Trp-Lys-D-Cys]-Thr-(Bzl)-Tyr-NH₂

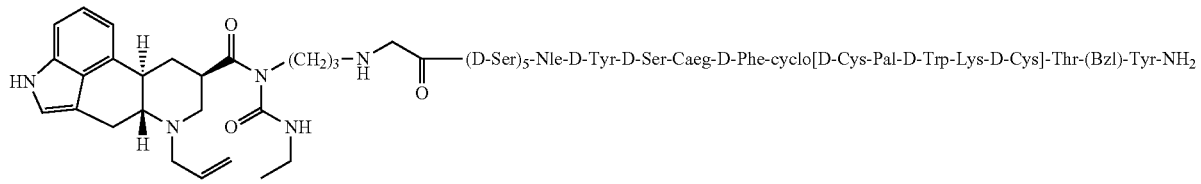
(D-Ser)₅-Nle-D-Tyr-D-Ser-Caeg-D-Phe-cyclo[D-Cys-Pal-D-Trp-Lys-D-Cys]-Thr-(Bzl)-Tyr-NH₂

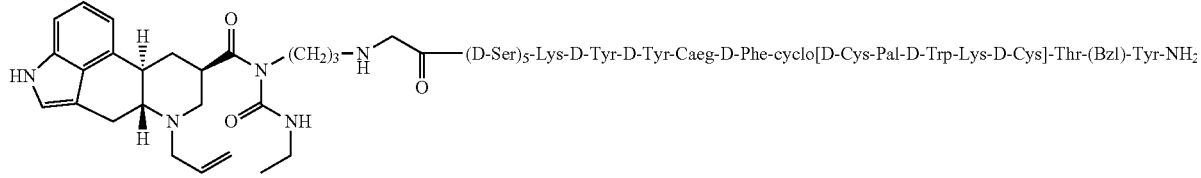
(D-Ser)₅-Lys-D-Tyr-D-Tyr-Caeg-D-Phe-cyclo[D-Cys-Pal-D-Trp-Lys-D-Cys]-Thr-(Bzl)-Tyr-NH₂

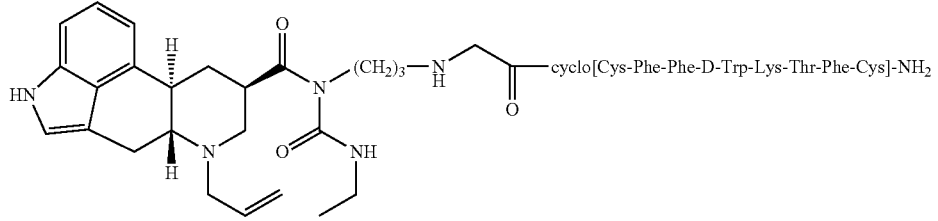
cyclo[Cys-Phe-Phe-D-Trp-Lys-Thr-Phe-Cys]-NH₂

-continued
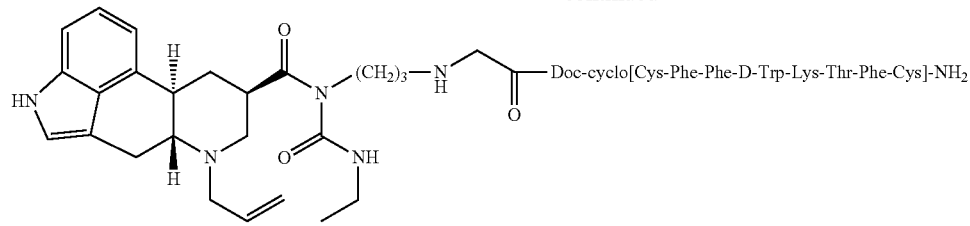
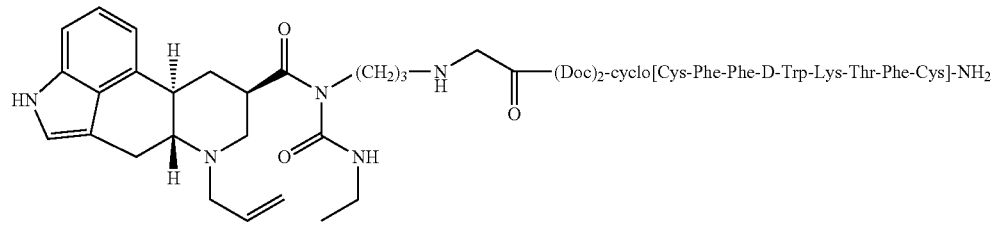
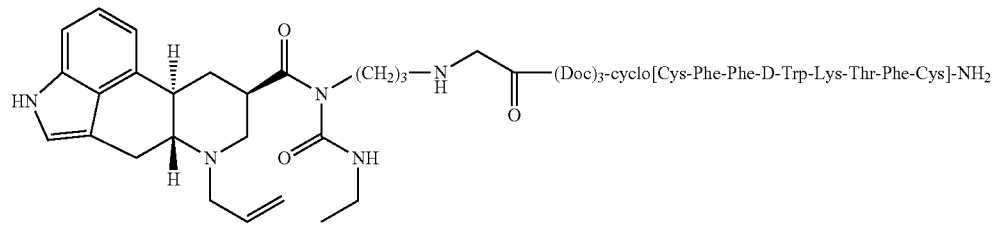
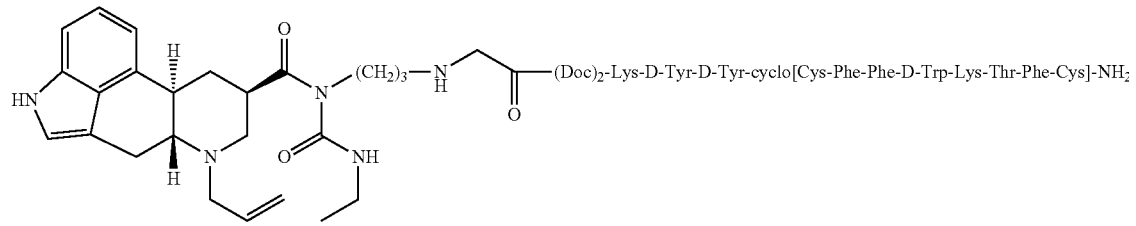
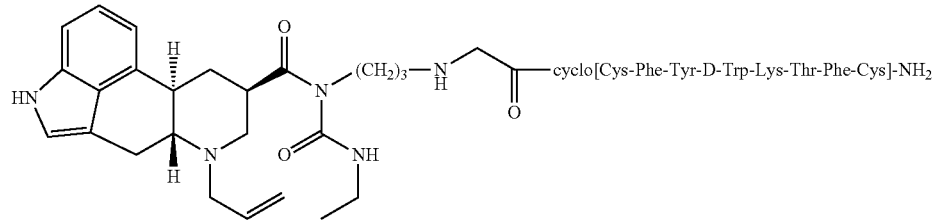
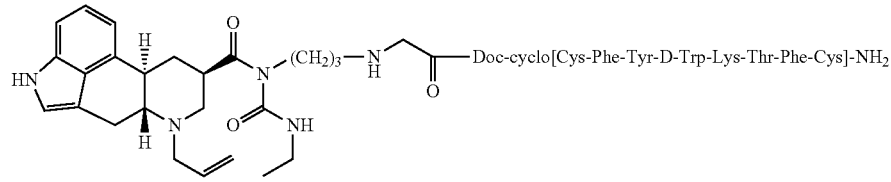
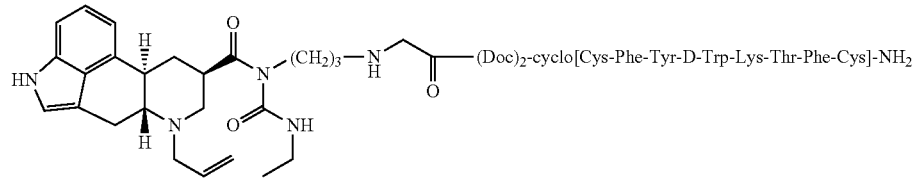
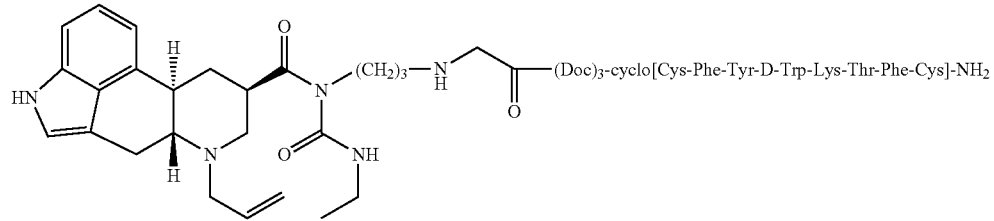

-continued
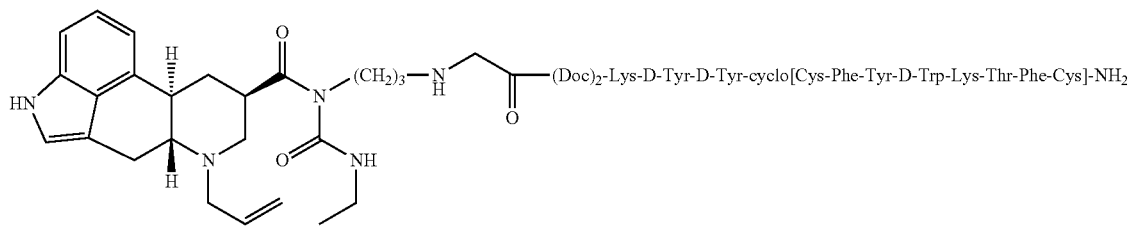
(Doc)₂-Lys-D-Tyr-D-Tyr-cyclo[Cys-Phe-Tyr-D-Trp-Lys-Thr-Phe-Cys]-NH₂
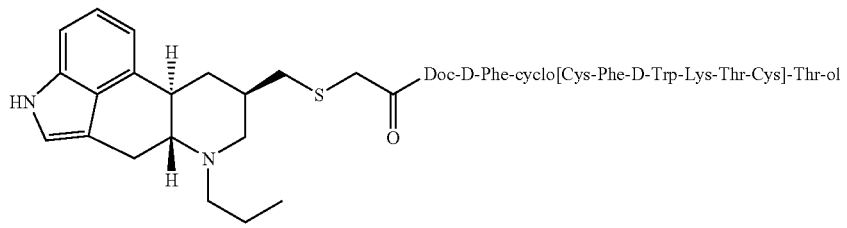
Doc-D-Phe-cyclo[Cys-Phe-D-Trp-Lys-Thr-Cys]-Thr-ol
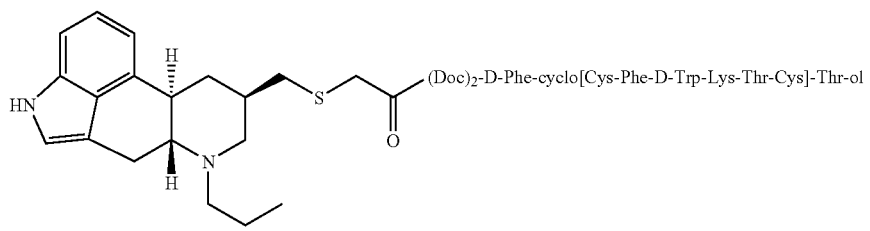
(Doc)₂-D-Phe-cyclo[Cys-Phe-D-Trp-Lys-Thr-Cys]-Thr-ol
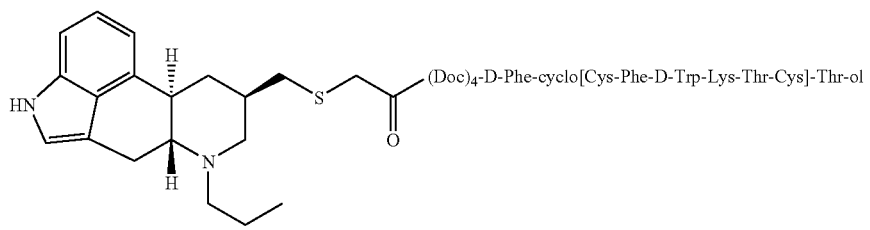
(Doc)₄-D-Phe-cyclo[Cys-Phe-D-Trp-Lys-Thr-Cys]-Thr-ol
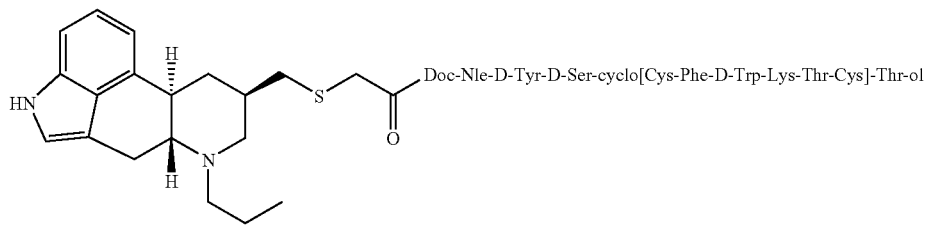
Doc-Nle-D-Tyr-D-Ser-cyclo[Cys-Phe-D-Trp-Lys-Thr-Cys]-Thr-ol
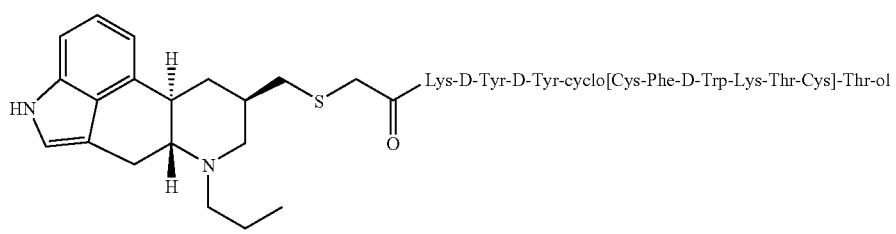
Lys-D-Tyr-D-Tyr-cyclo[Cys-Phe-D-Trp-Lys-Thr-Cys]-Thr-ol
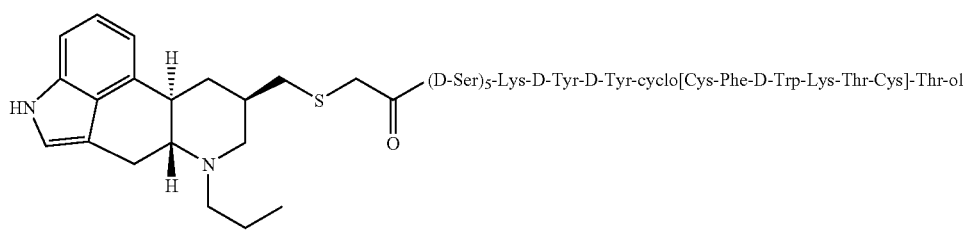
(D-Ser)₅-Lys-D-Tyr-D-Tyr-cyclo[Cys-Phe-D-Trp-Lys-Thr-Cys]-Thr-ol

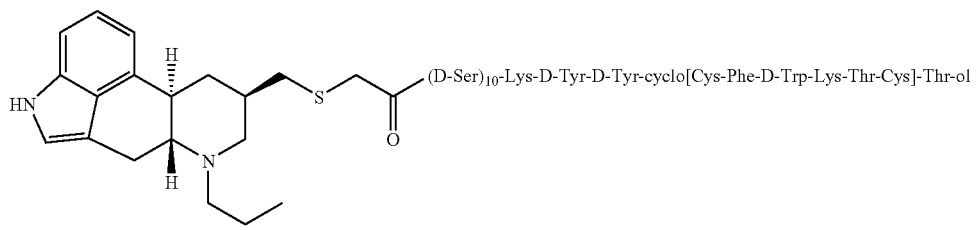
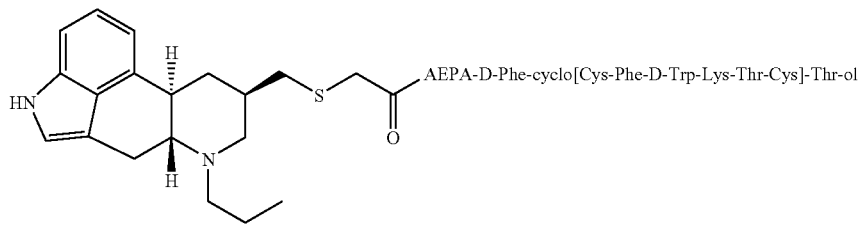
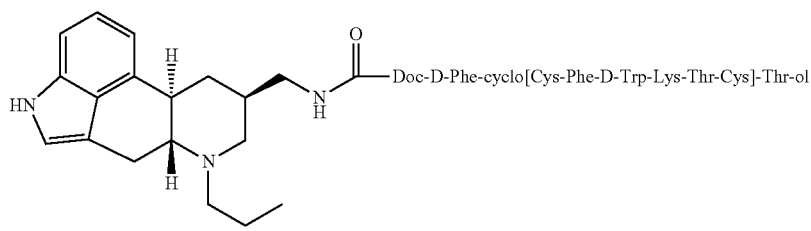
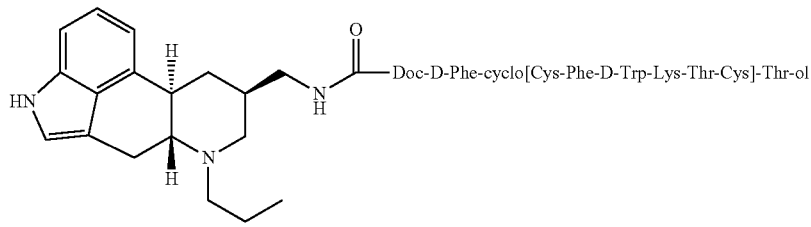
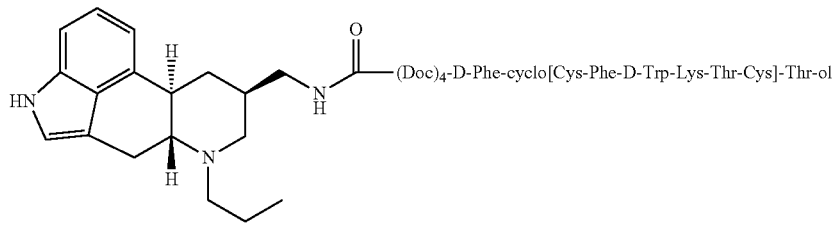
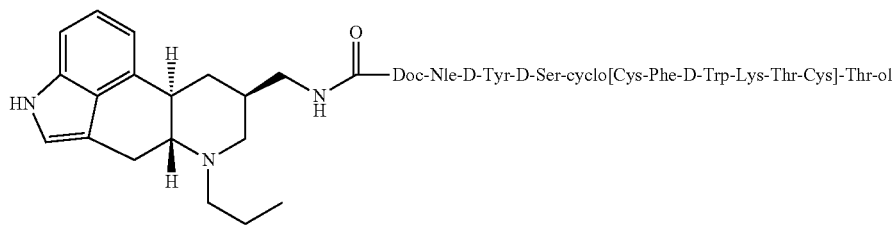
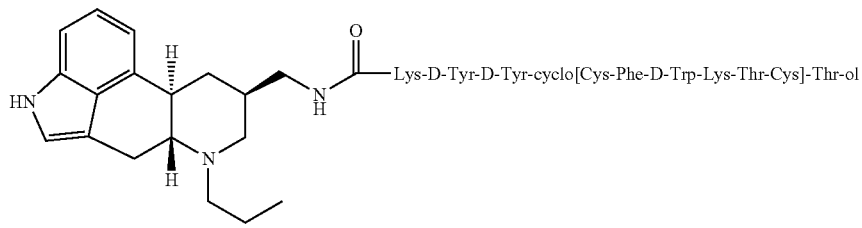

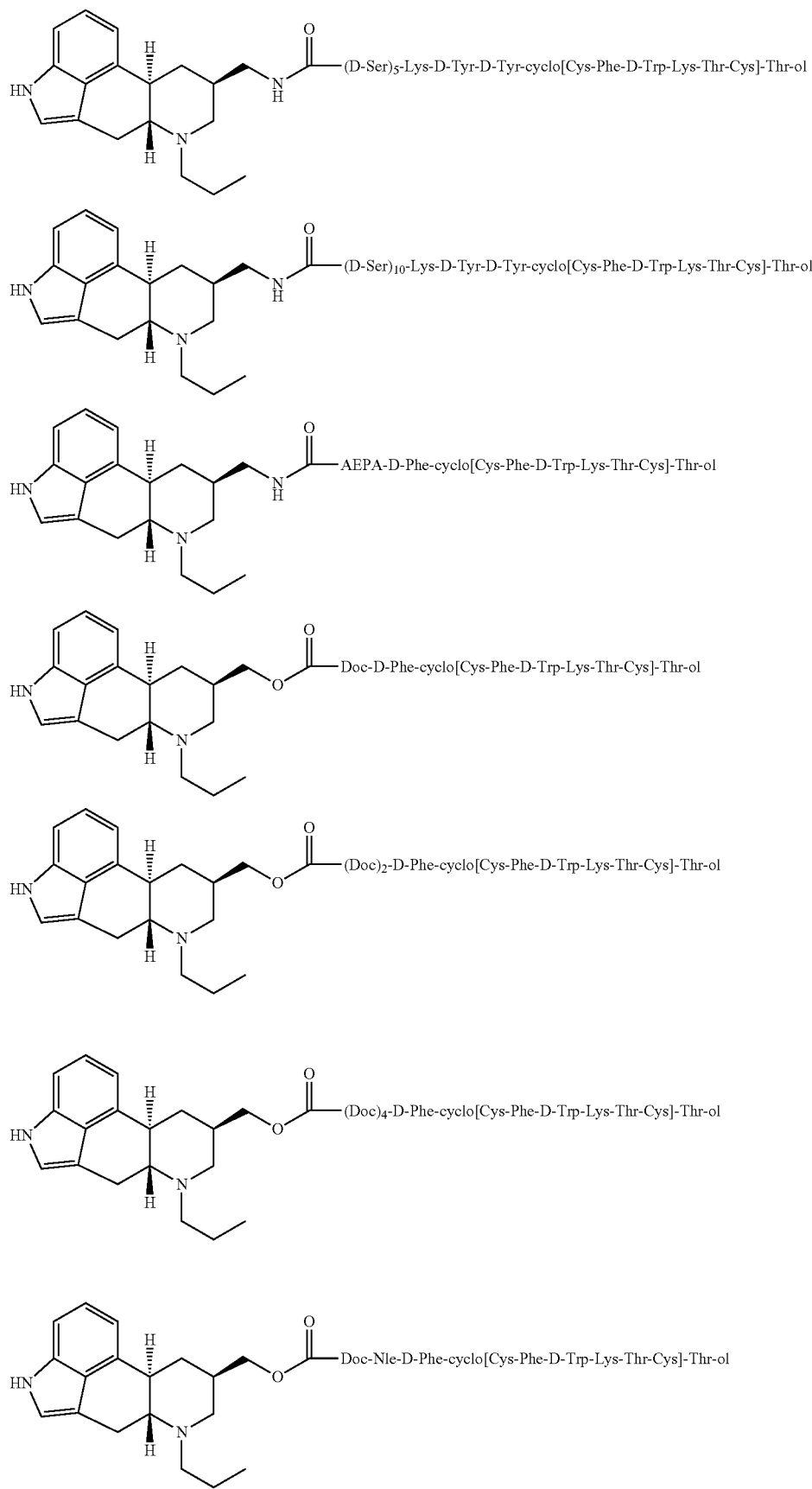

-continued
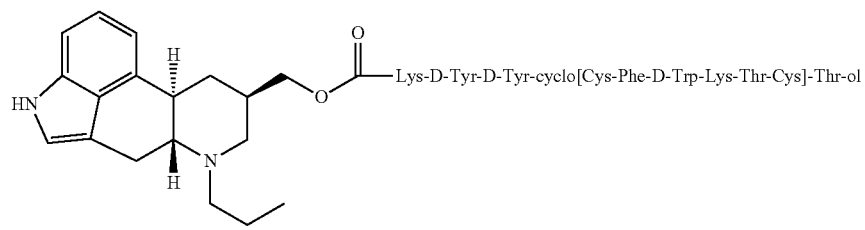
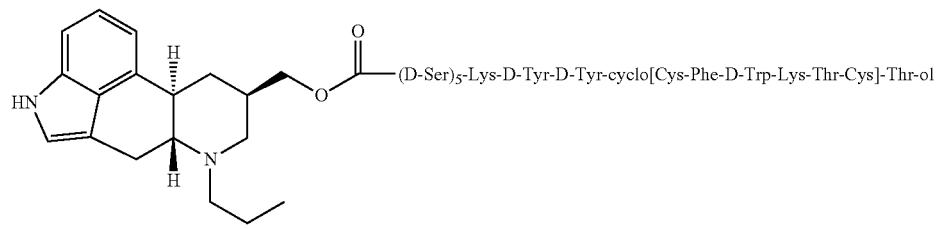
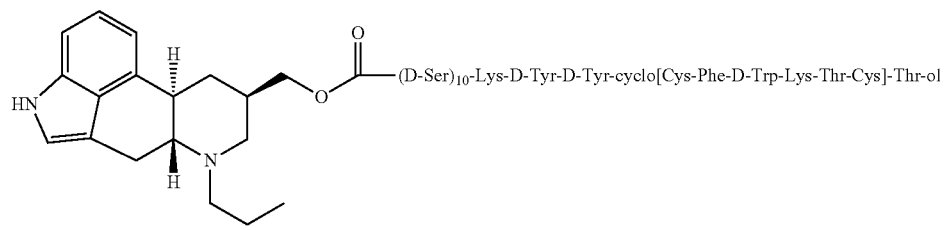
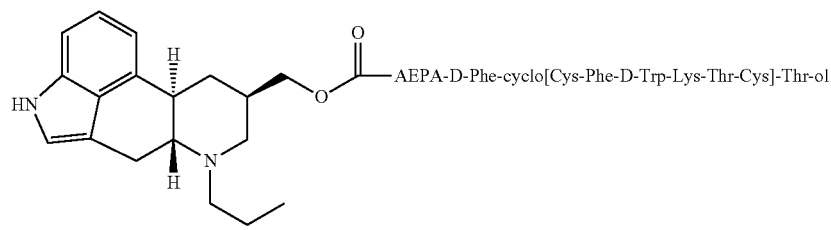
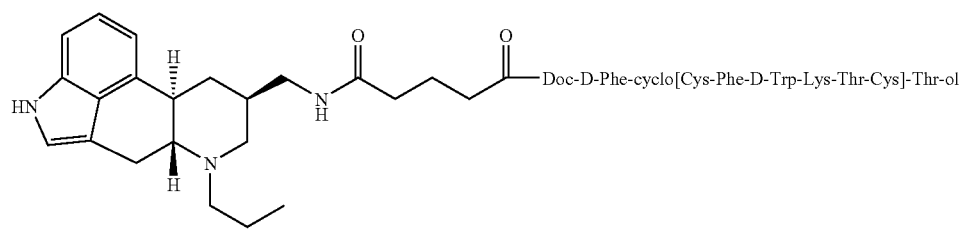
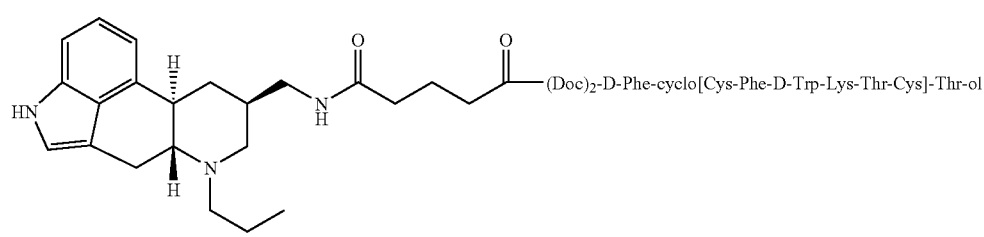
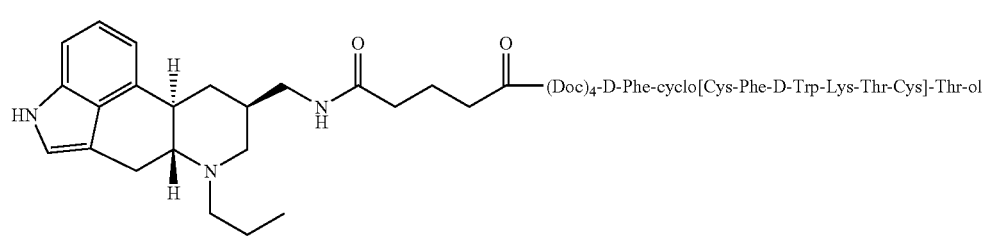

-continued
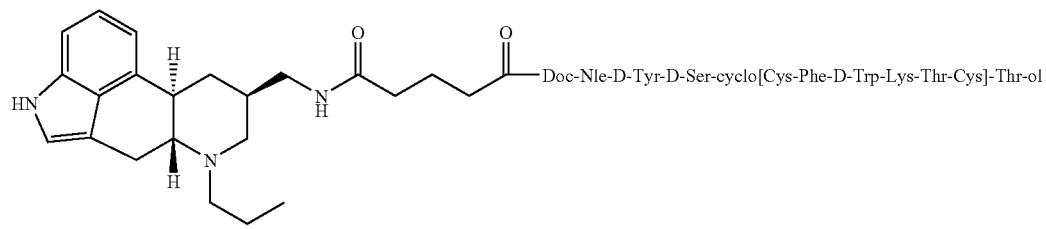
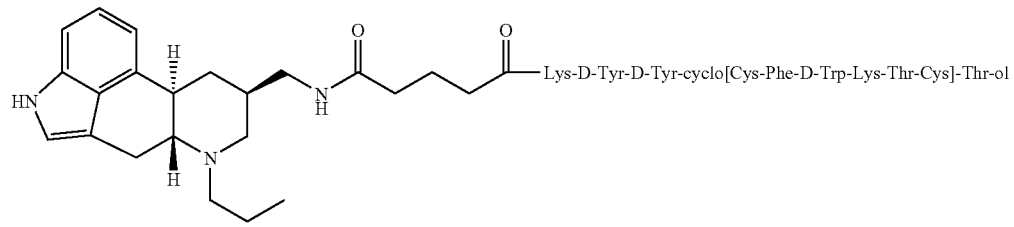
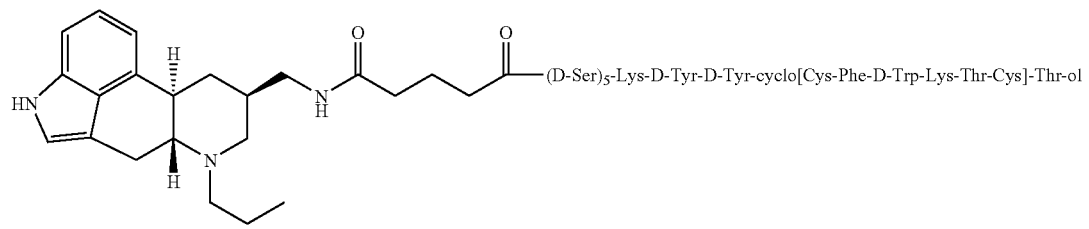
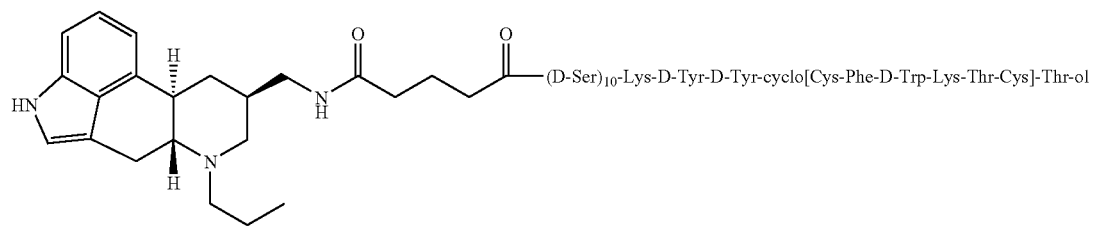
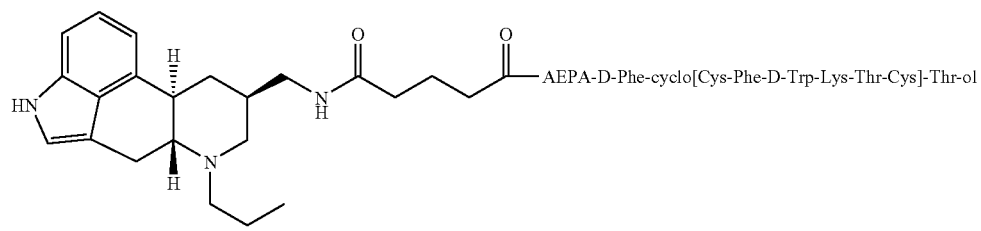
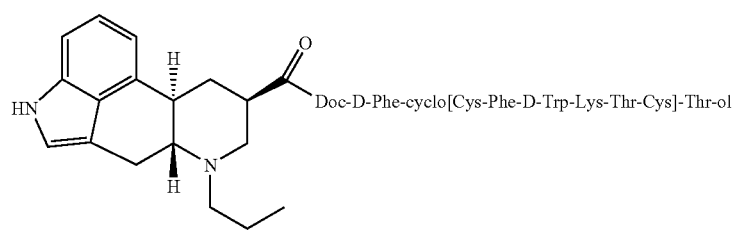
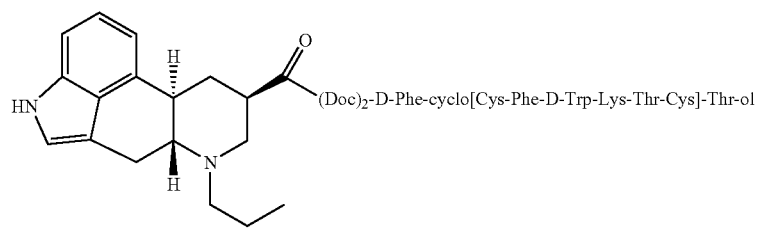

-continued
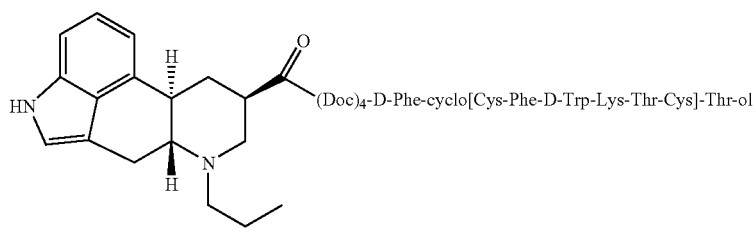
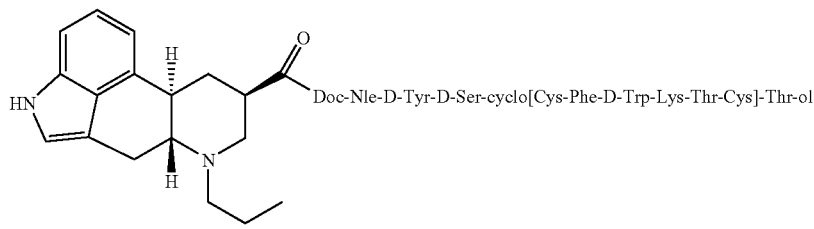
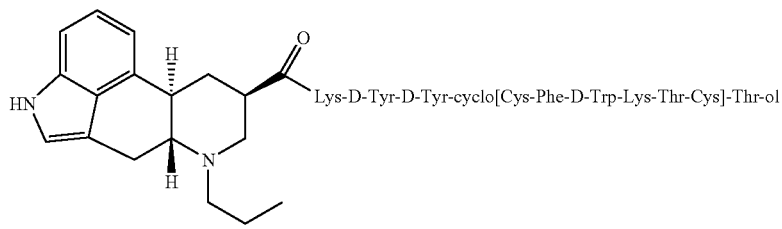
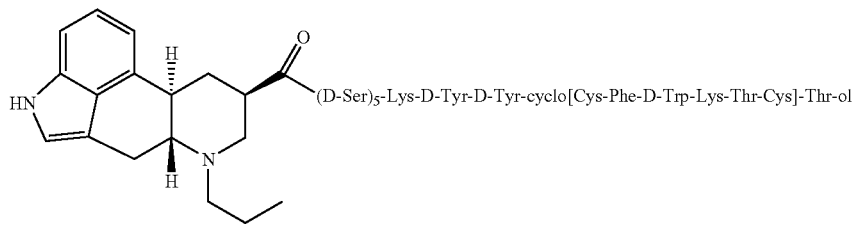
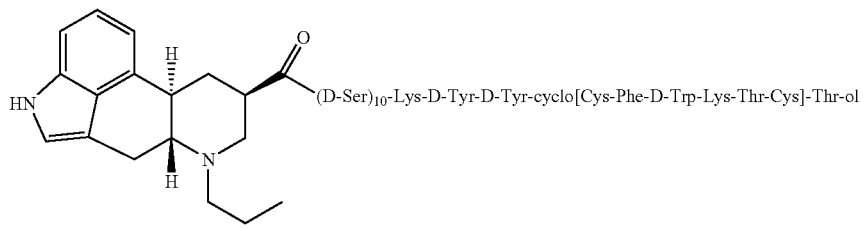
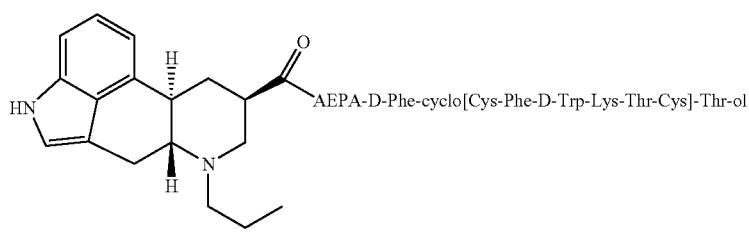
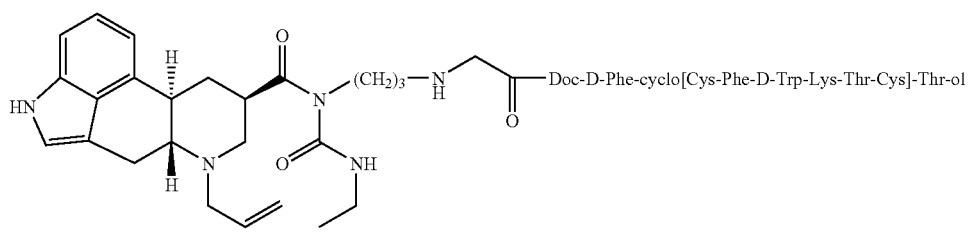

-continued
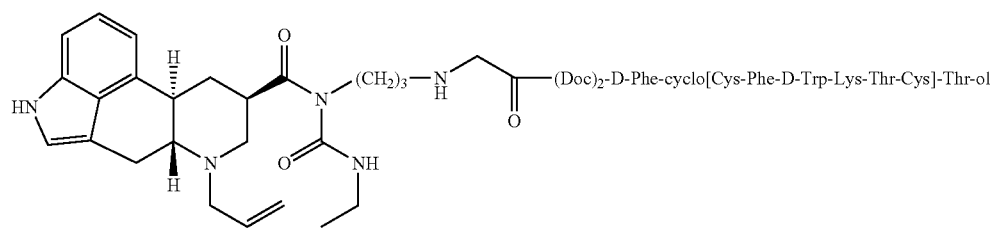
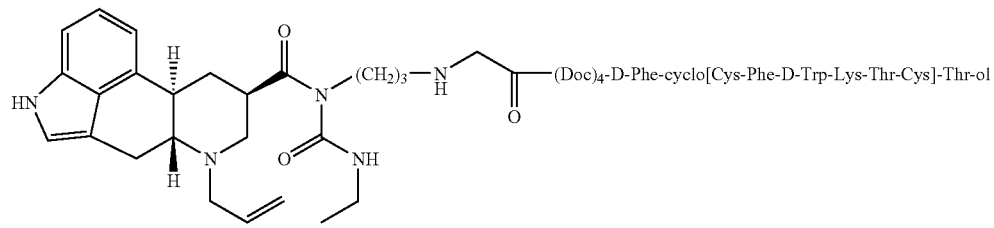
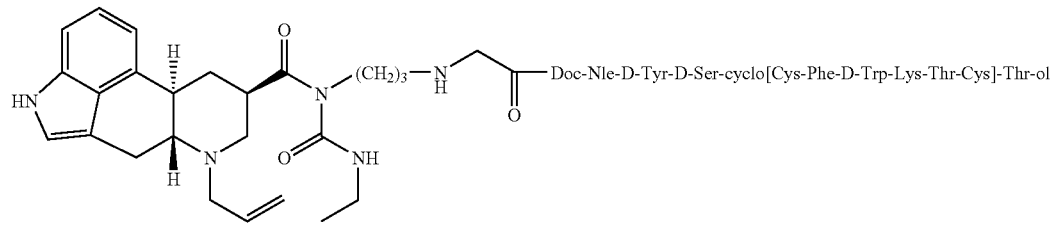
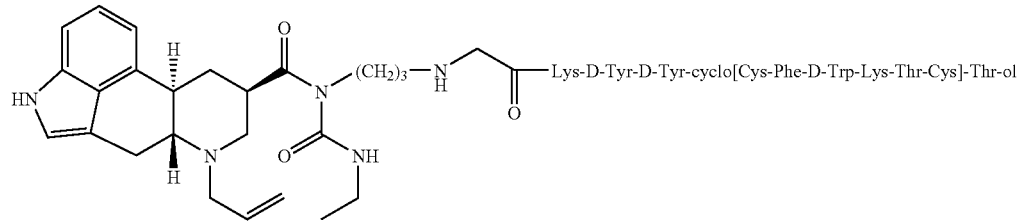
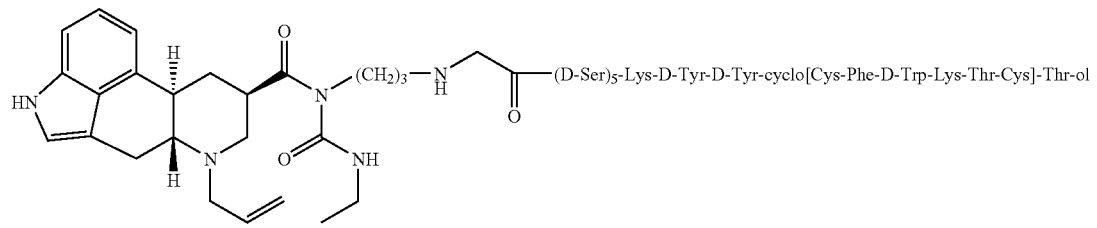
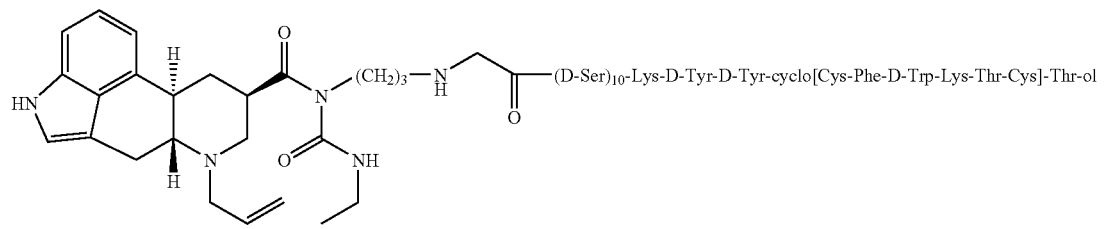
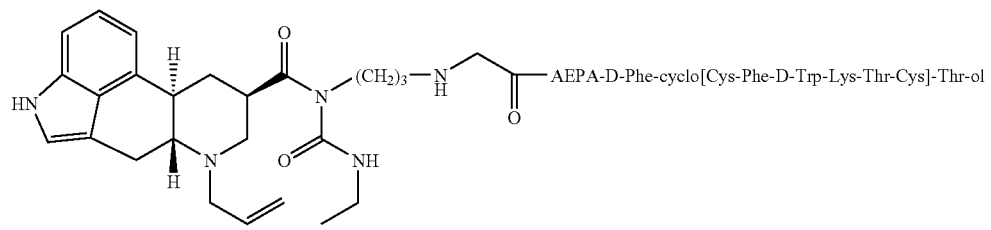

-continued
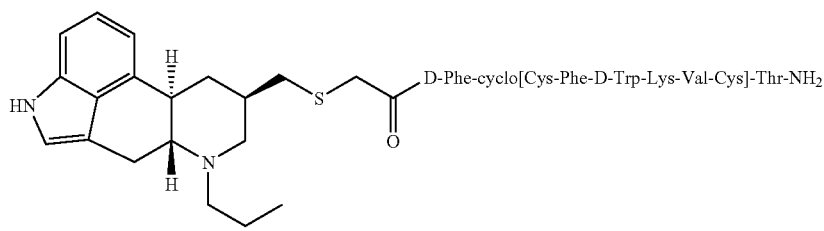
D-Phe-cyclo[Cys-Phe-D-Trp-Lys-Val-Cys]-Thr-NH$_2$
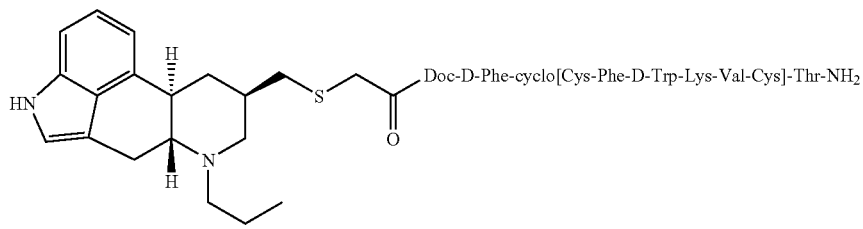
Doc-D-Phe-cyclo[Cys-Phe-D-Trp-Lys-Val-Cys]-Thr-NH$_2$
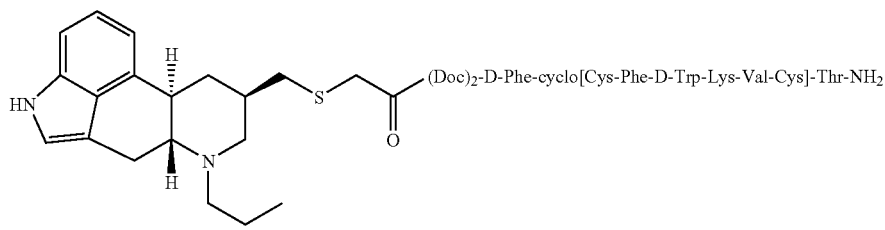
(Doc)$_2$-D-Phe-cyclo[Cys-Phe-D-Trp-Lys-Val-Cys]-Thr-NH$_2$
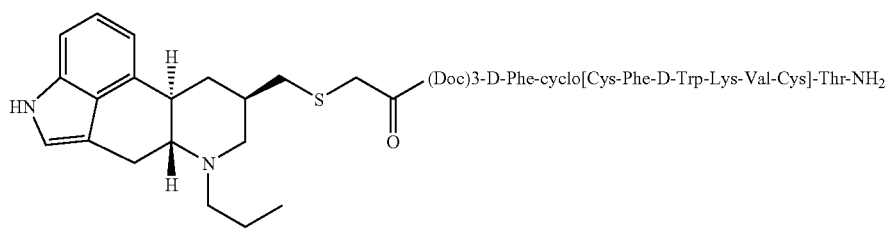
(Doc)$_3$-D-Phe-cyclo[Cys-Phe-D-Trp-Lys-Val-Cys]-Thr-NH$_2$
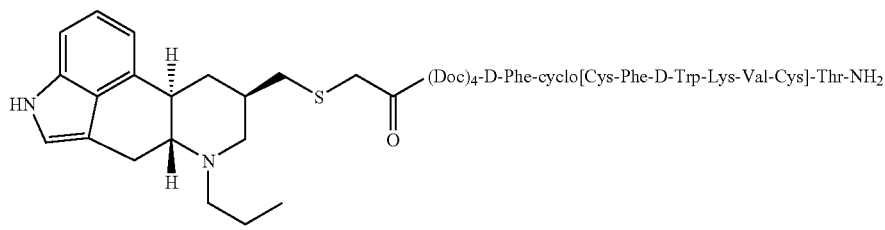
(Doc)$_4$-D-Phe-cyclo[Cys-Phe-D-Trp-Lys-Val-Cys]-Thr-NH$_2$
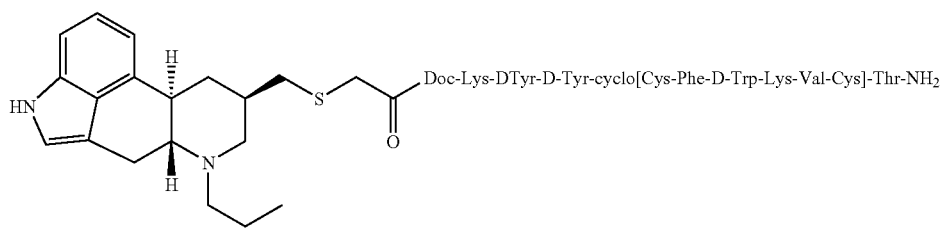
Doc-Lys-DTyr-D-Tyr-cyclo[Cys-Phe-D-Trp-Lys-Val-Cys]-Thr-NH$_2$
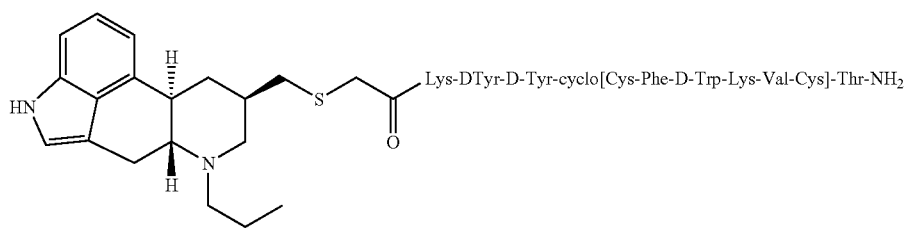
Lys-DTyr-D-Tyr-cyclo[Cys-Phe-D-Trp-Lys-Val-Cys]-Thr-NH$_2$ -continued
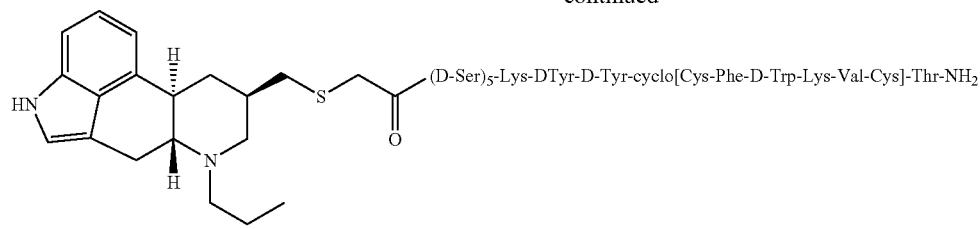
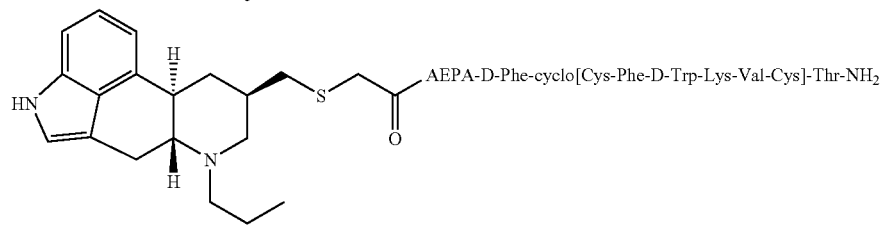
AEPA=4-(2-aminoethyl)-1-carboxymethyl-piperazine
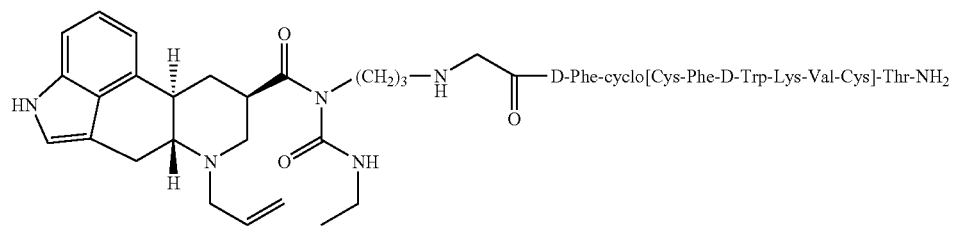
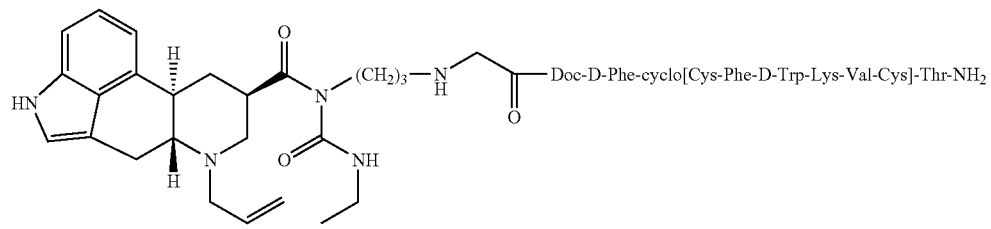
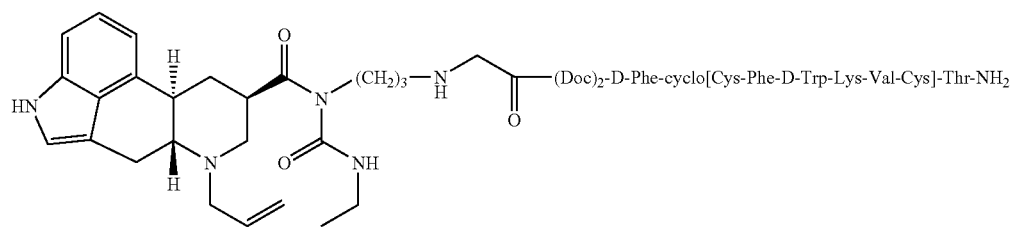
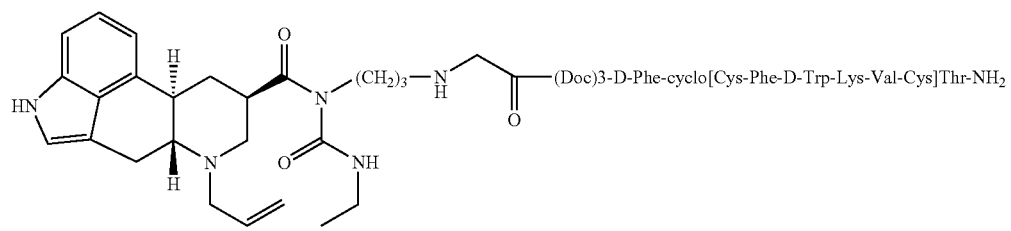
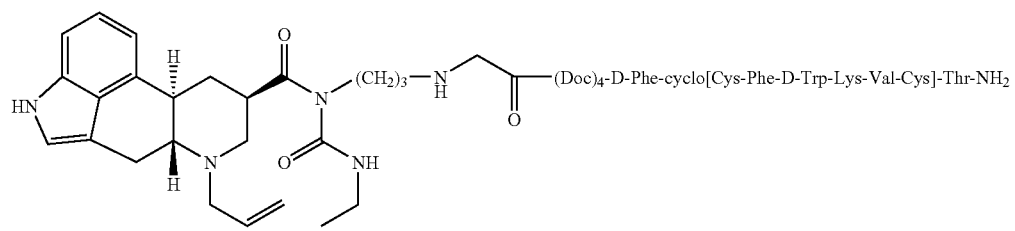

-continued
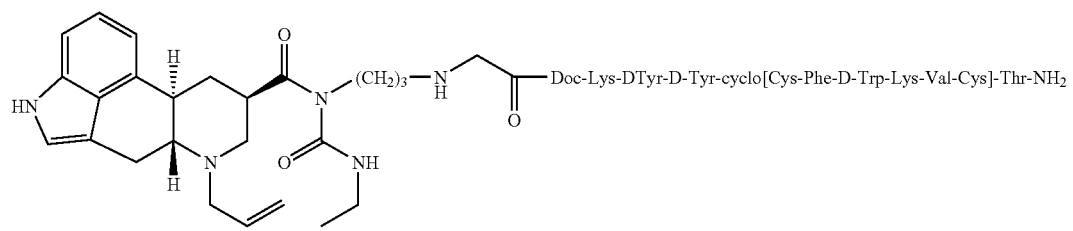
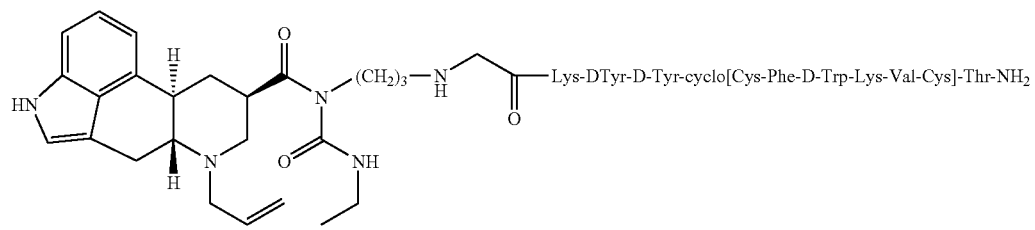
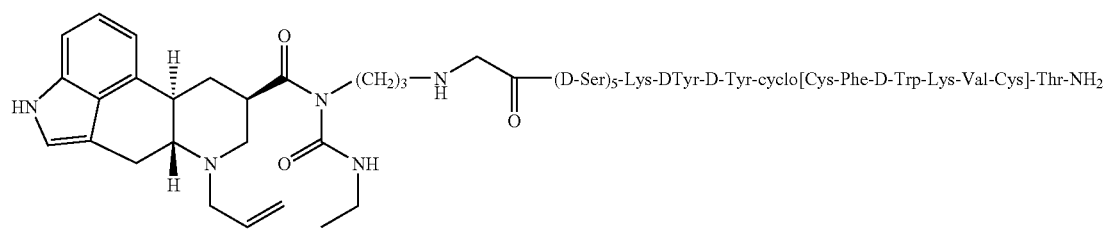
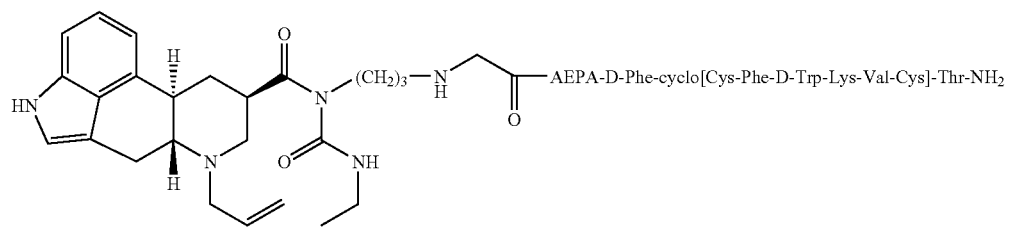
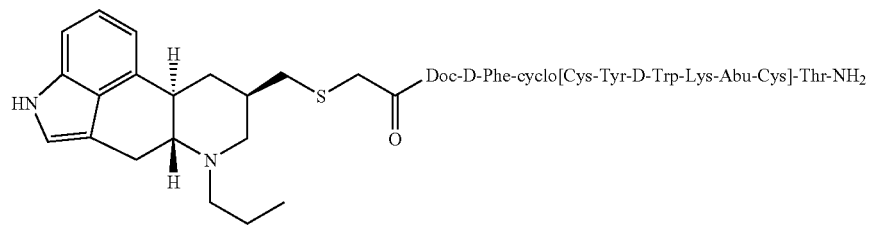
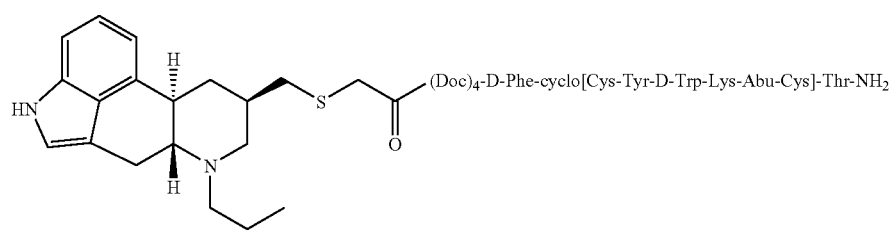
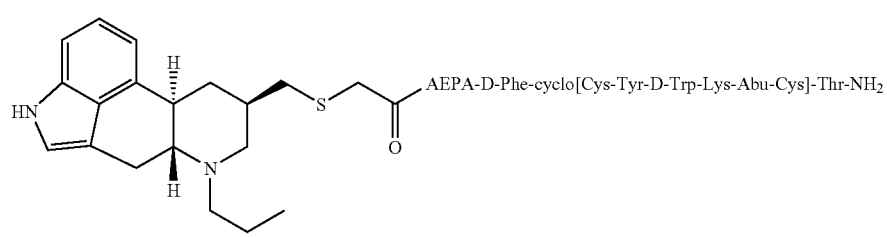

-continued
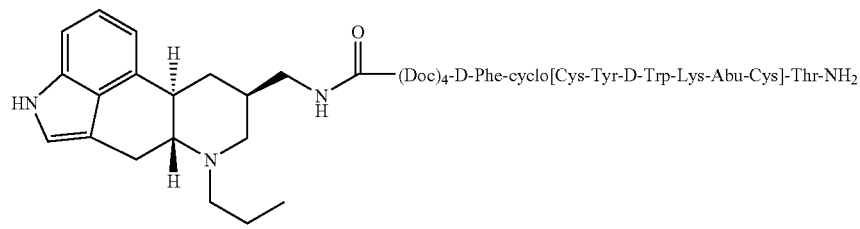
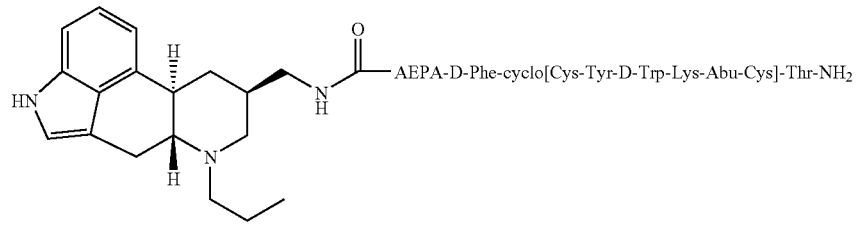
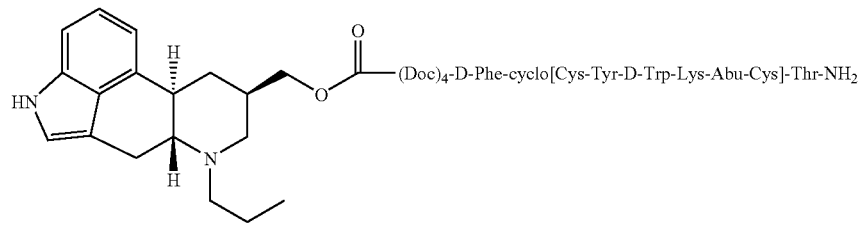
Compound C
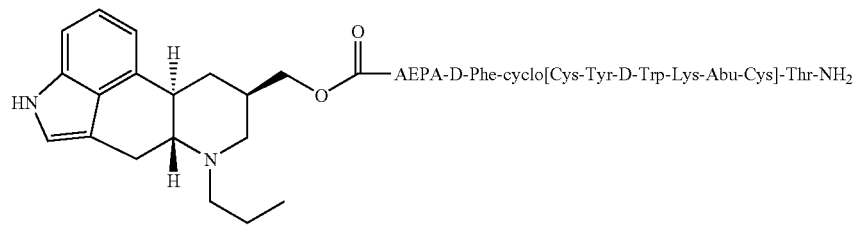
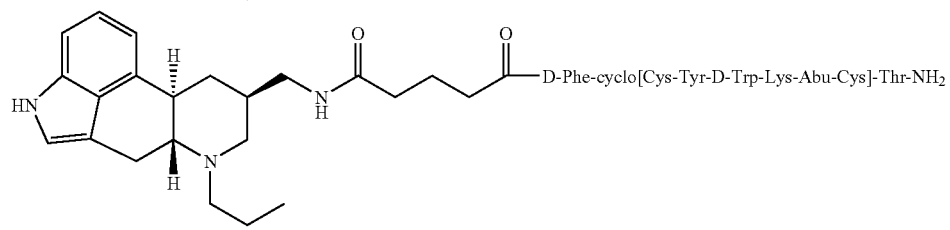
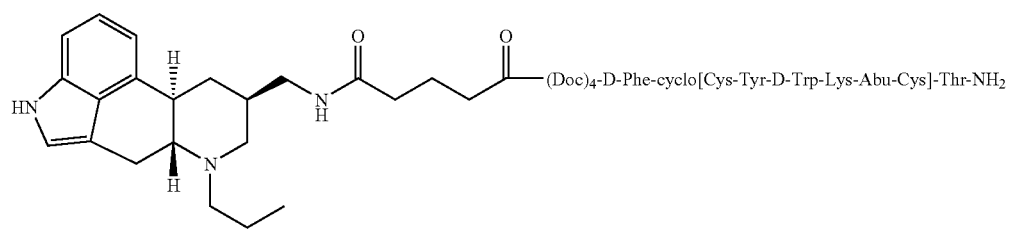
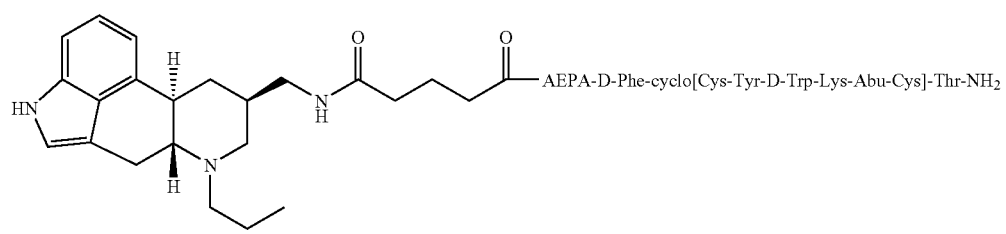

-continued
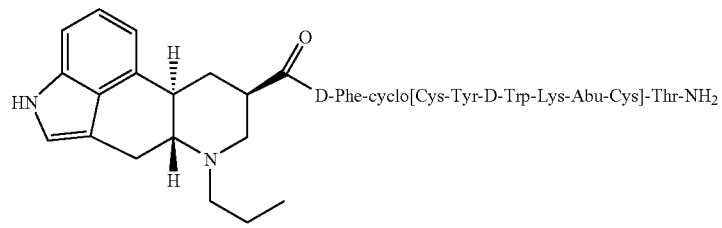
D-Phe-cyclo[Cys-Tyr-D-Trp-Lys-Abu-Cys]-Thr-NH$_2$
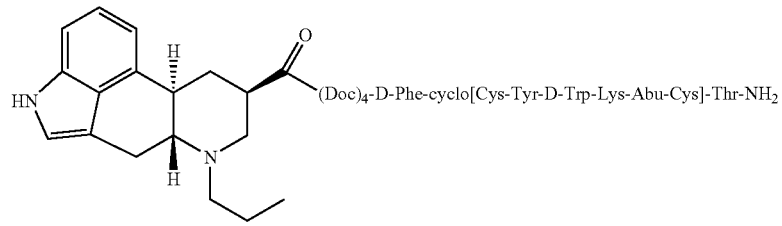
(Doc)$_4$-D-Phe-cyclo[Cys-Tyr-D-Trp-Lys-Abu-Cys]-Thr-NH$_2$
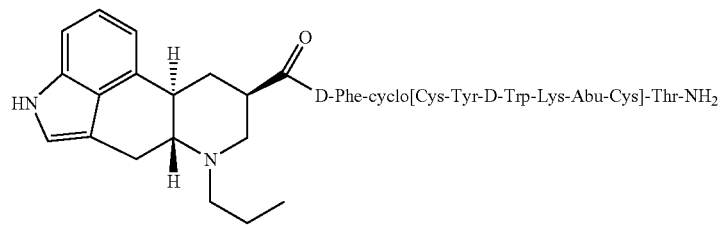
D-Phe-cyclo[Cys-Tyr-D-Trp-Lys-Abu-Cys]-Thr-NH$_2$
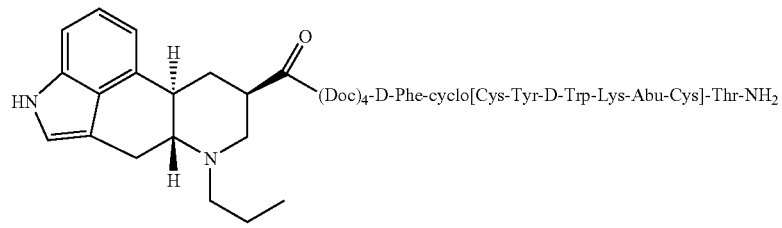
(Doc)$_4$-D-Phe-cyclo[Cys-Tyr-D-Trp-Lys-Abu-Cys]-Thr-NH$_2$
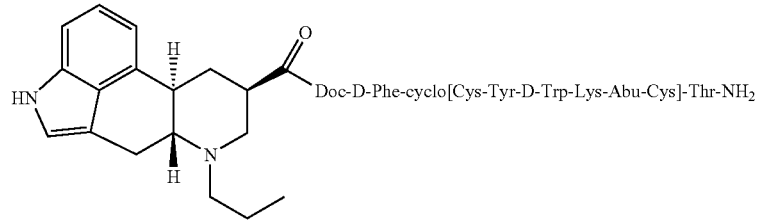
Doc-D-Phe-cyclo[Cys-Tyr-D-Trp-Lys-Abu-Cys]-Thr-NH$_2$
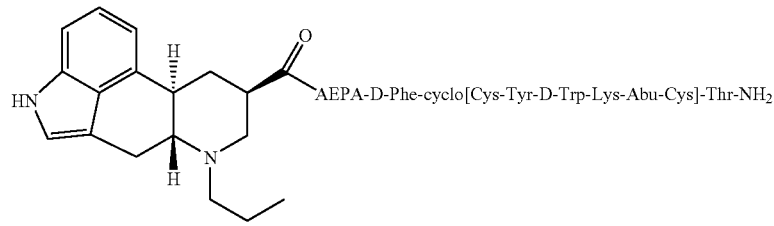
AEPA-D-Phe-cyclo[Cys-Tyr-D-Trp-Lys-Abu-Cys]-Thr-NH$_2$
Compound D
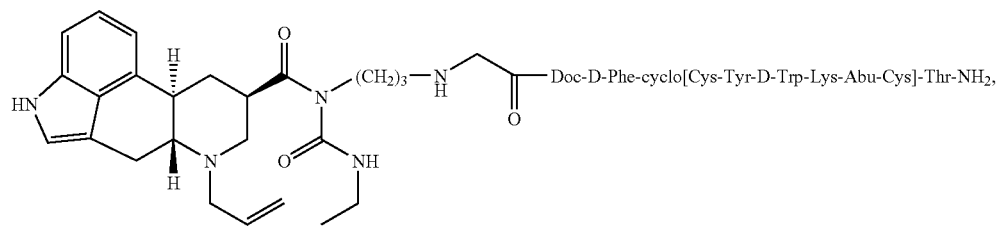
Doc-D-Phe-cyclo[Cys-Tyr-D-Trp-Lys-Abu-Cys]-Thr-NH$_2$,

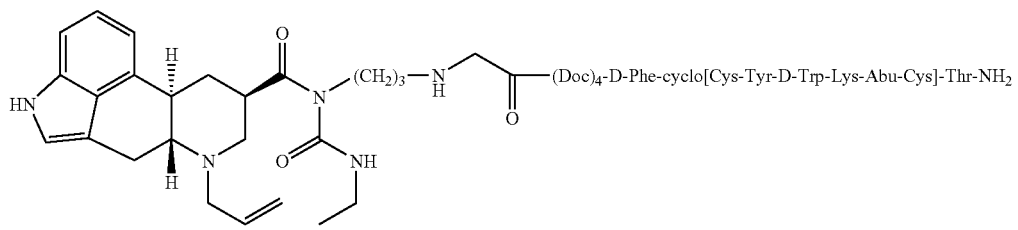
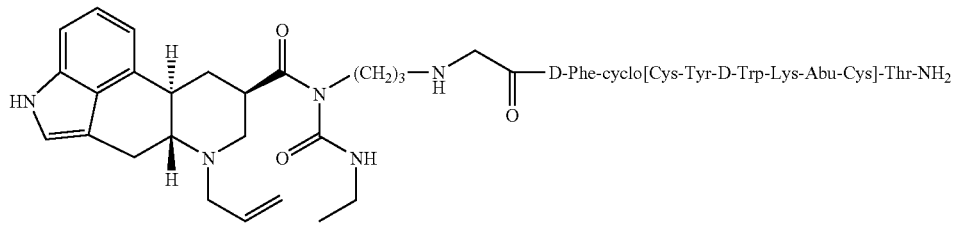
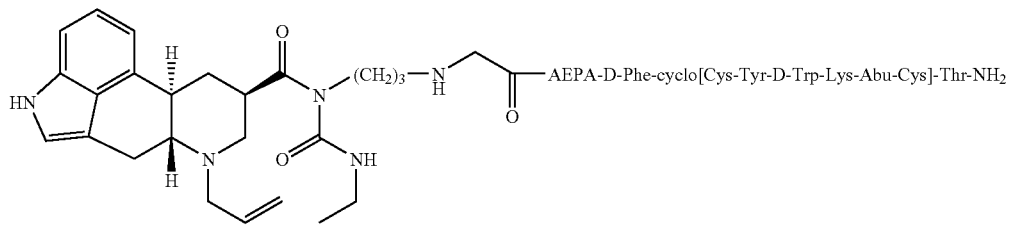
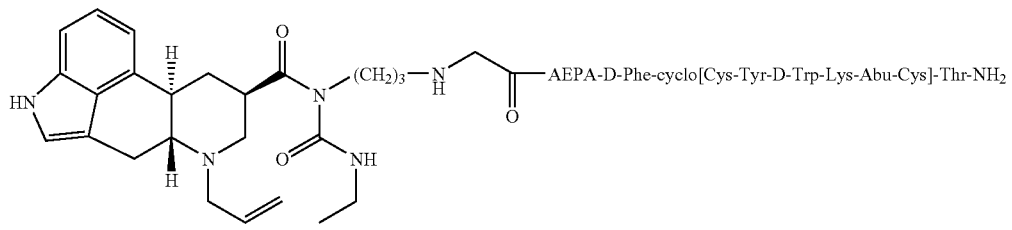
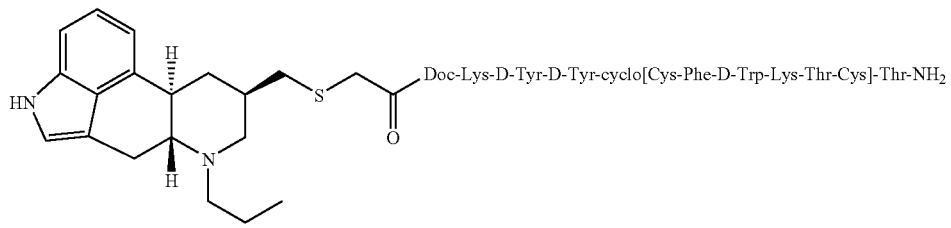
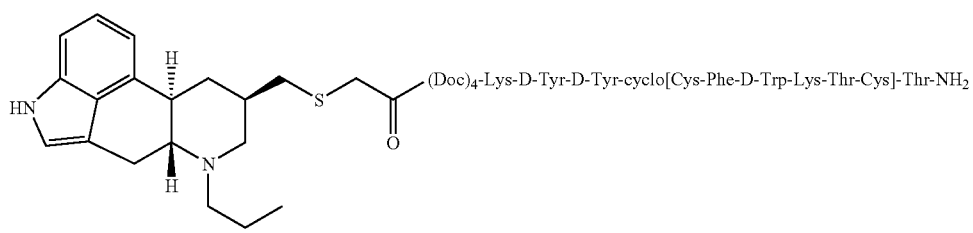
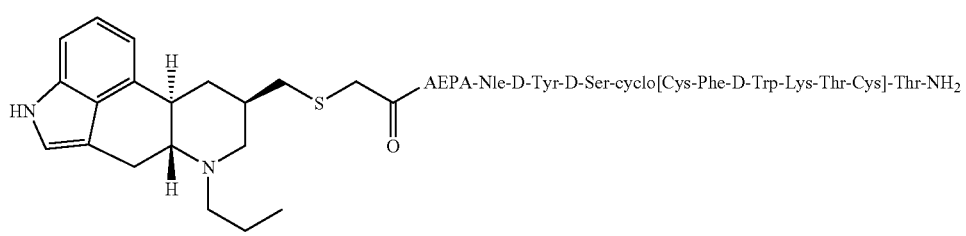

-continued
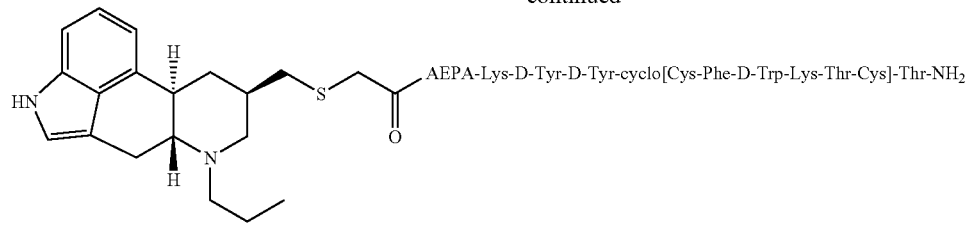
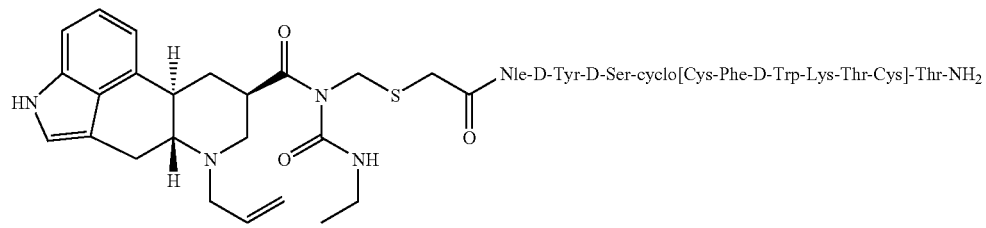
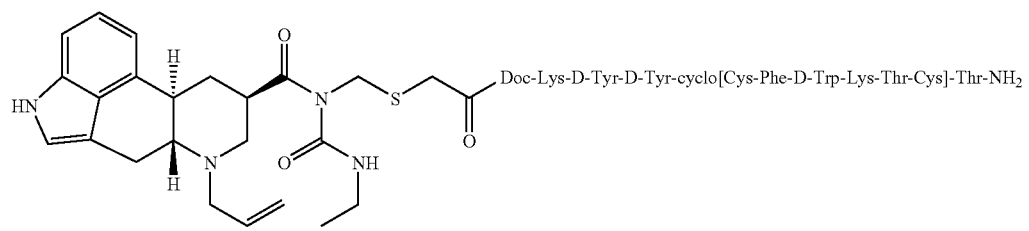
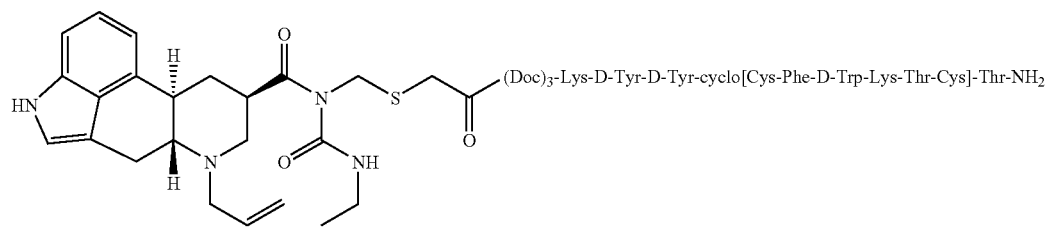
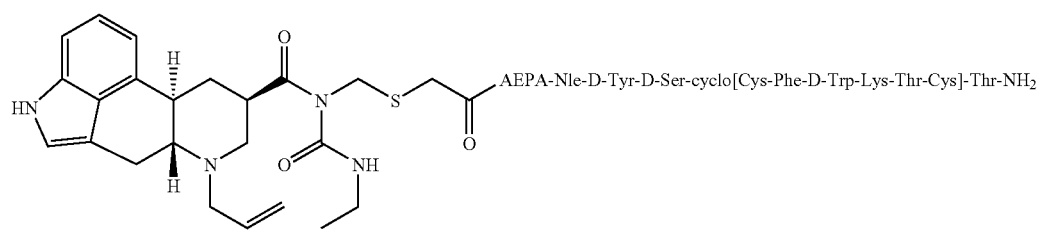
and
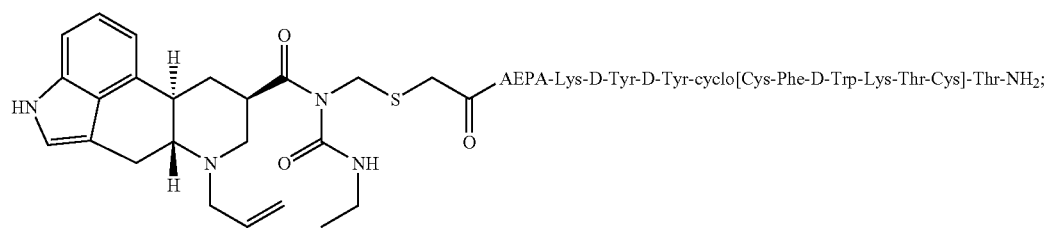
or a pharmaceutically acceptable salt thereof.

In another embodiment the invention features a compound according to the formula:

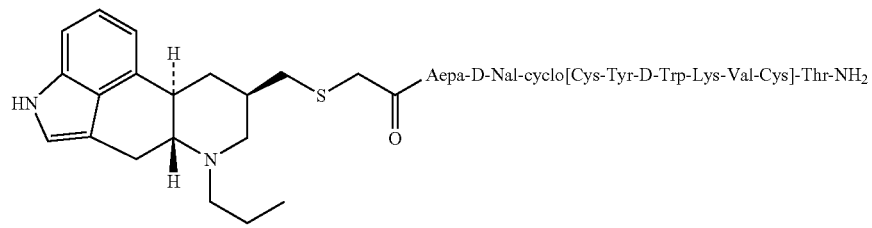
Aepa-D-Nal-cyclo[Cys-Tyr-D-Trp-Lys-Val-Cys]-Thr-NH$_2$

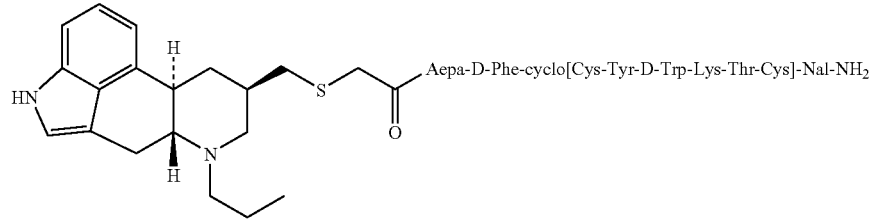
Aepa-D-Phe-cyclo[Cys-Tyr-D-Trp-Lys-Thr-Cys]-Nal-NH$_2$

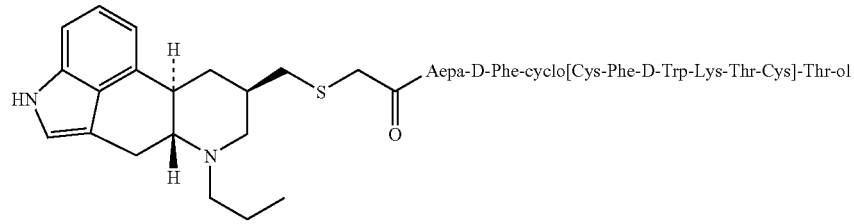
Aepa-D-Phe-cyclo[Cys-Phe-D-Trp-Lys-Thr-Cys]-Thr-ol

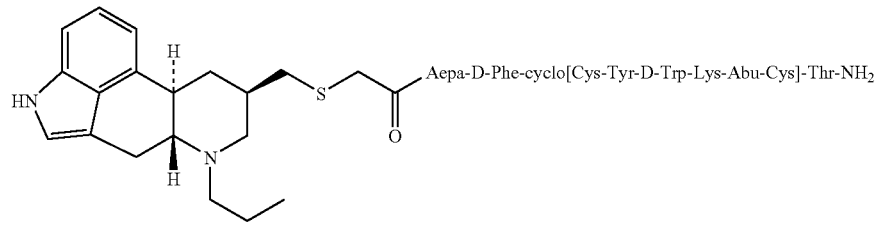
Aepa-D-Phe-cyclo[Cys-Tyr-D-Trp-Lys-Abu-Cys]-Thr-NH$_2$

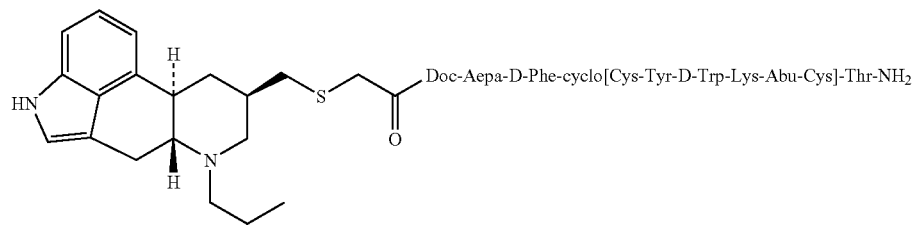
Doc-Aepa-D-Phe-cyclo[Cys-Tyr-D-Trp-Lys-Abu-Cys]-Thr-NH$_2$

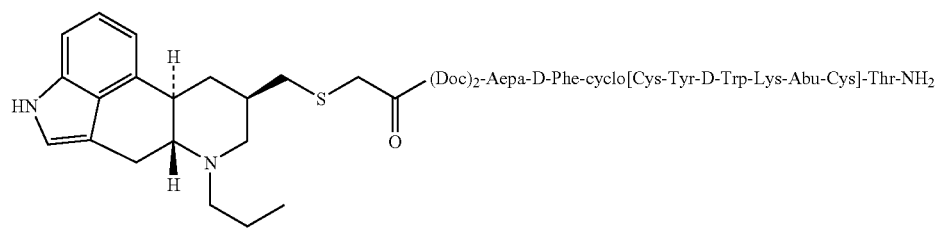
(Doc)$_2$-Aepa-D-Phe-cyclo[Cys-Tyr-D-Trp-Lys-Abu-Cys]-Thr-NH$_2$

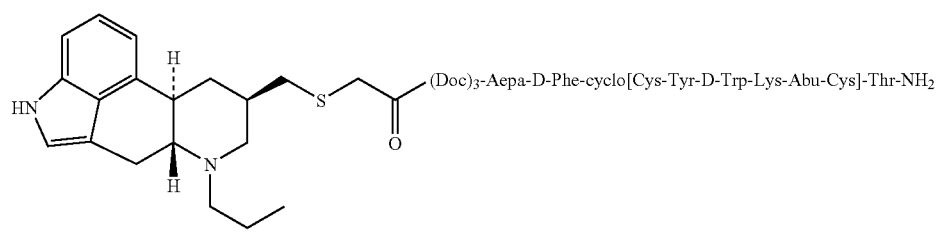
(Doc)$_3$-Aepa-D-Phe-cyclo[Cys-Tyr-D-Trp-Lys-Abu-Cys]-Thr-NH$_2$

-continued

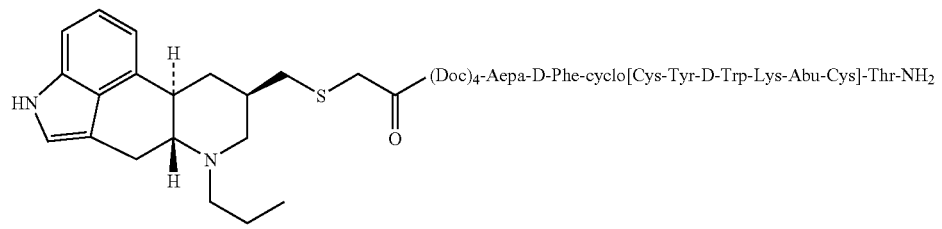
(Doc)₄-Aepa-D-Phe-cyclo[Cys-Tyr-D-Trp-Lys-Abu-Cys]-Thr-NH₂

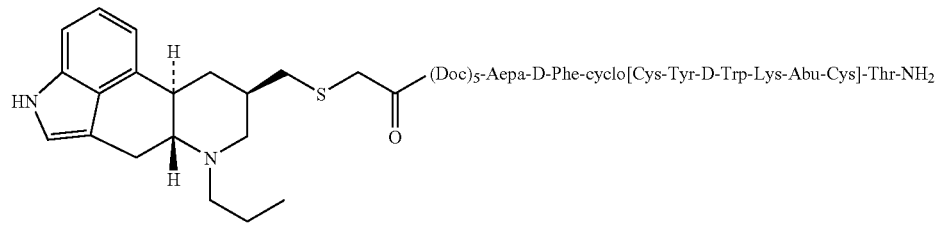
(Doc)₅-Aepa-D-Phe-cyclo[Cys-Tyr-D-Trp-Lys-Abu-Cys]-Thr-NH₂

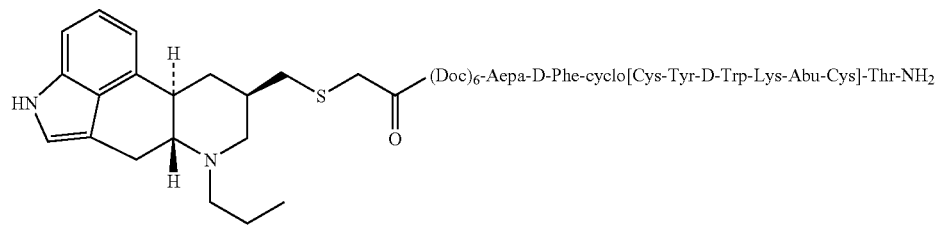
(Doc)₆-Aepa-D-Phe-cyclo[Cys-Tyr-D-Trp-Lys-Abu-Cys]-Thr-NH₂

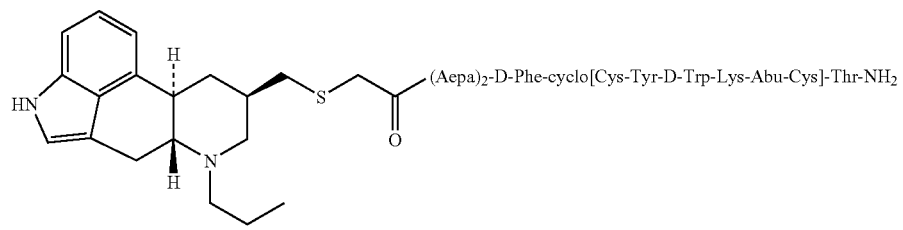
(Aepa)₂-D-Phe-cyclo[Cys-Tyr-D-Trp-Lys-Abu-Cys]-Thr-NH₂

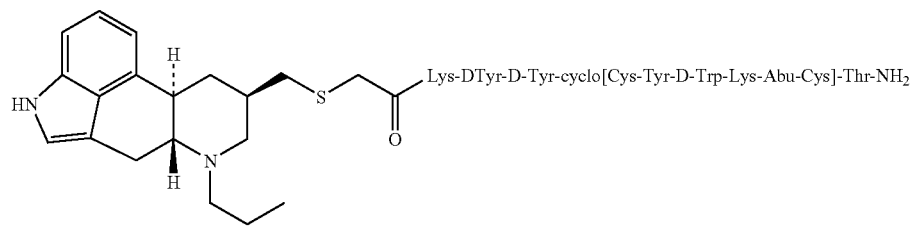
Lys-DTyr-D-Tyr-cyclo[Cys-Tyr-D-Trp-Lys-Abu-Cys]-Thr-NH₂

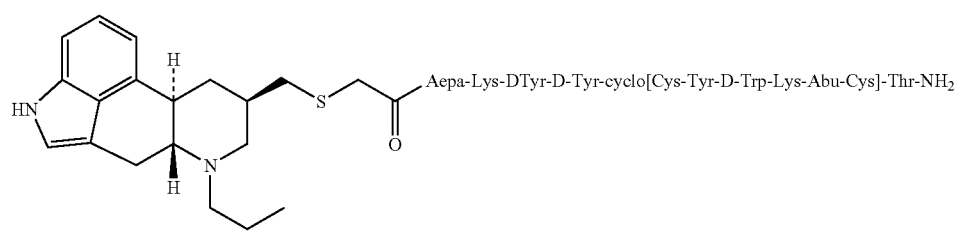
Aepa-Lys-DTyr-D-Tyr-cyclo[Cys-Tyr-D-Trp-Lys-Abu-Cys]-Thr-NH₂

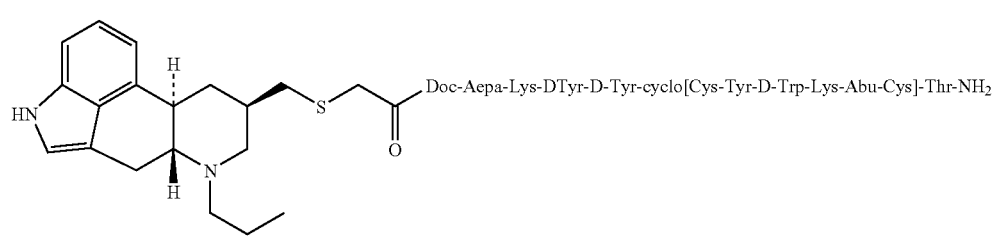
Doc-Aepa-Lys-DTyr-D-Tyr-cyclo[Cys-Tyr-D-Trp-Lys-Abu-Cys]-Thr-NH₂

-continued

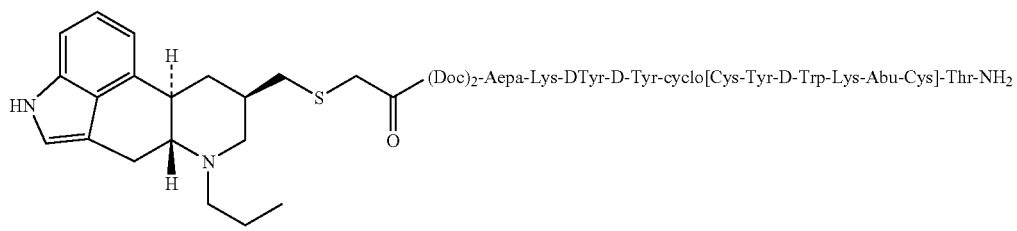
(Doc)₂-Aepa-Lys-DTyr-D-Tyr-cyclo[Cys-Tyr-D-Trp-Lys-Abu-Cys]-Thr-NH₂

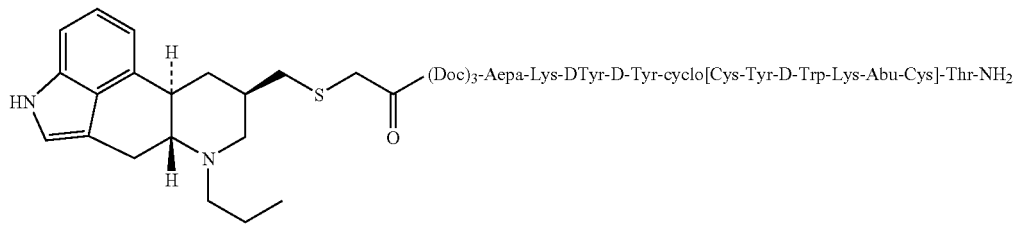
(Doc)₃-Aepa-Lys-DTyr-D-Tyr-cyclo[Cys-Tyr-D-Trp-Lys-Abu-Cys]-Thr-NH₂

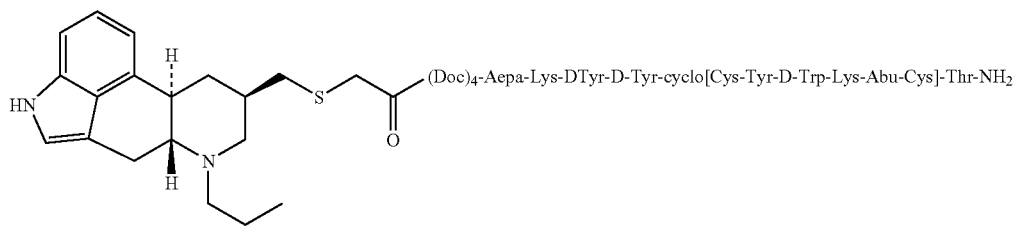
(Doc)₄-Aepa-Lys-DTyr-D-Tyr-cyclo[Cys-Tyr-D-Trp-Lys-Abu-Cys]-Thr-NH₂

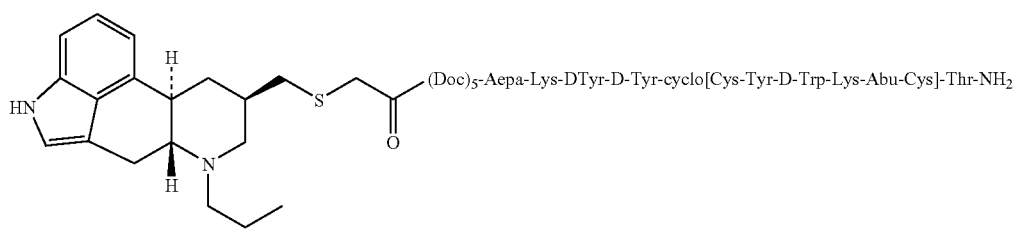
(Doc)₅-Aepa-Lys-DTyr-D-Tyr-cyclo[Cys-Tyr-D-Trp-Lys-Abu-Cys]-Thr-NH₂

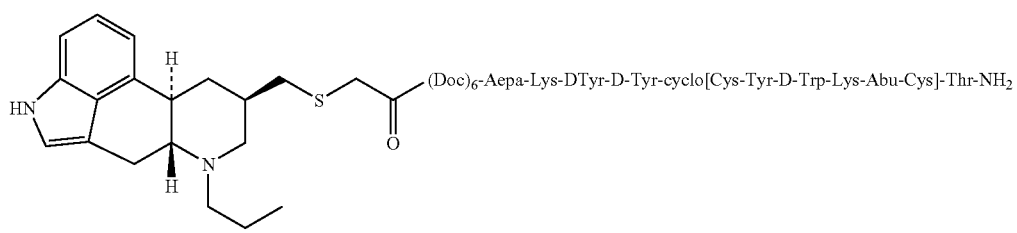
(Doc)₆-Aepa-Lys-DTyr-D-Tyr-cyclo[Cys-Tyr-D-Trp-Lys-Abu-Cys]-Thr-NH₂

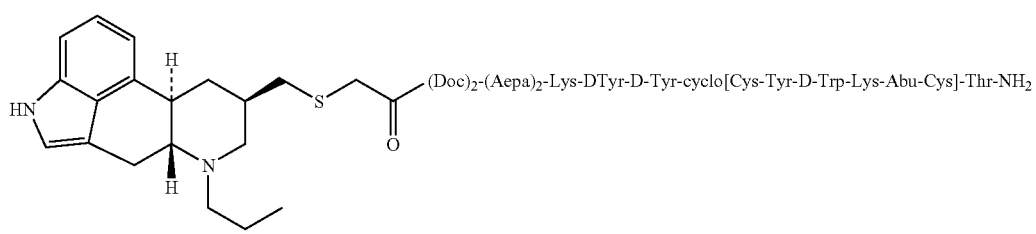
(Doc)₂-(Aepa)₂-Lys-DTyr-D-Tyr-cyclo[Cys-Tyr-D-Trp-Lys-Abu-Cys]-Thr-NH₂

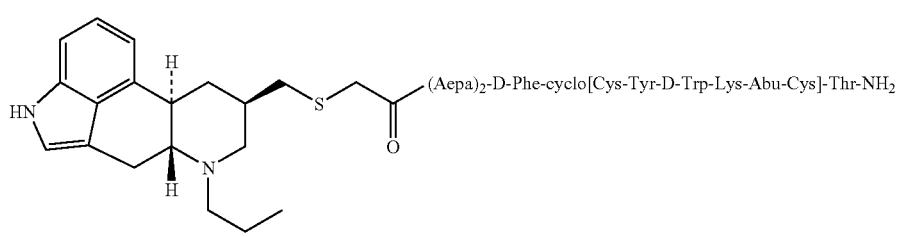
(Aepa)₂-D-Phe-cyclo[Cys-Tyr-D-Trp-Lys-Abu-Cys]-Thr-NH₂

-continued

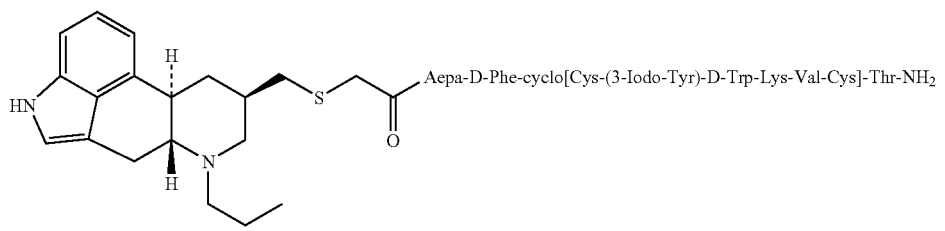
Aepa-D-Phe-cyclo[Cys-(3-Iodo-Tyr)-D-Trp-Lys-Val-Cys]-Thr-NH$_2$

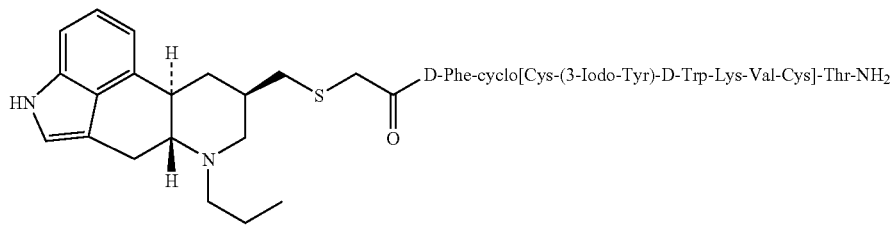
D-Phe-cyclo[Cys-(3-Iodo-Tyr)-D-Trp-Lys-Val-Cys]-Thr-NH$_2$

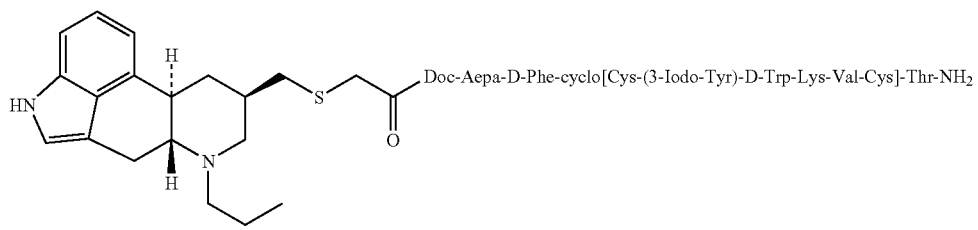
Doc-Aepa-D-Phe-cyclo[Cys-(3-Iodo-Tyr)-D-Trp-Lys-Val-Cys]-Thr-NH$_2$

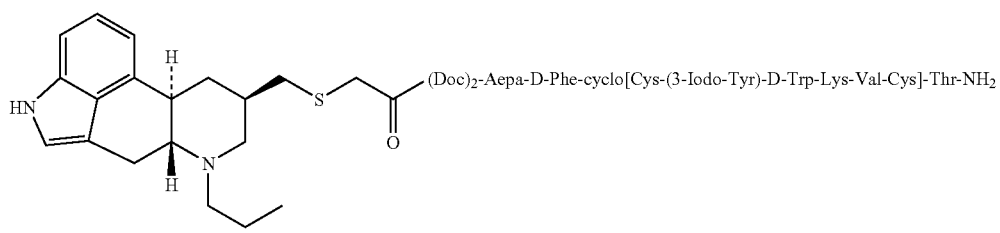
(Doc)$_2$-Aepa-D-Phe-cyclo[Cys-(3-Iodo-Tyr)-D-Trp-Lys-Val-Cys]-Thr-NH$_2$

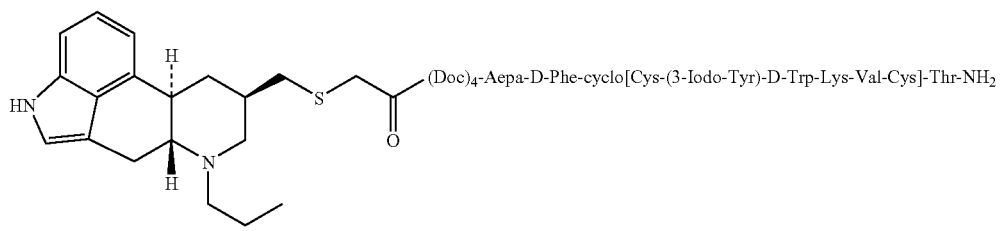
(Doc)$_4$-Aepa-D-Phe-cyclo[Cys-(3-Iodo-Tyr)-D-Trp-Lys-Val-Cys]-Thr-NH$_2$

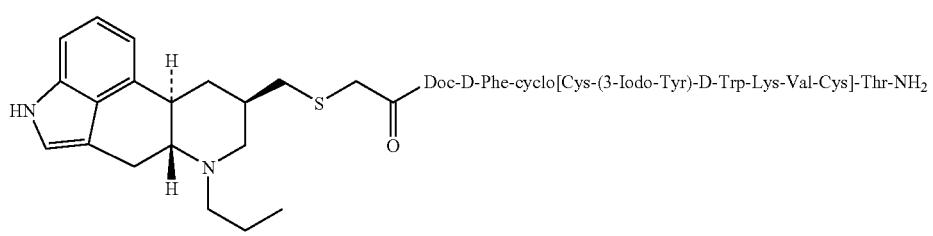
Doc-D-Phe-cyclo[Cys-(3-Iodo-Tyr)-D-Trp-Lys-Val-Cys]-Thr-NH$_2$

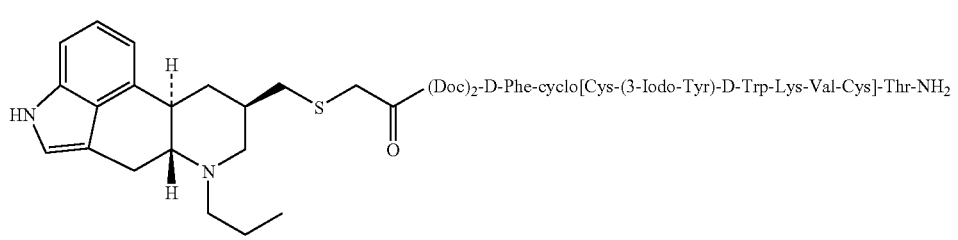
(Doc)$_2$-D-Phe-cyclo[Cys-(3-Iodo-Tyr)-D-Trp-Lys-Val-Cys]-Thr-NH$_2$

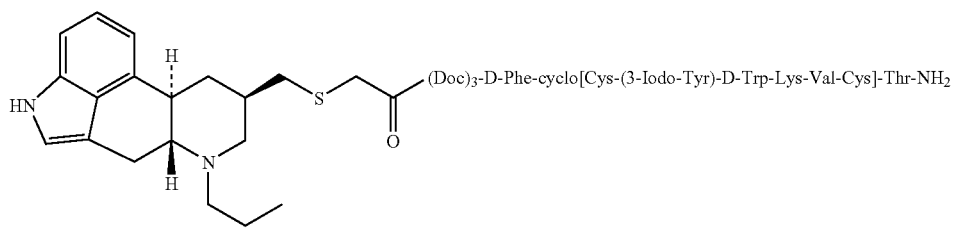
(Doc)₃-D-Phe-cyclo[Cys-(3-Iodo-Tyr)-D-Trp-Lys-Val-Cys]-Thr-NH₂

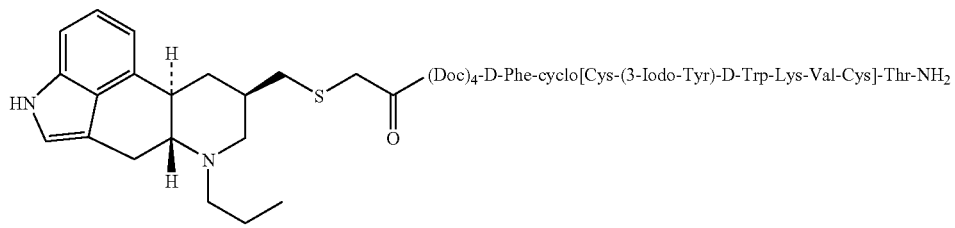
(Doc)₄-D-Phe-cyclo[Cys-(3-Iodo-Tyr)-D-Trp-Lys-Val-Cys]-Thr-NH₂

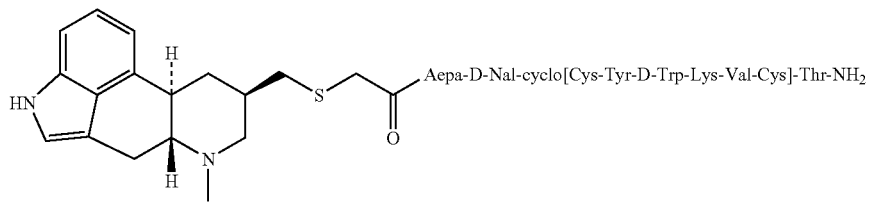
Aepa-D-Nal-cyclo[Cys-Tyr-D-Trp-Lys-Val-Cys]-Thr-NH₂

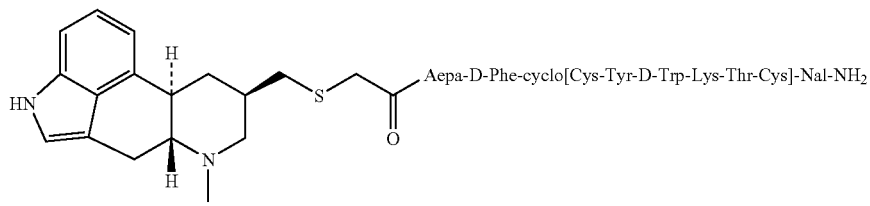
Aepa-D-Phe-cyclo[Cys-Tyr-D-Trp-Lys-Thr-Cys]-Nal-NH₂

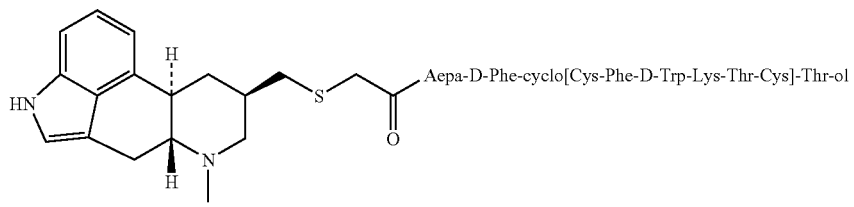
Aepa-D-Phe-cyclo[Cys-Phe-D-Trp-Lys-Thr-Cys]-Thr-ol

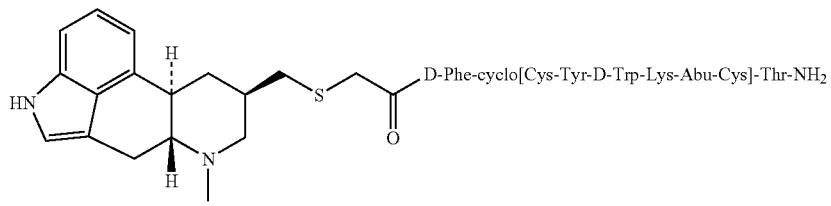
D-Phe-cyclo[Cys-Tyr-D-Trp-Lys-Abu-Cys]-Thr-NH₂

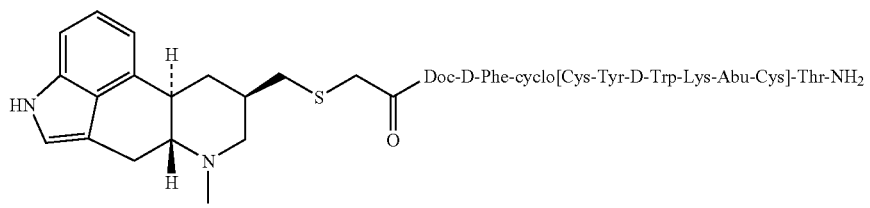
Doc-D-Phe-cyclo[Cys-Tyr-D-Trp-Lys-Abu-Cys]-Thr-NH₂

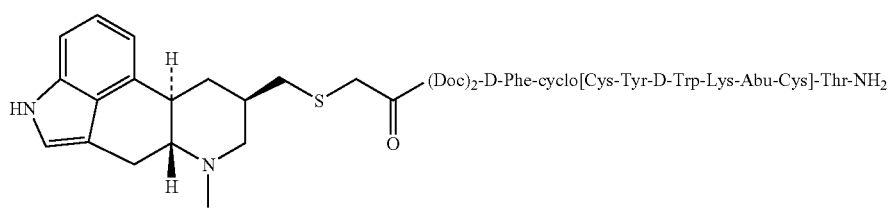
(Doc)₂-D-Phe-cyclo[Cys-Tyr-D-Trp-Lys-Abu-Cys]-Thr-NH₂

-continued

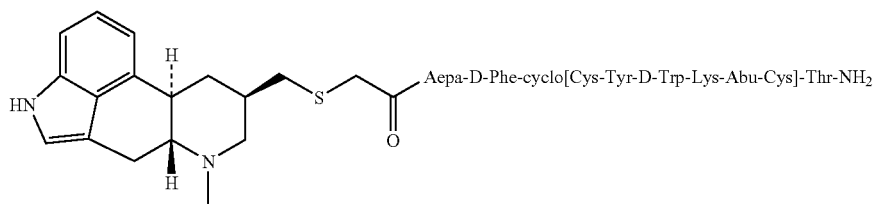
Aepa-D-Phe-cyclo[Cys-Tyr-D-Trp-Lys-Abu-Cys]-Thr-NH$_2$

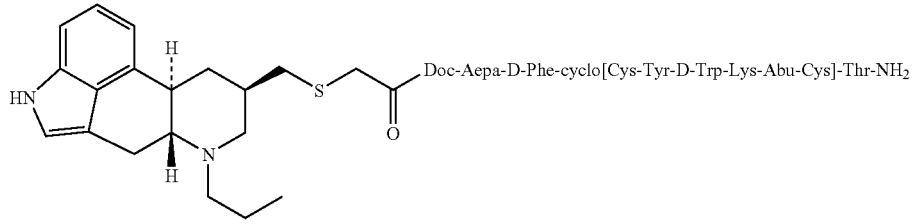
Doc-Aepa-D-Phe-cyclo[Cys-Tyr-D-Trp-Lys-Abu-Cys]-Thr-NH$_2$

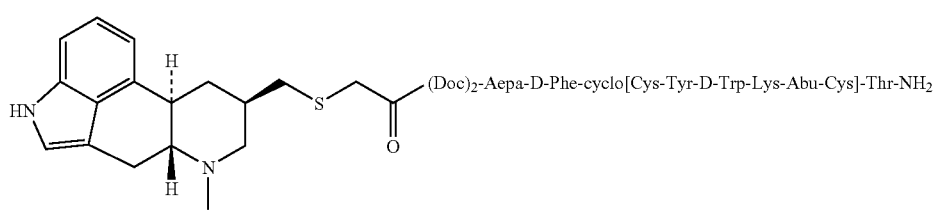
(Doc)$_2$-Aepa-D-Phe-cyclo[Cys-Tyr-D-Trp-Lys-Abu-Cys]-Thr-NH$_2$

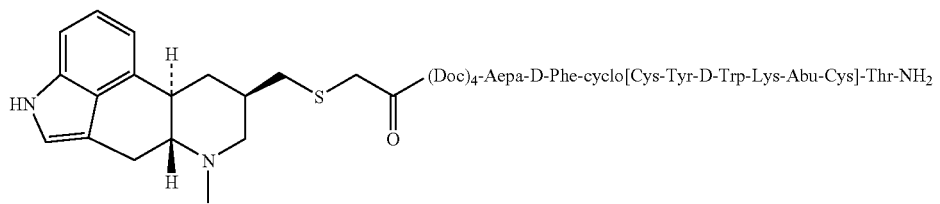
(Doc)$_4$-Aepa-D-Phe-cyclo[Cys-Tyr-D-Trp-Lys-Abu-Cys]-Thr-NH$_2$

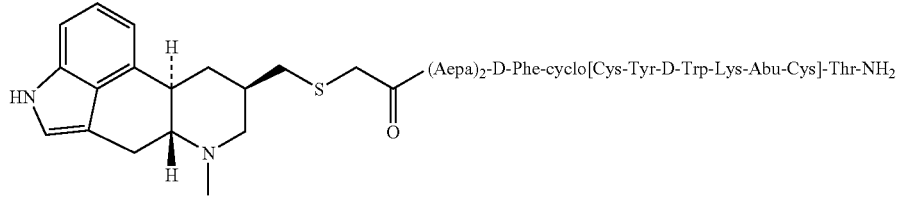
(Aepa)$_2$-D-Phe-cyclo[Cys-Tyr-D-Trp-Lys-Abu-Cys]-Thr-NH$_2$

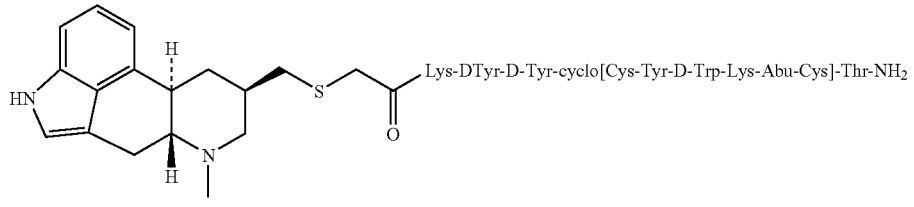
Lys-DTyr-D-Tyr-cyclo[Cys-Tyr-D-Trp-Lys-Abu-Cys]-Thr-NH$_2$

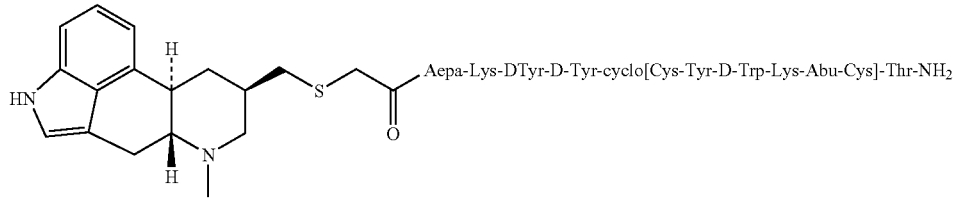
Aepa-Lys-DTyr-D-Tyr-cyclo[Cys-Tyr-D-Trp-Lys-Abu-Cys]-Thr-NH$_2$

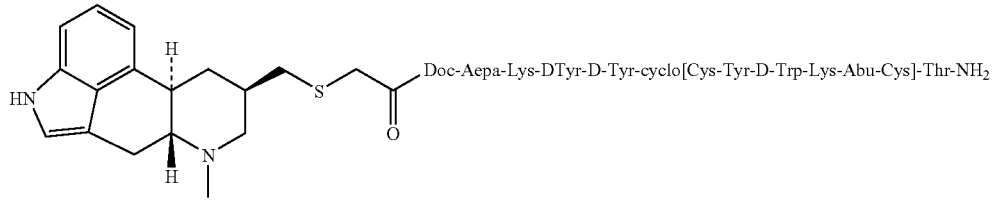
Doc-Aepa-Lys-DTyr-D-Tyr-cyclo[Cys-Tyr-D-Trp-Lys-Abu-Cys]-Thr-NH$_2$

-continued
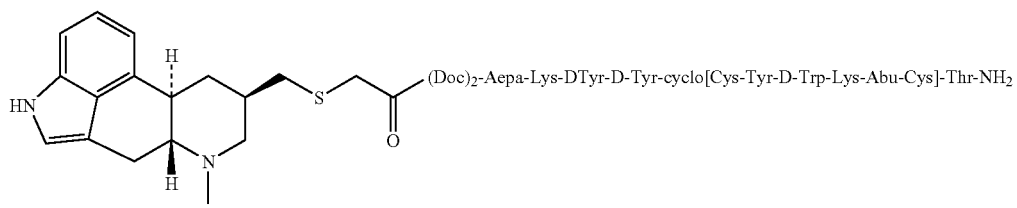
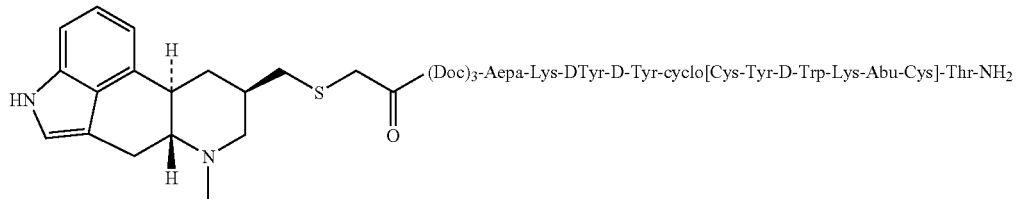
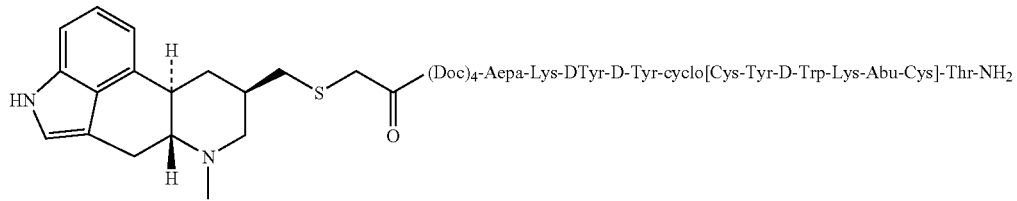
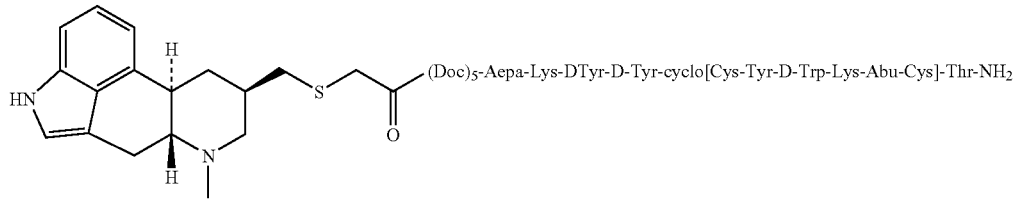
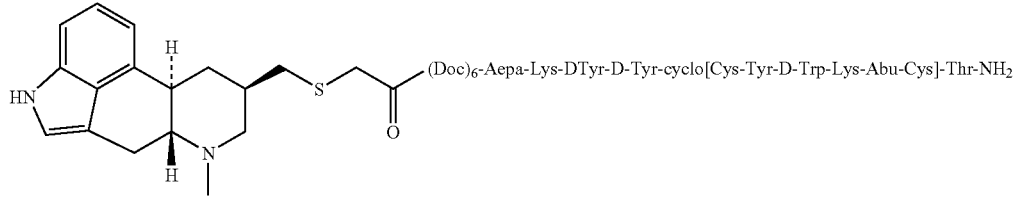
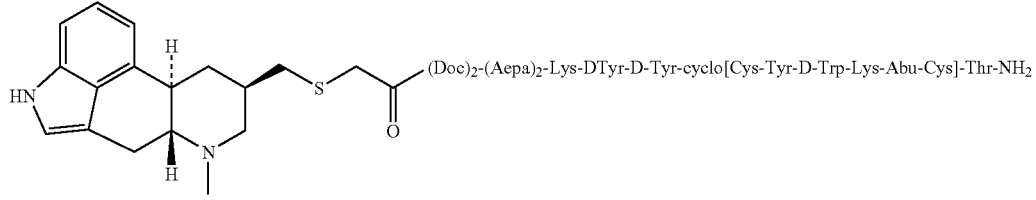
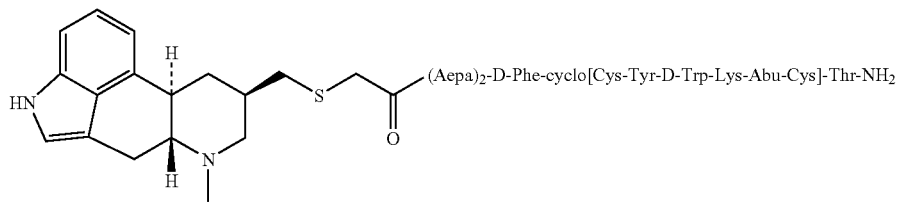
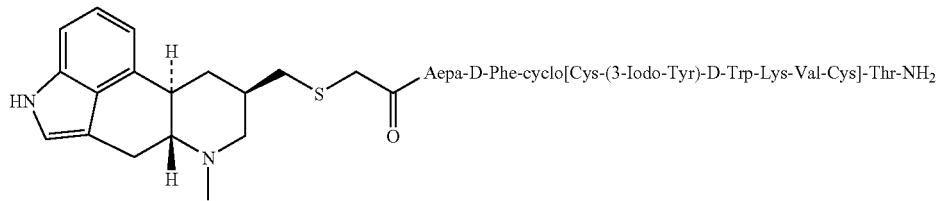

-continued

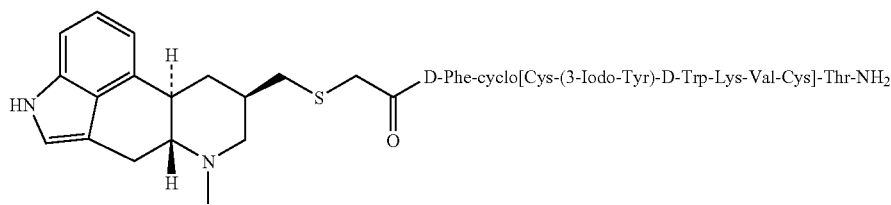
D-Phe-cyclo[Cys-(3-Iodo-Tyr)-D-Trp-Lys-Val-Cys]-Thr-NH$_2$

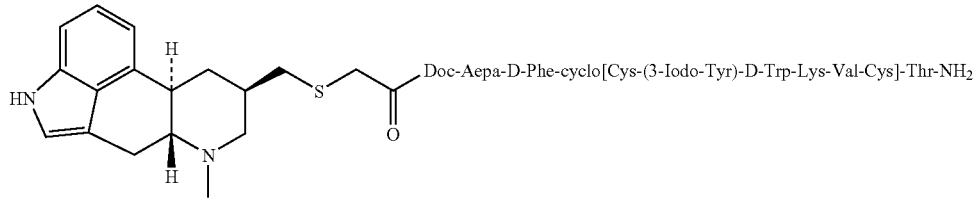
Doc-Aepa-D-Phe-cyclo[Cys-(3-Iodo-Tyr)-D-Trp-Lys-Val-Cys]-Thr-NH$_2$

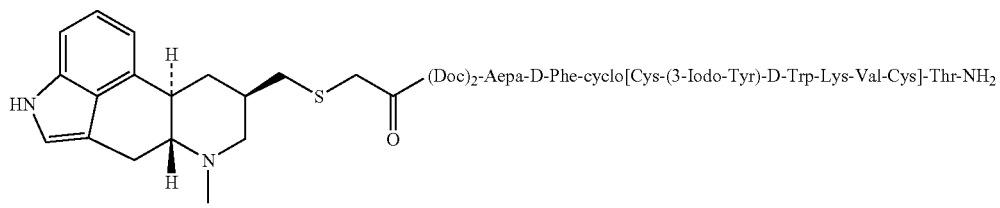
(Doc)$_2$-Aepa-D-Phe-cyclo[Cys-(3-Iodo-Tyr)-D-Trp-Lys-Val-Cys]-Thr-NH$_2$

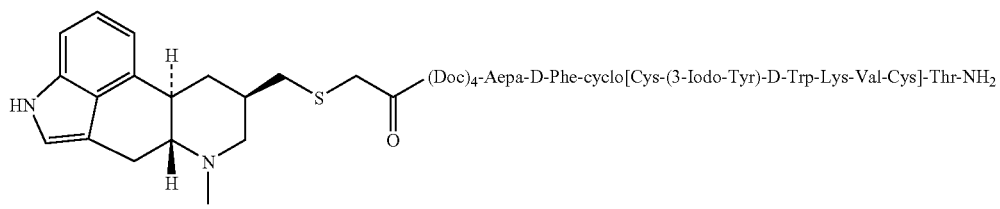
(Doc)$_4$-Aepa-D-Phe-cyclo[Cys-(3-Iodo-Tyr)-D-Trp-Lys-Val-Cys]-Thr-NH$_2$

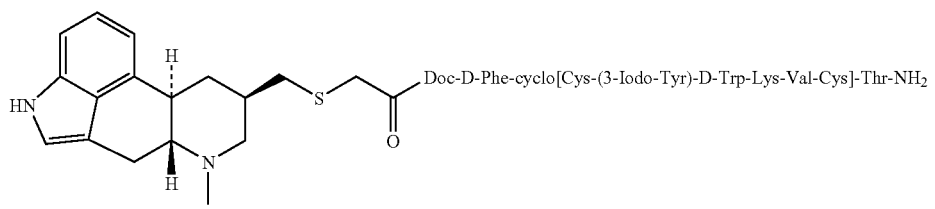
Doc-D-Phe-cyclo[Cys-(3-Iodo-Tyr)-D-Trp-Lys-Val-Cys]-Thr-NH$_2$

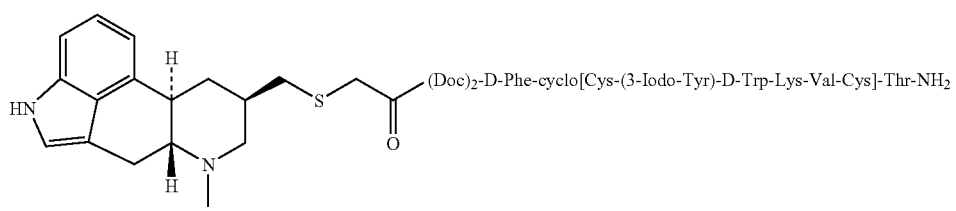
(Doc)$_2$-D-Phe-cyclo[Cys-(3-Iodo-Tyr)-D-Trp-Lys-Val-Cys]-Thr-NH$_2$

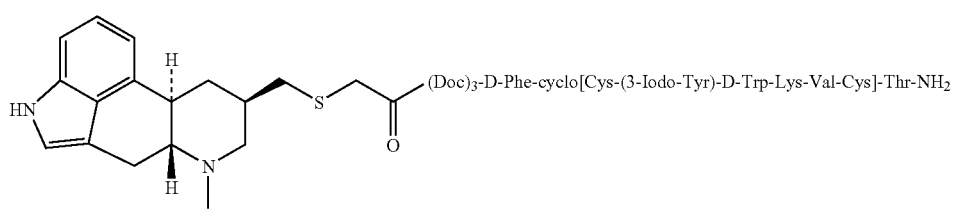
(Doc)$_3$-D-Phe-cyclo[Cys-(3-Iodo-Tyr)-D-Trp-Lys-Val-Cys]-Thr-NH$_2$

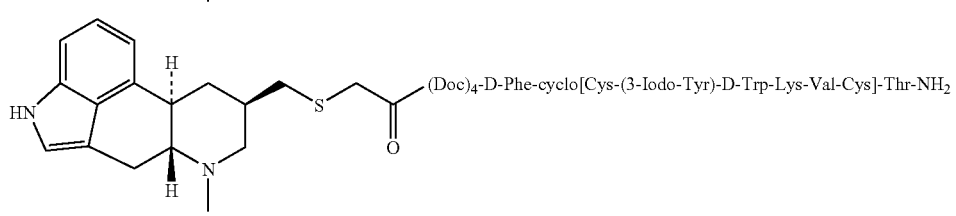
(Doc)$_4$-D-Phe-cyclo[Cys-(3-Iodo-Tyr)-D-Trp-Lys-Val-Cys]-Thr-NH$_2$ -continued
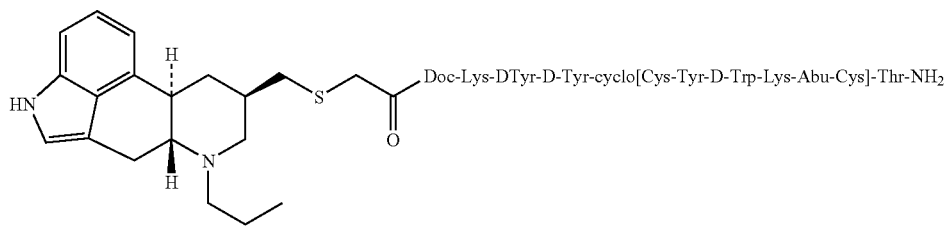
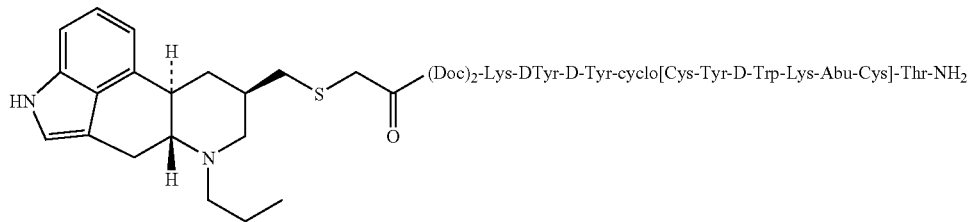
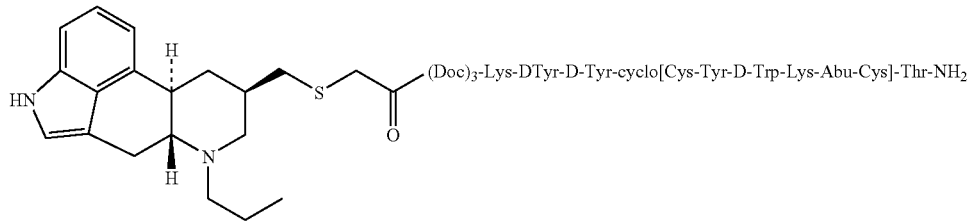
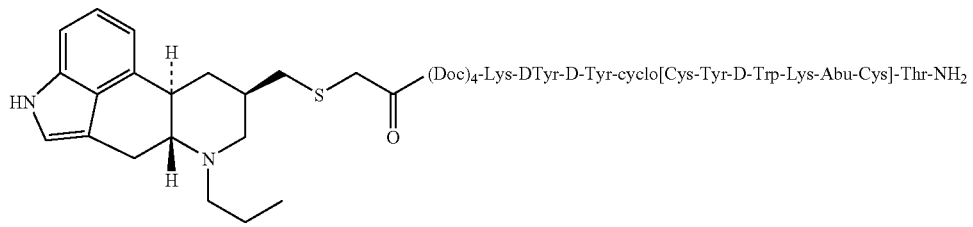
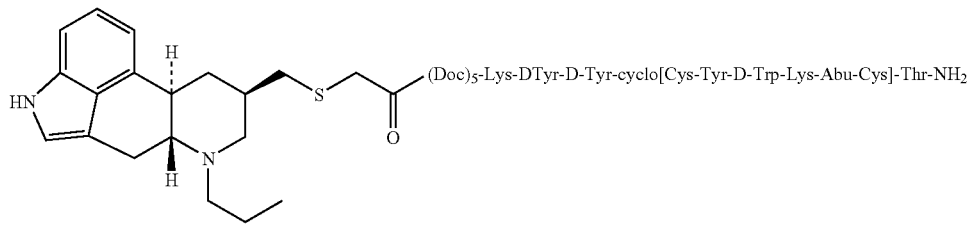
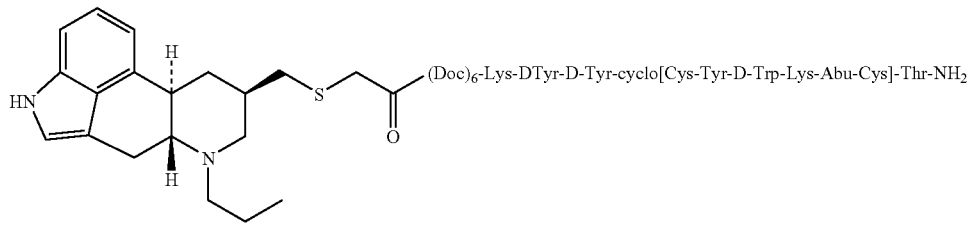
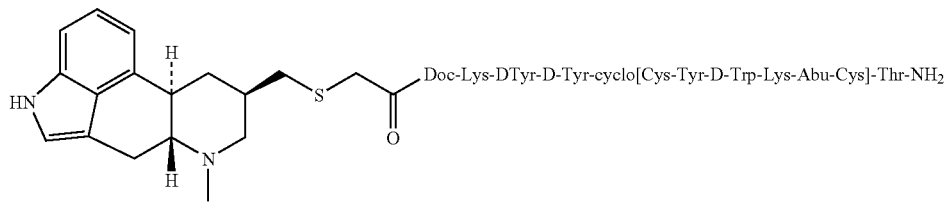

-continued
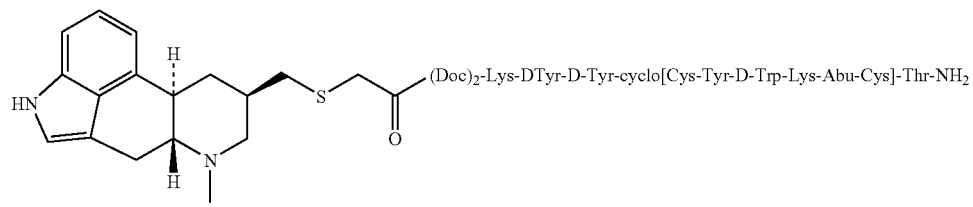
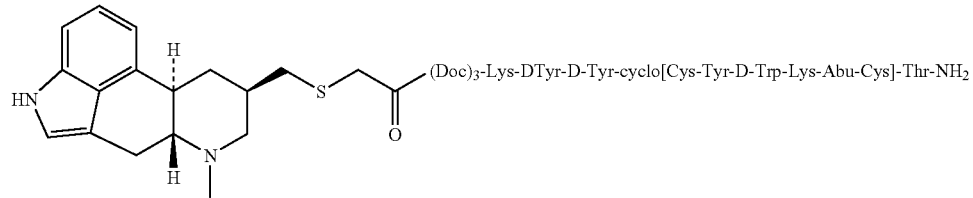
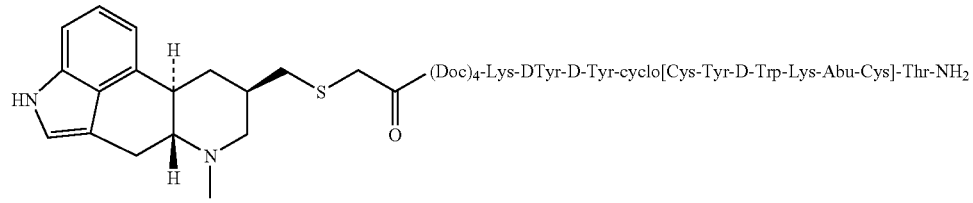
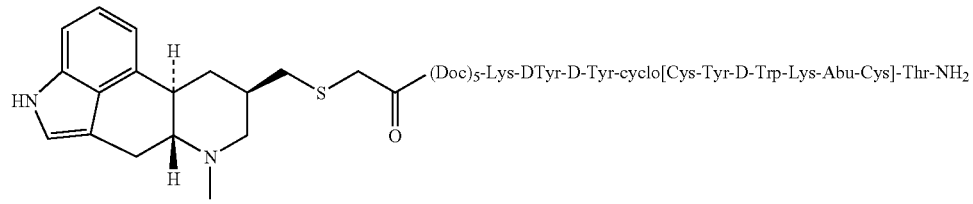
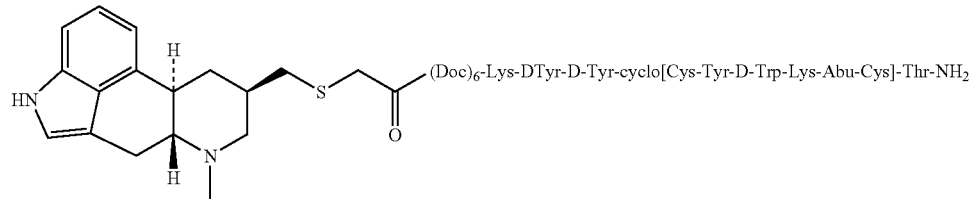
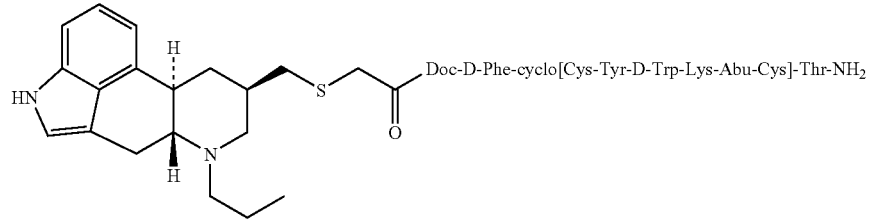
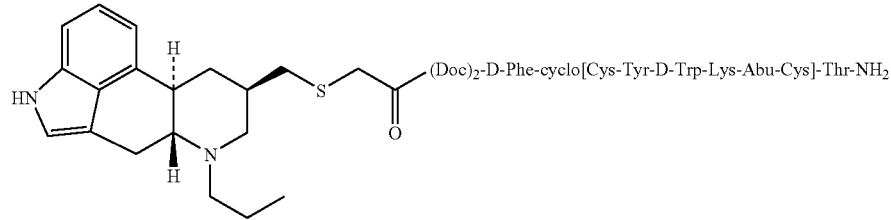
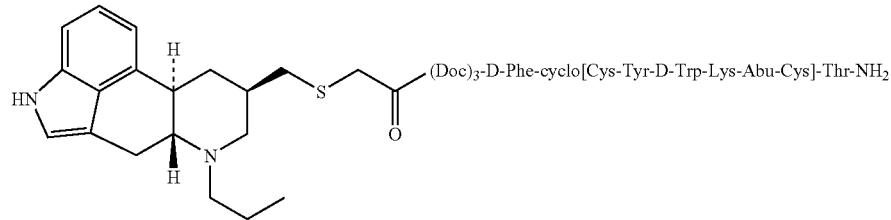

-continued

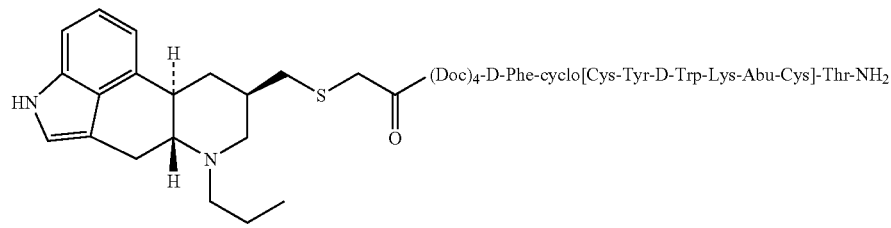
(Doc)₄-D-Phe-cyclo[Cys-Tyr-D-Trp-Lys-Abu-Cys]-Thr-NH₂

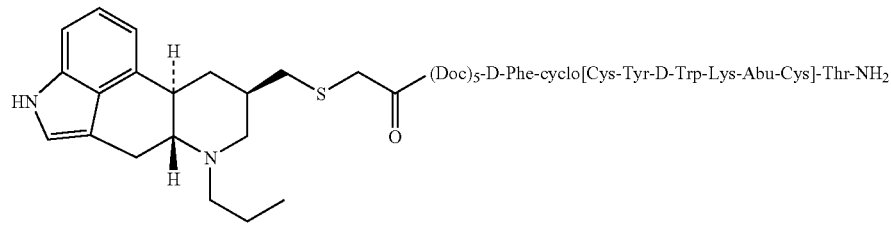
(Doc)₅-D-Phe-cyclo[Cys-Tyr-D-Trp-Lys-Abu-Cys]-Thr-NH₂

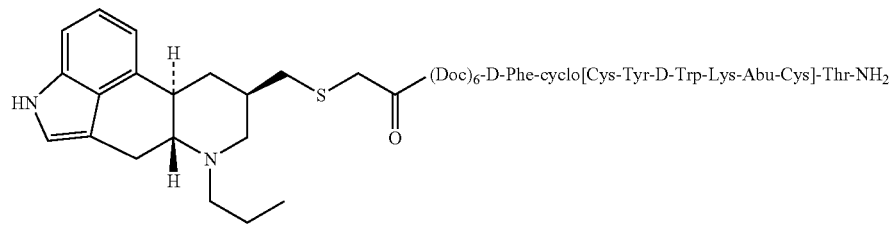
(Doc)₆-D-Phe-cyclo[Cys-Tyr-D-Trp-Lys-Abu-Cys]-Thr-NH₂

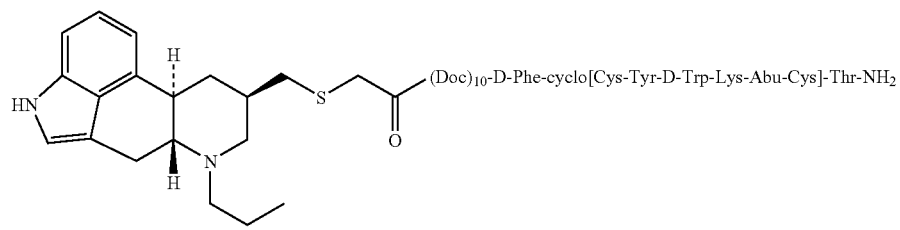
(Doc)₁₀-D-Phe-cyclo[Cys-Tyr-D-Trp-Lys-Abu-Cys]-Thr-NH₂

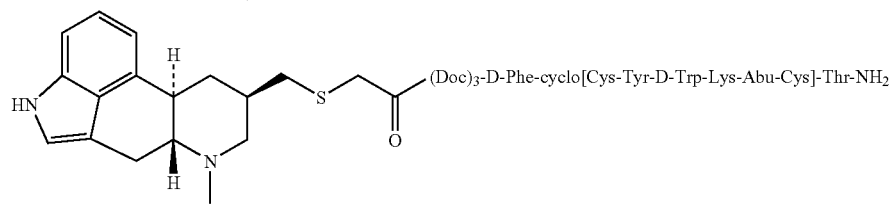
(Doc)₃-D-Phe-cyclo[Cys-Tyr-D-Trp-Lys-Abu-Cys]-Thr-NH₂

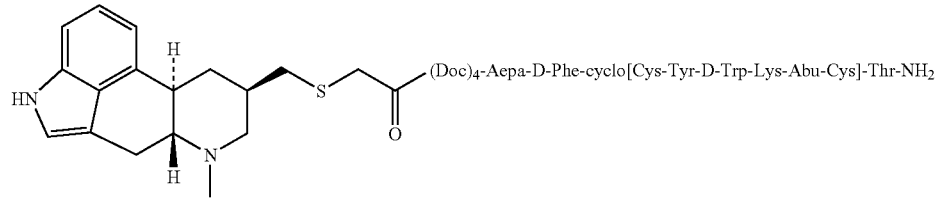
(Doc)₄-Aepa-D-Phe-cyclo[Cys-Tyr-D-Trp-Lys-Abu-Cys]-Thr-NH₂

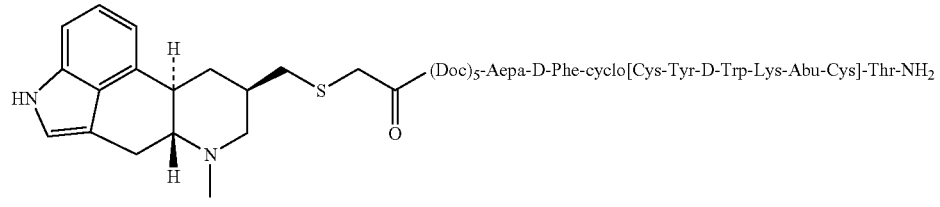
(Doc)₅-Aepa-D-Phe-cyclo[Cys-Tyr-D-Trp-Lys-Abu-Cys]-Thr-NH₂

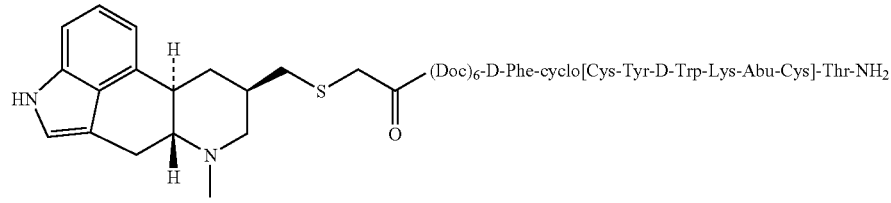
(Doc)₆-D-Phe-cyclo[Cys-Tyr-D-Trp-Lys-Abu-Cys]-Thr-NH₂

-continued
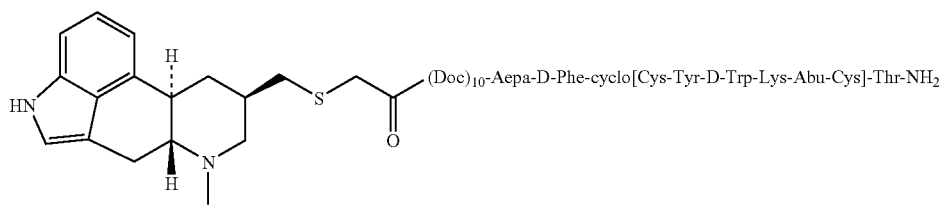
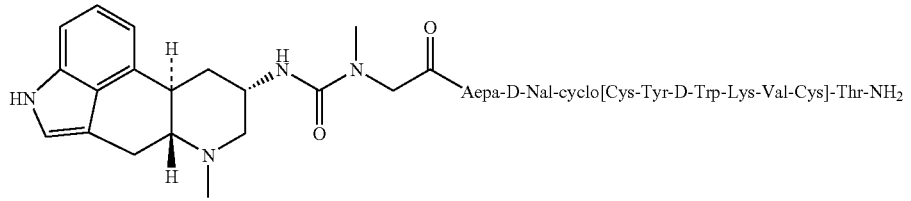
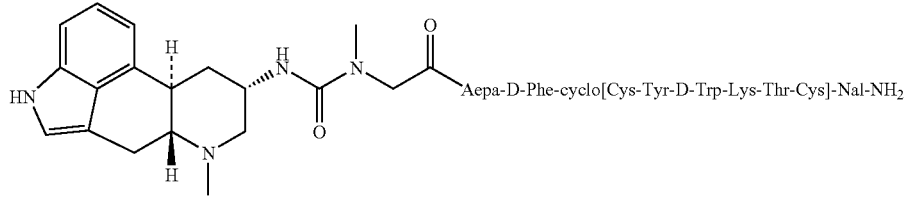
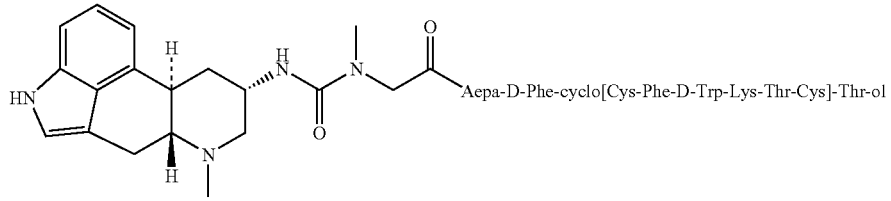
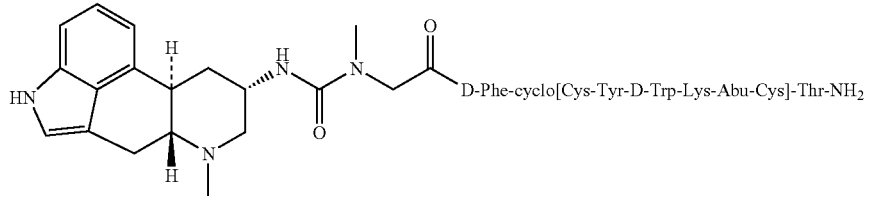
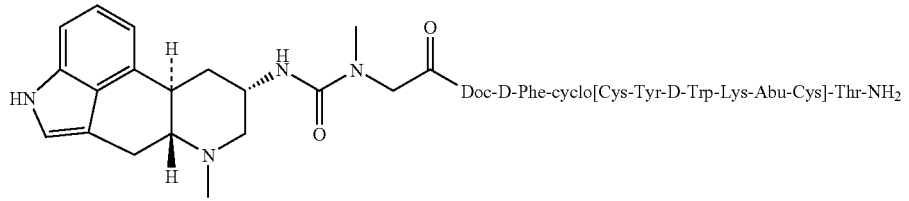
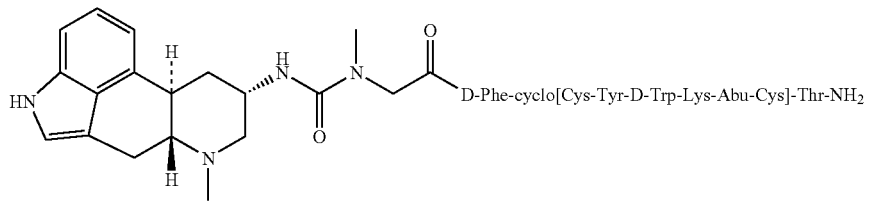
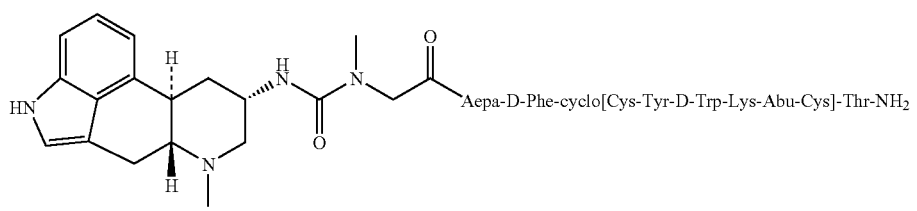

-continued

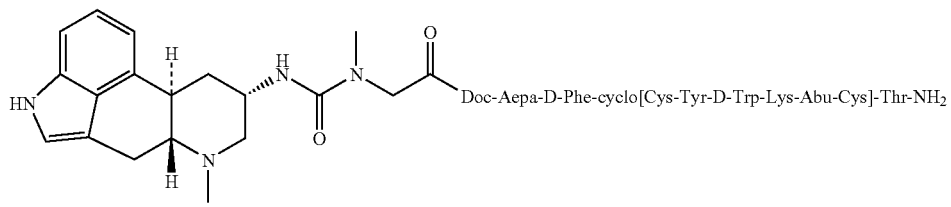
Doc-Aepa-D-Phe-cyclo[Cys-Tyr-D-Trp-Lys-Abu-Cys]-Thr-NH$_2$

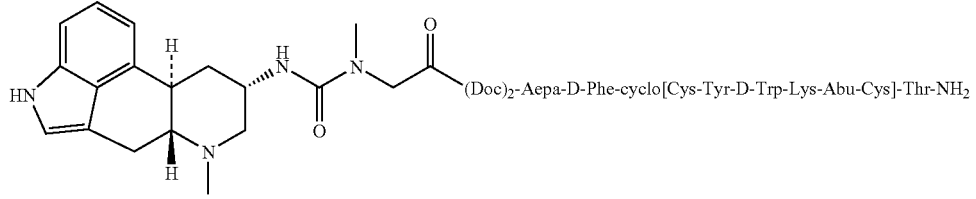
(Doc)$_2$-Aepa-D-Phe-cyclo[Cys-Tyr-D-Trp-Lys-Abu-Cys]-Thr-NH$_2$

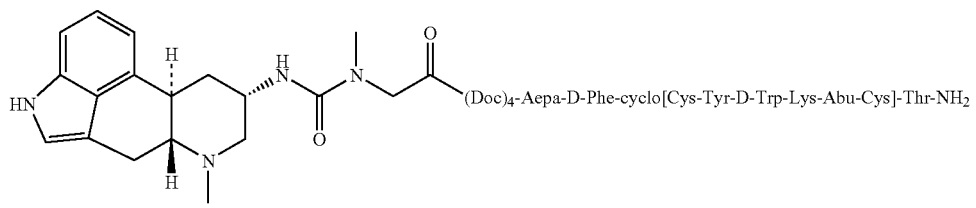
(Doc)$_4$-Aepa-D-Phe-cyclo[Cys-Tyr-D-Trp-Lys-Abu-Cys]-Thr-NH$_2$

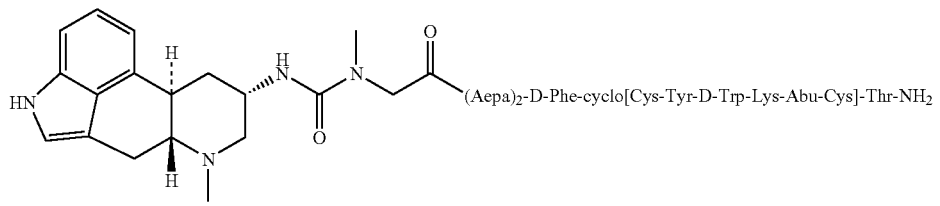
(Aepa)$_2$-D-Phe-cyclo[Cys-Tyr-D-Trp-Lys-Abu-Cys]-Thr-NH$_2$

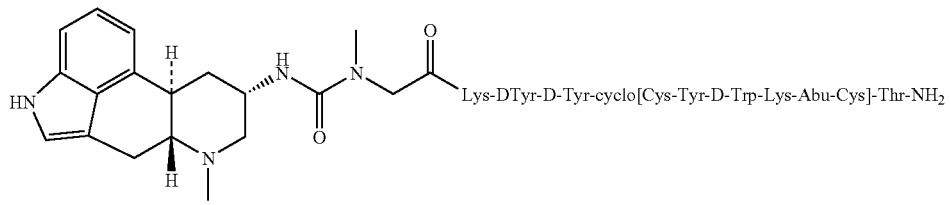
Lys-DTyr-D-Tyr-cyclo[Cys-Tyr-D-Trp-Lys-Abu-Cys]-Thr-NH$_2$

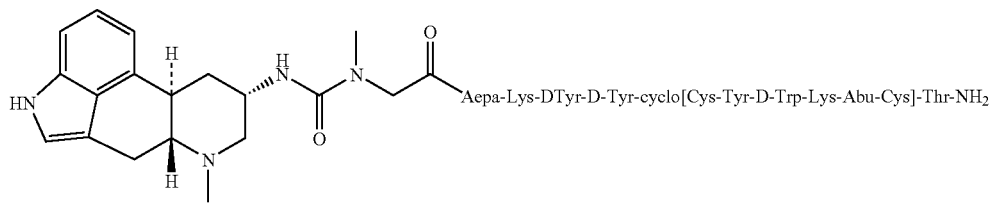
Aepa-Lys-DTyr-D-Tyr-cyclo[Cys-Tyr-D-Trp-Lys-Abu-Cys]-Thr-NH$_2$

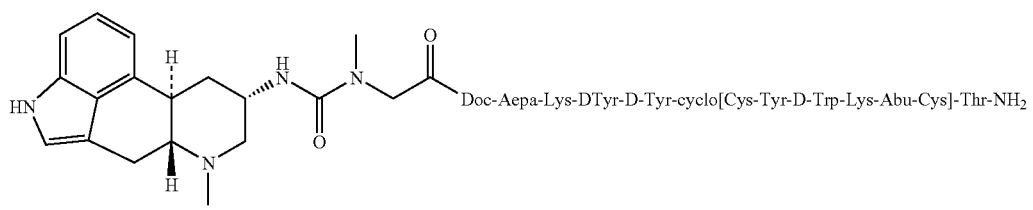
Doc-Aepa-Lys-DTyr-D-Tyr-cyclo[Cys-Tyr-D-Trp-Lys-Abu-Cys]-Thr-NH$_2$

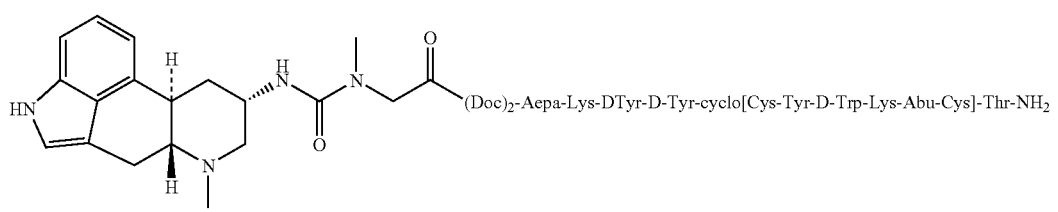
(Doc)$_2$-Aepa-Lys-DTyr-D-Tyr-cyclo[Cys-Tyr-D-Trp-Lys-Abu-Cys]-Thr-NH$_2$ -continued

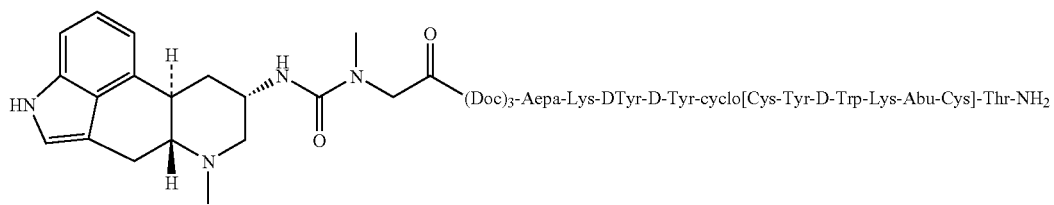
(Doc)₃-Aepa-Lys-DTyr-D-Tyr-cyclo[Cys-Tyr-D-Trp-Lys-Abu-Cys]-Thr-NH₂

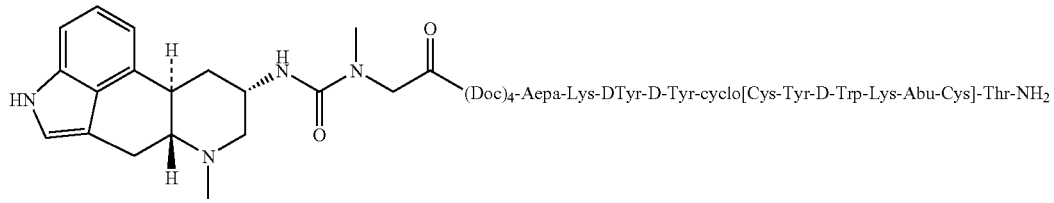
(Doc)₄-Aepa-Lys-DTyr-D-Tyr-cyclo[Cys-Tyr-D-Trp-Lys-Abu-Cys]-Thr-NH₂

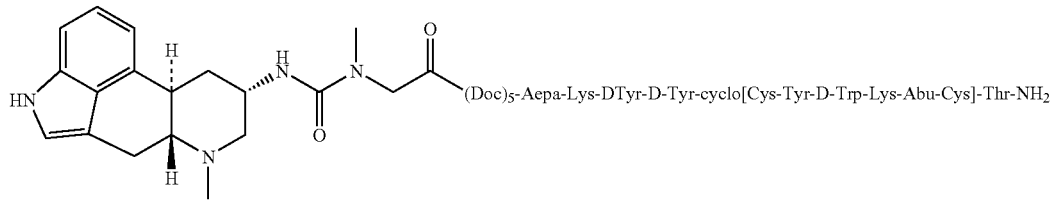
(Doc)₅-Aepa-Lys-DTyr-D-Tyr-cyclo[Cys-Tyr-D-Trp-Lys-Abu-Cys]-Thr-NH₂

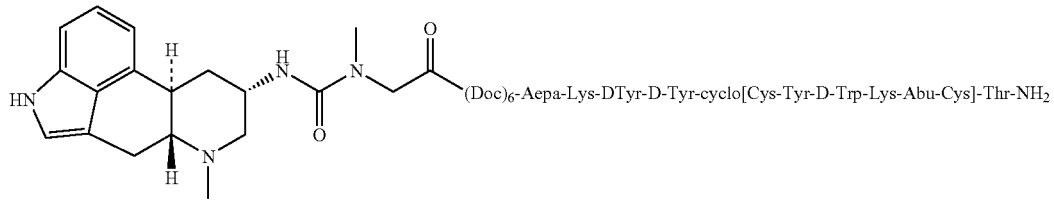
(Doc)₆-Aepa-Lys-DTyr-D-Tyr-cyclo[Cys-Tyr-D-Trp-Lys-Abu-Cys]-Thr-NH₂

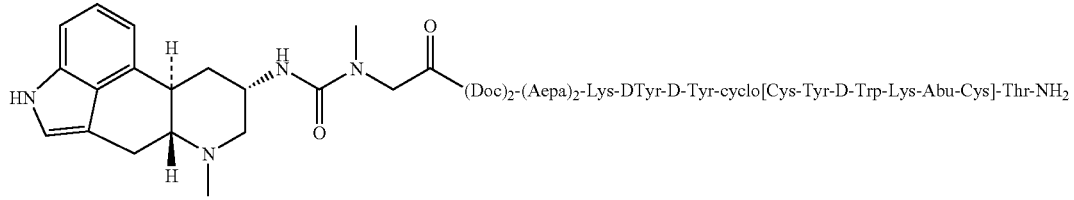
(Doc)₂-(Aepa)₂-Lys-DTyr-D-Tyr-cyclo[Cys-Tyr-D-Trp-Lys-Abu-Cys]-Thr-NH₂

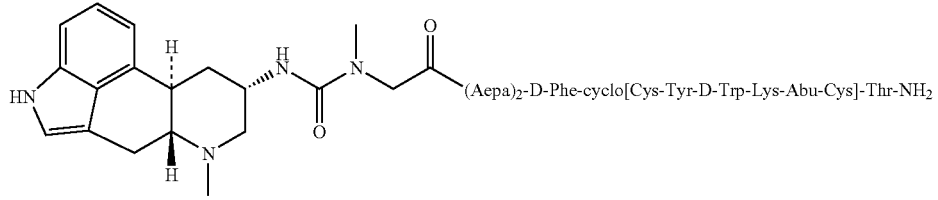
(Aepa)₂-D-Phe-cyclo[Cys-Tyr-D-Trp-Lys-Abu-Cys]-Thr-NH₂

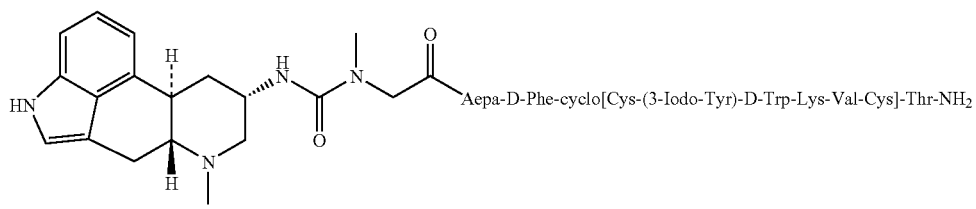
Aepa-D-Phe-cyclo[Cys-(3-Iodo-Tyr)-D-Trp-Lys-Val-Cys]-Thr-NH₂

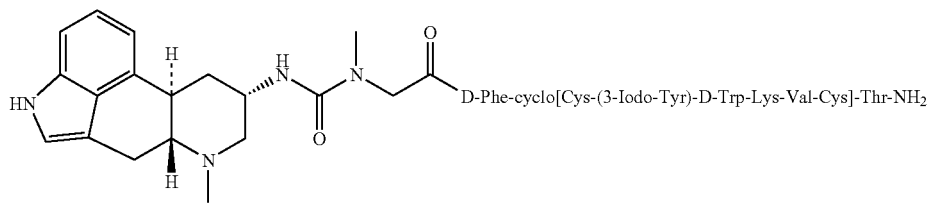
D-Phe-cyclo[Cys-(3-Iodo-Tyr)-D-Trp-Lys-Val-Cys]-Thr-NH₂

-continued

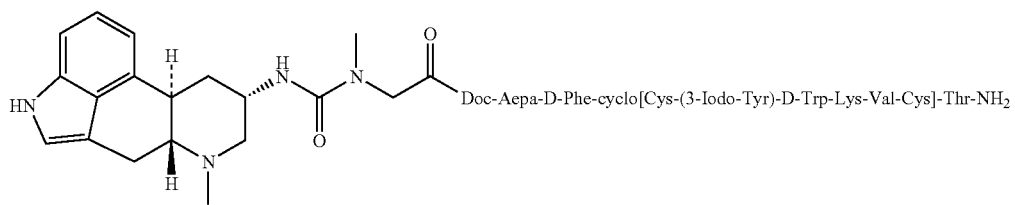
Doc-Aepa-D-Phe-cyclo[Cys-(3-Iodo-Tyr)-D-Trp-Lys-Val-Cys]-Thr-NH$_2$

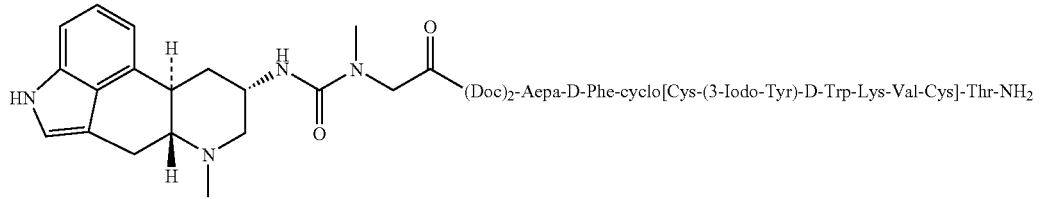
(Doc)$_2$-Aepa-D-Phe-cyclo[Cys-(3-Iodo-Tyr)-D-Trp-Lys-Val-Cys]-Thr-NH$_2$

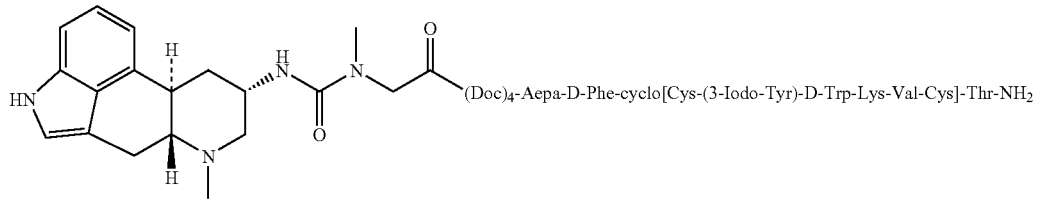
(Doc)$_4$-Aepa-D-Phe-cyclo[Cys-(3-Iodo-Tyr)-D-Trp-Lys-Val-Cys]-Thr-NH$_2$

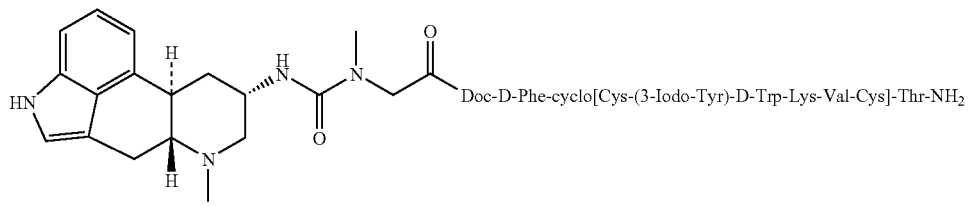
Doc-D-Phe-cyclo[Cys-(3-Iodo-Tyr)-D-Trp-Lys-Val-Cys]-Thr-NH$_2$

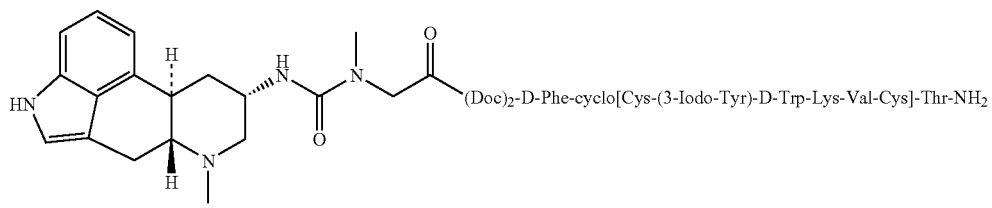
(Doc)$_2$-D-Phe-cyclo[Cys-(3-Iodo-Tyr)-D-Trp-Lys-Val-Cys]-Thr-NH$_2$

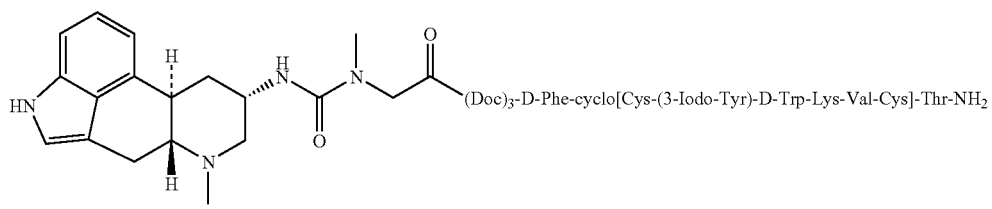
(Doc)$_3$-D-Phe-cyclo[Cys-(3-Iodo-Tyr)-D-Trp-Lys-Val-Cys]-Thr-NH$_2$

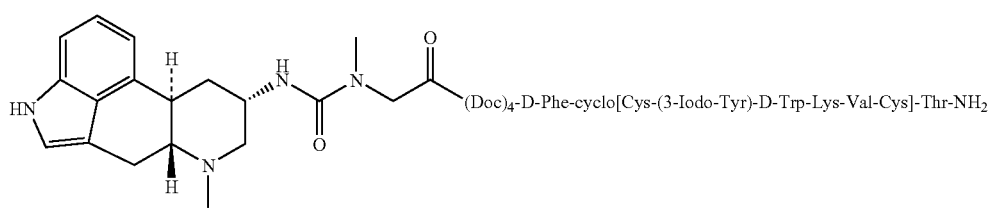
(Doc)$_4$-D-Phe-cyclo[Cys-(3-Iodo-Tyr)-D-Trp-Lys-Val-Cys]-Thr-NH$_2$

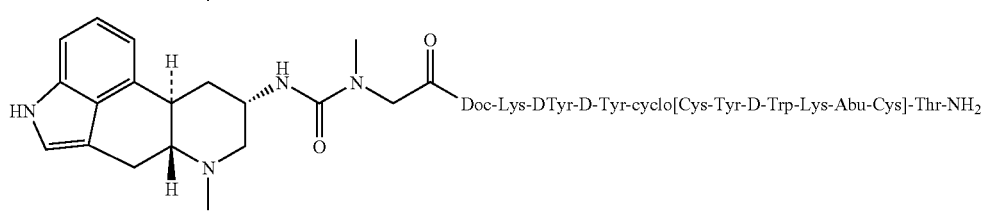
Doc-Lys-DTyr-D-Tyr-cyclo[Cys-Tyr-D-Trp-Lys-Abu-Cys]-Thr-NH$_2$

-continued
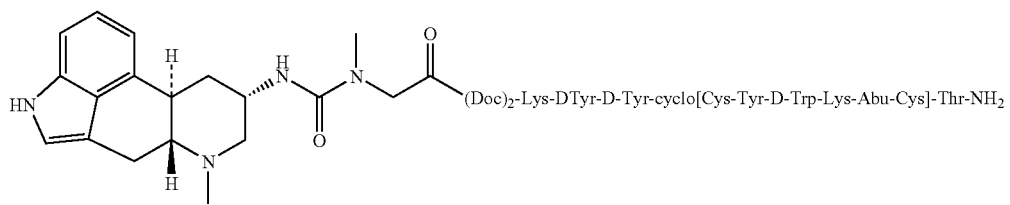
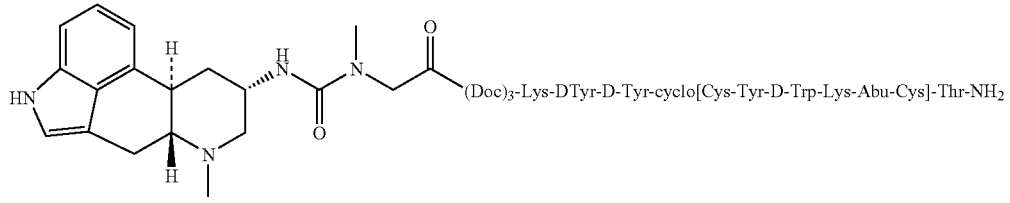
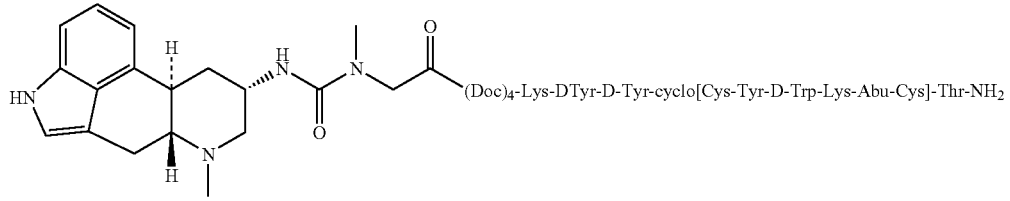
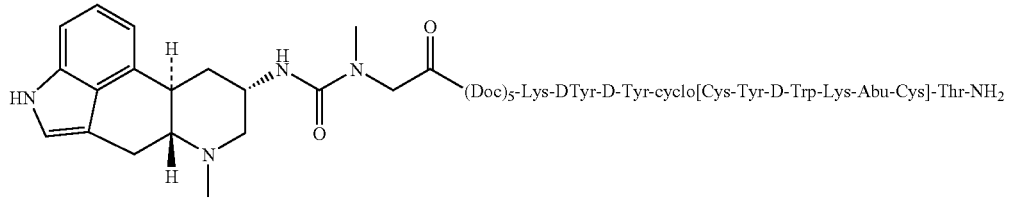
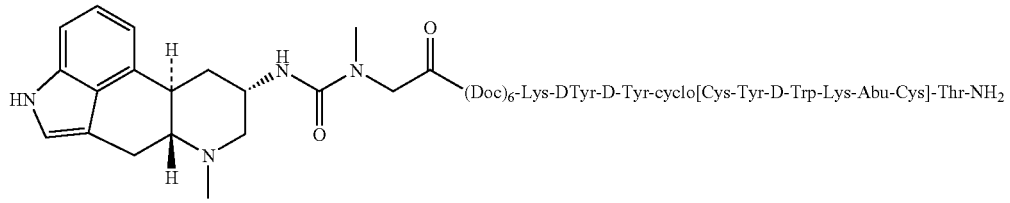
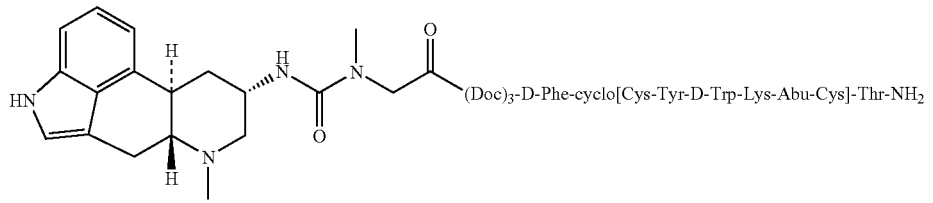
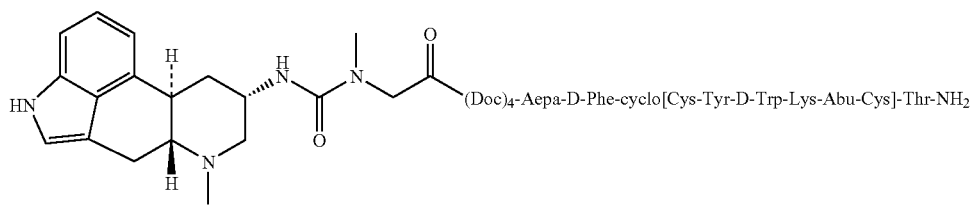
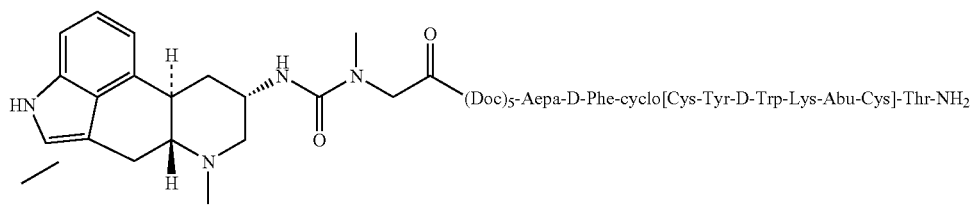

-continued

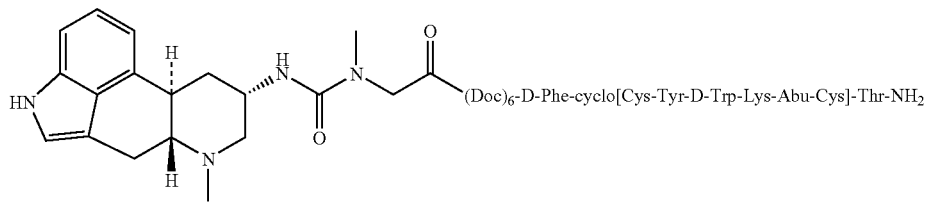
(Doc)₆-D-Phe-cyclo[Cys-Tyr-D-Trp-Lys-Abu-Cys]-Thr-NH₂

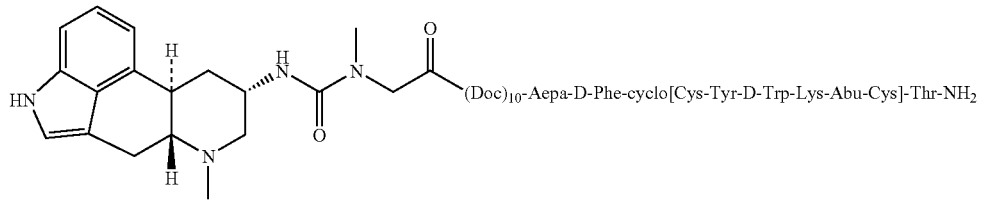
(Doc)₁₀-Aepa-D-Phe-cyclo[Cys-Tyr-D-Trp-Lys-Abu-Cys]-Thr-NH₂

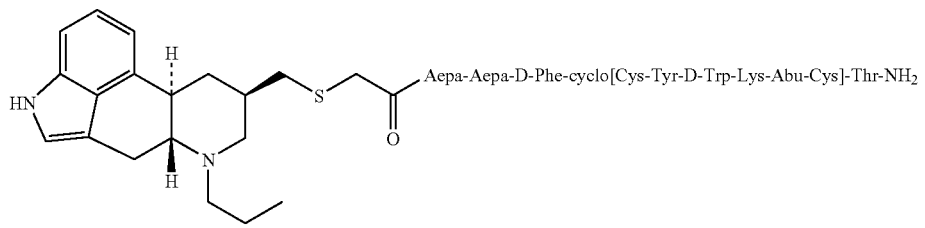
Aepa-Aepa-D-Phe-cyclo[Cys-Tyr-D-Trp-Lys-Abu-Cys]-Thr-NH₂

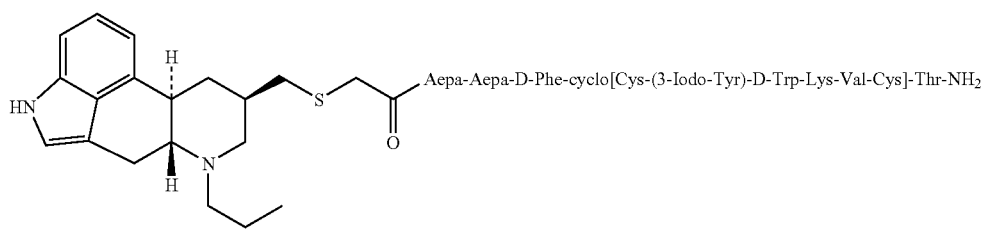
Aepa-Aepa-D-Phe-cyclo[Cys-(3-Iodo-Tyr)-D-Trp-Lys-Val-Cys]-Thr-NH₂

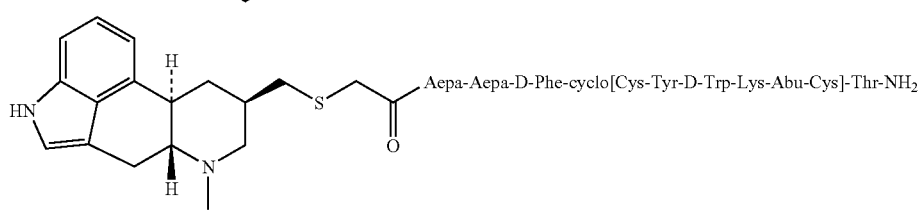
Aepa-Aepa-D-Phe-cyclo[Cys-Tyr-D-Trp-Lys-Abu-Cys]-Thr-NH₂

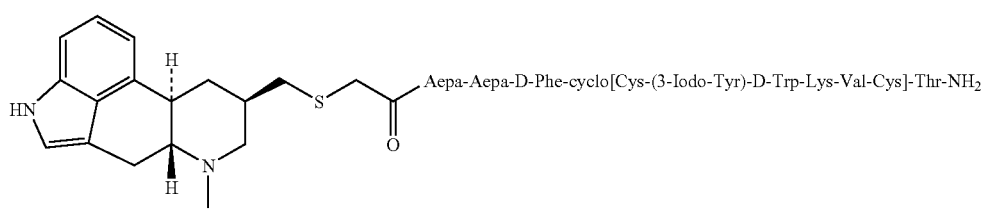
Aepa-Aepa-D-Phe-cyclo[Cys-(3-Iodo-Tyr)-D-Trp-Lys-Val-Cys]-Thr-NH₂

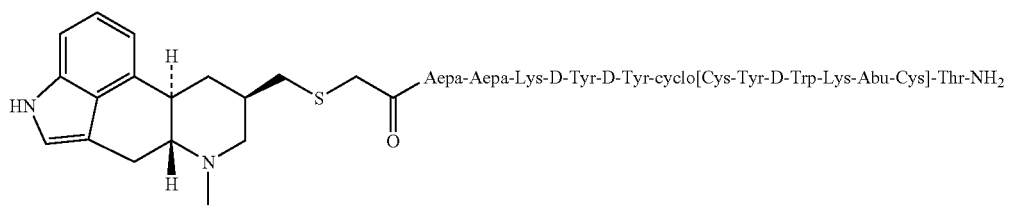
Aepa-Aepa-Lys-D-Tyr-D-Tyr-cyclo[Cys-Tyr-D-Trp-Lys-Abu-Cys]-Thr-NH₂

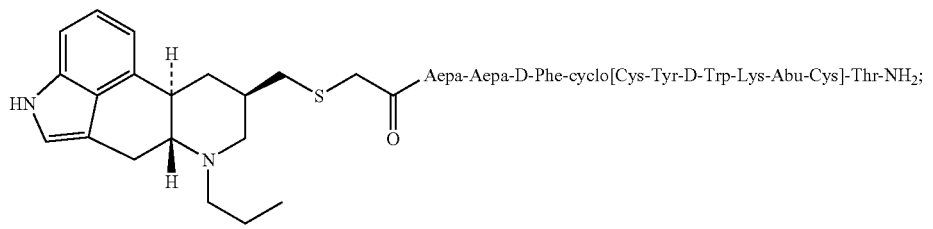
Aepa-Aepa-D-Phe-cyclo[Cys-Tyr-D-Trp-Lys-Abu-Cys]-Thr-NH₂;

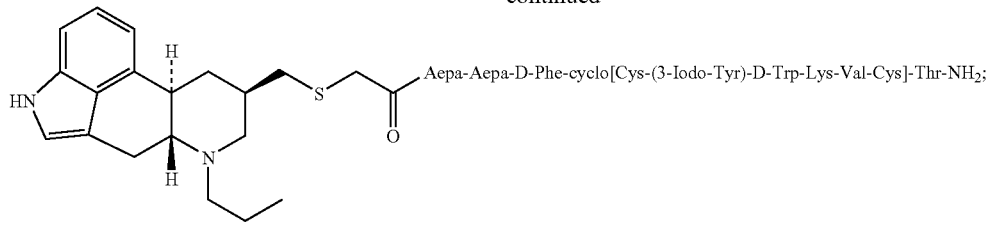
Aepa-Aepa-D-Phe-cyclo[Cys-(3-Iodo-Tyr)-D-Trp-Lys-Val-Cys]-Thr-NH$_2$;

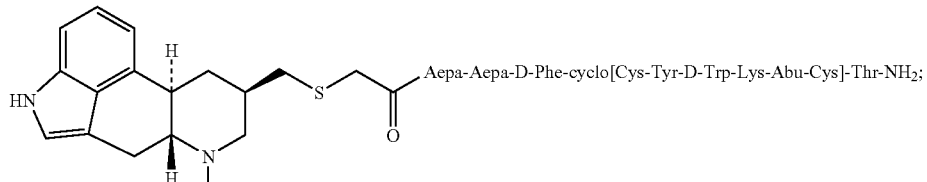
Aepa-Aepa-D-Phe-cyclo[Cys-Tyr-D-Trp-Lys-Abu-Cys]-Thr-NH$_2$;

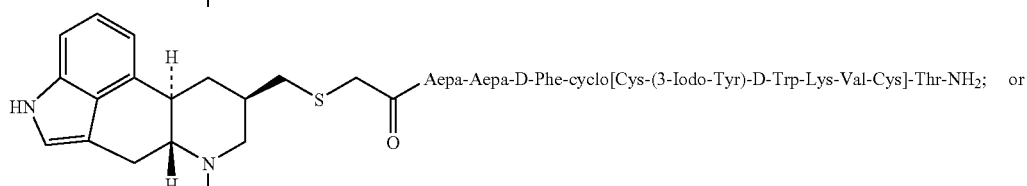
Aepa-Aepa-D-Phe-cyclo[Cys-(3-Iodo-Tyr)-D-Trp-Lys-Val-Cys]-Thr-NH$_2$; or

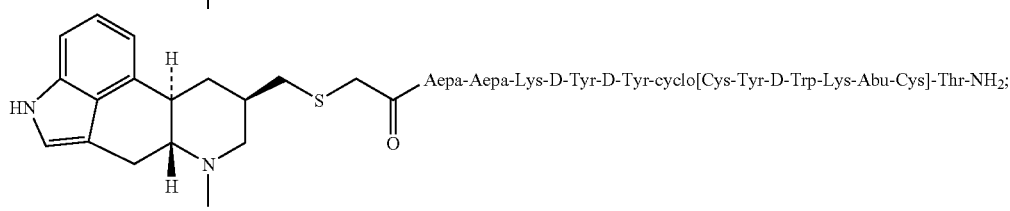
Aepa-Aepa-Lys-D-Tyr-D-Tyr-cyclo[Cys-Tyr-D-Trp-Lys-Abu-Cys]-Thr-NH$_2$;

or a pharmaceutically acceptable salt thereof.

In one aspect the invention features a method of eliciting a dopamine receptor agonist effect in a subject in need thereof, wherein said method comprises administering to said subject an effective amount of a compound according to formula (I) or formula (II), or a pharmaceutically acceptable salt thereof. In a preferred embodiment of this aspect the compound is selected from among the compounds specifically disclosed herein.

In another aspect the invention features a method of eliciting a somatostatin receptor agonist effect in a subject in need thereof, wherein said method comprises administering to said subject an effective amount of a compound according to formula (I) or formula (II), or a pharmaceutically acceptable salt thereof. In a preferred embodiment of this aspect the compound is selected from among the compounds specifically disclosed herein.

In another aspect the invention features a method of simultaneously eliciting both a dopamine receptor agonist effect and a somatostatin receptor agonist effect in a subject in need thereof, wherein said method comprises administering to said subject an effective amount of a compound according to formula (I) or formula (II), or a pharmaceutically acceptable salt thereof. In a preferred embodiment of this aspect the compound is selected from among the compounds specifically disclosed herein.

In another aspect the invention features a pharmaceutical composition comprising an effective amount of a compound according to formula (I) or formula (II), or a pharmaceutically acceptable salt thereof, and a pharmaceutically acceptable carrier. In a preferred embodiment of this aspect the compound is selected from among the compounds specifically disclosed herein.

In another aspect the invention features a method of treating a disease or condition in a subject, said method comprising administering to said subject a therapeutically effective amount of a compound of formula (I) or formula (II), or a pharmaceutically acceptable salt thereof, wherein said disease is selected from the list consisting of lung cancer, glioma, anorexia, hypothyroidism, hyperaldosteronism, *H. pylori* proliferation, acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, gonadotropinoma, hyperparathyroidism, Graves' Disease, diabetic neuropathy, Paget's disease, polycystic ovary disease, thyroid cancer, hepatome, leukemia, meningioma, cancer cachexia, orthostatic hypotension, postprandial hypotension, panic attacks, GH secreting adenomas, Acromegaly, TSH secreting adenomas, prolactin secreting adenomas, insulinoma, glucagonoma, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous fistula, pancreaticocutaneous fistula, Dumping syndrome, watery diarrhea syndrome, pancreatitis, gastrointestinal hormone secreting tumor, angiogenesis, arthritis, allograft rejection, graft vessel bleeding, portal hypertension, gastrointestinal bleeding, obesity, and opioid overdose. In a preferred embodiment of this aspect the compound is selected from among the compounds specifically disclosed herein. In a more preferred embodiment of this aspect of the invention said disease or condition is acromegaly.

In a particularly preferred embodiment of each of the foregoing methods the compound is selected from the list of compounds consisting of Compound A through Compound K, or from among the list of compounds consisting of Example L through Example V, as disclosed hereinbelow under the heading "Synthesis of Somatostatin-Dopamine Chimers".

In another aspect of the invention is featured a dopamine agonist according the formula (I) or formula (II), hereinabove, wherein the somatostatin analog "z" is replaced by a moiety comprising —H, —OH, ($C_1$-$C_6$)alkoxy, arylalkoxy, (e.g., benzyl, substituted benzyl, and the like), —$NH_2$, —NR9R10, where R9 and R10 are as defined in formula (II). In a preferred embodiment of this aspect said dopamine agonist is selected from among the dopamine moiety components of the dopamine-somatostatin chimers disclosed herein, or a pharmaceutically acceptable salt thereof. In a most preferred embodiment of this aspect said dopamine agonist is:

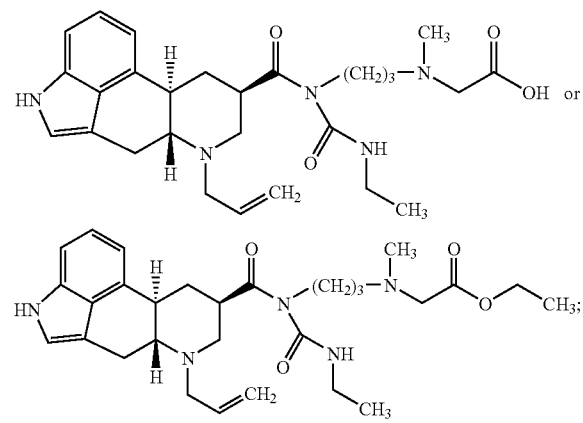

or a pharmaceutically acceptable salt thereof.

DETAILED DESCRIPTION OF THE INVENTION

It is believed that one skilled in the art can, based on the description herein, utilise the present invention to its fullest extent. The following specific embodiments are, therefore, to be construed as merely illustrative, and not limitative of the remainder of the disclosure in any was whatsoever.

Unless defined otherwise, all technical and scientific terms used herein have the same meaning as commonly understood by one of ordinary skill in the art to which this invention belongs. Also, all publications, patent applications, patents, and other references mentioned herein are incorporated by reference, each in its entirety.

Various somatostatin receptors (SSTR's) have been isolated, e.g., SSTR-1, SSTR-2, SSTR-3, SSTR-4, and SSTR-5. Thus, a somatostatin agonist may be one or more of an SSTR-1 agonist, SSTR-2 agonist, SSTR-3 agonist, SSTR-4 agonist or a SSTR-5 agonist. What is meant by, e.g., a somatostatin type-2 receptor agonist (i.e., SSTR-2 agonist) is a compound which has a high binding affinity (e.g., Ki of less than 100 nM, or preferably less than 10 nm, or more preferably less than 1 nM) for SSTR-2 (e.g., as defined by the receptor binding assay described below). What is meant by, e.g., a somatostatin type-2 receptor selective agonist is a somatostatin type-2 receptor agonist which has a higher binding affinity (i.e., lower Ki) for SSTR-2 than for any other somatostatin receptor.

In one embodiment the SSTR-2 agonist is also a SSTR-2 selective agonist. Examples of SSTR-2 agonists which may be used to practice the present invention include, but are not limited to:
D-NaI-cyclo[Cys-Tyr-D-Trp-Lys-Val-Cys]-Thr-$NH_2$;
cyclo[Tic-Tyr-D-Trp-Lys-Abu-Phe];
4-(2-Hydroxyethyl)-1-piperazinylacetyl-D-Phe-cyclo(Cys-Tyr-D-Trp-Lys-Abu-Cys)-Thr-$NH_2$; and
4-(2-Hydroxyethyl)-1-piperazine-2-ethanesulfonyl-D-Phe-cyclo(Cys-Tyr-D-Trp-Lys-Abu-Cys)-Thr-$NH_2$.

Further examples of somatostatin agonists are those covered by formulae or those specifically recited in the publications set forth below, each of which is hereby incorporated by reference in its entirety.

EP Application No. P5 164 EU (Inventor: G. Keri);
Van Binst, G. et al. Peptide Research 5:8 (1992);
Horvath, A. et al. Abstract, "Conformations of Somatostatin Analogs Having Antitumor Activity", 22nd European peptide Symposium, Sep. 13-19, 1992, Interlaken, Switzerland;
PCT Application No. WO 91/09056 (1991);
EP Application No. 0 363 589 A2 (1990);
U.S. Pat. No. 4,904,642 (1990);
U.S. Pat. No. 4,871,717 (1989);
U.S. Pat. No. 4,853,371 (1989);
U.S. Pat. No. 4,725,577 (1988);
U.S. Pat. No. 4,684,620 (1987);
U.S. Pat. No. 4,650,787 (1987);
U.S. Pat. No. 4,603,120 (1986);
U.S. Pat. No. 4,585,755 (1986);
EP Application No. 0 203 031 A2 (1986);
U.S. Pat. No. 4,522,813 (1985);
U.S. Pat. No. 4,486,415 (1984);
U.S. Pat. No. 4,485,101 (1984);
U.S. Pat. No. 4,435,385 (1984);
U.S. Pat. No. 4,395,403 (1983);
U.S. Pat. No. 4,369,179 (1983);
U.S. Pat. No. 4,360,516 (1982);
U.S. Pat. No. 4,358,439 (1982);
U.S. Pat. No. 4,328,214 (1982);
U.S. Pat. No. 4,316,890 (1982);
U.S. Pat. No. 4,310,518 (1982);
U.S. Pat. No. 4,291,022 (1981);
U.S. Pat. No. 4,238,481 (1980);
U.S. Pat. No. 4,235,886 (1980);
U.S. Pat. No. 4,224,199 (1980);
U.S. Pat. No. 4,211,693 (1980);
U.S. Pat. No. 4,190,648 (1980);
U.S. Pat. No. 4,146,612 (1979);
U.S. Pat. No. 4,133,782 (1979);
U.S. Pat. No. 5,506,339 (1996);
U.S. Pat. No. 4,261,885 (1981);
U.S. Pat. No. 4,728,638 (1988);
U.S. Pat. No. 4,282,143 (1981);
U.S. Pat. No. 4,215,039 (1980);
U.S. Pat. No. 4,209,426 (1980);
U.S. Pat. No. 4,190,575 (1980);
EP Patent No. 0 389 180 (1990);
EP Application No. 0 505 680 (1982);
EP Application No. 0 083 305 (1982);
EP Application No. 0 030 920 (1980);
PCT Application No. WO 88/05052 (1988);
PCT Application No. WO 90/12811 (1990);
PCT Application No. WO 97/01579 (1997);
PCT Application No. WO 91/18016 (1991);
U.K. Application No. GB 2,095,261 (1981); and
French Application No. FR 2,522,655 (1983).

Note that for all somatostatin agonists described herein, each amino acid residue represents the structure of —NH—C(R)H—CO—, in which R is the side chain (e.g., CH$_3$ for Ala). Lines between amino acid residues represent peptide bonds which join the amino acids. Also, where the amino acid residue is optically active, it is the L-form configuration that is intended unless D-form is expressly designated. For clarity, disulfide bonds (e.g., disulfide bridge) which exist between two free thiols of Cys residues are not shown. Abbreviations of the common amino acids are in accordance with IUPAC-IUB recommendations.

Synthesis of Somatostatin Agonists

The methods for synthesizing peptide somatostatin agonists are well documented and are within the ability of a person of ordinary skill in the art. For example, peptides are synthesized on Rink amide MBHA resin (4-(2'4'-dimethoxyphenyl-Fmoc-aminomethyl)-phenoxyacetamido-norleucyl-MBHA resin) using a standard solid phase protocol of Fmoc chemistry. The peptide-resin with free amino functional at the N-terminus is then treated with the corresponding compound containing dopamine moiety. The final product is cleaved off from resin with TFA/water/triisopropylsilane (TIS) mixture.

For example, synthesis of H-D-Phe-Phe-Phe-D-Trp-Lys-Thr-Phe-Thr-NH$_2$, can be achieved by following the protocol set forth in Example I of European Patent Application 0 395 417 A1. The synthesis of somatostatin agonists with a substituted N-terminus can be achieved, for example, by following the protocol set forth in PCT Publication No. WO 88/02756, PCT Publication No. WO 94/04752, and/or European Patent Application No. 0 329 295.

Peptides can be and were cyclized by using iodine solution in MeOH/water and purified on C18 reverse-phase prep. HPLC, using acetonitrile-0.1% TFA/water-0.1% TFA buffers. Homogeneity was assessed by analytical HPLC and mass spectrometry and determined to be >95% for each peptide.

Certain uncommon amino acids were purchased from the following vendors: Fmoc-Doc-OH and Fmoc-AEPA were purchased from Chem-Impex International, Inc. (Wood Dale, Ill., USA). Fmoc-Caeg(Bhoc)-OH was purchased from PerSeptive Biosystems (Framingham Mass., USA). Bhoc stands for benzhydryloxycarbonyl.

Synthesis of Dopamine Agonists

The methods for synthesizing many dopamine agonists are also well documented and are within the ability of a person of ordinary skill in the art. Further synthetic procedures are provided in the following reaction schemes and examples.

Scheme 1

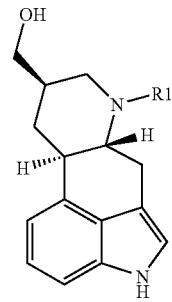

1

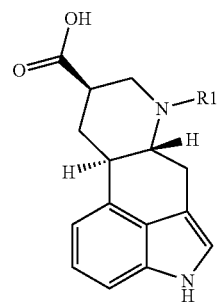

2

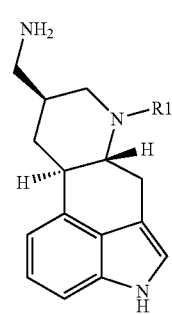

3

Scheme 2

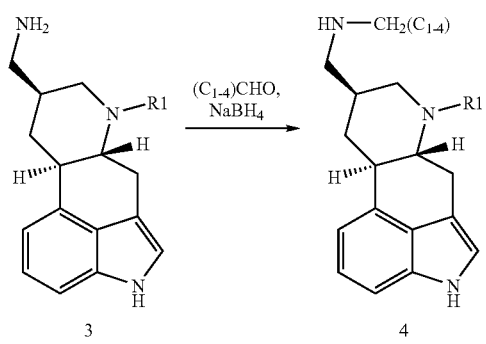

Scheme 3:
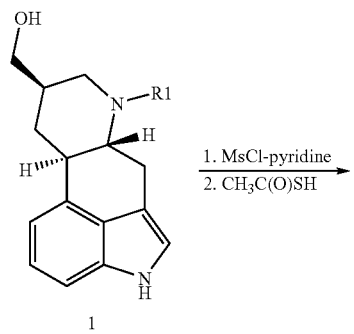
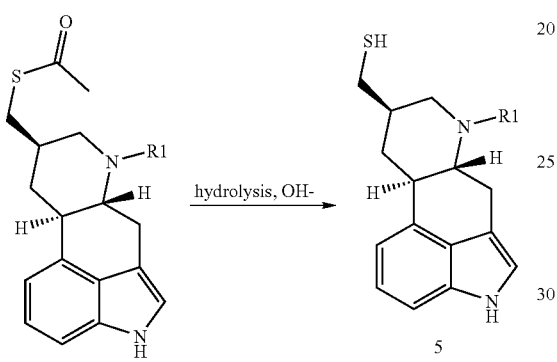
Scheme 4:
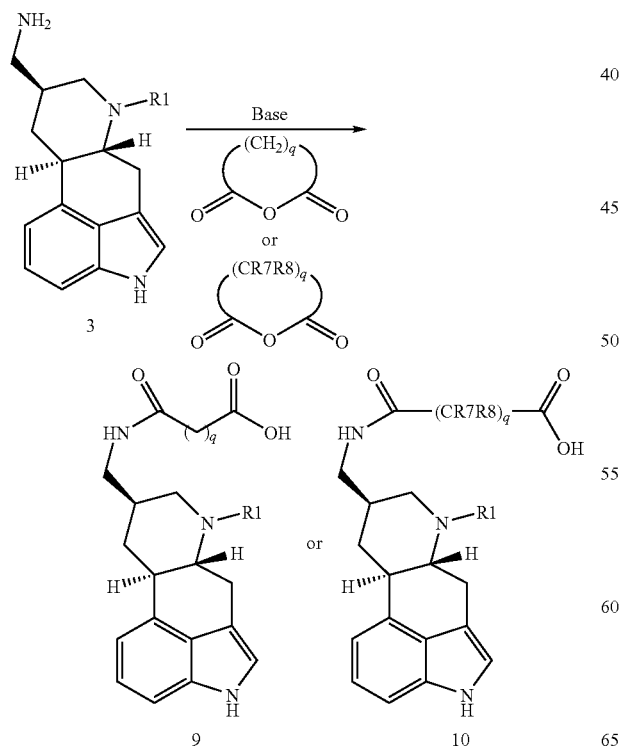
Scheme 5:
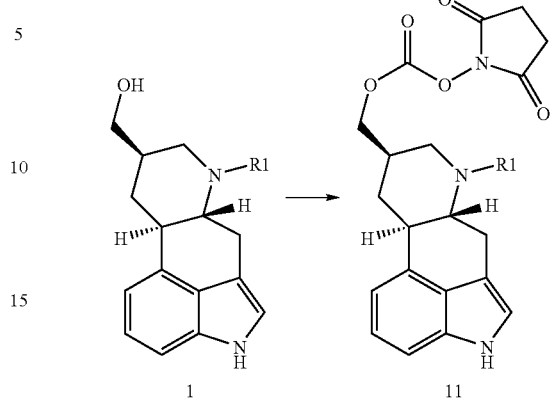
Scheme 6:
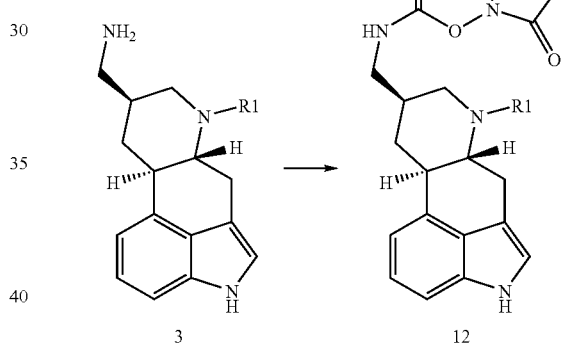
Scheme 7:
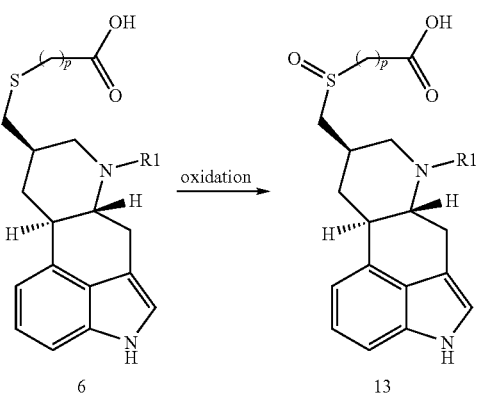

Scheme 8:
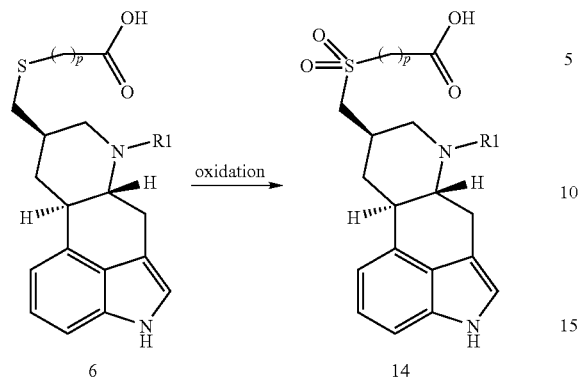
Scheme 9:
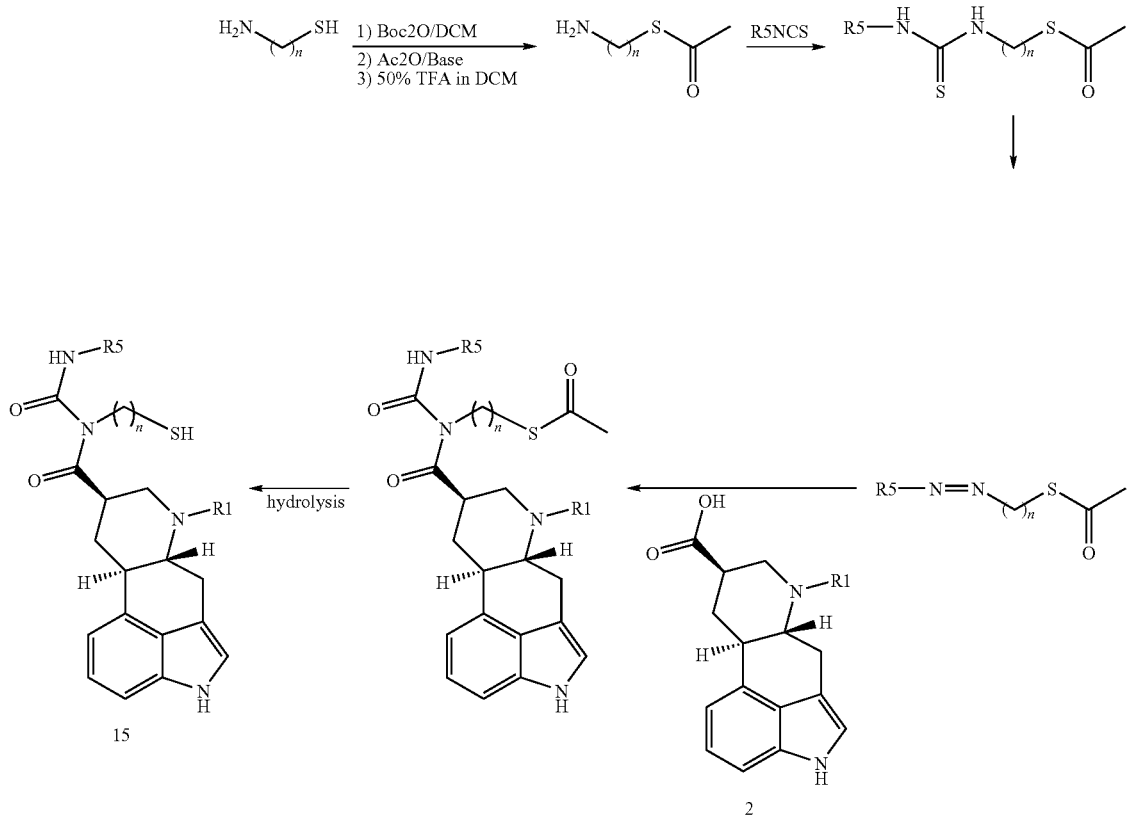
Scheme 10:
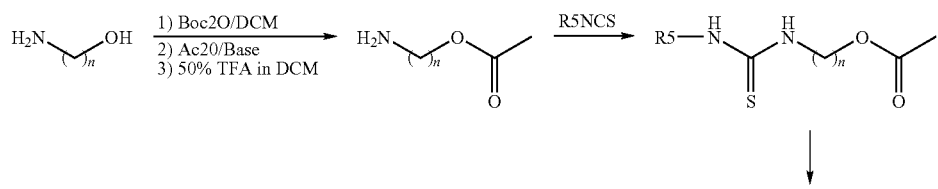

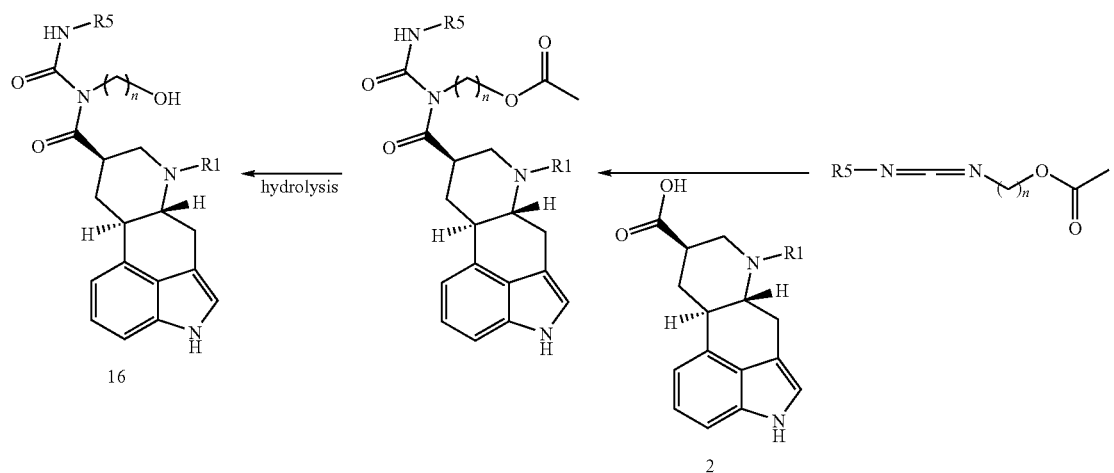
Scheme 11:
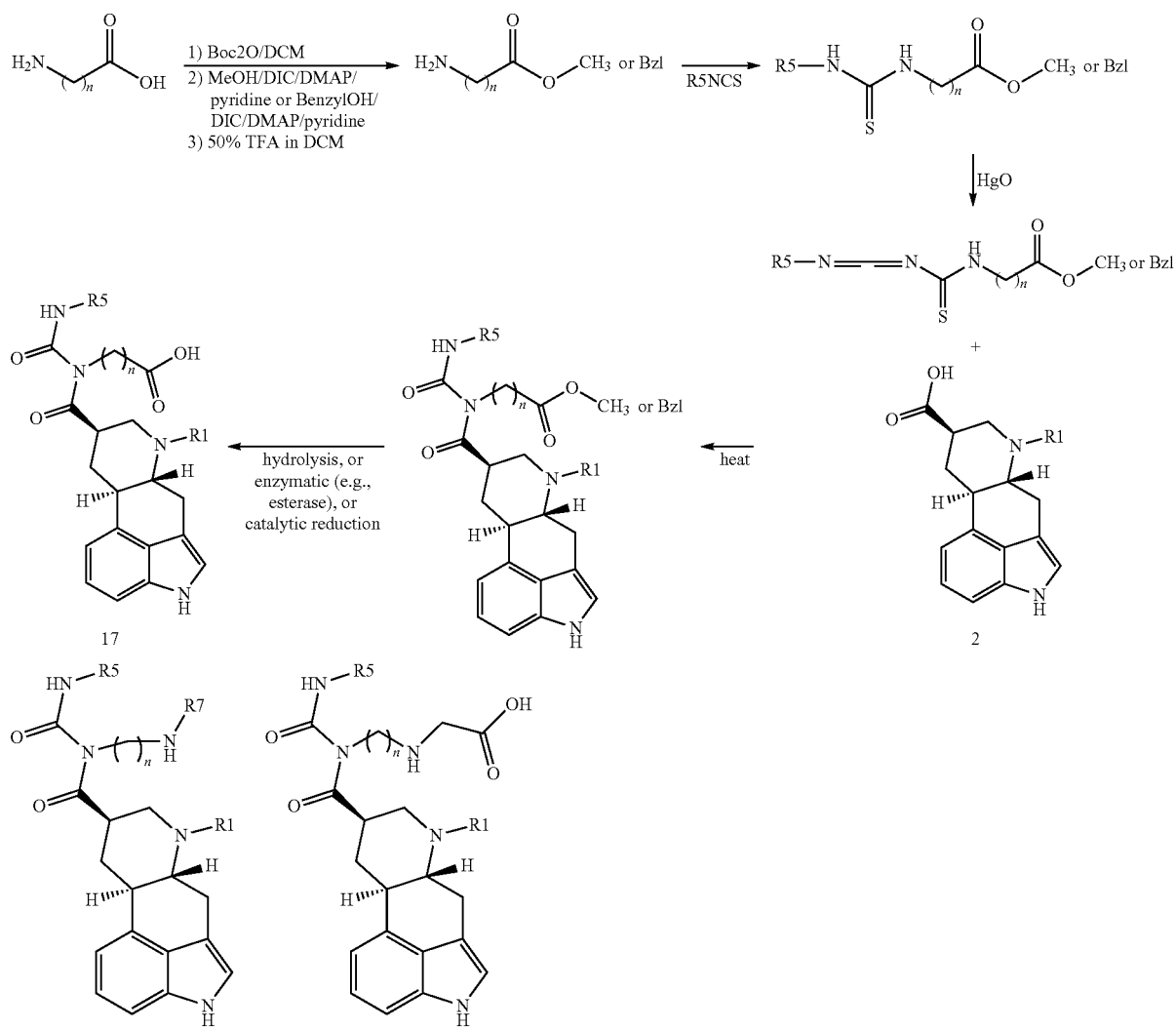

Scheme 12:
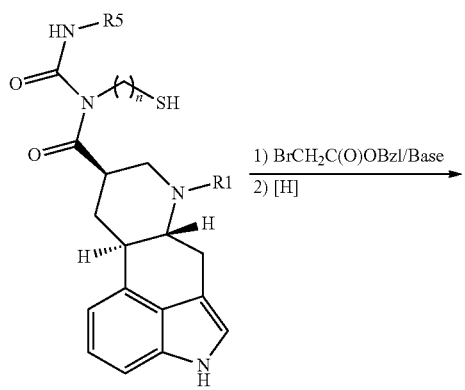
1) BrCH₂C(O)OBzl/Base
2) [H]
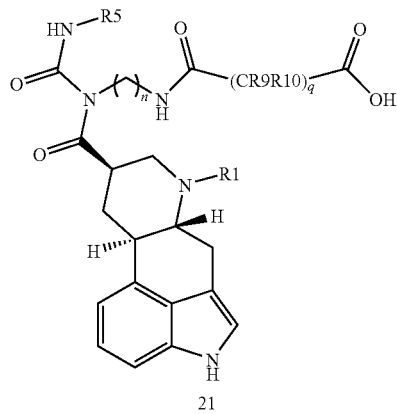
21
Scheme 13:
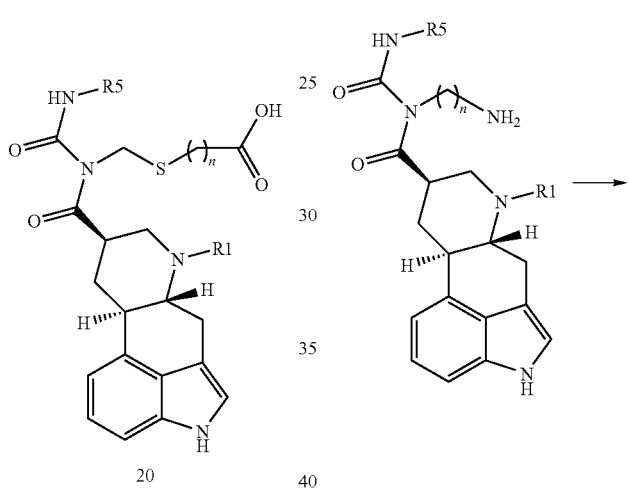
20
Scheme 14:
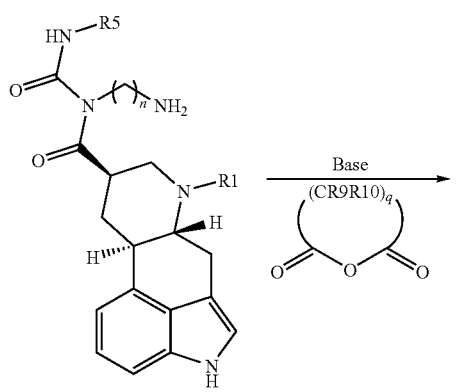
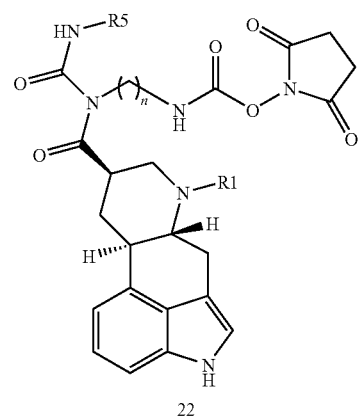
22

Scheme 15:
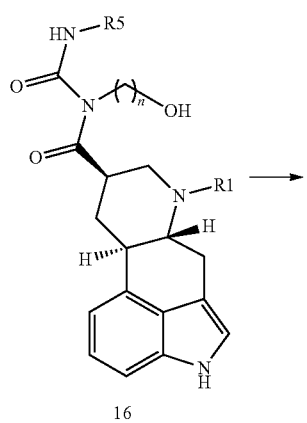
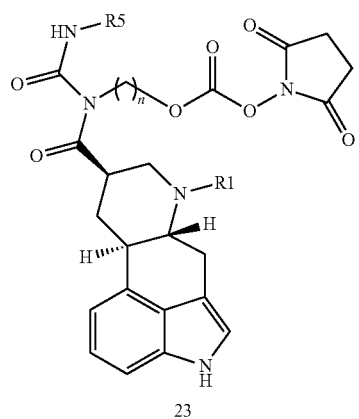
Scheme I
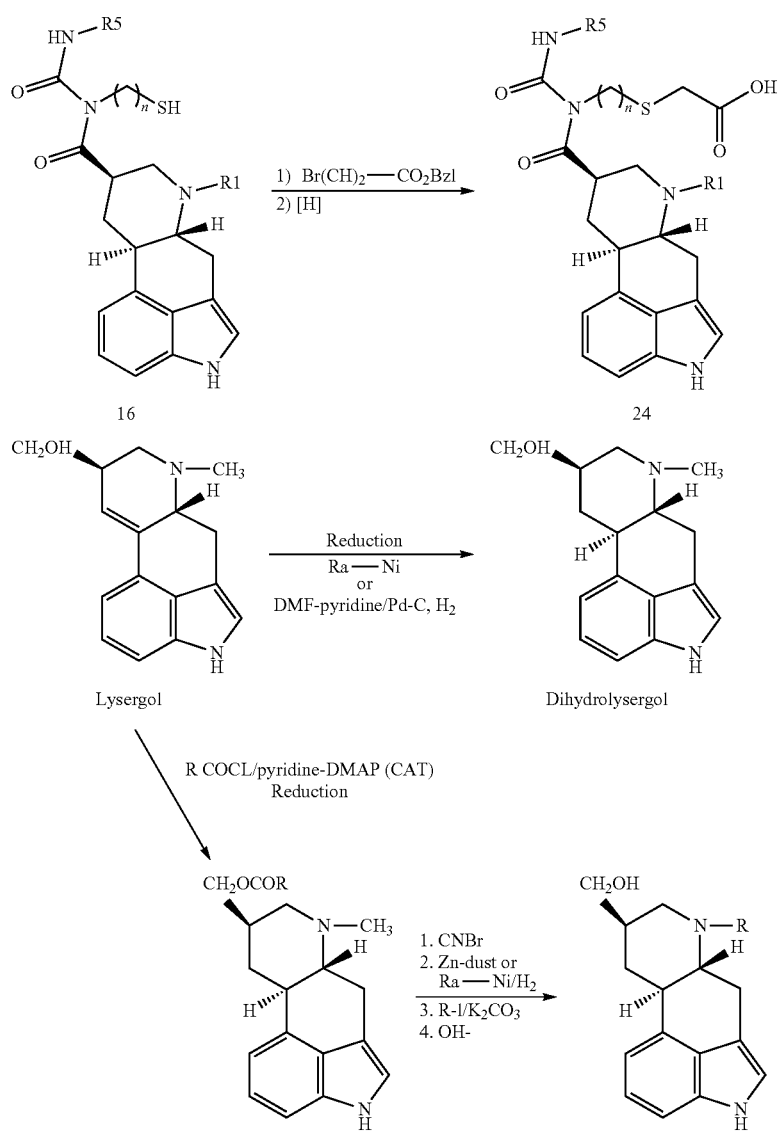

-continued
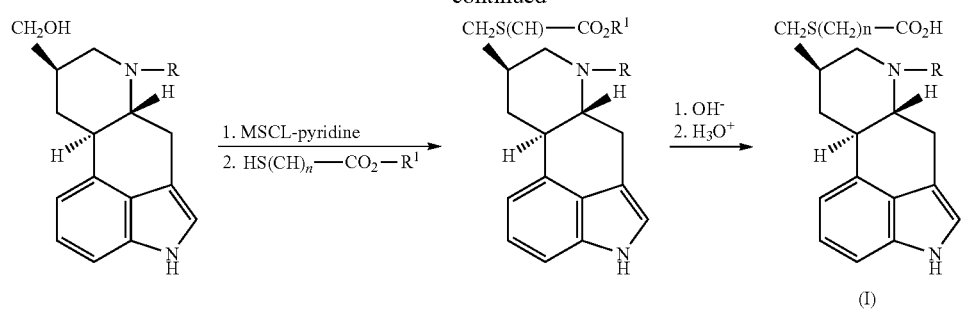
Similarly for compunds 6, 7 and 8:
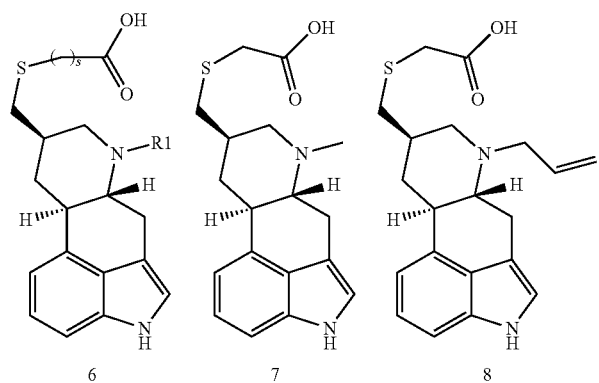
Scheme II
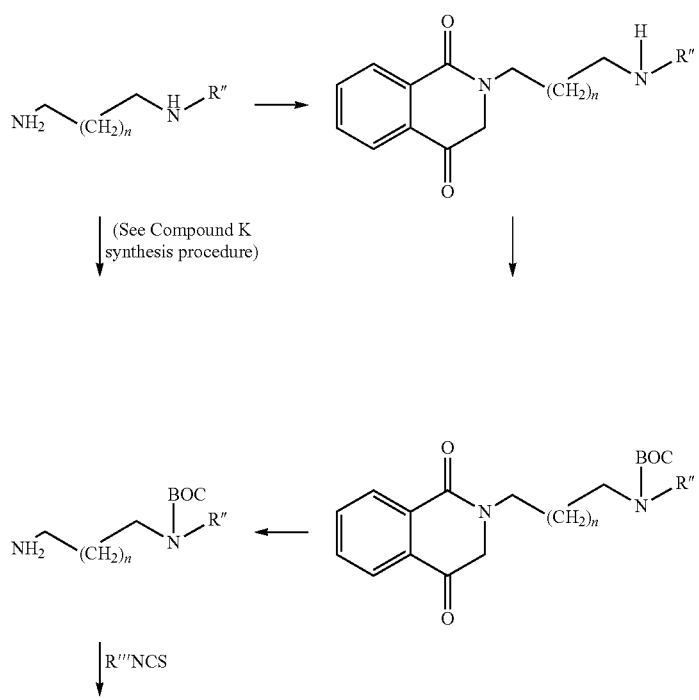

-continued
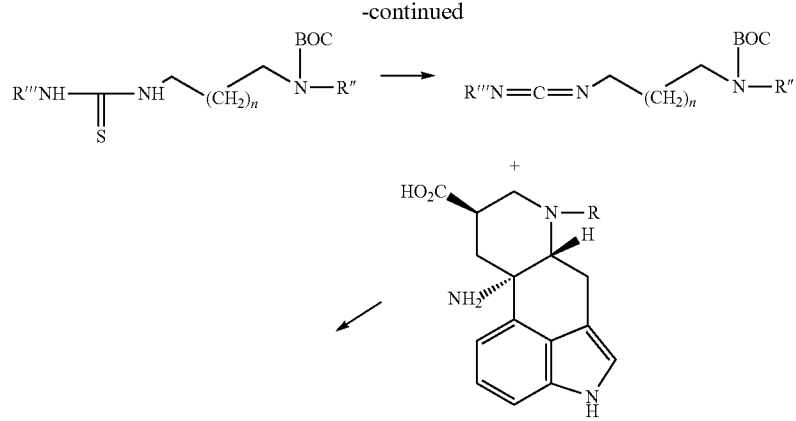
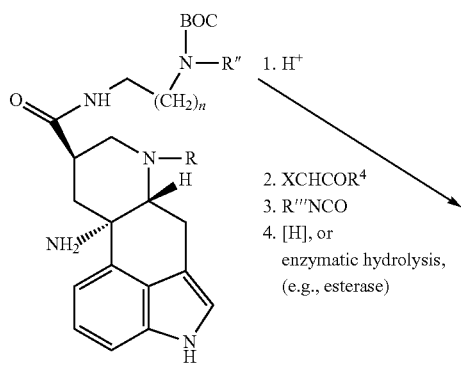
1. H⁺
2. XCHCOR⁴
3. R'''NCO
4. [H], or enzymatic hydrolysis, (e.g., esterase)
18
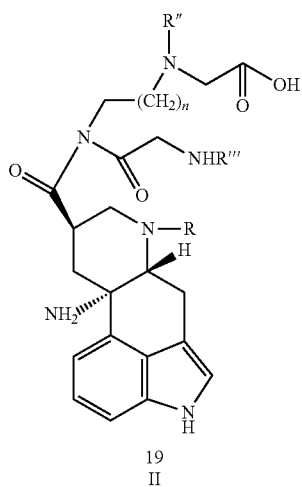
19
II
Where R" and R''' are, independentyl, H or C₁-C₄alkyl Scheme III
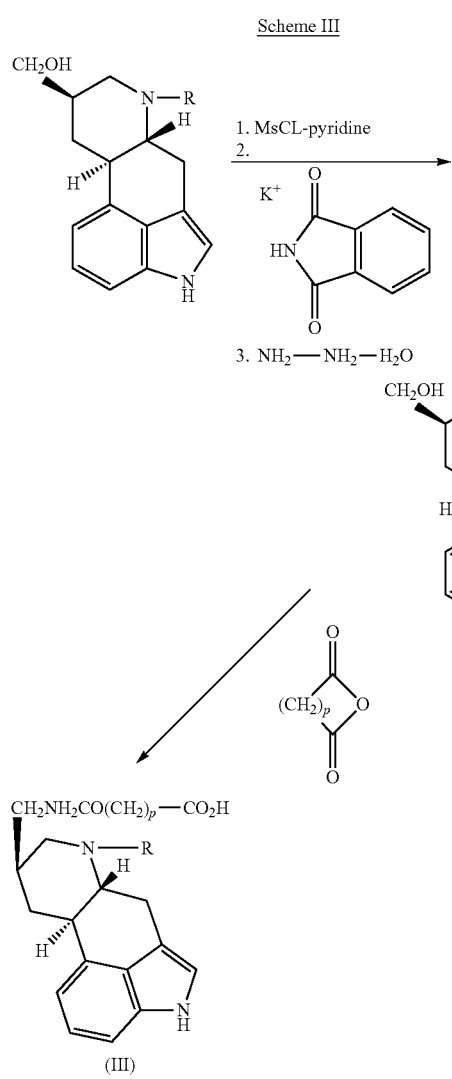
(III)
Scheme IV
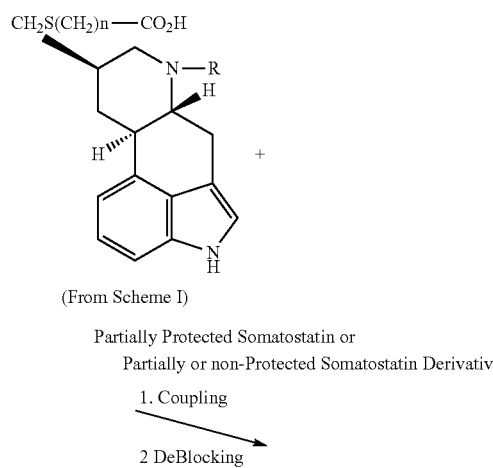
(From Scheme I)
Partially Protected Somatostatin or
Partially or non-Protected Somatostatin Derivative
1. Coupling
2. DeBlocking
-continued
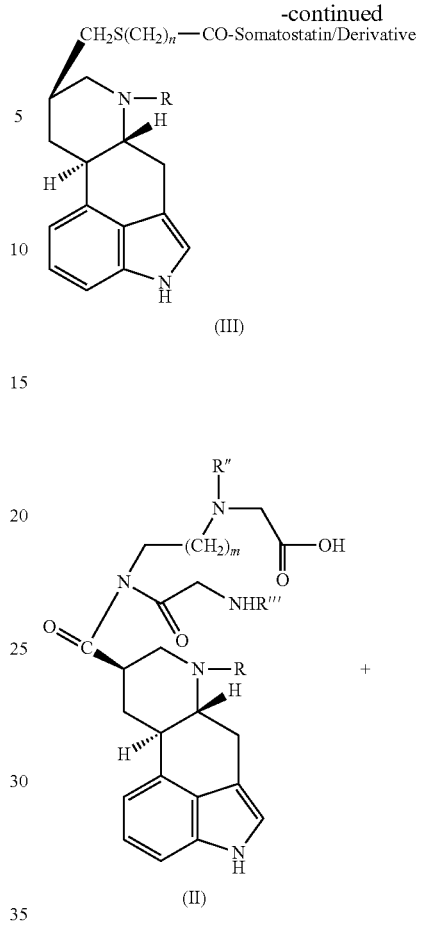
(III)
(II)
Partially Protected Somatostatin or
Partially or non-Protected Somatostatin Derivative
1. Coupling
2. DeBlocking
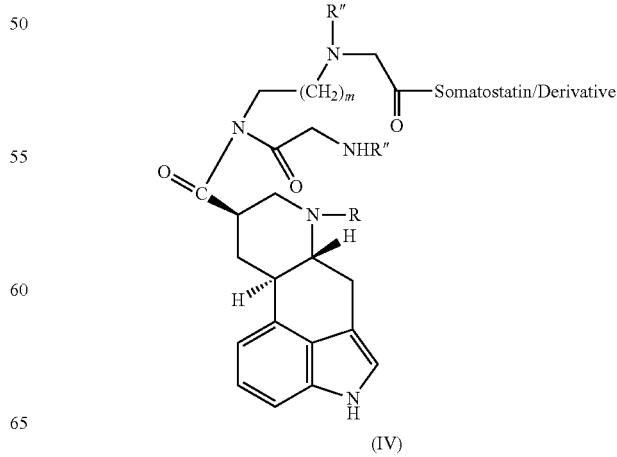
(IV)

153

Scheme V

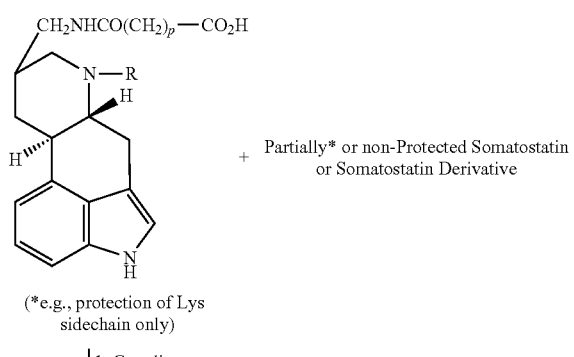

(*e.g., protection of Lys sidechain only)

+ Partially* or non-Protected Somatostatin or Somatostatin Derivative

1. Coupling
2. DeBlocking

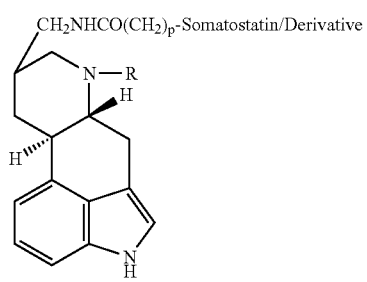

Scheme VI

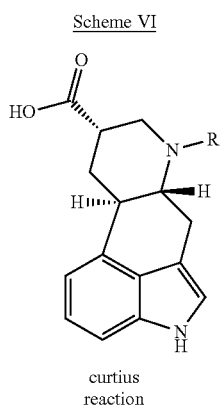

curtius reaction

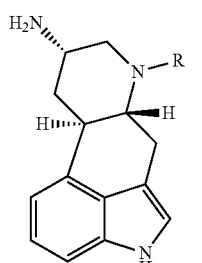

N,N-DSSIC*/base
*N,N'-disuccinimidyl carbonate

154

-continued

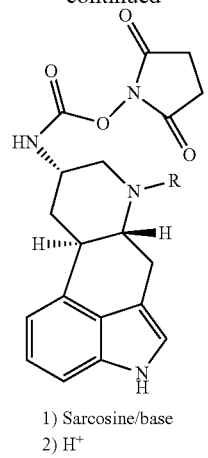

1) Sarcosine/base
2) H$^+$

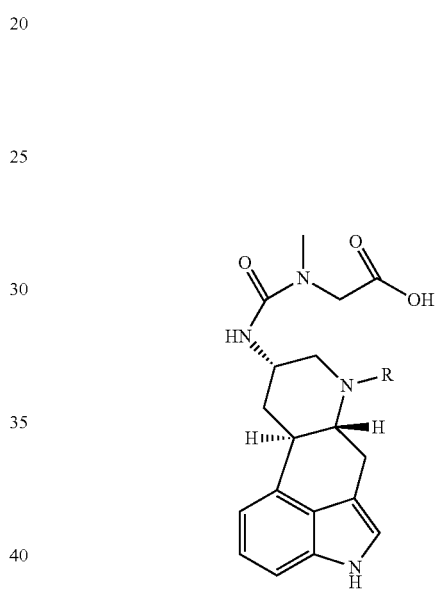

Synthesis of Somatostatin-Dopamine Chimers

The somatostatin-dopamine chimers may be synthesized according to the following reaction schemes and examples. Starting material and intermediates for compounds (I), (II) and (III), depicted in Scheme I, II, and III, respectively, are commercially available or prepared by the literatures; Pharmazie 39, 537 (1984); collect Czech. Chem. Commun. 33, (1966); Helv. Chim. Acta 32, 1947, (1949)' U.S. Pat. No. 5,097,031; U.S. Pat. No. 3,901,894; EP 0003667; U.S. Pat. No. 4,526,892. The synthesis of peptides are within the scope of a skilled person in the art, and in any event, is readily available in the literature. See, e.g., Stewart et al., Solid Phase Synthesis, Pierce Chemical, 2$^{nd}$ Ed. 1984; G. A. Grant; Synthetic peptide. WH., Freenand Co., New York, 1992; M. Bodenszky A. Bodanszky, The Practice of Peptide Synthesis. Spring Verlag. N.Y. 1984.

Preparation of Compound A:

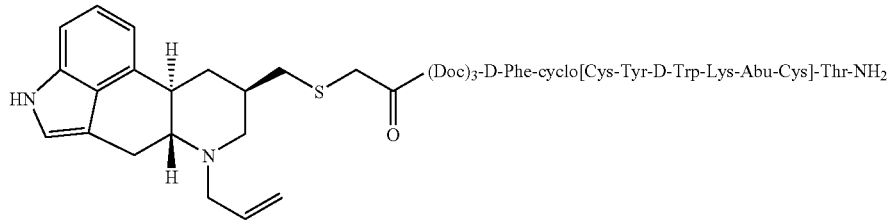

Compound 8 (3 eq.) is mixed with H-(Doc)₃-D-Phe-Cys(Acm)-Tyr(tBu)-D-Trp(Boc)-Lys(Boc)-Abu-Cys(Acm)-Thr(tBu)-Rink amide MBHA resin (1 eq.), HBTU (2.9 eq), HOBt (3.0 eq.) and DIEA (6 eq) in DMF. The mixture is shaken at room temperature for 4 hours. The resin is washed with DMF and DCM and dried under reduced pressure to dryness. The dry resin is treated with TFA/TIS/water (92/5/3, v/v) for 1 hour at room temperature. The solution is filtered and concentrated. To the concentrated solution is added cold ether. The precipitate is collected and dissolved in water-methanol solvent system. To the solution is added iodine solution in methanol until the brown color appears. The solution then stands at room temperature for 1 hour. To the solution is added $Na_2S_2O_3$ aqueous solution until the brown color disappears. The resulting solution is purified by using a C18 reverse-phase prep HPLC, eluting with a linear gradient of buffer A (1% TFA in Water)/buffer B (1% TFA in $CH_3CN$). The fractions are checked by analytical HPLC. The fractions containing pure desired compound are pooled and lyophilized to dryness. The molecular weight of the compound is measured by using MS fitted with an electrospray source.

Preparation of Compound B:

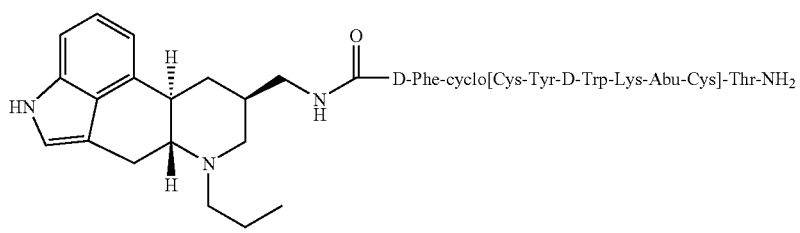

Compound 12 where R1 is n-propyl (1.5 eq.) is mixed with H-D-Phe-Cys(Acm)-Tyr(tBu)-D-Trp(Boc)-Lys(Boc)-Abu-Cys(Acm)-Thr(tBu) Rink amide MBHA resin (1 eq) and DIEA (2 eq) in DMF. The mixture is shaken at room temperature for 5 hours. The resin is washed with DMF and DCM and dried under reduced pressure to dryness. The dry resin is treated with TFA/TIS/water (92/5/3, v/v) for 1 hour at room temperature. The solution is filtered and concentrated. To the concentrated solution is added cold ether. The precipitate is collected and dissolved in water-methanol solvent system. To the solution is added iodine solution in methanol until the brown color appears. The solution then stands at room temperature for 1 hour. To the solution is added $Na_2S_2O_3$ aqueous solution until the brown color disappears. The resulting solution is purified by using a C18 reverse-phase prep HPLC, eluting with a linear gradient of buffer A (1% TFA in Water)/buffer B (1% TFA in $CH_3CN$). The fractions are checked by analytical HPLC. The fractions containing pure desired compound are pooled and lyophilized to dryness. The molecular weight of the compound is measured by using MS fitted with an electrospray source.

Preparation of Compound C:

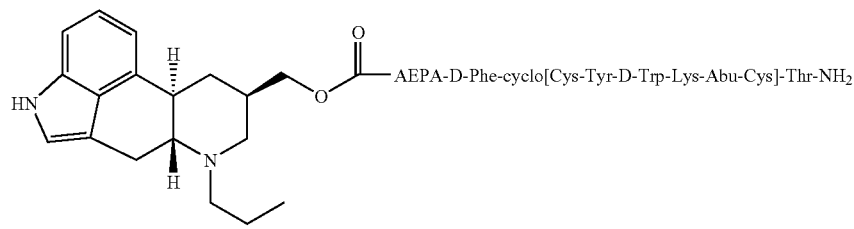

Compound 11 where R1 is n-propyl (1.5 eq.) is mixed with H-AEPA-D-Phe-Cys(Acm)-Tyr(tBu)-D-Trp(Boc)-Lys(Boc)-Abu-Cys(Acm)-Thr(tBu)-Rink amide MBHA resin (1 eq) and DIEA (2 eq) in DMF. The mixture is shaken at room temperature for 5 hours. The resin is washed with DMF and DCM and dried under reduced pressure to dryness. The dry resin is treated with TFA/TIS/water (92/5/3, v/v) for 1 hour at room temperature. The solution is filtered and concentrated. To the concentrated solution is added cold ether. The precipitate is collected and dissolved in water-methanol solvent system. To the solution is added iodine solution in methanol until the brown color appears. The solution then stands at room temperature for 1 hour. To the solution is added $Na_2S_2O_3$ aqueous solution until the brown color disappears. The resulting solution is purified by using a C18 reverse-phase prep HPLC, eluting with a linear gradient of buffer A (1% TFA in Water)/buffer B (1% TFA in $CH_3CN$). The fractions are checked by analytical HPLC. The fractions containing pure desired compound are pooled and lyophilized to dryness. The molecular weight of the compound is measured by using MS fitted with an electrospray source.

Preparation of Compound D:

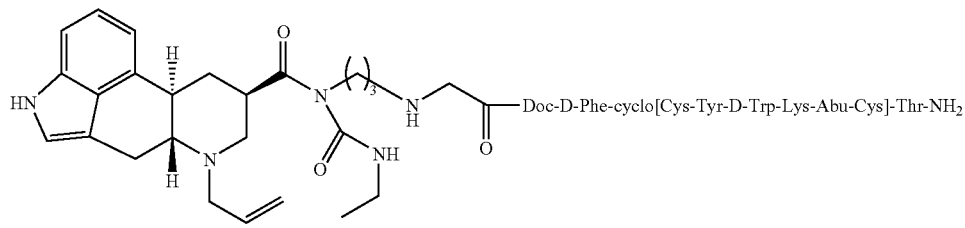

Compound 25 (3 eq.) is mixed with H-Doc-D-Phe-Cys(Acm)-Tyr(tBu)-D-Trp(Boc)-Lys(Boc)-Abu-Cys(Acm)-Thr(tBu)-Rink amide MBHA resin (1 eq.), HBTU (2.9 eq), HOBt (3.0 eq.) and DIEA (6 eq) in DMF. The mixture is shaken at room temperature for 4 hours. The resin is washed with DMF and DCM and dried under reduced pressure to dryness. The dry resin is treated with TFA/TIS/water (92/5/3, v/v) for 1 hour at room temperature. The solution is filtered and concentrated. To it is added cold ether, the precipitate is collected and dissolved in water-methanol solvent system. To the solution is added iodine solution in methanol until the brown color appears. The solution is then stands at room temperature for 1 hour. To the solution is added $Na_2S_2O_3$ aqueous solution until the brown color disappears. The resulting solution is purified by using a C18 reverse-phase prep HPLC, eluting with a linear gradient of buffer A (1% TFA in Water)/buffer B (1% TFA in $CH_3CN$). The fractions are checked by analytical HPLC. The fractions containing pure desired compound are pooled and lyophilized to dryness. The molecular weight of the compound is measured by using MS fitted with an electrospray source.

Preparation of Compound E:

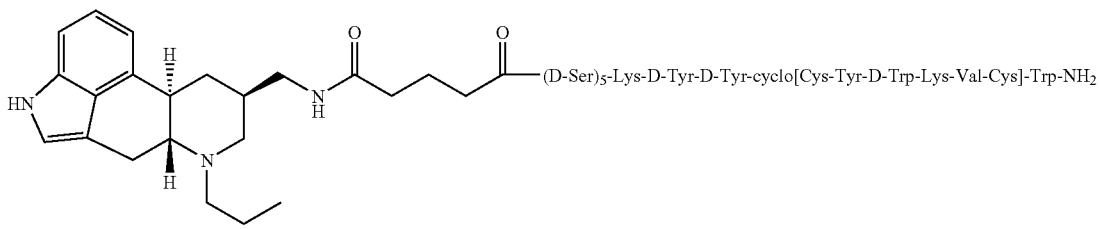

Compound 26 (3 eq.) is mixed with H-(D-Ser(tBu))$_5$-Lys (Boc)-D-Tyr(tBu)-D-Tyr(tBu)-Cys(Acm)-Tyr(tBu)-D-Trp (Boc)-Lys(Boc)-Val-Cys(Acm)-Trp(Boc)-Rink amide MBHA resin (1 eq.), HBTU (2.9 eq), HOBt (3.0 eq.) and DIEA (6 eq) in DMF. The mixture is shaken at room temperature for 4 hours. The resin is washed with DMF and DCM and dried under reduced pressure to dryness. The dry resin is treated with TFA/TIS/water (92/5/3, v/v) for 1 hour at room temperature. The solution is filtered and concentrated. To the concentrated solution is added cold ether. The precipitate is collected and dissolved in water-methanol solvent system. To the solution is added iodine solution in methanol until the brown color appears. The solution then stands at room temperature for 1 hour. To the solution is added Na$_2$S$_2$O$_3$ aqueous solution until the brown color disappears. The resulting solution is purified by using a C18 reverse-phase prep HPLC, eluting with a linear gradient of buffer A (1% TFA in Water)/buffer B (1% TFA in CH$_3$CN). The fractions are checked by analytical HPLC. The fractions containing pure desired compound are pooled and lyophilized to dryness. The molecular weight of the compound is measured by using MS fitted with an electrospray source.

Preparation of Compound F:

Ethyl-[6-methyl-8β-ergolinylmethyl]thioacetate

To a solution of dihydrolysergol (240 mg) in 10 ml pyridine was added 250 μl methanesulfonyl chloride. After stirring at room temperature for 2 hours, the reaction mixture was poured into 100 ml water, it was extracted with chloroform (2×20 ml). Organic layer was washed with water, then dried over MgSO$_4$ and solvent was removed in vacuo to dryness to give 140 mg of pale brown solid. Further extraction from aqueous solution after basification with NaHCO$_3$ gave another 100 mg of product. Overall 240 mg. Mass Spec (Electrospray) 335.2.

To a solution of the above D-6-methyl-8β-mesyloxymethyl-ergoline (140 ng) in 3 ml dimethylformide was added powdered K$_2$CO$_3$ (150 mg) followed by 150 μl ethyl-2-mercaptoacetate and the mixture was heated at 40° C. for 2 hours under nitrogen atmosphere. Solvent was removed in vacuo to dryness, and the residue partitioned between chloroform and water. Organic layer was then dried (MgSO$_4$), and after evaporation of solvent the residue was subject to preparative silica gel thin layer chromatography using chloroform/methanol (9:1) as developing solvents. Appropriate portion was isolated, extracted with chloroform-methanol and solvents were removed in vacuo to dryness. Pale brown solid. 100 mg Mass spec (Electrospray) 359.2.

Preparation of Compound G:

6-Methyl-8β-ergolinylmethylthioacetyl-D-Phe-c(Cys-Tyr-D-Trp-Lys-Abu-Cys)-Thr-NH$_2$ To a solution of 6-Methyl-8β-ergolinylmethylthioacetyl acid (Scheme I, compound 7) (50 mg) and D-Phe-c(Cys-Tyr(OBT)-D-Trp-Lys(BOC)-Abu-Cys)-Thr-NH$_2$ (100 mg) prepared by solid-phase synthesis using Fmoc-chemistry in 10 ml dimethylformide was added 200 mg of EDC (1-[3-(dimethylamino)-propyl]-3-ethylcarbodiimide-HCL), 100 mg of HOAT (1-Hydroxy-7-azabenzotriazole) followed by 200 μl diisopropylethylamine and the mixture was stirred at room temperature overnight. Volatile substances were removed in vacuo to dryness. The residue was partitioned between chloroform methanol and brine. The organic layer was washed with aqueous NaHCO$_3$, dried over MgSO$_4$. After evaporation of solvent, the residue was subject to preparative thin-layer chromatography using chloroform-methanol (85:15) as developing solvents. Appropriate portion was isolated, extracted with chloroform-methanol and solvents were removed in Vacuo to give 40 mg of protected product. Mass Spec. (Electrospray) 1500.7.

The protected product was then treated with 30% trifluoroacetic acid in dichloromethyl (10 ml) containing a few drops of triisopropyl silane for 30 minutes. Volatile substances were removed in vacuo to dryness. The residue was purified using vydac C$_{18}$ HPLC and CH$_3$CN/0.1% aqueous TFA, resulting in 17 mg of white solid. Mass Spec (Electrospray). 1344.8, 673.2.

Preparation of Compound H:

Ethyl-(6-n-propyl-8β-ergolinyl)methylthioacetate

This compound was prepared analogously to Compound F, starting with D-n-propyl-8β-hydroxymethylergoline which can be made according to EP 000.667. Pale yellow solid. Mass Spec (Electrospray) 387.2.

Preparation of compound I:

6-n-propyl-8β-ergolinyl methylthioacetyl-D-Phe-c(Cys-Tyr-D-Trp-Lys-Abu-Cys)-Thr-NH$_2$ This compound was prepared analogously to Compound G, starting with 6-n-propyl-8β-ergolinyl)methylthioacetic acid (Scheme I, compound 6, where R1=propyl and s=1) and D-Phe-c(Cys-Tyr(OBT)-D-Trp-Lys(BOC)-Abu-Cys)-Thr-NH$_2$. White solid. Mass Spec. (Electrospray) 1372.5, 687.3.

Preparation of Compound J:

6-D-Methyl-8β-ergolinylmethylthlaminosuccinoyl-D-Phe-c(Cys-Tyr-D-Trp-Lys-Abu-Cys)-Thr-NH$_2$ This compound was prepared analogously to Compound G starting with 6-D-Methyl-8β-succinoylaminomethylergoline and D-Phe-c(Cys-Tyr(OBT)-D-Trp-Lys(BOC)-Abu-Cys)-Thr-NH$_2$, White solid. Mass Spec (Electrospray) 1344.8, 673.2.

Preparation of Compound K:

6-allyl-8β-(1-ethyl-(3-N-methyl-3-carbonylmethyl)aminopropyl-ureidocarbonyl-ergoline-D-Phe-c(Cys-Tyr-D-Trp-Lys-Abu-Cys)-Thr-NH$_2$, i.e., a compound according to the following structure:

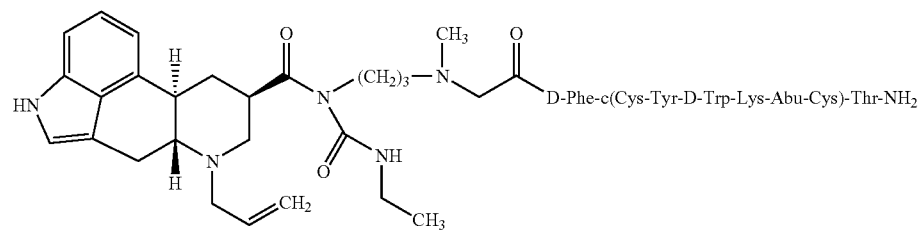

A. 1-[[6-allylergolin-8β-yl]carbonyl]-1-[3-(N-(ethoxycarbonyl)methyl,N-methyl)amino-propyl]-3-ethylurea, i.e., a compound according to the following structure:

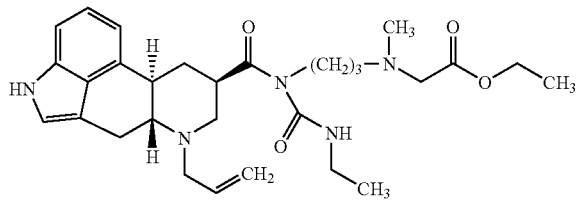

(1) 3,3-BOC, N-Methylpropanediamine

To a solution of 3 N-Methyl propanediamine (1.8 g) in dichloromethane (30 ml) was added anhydrous MgSO4 (5.5 gm) followed by benzaldehyde (2.3 g) and the mixture was stirred at room temperature overnight. After filtration, the filtrate was treated with (BOC)$_2$ (4.3 g) and DMAP (0.35 g) and stirred for about 1 hour. The mixture was then washed with 5% aqueous citric acid, then 5% NaHCO$_3$, and then dried over MgSO4.

After evaporation of solvent, the residue was dissolved in ethanol (50 ml). Pd(OH)$_2$ (600 mg), acetic acid (1 ml), and cyclohexene (3 ml) were added and hydrogenation was carried out overnight. The mixture was filtered through a celite pad and the filtrate was evaporated in vacuo to dryness to produce 3,3-BOC,N-Methylpropanediamine as a colorless liquid. 2.3 g. Mass Spec (Electrospray)=189.1.

(2) 6-allyl-8β-(3,3-BOC,N-Methyl-aminopropyl-carbamoyl)-ergoline

To a solution of 6-allyl-dihydrolysersic acid (150 mg), prepared according to the procedure disclosed in EP 0 003667, and 3,3-BOC,N-Methyl-propanediamine (150 mg) in DMF (5 ml) was added diisopropylethylamine (175 µl) followed by diethylcyanophosphonate (150 µl) and the mixture was stirred at room temperature overnight. Volatile substances were removed in vacuo to dryness. The residue was partitioned between CHCl$_3$ and water. The organic layer was then washed with aqueous NaHCO$_3$ and dried over MgSO$_4$. Solvent was removed in vacuo to give 6-allyl-8β-(3,3-BOC, N-Methyl-aminopropyl-carbamoyl)-ergoline.

(3) 6-allyl-8β-(3-N-Methyl-aminopropyl-carbamoyl)-ergoline, TFA salt 6-allyl-8β-(3,3-BOC,N-Methyl-aminopropyl-carbamoyl)-ergoline from the previous step was treated with 30% TFA in dichloromethane for 30 minutes and volatile substances were removed in vacuo to dryness yielding 250 mg of 6-allyl-8β-(3-N-Methyl-aminopropyl-carbamoyl)-ergoline, TFA salt. Mass spec (Electrospray)=367.2.

(4) 6-allyl-8β-(3-N-Methyl,3-carbethoxymethyl)aminopropyl-carbamoyl-ergoline

To a solution of 6-allyl-8β-(3-N-Methyl-aminopropyl-carbamoyl)-ergoline TFA salt (250 mg) and K$_2$CO$_3$ (140 mg) in DMF (5 ml) was added ethyl bromoacetate (70111) and the mixture was stirred at room temperature overnight. After evaporation of solvent, the residue was partitioned between chloroform and water. The organic layer was dried using MgSO$_4$ and then solvent was removed in vacuo to give crude 6-allyl-8β-(3-N-Methyl,3-carbethoxymethyl)aminopropyl-carbamoyl-ergoline (240 mg). Mass Spec (Electrospray)= 453.2.

(5) 6-allyl-8β-(1-ethyl-(3-N-methyl-3-carbethoxymethyl)aminopropyl-ureidocarbonyl-ergoline 6-allyl-8β-(3-N-Methyl,3-carbethoxymethyl)aminopropyl-carbamoyl-ergoline from the previous step was dissolved in toluene (10 ml) and ethylisocyanate (3 ml) was added. The mixture was refluxed under nitrogen atmosphere for 3 days and after evaporation of volatile substances, the residue was subject to preparative silica gel chromatography using chloroform/methanol (19 to 1) as developing solvents. Appropriate portion was extracted with chloroform/methanol and solvents were removed in vacuo to give 6-allyl-8β-(1-ethyl-(3-N-methyl-3-carbethoxymethyl)aminopropyl-ureidocarbonyl-ergoline as a pale yellow viscous substance (30 mg). Mass Spec (Electrospray)=524.3.

B. 6-allyl-8β-(1-ethyl-(3-N-methyl-3-carboxymethyl)aminopropyl-ureidocarbonyl-ergoline, i.e., a compound according to the following structure:

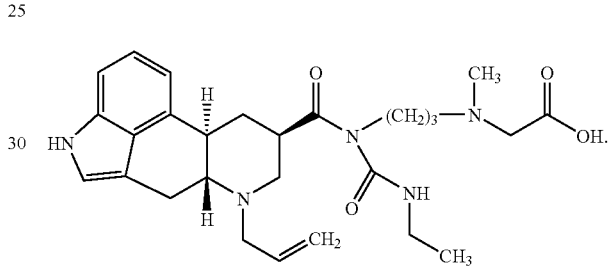

To a mixture of 6-allyl-8β-(1-ethyl-(3-N-methyl-3-carbethoxymethyl)aminopropyl-ureidocarbonyl-ergoline (520 mg) in 10 ml of acetone are added 15 ml of 0.2M phosphate buffer (pH=approx. 7) and 0.6 ml ChiroCLEC-BL (Altus Biologics, Cambridge, Mass.). The mixture is incubated on a rotary shaker at approximately 40 C overnight. The mixture is acidified with 5% aqueous citric acid and extracted with CHCl$_3$-Methanol. The organic extract is dried and the solvents are removed in vacuo to yield 6-allyl-8β-(1-ethyl-(3-N-methyl-3-carboxymethyl)aminopropyl-ureidocarbonyl-ergoline.

C. 6-allyl-8β-(1-ethyl-(3-N-methyl-3-carbonylmethyl)aminopropyl-ureidocarbonyl-ergoline-D-Phe-c(Cys-Tyr-D-Trp-Lys-Abu-Cys)-Thr-NH$_2$, i.e., Compound K To a solution of 6-allyl-8β-(1-ethyl-(3-N-methyl-3-carboxymethyl)aminopropyl-ureidocarbonyl-ergoline (50 mg) and D-Phe-c(Cys-Tyr-D-Trp-Lys(FMOC)-Abu-Cys)-Thr-NH$_2$ (100 mg, prepared by solid-phase synthesis), in 10 ml dimethylformide is added 200 mg of EDC (1-[3-(dimethylamino)-propyl]-3-ethylcarbodiimide-HCL), 100 mg of HOAT (1-Hydroxy-7-azabenzotriazole) followed by 200 µl diisopropylethylamine and the mixture is stirred at room temperature overnight. Volatile substances are removed in vacuo to dryness. The residue is partitioned between chloroform methanol and brine. The organic layer is washed with aqueous NaHCO$_3$ and then dried over MgSO$_4$. After evaporation of solvent the protected product is then treated with 5% piperidine in DMF (10 ml) for 30 minutes. Volatile substances are removed in vacuo to a small volume (about 2 ml). It is purified using VYDAC C$_{18}$ HPLC and CH$_3$CN/0.1% aqueous TFA to yield the purified, de-protected product.

Example L

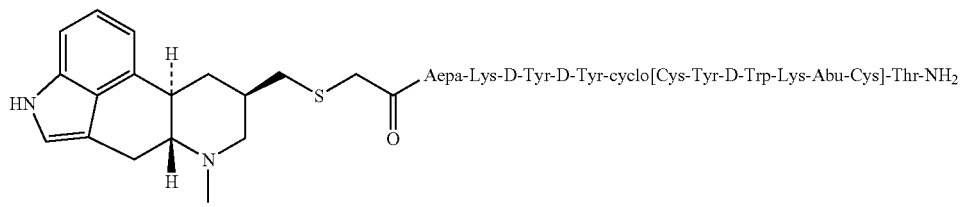

A. H-Aepa-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin The protected peptide-resin was automatically synthesized on an Applied Biosystems (Foster City, Calif.) model 433A peptide synthesizer by using Fluorenylmethyloxycarbonyl (Fmoc) chemistry. A Rink Amide MBHA resin (Novabiochem., San Diego, Calif.) with substitution of 0.72 mmol/g was used. The Fmoc amino acids (AnaSpec, San Jose, Calif.) were used with the following side chain protection: Fmoc-Thr(tBu)-OH, Fmoc-Cys(Trt)-OH, Fmoc-Lys(Boc)-OH, Fmoc-DTrp(Boc)-OH, Fmoc-Tyr(tBu)-OH, Fmoc-DTyr(tBu)-OH Fmoc-Phe-OH, Fmoc-Cys(Trt)-OH, Fmoc-Thr(tBu)-OH and Fmoc-Abu-OH. Fmoc-Aepa-OH was purchased from Chem-Impex International, Inc. (Wood Dale, Ill.). The synthesis was carried out on a 0.25 mmol scale. The Fmoc groups were removed by treatment with 20% piperidine in N-methylpyrrolidone (NMP) for 30 min. In each coupling step, the Fmoc amino acid (4 eq, 1 mmol) was first pre-activated in 2 mL solution of 0.45M 2-(1-H-benzotriazole-1-yl)-1,1,2,3-tetramethyluronium hexafluorophosphate/1-hydroxy-benzotriazole (HBTU/HOBT) in N,N-dimethylformamide (DMF). This activated amino acid ester, 1 mL of diisopropylethylamine (DIEA) and 1 mL of NMP were added to the resin. The ABI 433A peptide synthesizer was programmed to perform the following reaction cycle: (1) washing with NMP, (2) removing Fmoc protecting group with 20% piperidine in NMP for 30 min, (3) washing with NMP, (4) coupling with pre-activated Fmoc amino acid for 1 h. The resin was coupled successively according to the sequence. After peptide chain was assembled, the Fmoc was removed and washed completely by using DMF and dichloromethane (DCM).

MBHA=4-methylbenzylhydrylamine
Aepa=

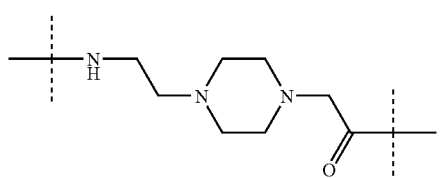

B. The resulting H-Aepa-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin (0.188 mmol) was mixed with compound 7 (92 mg, 0.28 mmol, 1.5 eq.), [7-azabenzotriazol-1-yloxytris(pyrrolidino)phosphonium-hexafluorophosphate] (PyAOP) (146 mg, 0.28 mmol, 1.5 eq.) and 1-hydroxy-7-azabenzotriazol (HOAT) (38 mg, 0.28 mmol, 1.5 eq.) in 5 mL of DCM. The mixture was shaken overnight. The resin was drained and washed successively with DMF, methanol and DCM. After drying in the air, the resin was treated with a mixture of TFA, $H_2O$ and triisopropylsilane (TIS) (9.5 ml/0.85 ml/0.8 ml) for 2 h. The resin was filtered off and the filtrate was poured into 50 mL of cold ether. The precipitate was collected after centrifuge. The crude product was dissolved in 100 ml of 5% AcOH aqueous solution, to which iodine methanol solution was added dropwise until yellow color maintained. The reaction solution was stirred for additional 1 h. 10% $Na_2S_2O_3$ water solution was added to quench excess iodine. The crude product in the solution was purified on preparative HPLC system with a column (4×43 cm) of C18 DYNAMAX-100 A$^0$ (Varian, Walnut Creek, Calif.). The column was eluted with a linear gradient from 80% A and 20% B to 55% A and 45% B in 50 min., where A was 0.1% TFA in water and B was 0.1% TFA in acetonitrile. The fractions were checked by an analytical HPLC. Those containing pure product were pooled and lyophilized to dryness. Yield: 40%. The purity was 96.8% based on analytical HPLC analysis. MS (Electro Spray): 1820.8 (in agreement with the calculated molecular weight of 1821.3).

Example M

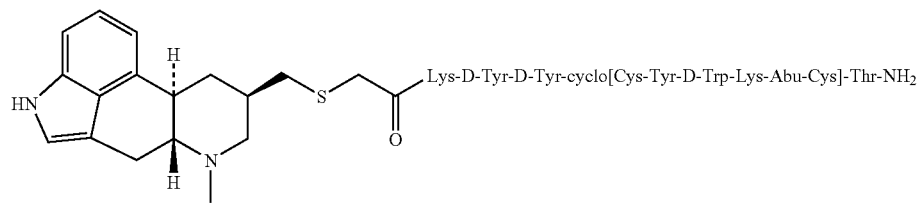

Example M was synthesized substantially according to the procedure described for Example L by using H-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin. Purity of the final product was 97.9% based on analytical HPLC analysis. MS (Electro Spray): 1652.1 (in agreement with the calculated molecular weight of 1652.03).

Example N

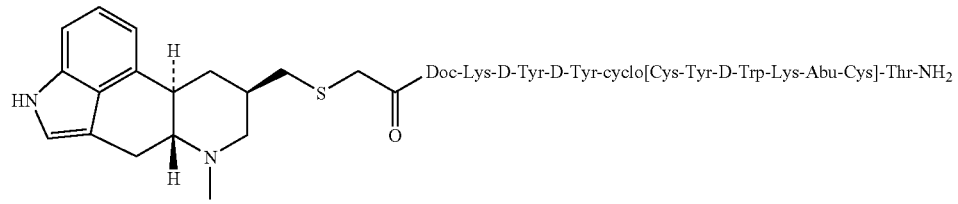

Example N was synthesized substantially according to the procedure described for Example L by using H-Doc-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin. Purity of the final product was 99.2% based on analytical HPLC analysis. MS (Electro Spray): 1797.1 (in agreement with the calculated molecular weight of 1797.19).

Fmoc-Doc-OH was purchased from Chem-Impex International, Inc. (Wood Dale, Ill.).

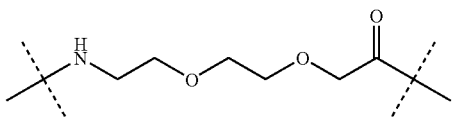

Doc=

Example O

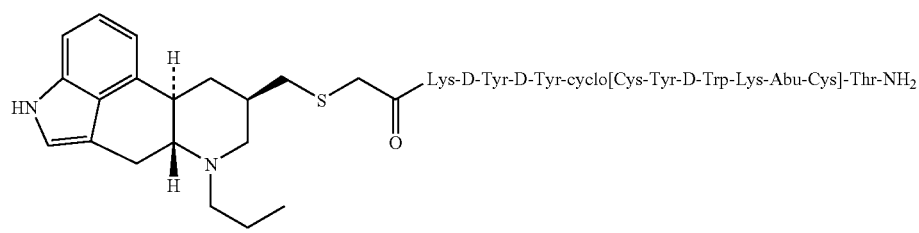

Example O was synthesized substantially according to the procedure described for Example L by using (6-N-propyl-8β-ergolinyl)methylthioacetic acid and H-Lys(Boc)-DTyr(tBu)-DTyr(tBu)-Cys(Trt)-Tyr(tBu)-DTrp(Boc)-Lys(Boc)-Abu-Cys(Trt)-Thr(tBu)-Rink Amide MBHA Resin. Purity of the final product was 97.4% based on analytical HPLC analysis. MS (Electro Spray): 1680.6 (in agreement with the calculated molecular weight of 1680.1).

Example P

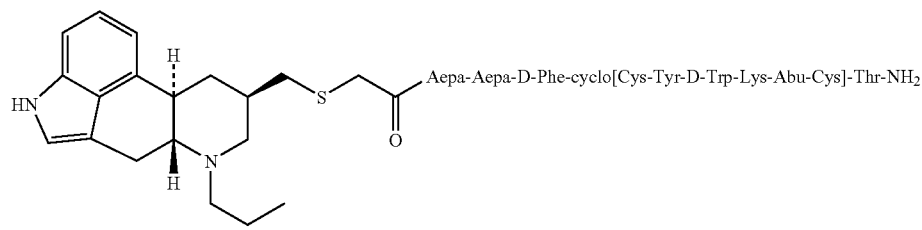

Example P was synthesized substantially according to the procedure described for Example L by using (6-N-propyl-8β-ergolinyl)methylthioacetic acid and H-Aepa-Aepa-D-Phe-Cys(Trt)-Tyr(tBu)-DTrp(Boc)-Lys(Boc)-Abu-Cys(Trt)-Thr(tBu)-Rink Amide MBHA Resin. Purity of the final product was 99.9% based on analytical HPLC analysis. MS (Electro Spray): 1710.7 (in agreement with the calculated molecular weight of 1711.2).

Example Q

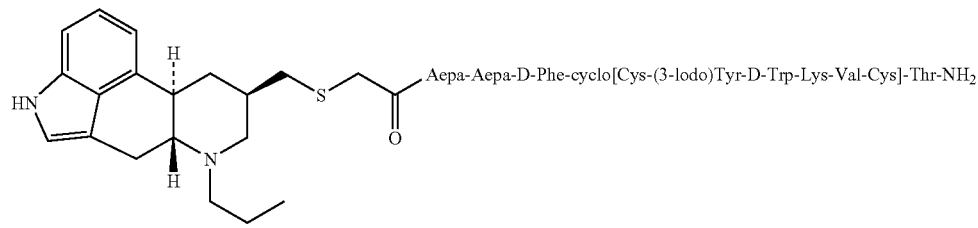

Example Q was synthesized substantially according to the procedure described for Example L by using (6-N-propyl-8β-ergolinyl)methylthioacetic acid and H-Aepa-Aepa-DPhe-Cys(Trt)-(3-Iodo)Tyr-DTrp(Boc)-Lys(Boc)-Val-Cys(Trt)-Thr(tBu)-Rink Amide MBHA Resin. Purity of the final product was 99% based on analytical HPLC analysis. MS (Electro Spray): 1851.1 (in agreement with the calculated molecular weight of 1851.1).
Fmoc-(3-Iodo)-Tyr-OH was purchased from Advanced ChemTech (Louisville, Ky.).
(3-Iodo)Tyr=

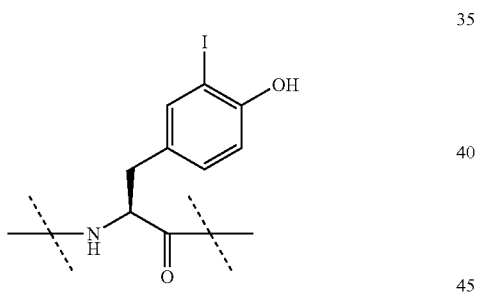

Example R

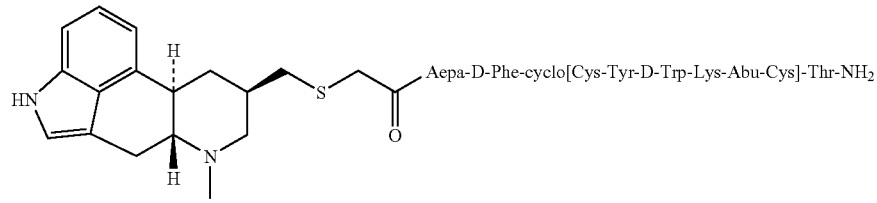

Example R was synthesized substantially according to the procedure described for Example L by using H-Aepa-DPhe-Cys(Trt)-Tyr(tBu)-DTrp(Boc)-Lys(Boc)-Abu-Cys(Trt)-Thr(tBu)-Rink Amide MBHA Resin. Purity of the final product was 98.3% based on analytical HPLC analysis. MS (Electro Spray): 1513.8 (in agreement with the calculated molecular weight of 1513.9).

Example S

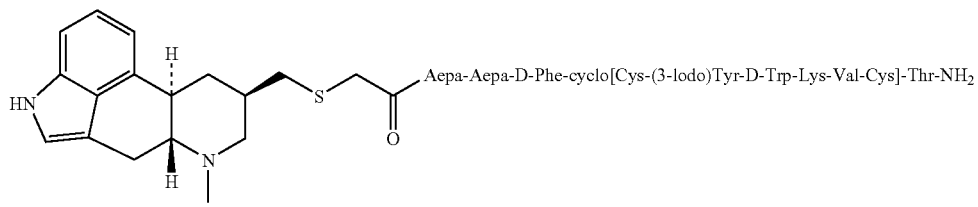

Example S was synthesized substantially according to the procedure described for Example L by using H-Aepa-Aepa-DPhe-Cys(Trt)-(3-Iodo)Tyr-DTrp(Boc)-Lys(Boc)-Val-Cys(Trt)-Thr(tBu)-Rink Amide MBHA Resin. Purity of the final product was 85.7% based on analytical HPLC analysis. MS (Electro Spray): 1822.9 (in agreement with the calculated molecular weight of 1823.06).

Example T

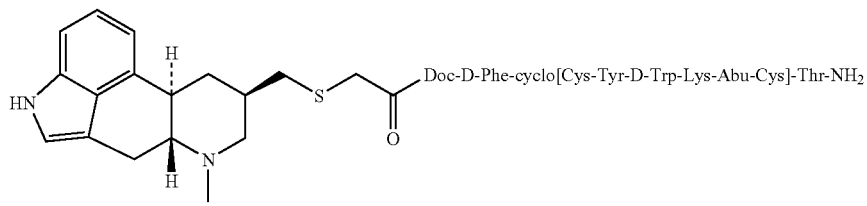

Example T was synthesized substantially according to the procedure described for Example L by using H-Doc-DPhe-Cys(Trt)-Tyr(tBu)-DTrp(Boc)-Lys(Boc)-Abu-Cys(Trt)-Thr(tBu)-Rink Amide MBHA Resin. Purity of the final product was 98.9% based on analytical HPLC analysis. MS (Electro Spray): 1489.6 (in agreement with the calculated molecular weight of 1489.84).

Example U

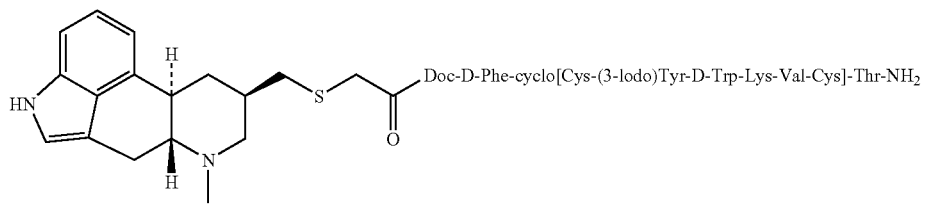

Example U was synthesized substantially according to the procedure described for Example L by using H-Doc-DPhe-Cys(Trt)-(3-Iodo)Tyr-DTrp(Boc)-Lys(Boc)-Val-Cys(Trt)-Thr(tBu)-Rink Amide MBHA Resin. MS (Electro Spray): 1629.8 (in agreement with the calculated molecular weight of 1629.7).

Example V

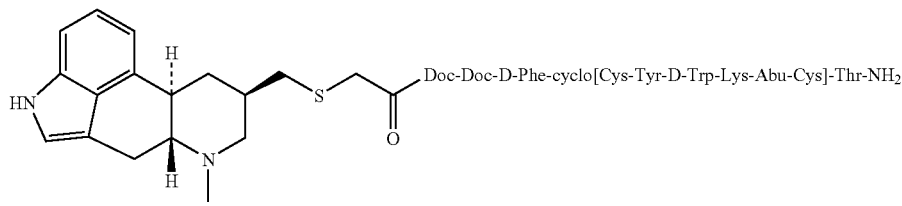

The titled compound was synthesized substantially according to the procedure described for Example L by using H-Doc-Doc-DPhe-Cys(Trt)-Tyr(tBu)-DTrp(Boc)-Lys(Boc)-Abu-Cys(Trt)-Thr(tBu)-Rink Amide MBHA Resin. Purity of the final product was 99% based on analytical HPLC analysis. MS (Electro Spray): 1635.0 (in agreement with the calculated molecular weight of 1633).

Some of the compounds of the instant invention can have at least one asymmetric center. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, are included within the scope of the instant invention.

The compounds of the instant invention generally can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The pharmaceutically acceptable salts can be formed by taking about 1 equivalent of a compound of the invention, (e.g., Compound C, below), and contacting it with about 1 equivalent or more of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention includes within its scope pharmaceutical compositions comprising, as an active ingredient, at least one compound of the invention in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

In general, an effective dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses.

Somatostatin Receptor Specificity and Selectivity Assay

Specificity and selectivity of the somatostatin analogues used to synthesize the somatostatin-dopamine chimers were determined by a radioligand binding assay on CHO-K1 cells stably transfected with each of the SSTR subtypes, as follows.

The complete coding sequences of genomic fragments of the SSTR 1, 2, 3, and 4 genes and a cDNA clone for SSTR 5 were subcloned into the mammalian expression vector pCMV (Life Technologies, Milano, Italy). Clonal cell lines stably expressing SSTR's 1-5 were obtained by transfection into CHO-K1 cells (ATCC, Manassas, Va., USA) using the calcium phosphate co-precipitation method (Davis L, et al., 1994 In: Basic methods in Molecular Biology, 2nd edition, Appleton & Lange, Norwalk, Conn., USA: 611-646). The plasmid pRSV-neo (ATCC) was included as a selectable marker. Clonal cell lines were selected in RPMI 1640 media containing 0.5 mg/ml of G418 (Life Technologies, Milano, Italy), ring cloned, and expanded into culture.

Membranes for in vitro receptor binding assays were obtained by homogenizing the CHO-K1 cells expressing the SSTR's subtypes in ice-cold 50 mM Tris-HCl and centrifuging twice at 39000 g (10 min), with an intermediate resuspension in fresh buffer. The final pellets were resuspended in 10 mM Tris-HCl for assay. For the SSTR 1, 3, 4, and 5 assays, aliquots of the membrane preparations were incubated 90 min. at 25° C. with 0.05 nM [$^{125}$I-Tyr11]SS-14 in 50 mM HEPES (pH 7.4) containing 10 mg/ml BSA, 5 mM MgCl$_2$, 200 KIU/ml Trasylol, 0.02 mg/ml bacitracin, and 0.02 mg/ml phenylmethylsuphonyl fluoride. The final assay volume was 0.3 ml. For the SSTR 2 assay, 0.05 nM [$^{125}$I]MK-678 was employed as the radioligand and the incubation time was 90 min at 25° C. The incubations were terminated by rapid filtration through GF/C filters (pre-soaked in 0.3% polyethylenimine) using a Brandel filtration manifold. Each tube and filter were then washed three times with 5 ml aliquots of ice-cold buffer. Specific binding was defined as the total radioligand bound minus that bound in the presence of 1000 nM SS-14 for SSTR 1, 3, 4, and 5, or 1000 nM MK-678 for SSTR2.

Dopamine Receptor Specificity and Selectivity Assay

Specificity and selectivity for the dopamine-2 receptor of the dopamine analogues used to synthesize the somatostatin-dopamine chimers may be determined by a radioligand binding assay as follows.

Crude membranes were prepared by homogenization of frozen rat corpus striatum (Zivic Laboratories, Pittsburgh, Pa.) in 20 ml of ice-cold 50 mM Tris-HCl with a Brinkman Polytron (setting 6, 15 sec). Buffer was added to obtain a final volume of 40 ml, and the homogenate was centrifuged in a Sorval SS-34 rotor at 39,000 g for 10 min at 0-4° C. The resulting supernatant was decanted and discarded. The pellet was rehomogenized in ice-cold buffer, pre-incubated at 37° C. for 10 min, diluted, and centrifuged as before. The final pellet was resuspended in buffer and held on ice for the receptor binding assay.

For assay, aliquots of the washed membrane preparations and test compounds were incubated for 15 min (37 C) with 0.25 nM [$^3$HI]spiperone (16.5 Ci.mmol, New England Nuclear, Boston, Mass.) in 50 mM Tris HCl, 120 mM NaCl, 5 mM KCl, 2 mM CaCl2, 1 mM MgCl2. The final assay volume was 1.0 ml. The incubations were terminated by rapid filtration through GF/B filters using a Brandel filtration manifold. Each tube and filter were then washed three times with 5-ml aliquots of ice-cold buffer. Specific binding was defined as the total radioligand bound minus that bound in the presence of 1000 nM (+) butaclamol.

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the claims. Also, all publications mentioned herein are hereby incorporated by reference in their entirety.

What is claimed is:

1. A method of treating acromegaly, GH secreting adenomas, or prolactin secreting adenomas in a subject, said method comprising administering to said subject a therapeutically effective amount of:

a) a compound of Formula (I),

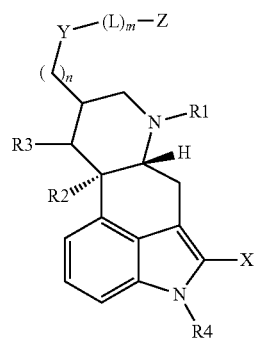

(I)

wherein:
X is H, Cl, Br, I, F, —CN, or $C_{1-5}$ alkyl;
R1 is H, $C_{1-4}$ alkyl, allyl, alkenyl or —CN;
R2 and R3, each are, independently H or absent, provided that when R2 and R3 are absent a double bond is present between the carbon atoms to which they are attached;
R4 is H or —CH$_3$;
Y is —O—, —C(O)—, —S—, —S—(CH$_2$)s-C(O)—, —S(O)—, —S(O)$_2$—, —SC(O)—, —OC(O)—, —N(R5)-C(O)—, or —N(R6)-;
R5, R6, R7 and R8 each is, independently, H or $C_{1-5}$ alkyl;
R6 is H or $C_{1-5}$ alkyl;
m is 0 or 1;
n is 0-10;
L is —(CH$_2$)p-C(O)—, when Y is —S—, —S(O)—, —S(O)$_2$—, —O— or —N(R6)-;
L is —C(O)—(CR7R8)q-C(O)—, when Y is —N(R6)-, —O—, or —S—;
L is -(Doc)t-, when Y is —C(O)—, SC(O)—, —OC(O)—, —S—(CH$_2$)s-C(O)—, or —N(R5)-C(O)—;
p is 1-10;
q is 2-4;
s is 1-10;
t is 1-10; and
z is a somatostatin analog or a moiety comprising —H, —OH, ($C_1$-$C_6$)alkoxy, arylalkoxy, —NH$_2$, or —NR9R10, wherein R9 and R10 each is, independently, H or $C_{1-5}$ alkyl;
or a pharmaceutically acceptable salt thereof; or b) a compound of Formula (II),

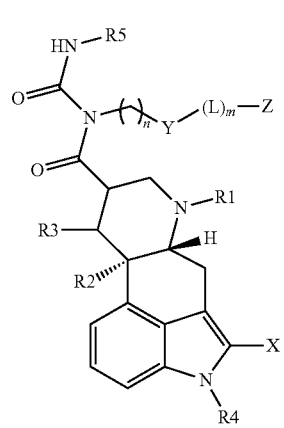

(II)

wherein:

X is H, Cl, Br, I, F, —CN, or $C_{1-5}$ alkyl;
R1 is C1-4 alkyl, H, allyl, alkenyl or —CN;
R2 and R3, each are, independently H or absent, provided that when R2 and R3 are absent a double bond is present between the carbon atoms to which they are attached;
R4 is H or —CH$_3$;
R5 is C1-5 alkyl group, or a group of the formula of —(CH$_2$)rN(CH$_3$)q;
Y is —O—, —C(O)—, —S—, —SC(O)—, —OC(O)—, —N(R6)-C(O)—, —N(R7)-, or —N(R8)-(CH$_2$)s-C(O)—;
R6, R7, R8, R9 and R10 each is, independently, H or $C_{1-5}$ alkyl;
L is —(CH$_2$)p-C(O)—, when Y is —S—, —O— or —N(R7)-;
L is —C(O)—(CR9R10)q—C(O)—, when Y is —N(R7)-, —O—, or —S—;
L is -(Doc)t-, when Y is —C(O)—, SC(O)—, —OC(O)—, —N(R8)-(CH$_2$)s-C(O)—, or —N(R6)-C(O)—;
m is 0 or 1;
n is 2-10;
r is 1-8;
q is 2-4;
p is 1-10;
s is 1-10;
t is 1-10; and
z is a somatostatin analog or a moiety comprising —H, —OH, ($C_1$-$C_6$)alkoxy, arylalkoxy, —NH$_2$, or —NR9R10;
or a pharmaceutically acceptable salt thereof; or
  c) a compound of formulae:

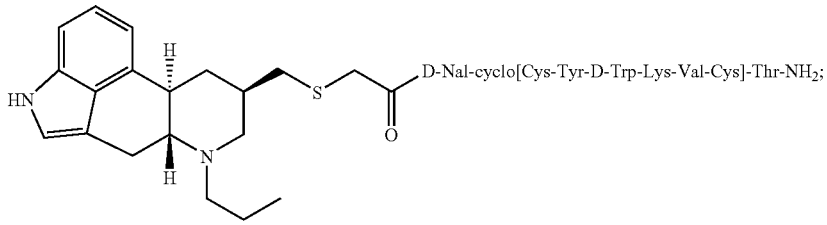
D-Nal-cyclo[Cys-Tyr-D-Trp-Lys-Val-Cys]-Thr-NH$_2$;

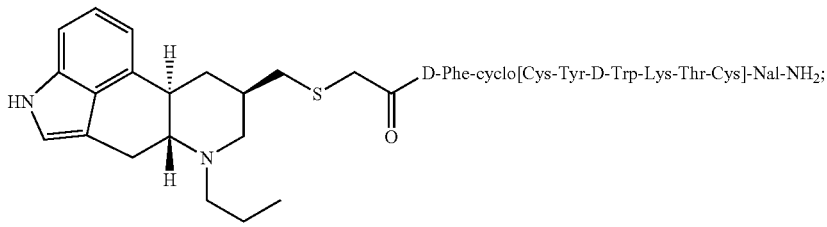
D-Phe-cyclo[Cys-Tyr-D-Trp-Lys-Thr-Cys]-Nal-NH$_2$;

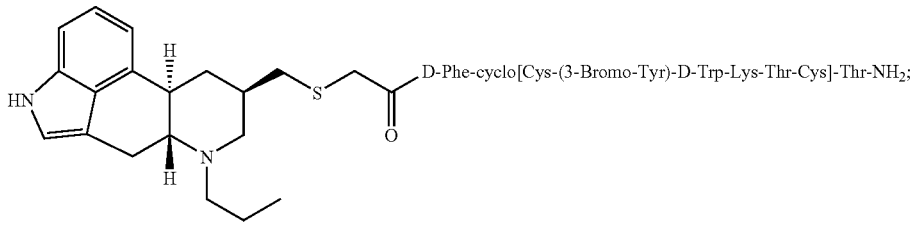
D-Phe-cyclo[Cys-(3-Bromo-Tyr)-D-Trp-Lys-Thr-Cys]-Thr-NH$_2$;

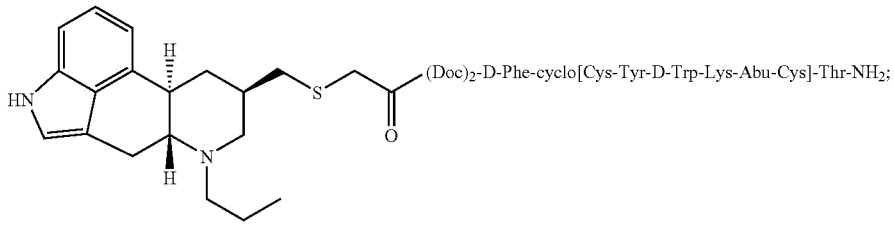
(Doc)$_2$-D-Phe-cyclo[Cys-Tyr-D-Trp-Lys-Abu-Cys]-Thr-NH$_2$;

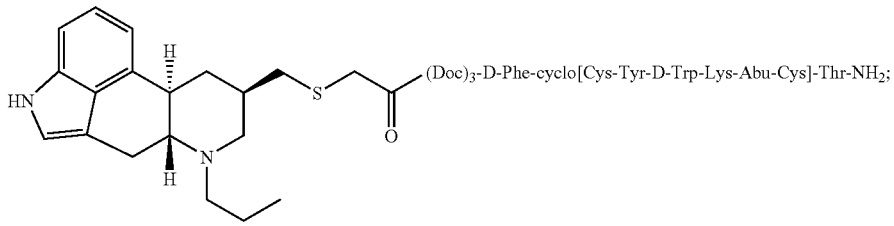
(Doc)$_3$-D-Phe-cyclo[Cys-Tyr-D-Trp-Lys-Abu-Cys]-Thr-NH$_2$;

-continued

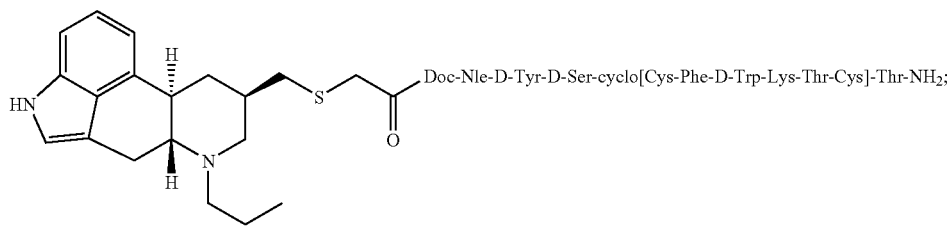
Doc-Nle-D-Tyr-D-Ser-cyclo[Cys-Phe-D-Trp-Lys-Thr-Cys]-Thr-NH$_2$;

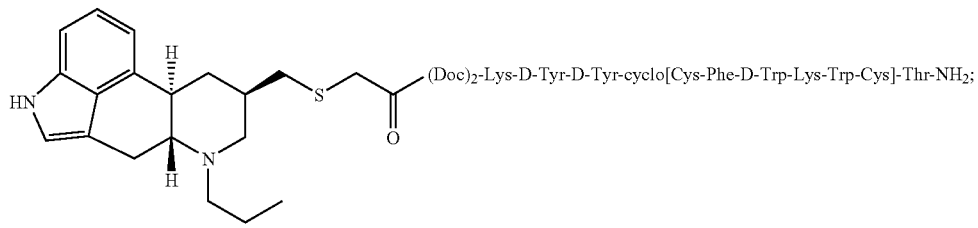
(Doc)$_2$-Lys-D-Tyr-D-Tyr-cyclo[Cys-Phe-D-Trp-Lys-Trp-Cys]-Thr-NH$_2$;

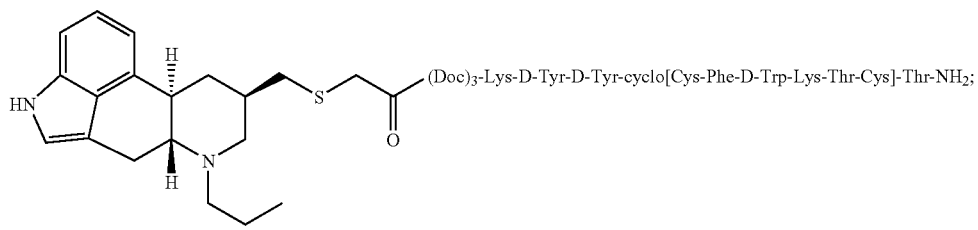
(Doc)$_3$-Lys-D-Tyr-D-Tyr-cyclo[Cys-Phe-D-Trp-Lys-Thr-Cys]-Thr-NH$_2$;

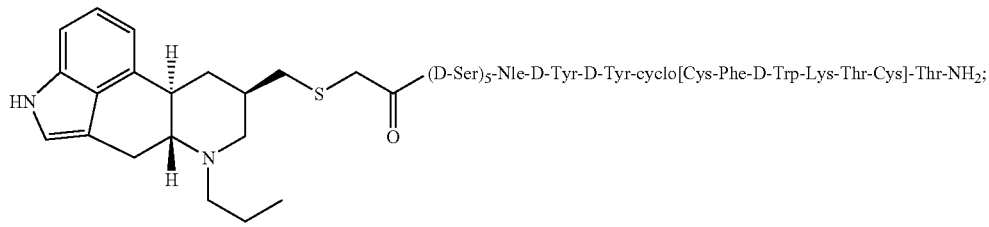
(D-Ser)$_5$-Nle-D-Tyr-D-Tyr-cyclo[Cys-Phe-D-Trp-Lys-Thr-Cys]-Thr-NH$_2$;

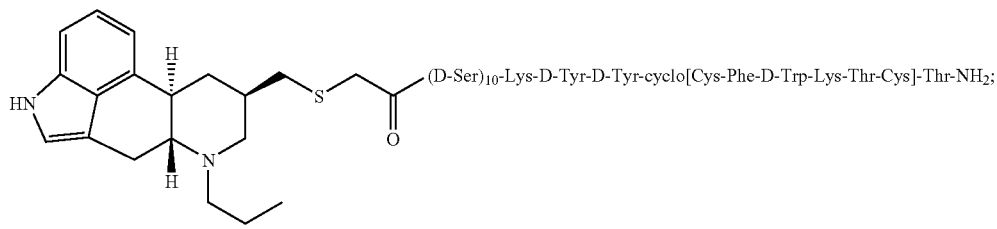
(D-Ser)$_{10}$-Lys-D-Tyr-D-Tyr-cyclo[Cys-Phe-D-Trp-Lys-Thr-Cys]-Thr-NH$_2$;

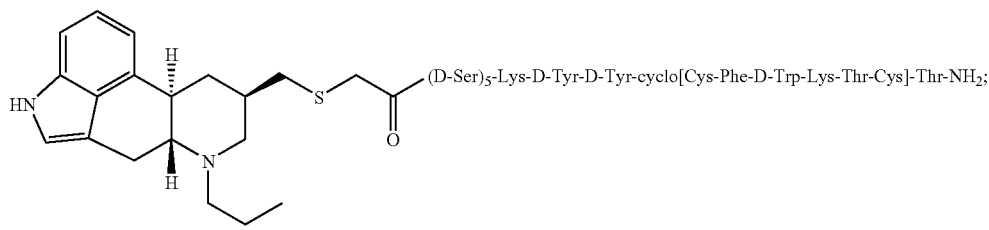
(D-Ser)$_5$-Lys-D-Tyr-D-Tyr-cyclo[Cys-Phe-D-Trp-Lys-Thr-Cys]-Thr-NH$_2$;

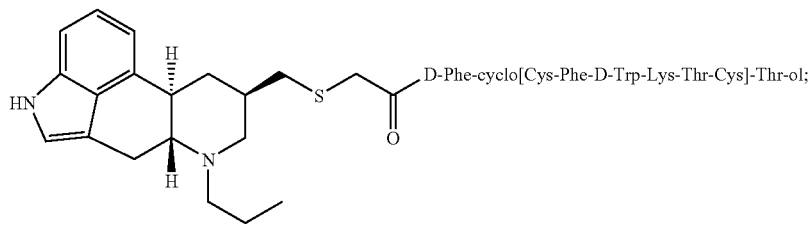
D-Phe-cyclo[Cys-Phe-D-Trp-Lys-Thr-Cys]-Thr-ol;

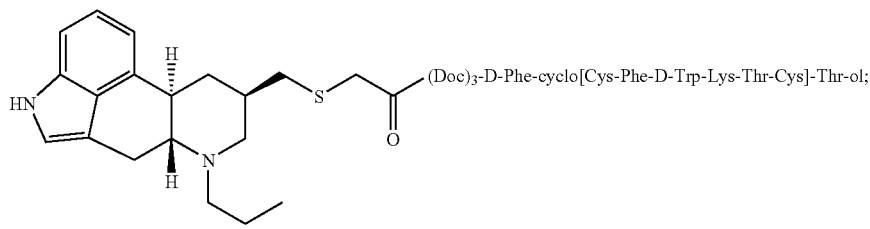(Doc)₃-D-Phe-cyclo[Cys-Phe-D-Trp-Lys-Thr-Cys]-Thr-ol;
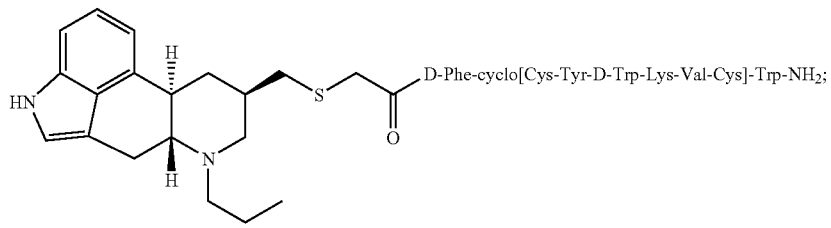D-Phe-cyclo[Cys-Tyr-D-Trp-Lys-Val-Cys]-Trp-NH₂;
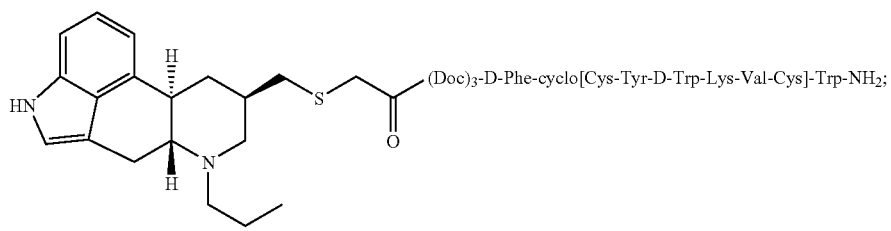(Doc)₃-D-Phe-cyclo[Cys-Tyr-D-Trp-Lys-Val-Cys]-Trp-NH₂;
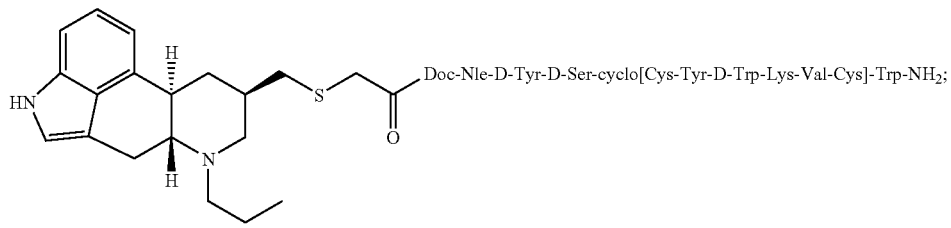Doc-Nle-D-Tyr-D-Ser-cyclo[Cys-Tyr-D-Trp-Lys-Val-Cys]-Trp-NH₂;
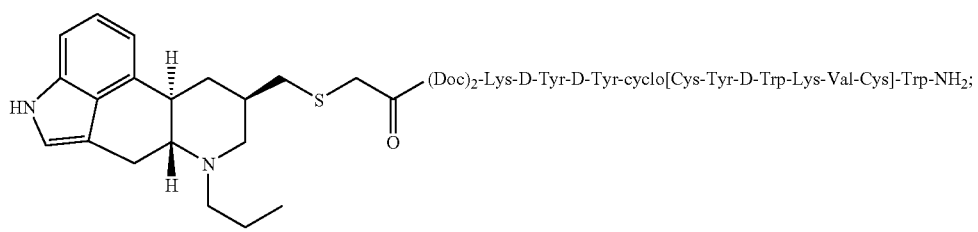(Doc)₂-Lys-D-Tyr-D-Tyr-cyclo[Cys-Tyr-D-Trp-Lys-Val-Cys]-Trp-NH₂;
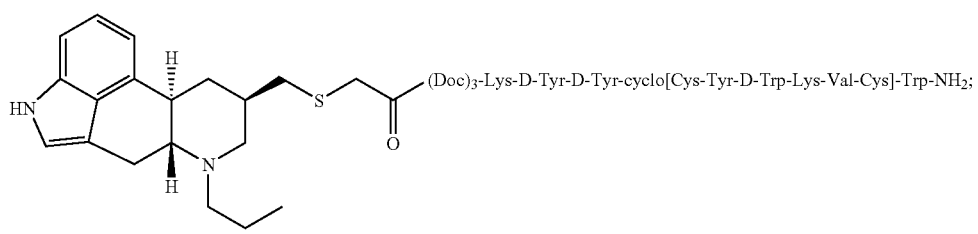(Doc)₃-Lys-D-Tyr-D-Tyr-cyclo[Cys-Tyr-D-Trp-Lys-Val-Cys]-Trp-NH₂;
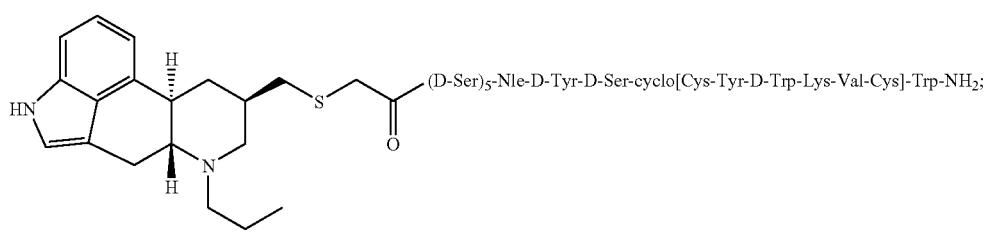(D-Ser)₅-Nle-D-Tyr-D-Ser-cyclo[Cys-Tyr-D-Trp-Lys-Val-Cys]-Trp-NH₂;

-continued

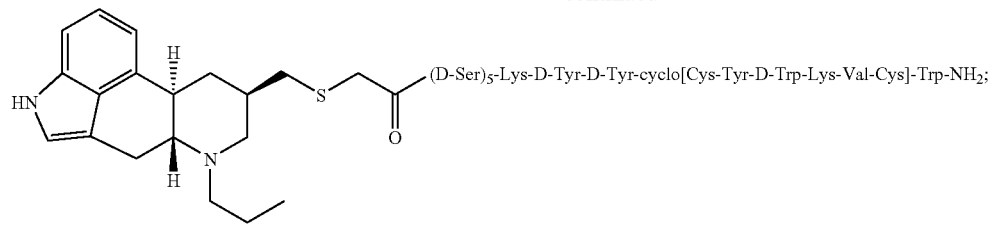(D-Ser)₅-Lys-D-Tyr-D-Tyr-cyclo[Cys-Tyr-D-Trp-Lys-Val-Cys]-Trp-NH₂;

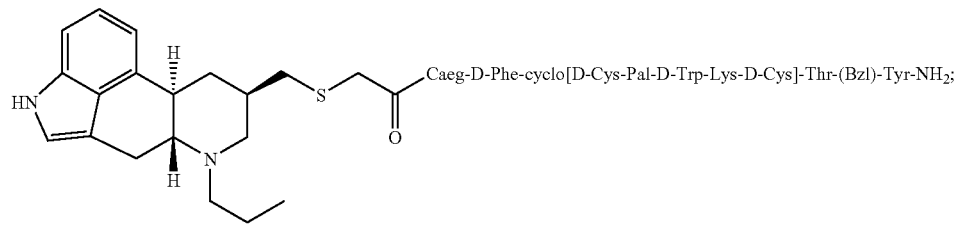Caeg-D-Phe-cyclo[D-Cys-Pal-D-Trp-Lys-D-Cys]-Thr-(Bzl)-Tyr-NH₂;

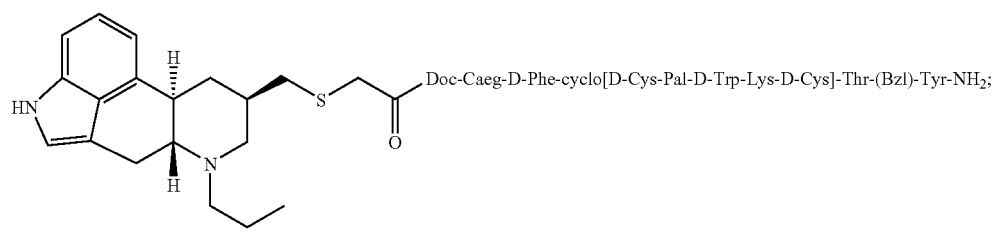Doc-Caeg-D-Phe-cyclo[D-Cys-Pal-D-Trp-Lys-D-Cys]-Thr-(Bzl)-Tyr-NH₂;

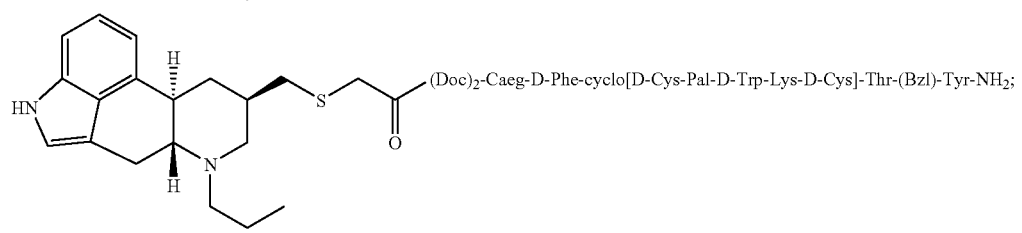(Doc)₂-Caeg-D-Phe-cyclo[D-Cys-Pal-D-Trp-Lys-D-Cys]-Thr-(Bzl)-Tyr-NH₂;

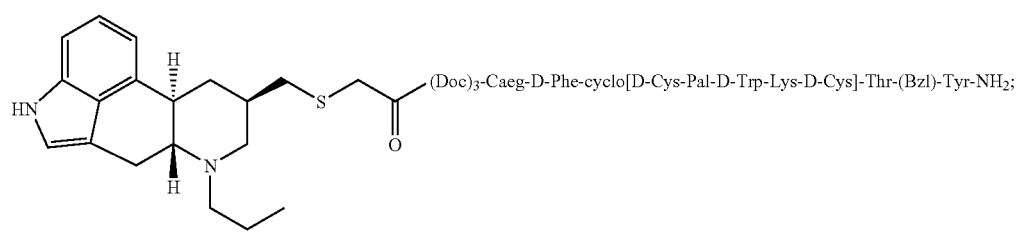(Doc)₃-Caeg-D-Phe-cyclo[D-Cys-Pal-D-Trp-Lys-D-Cys]-Thr-(Bzl)-Tyr-NH₂;

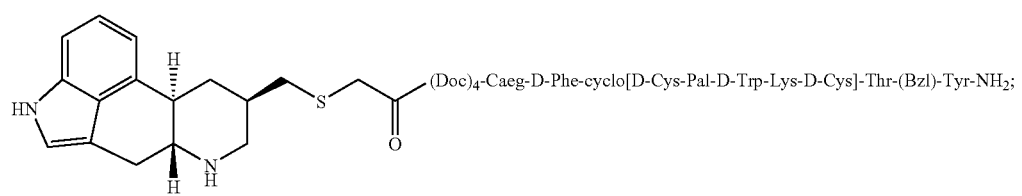(Doc)₄-Caeg-D-Phe-cyclo[D-Cys-Pal-D-Trp-Lys-D-Cys]-Thr-(Bzl)-Tyr-NH₂;

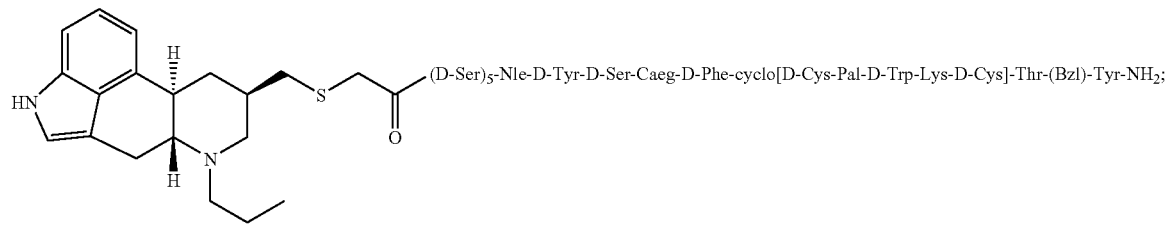(D-Ser)₅-Nle-D-Tyr-D-Ser-Caeg-D-Phe-cyclo[D-Cys-Pal-D-Trp-Lys-D-Cys]-Thr-(Bzl)-Tyr-NH₂;

-continued
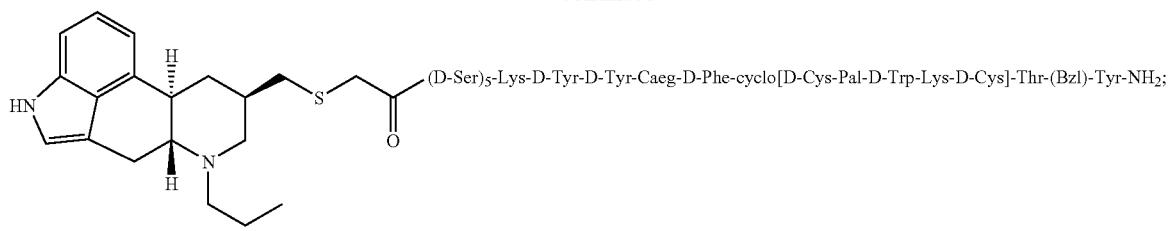
(D-Ser)5-Lys-D-Tyr-D-Tyr-Caeg-D-Phe-cyclo[D-Cys-Pal-D-Trp-Lys-D-Cys]-Thr-(Bzl)-Tyr-NH2;
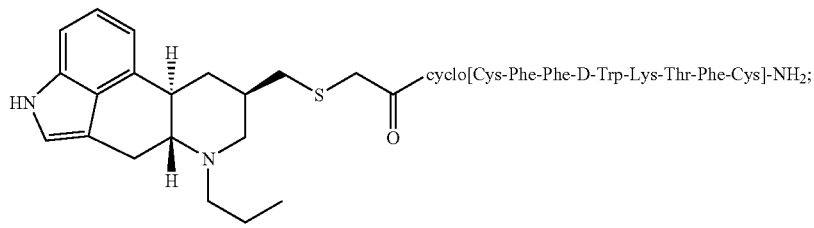
cyclo[Cys-Phe-Phe-D-Trp-Lys-Thr-Phe-Cys]-NH2;
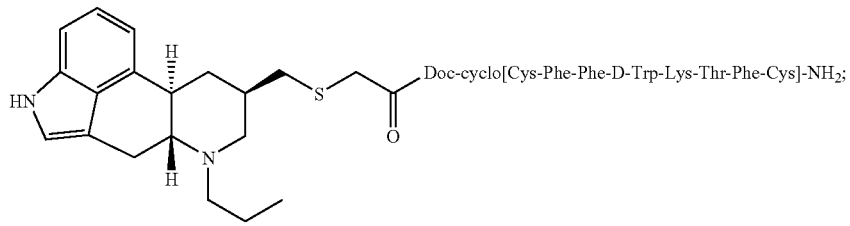
Doc-cyclo[Cys-Phe-Phe-D-Trp-Lys-Thr-Phe-Cys]-NH2;
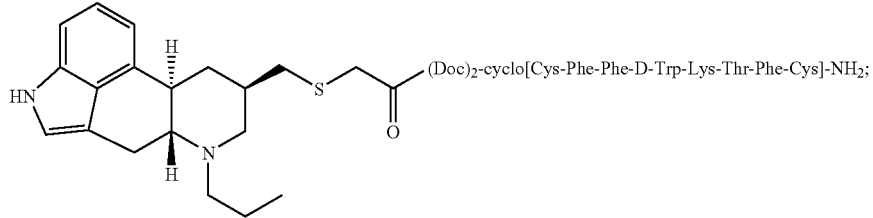
(Doc)2-cyclo[Cys-Phe-Phe-D-Trp-Lys-Thr-Phe-Cys]-NH2;
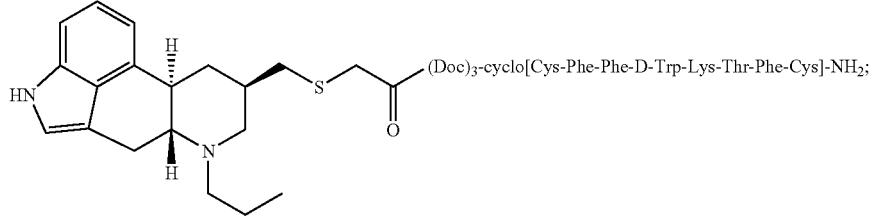
(Doc)3-cyclo[Cys-Phe-Phe-D-Trp-Lys-Thr-Phe-Cys]-NH2;
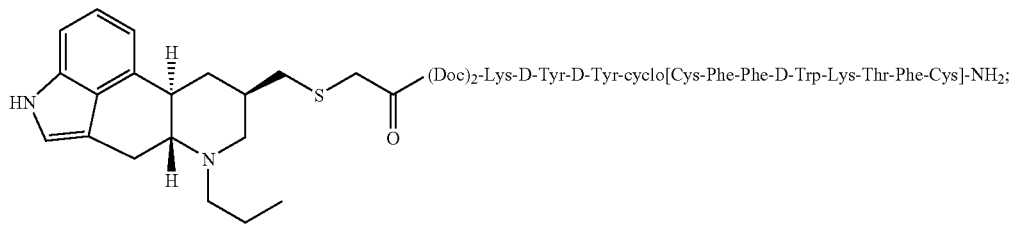
(Doc)2-Lys-D-Tyr-D-Tyr-cyclo[Cys-Phe-Phe-D-Trp-Lys-Thr-Phe-Cys]-NH2;
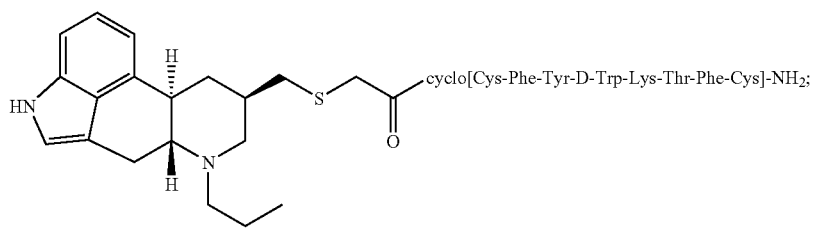
cyclo[Cys-Phe-Tyr-D-Trp-Lys-Thr-Phe-Cys]-NH2;

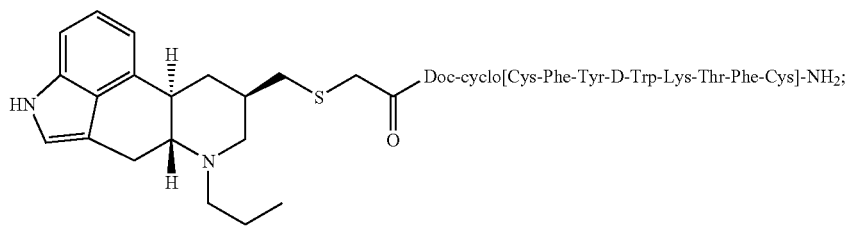
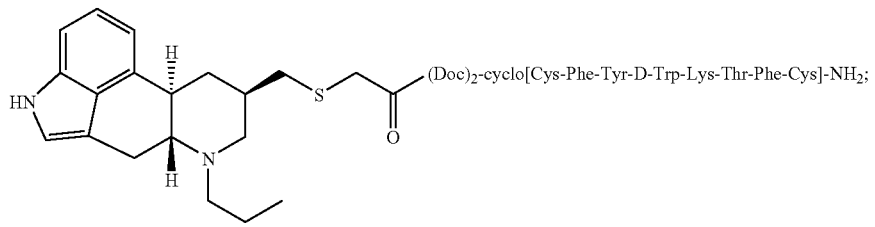
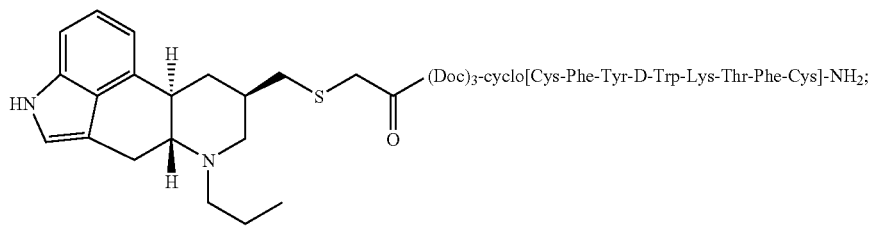
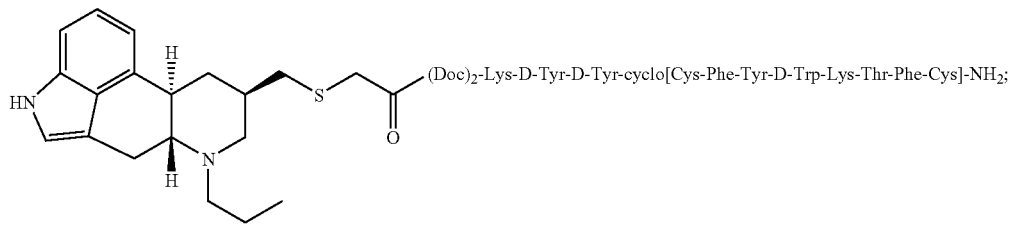
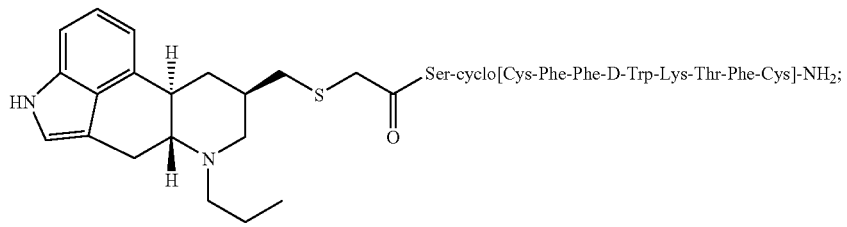
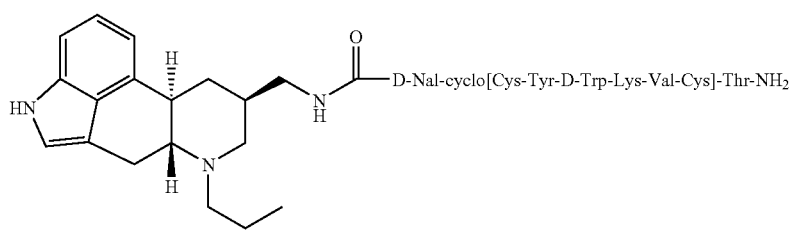
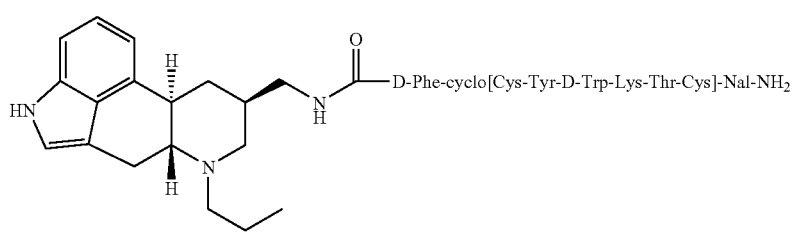

-continued
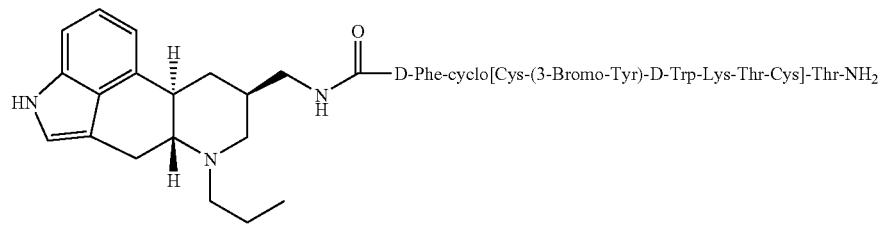
D-Phe-cyclo[Cys-(3-Bromo-Tyr)-D-Trp-Lys-Thr-Cys]-Thr-NH₂
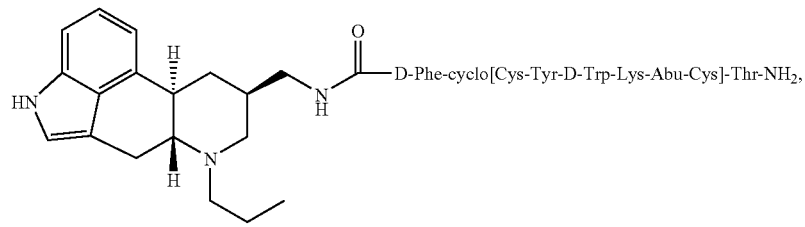
D-Phe-cyclo[Cys-Tyr-D-Trp-Lys-Abu-Cys]-Thr-NH₂,
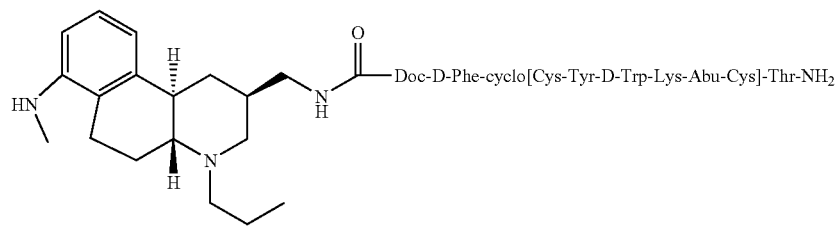
Doc-D-Phe-cyclo[Cys-Tyr-D-Trp-Lys-Abu-Cys]-Thr-NH₂
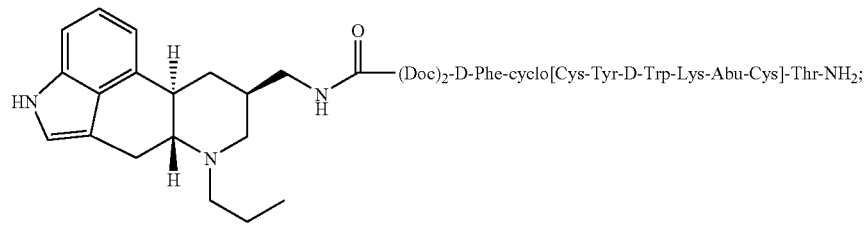
(Doc)₂-D-Phe-cyclo[Cys-Tyr-D-Trp-Lys-Abu-Cys]-Thr-NH₂;
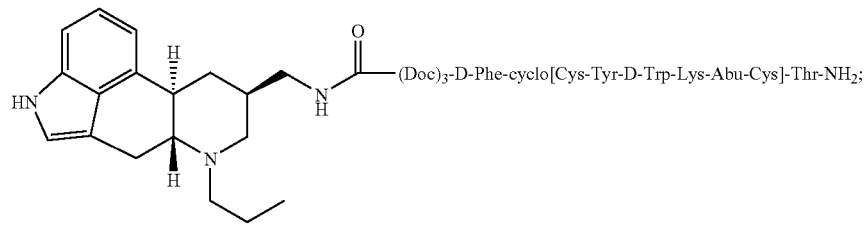
(Doc)₃-D-Phe-cyclo[Cys-Tyr-D-Trp-Lys-Abu-Cys]-Thr-NH₂;
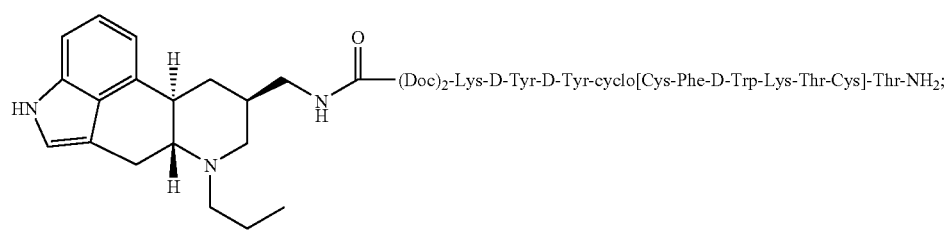
(Doc)₂-Lys-D-Tyr-D-Tyr-cyclo[Cys-Phe-D-Trp-Lys-Thr-Cys]-Thr-NH₂;
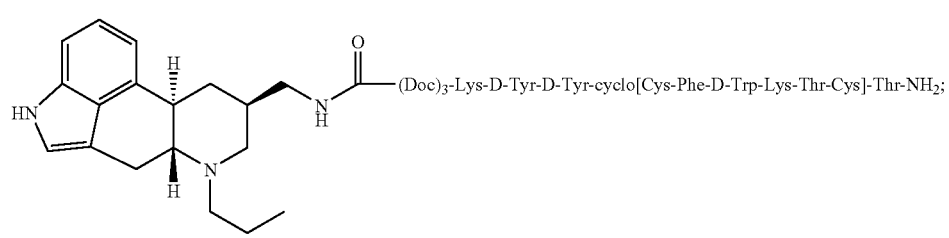
(Doc)₃-Lys-D-Tyr-D-Tyr-cyclo[Cys-Phe-D-Trp-Lys-Thr-Cys]-Thr-NH₂;

-continued
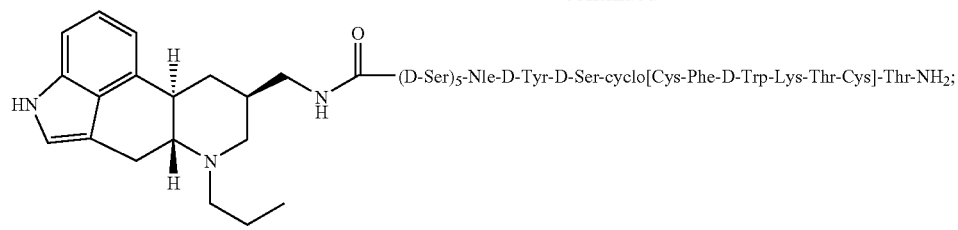
(D-Ser)₅-Nle-D-Tyr-D-Ser-cyclo[Cys-Phe-D-Trp-Lys-Thr-Cys]-Thr-NH₂;
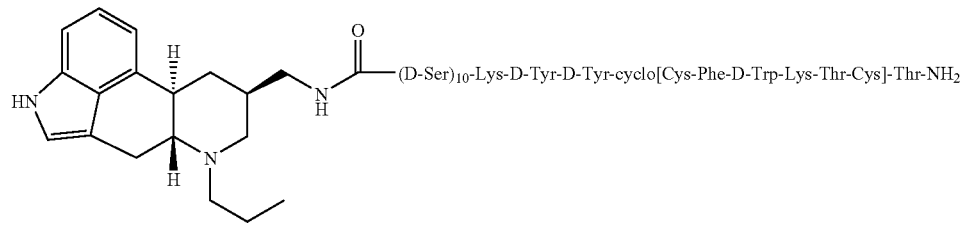
(D-Ser)₁₀-Lys-D-Tyr-D-Tyr-cyclo[Cys-Phe-D-Trp-Lys-Thr-Cys]-Thr-NH₂
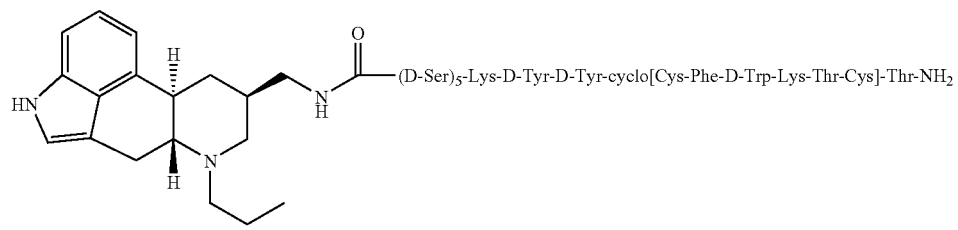
(D-Ser)₅-Lys-D-Tyr-D-Tyr-cyclo[Cys-Phe-D-Trp-Lys-Thr-Cys]-Thr-NH₂
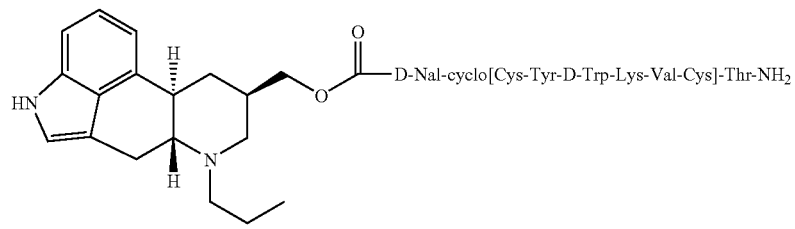
D-Nal-cyclo[Cys-Tyr-D-Trp-Lys-Val-Cys]-Thr-NH₂
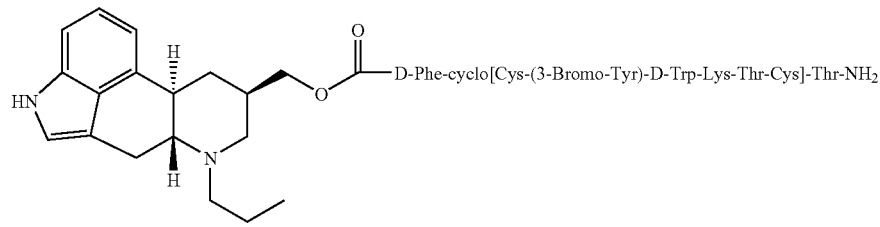
D-Phe-cyclo[Cys-(3-Bromo-Tyr)-D-Trp-Lys-Thr-Cys]-Thr-NH₂
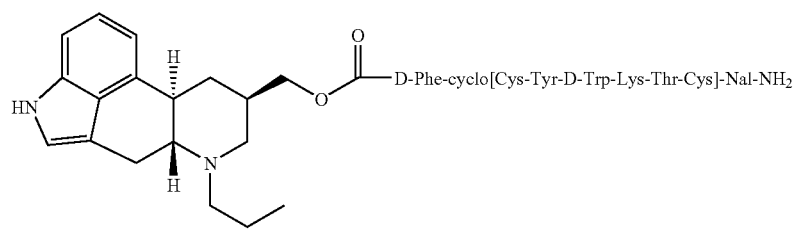
D-Phe-cyclo[Cys-Tyr-D-Trp-Lys-Thr-Cys]-Nal-NH₂
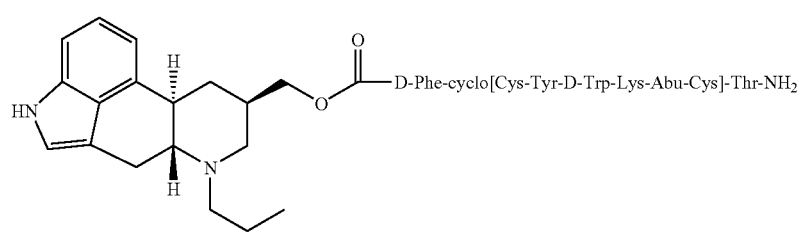
D-Phe-cyclo[Cys-Tyr-D-Trp-Lys-Abu-Cys]-Thr-NH₂

-continued
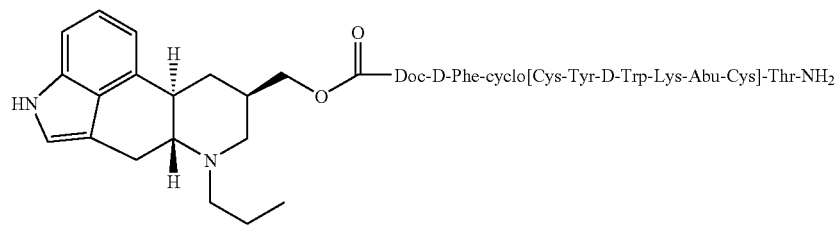
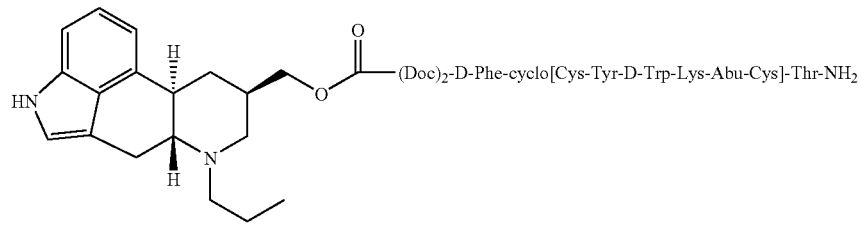
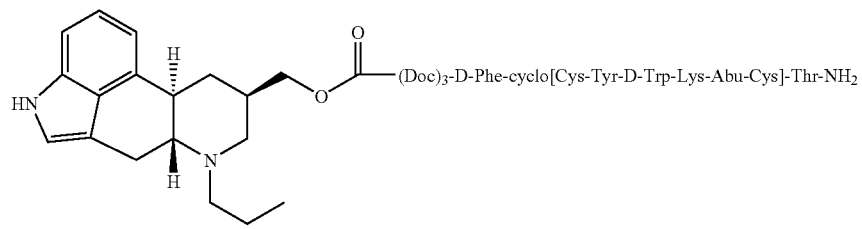
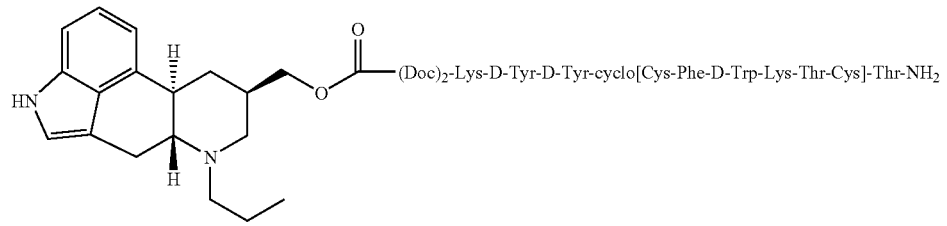
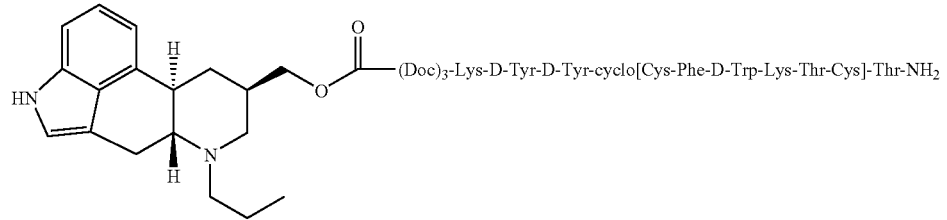
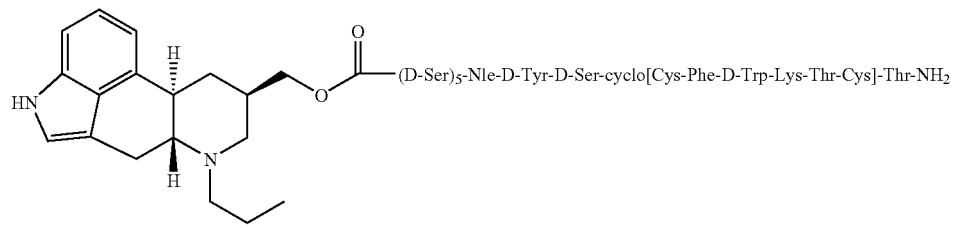
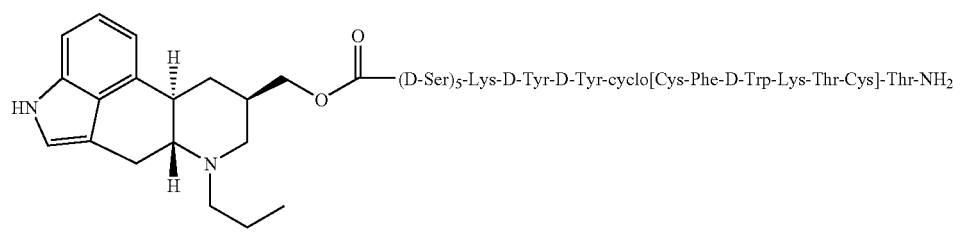

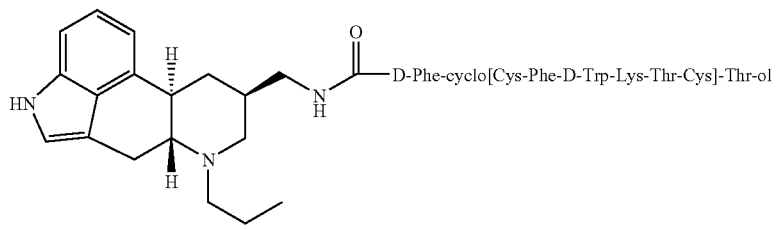
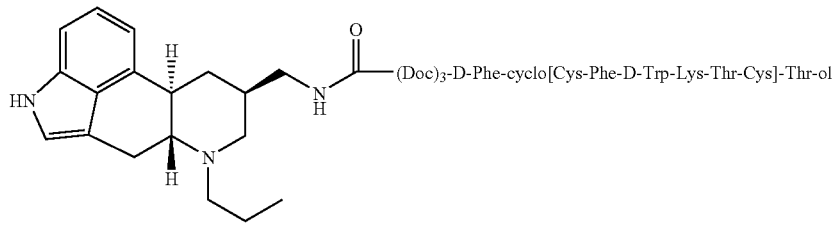
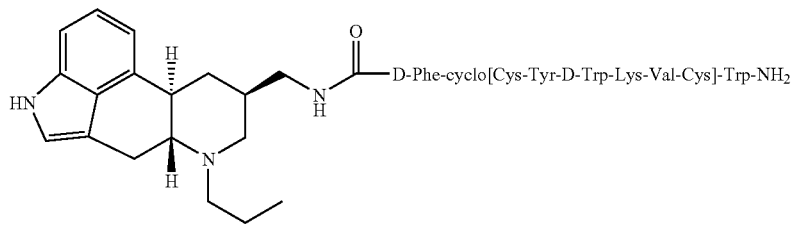
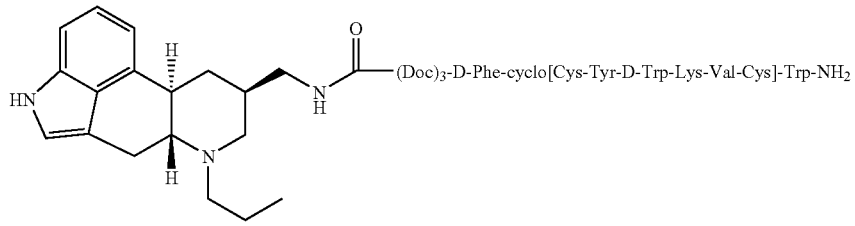
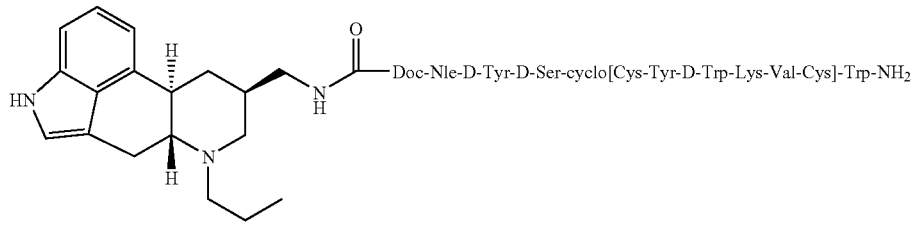
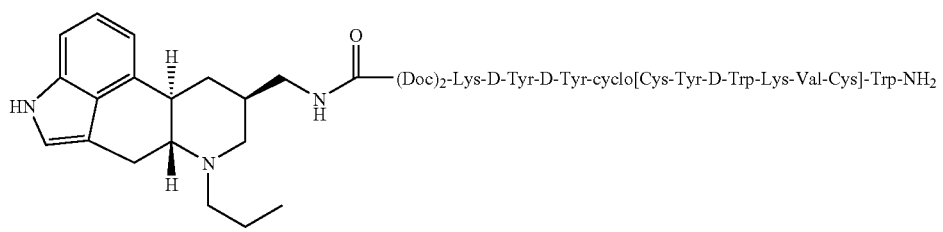
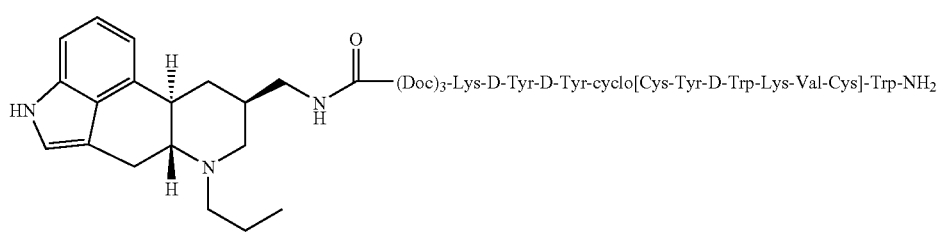

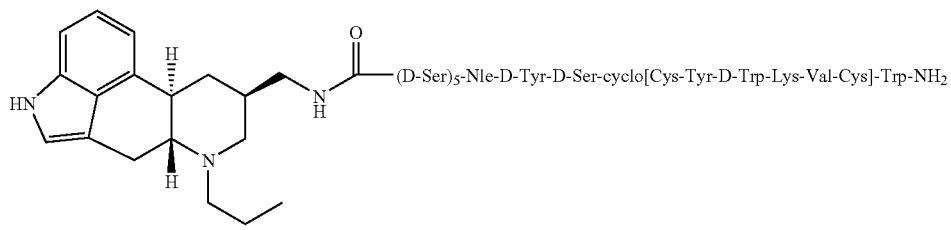
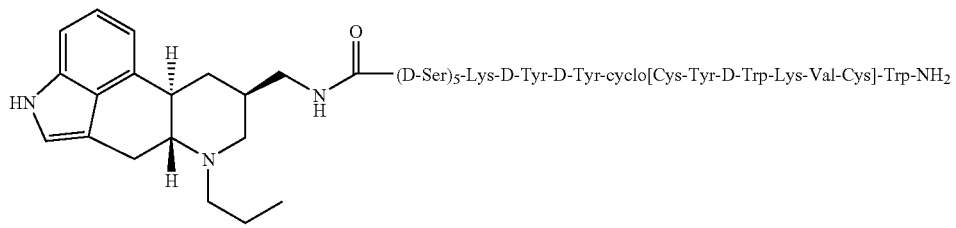
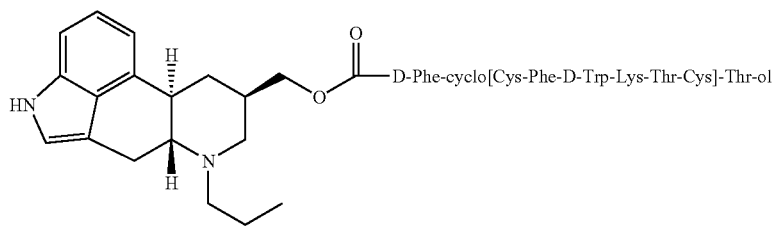
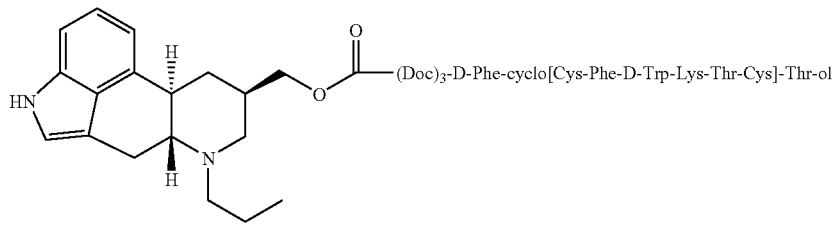
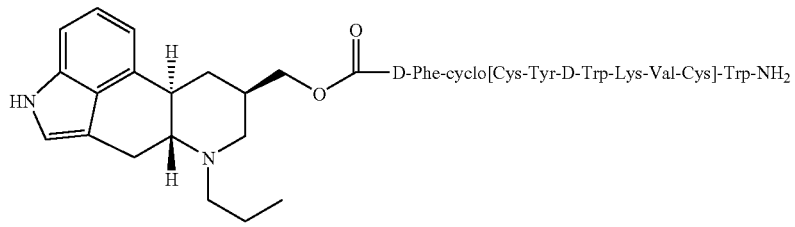
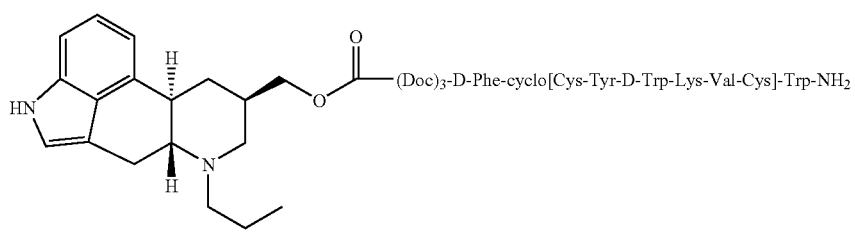
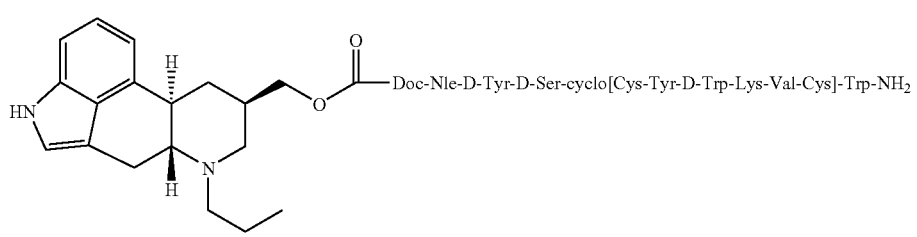

-continued
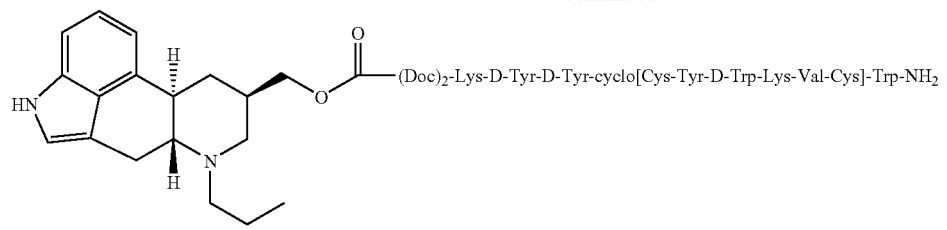
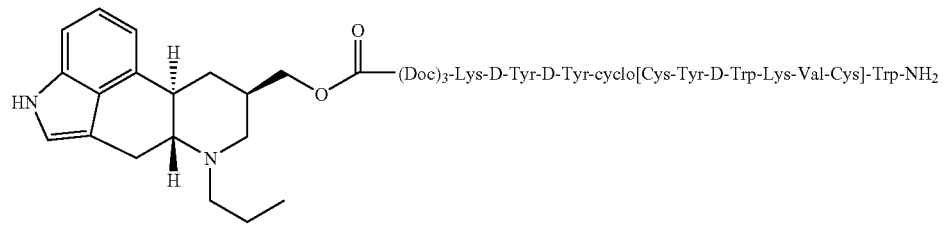
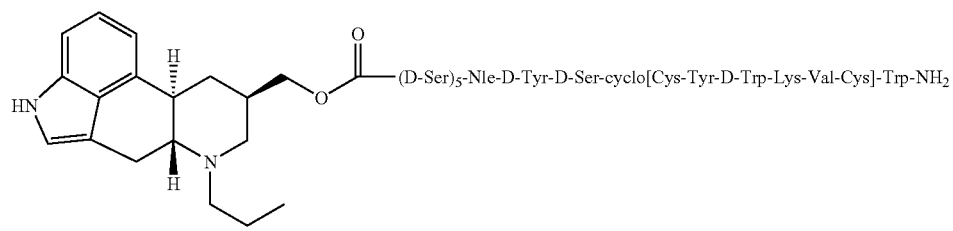
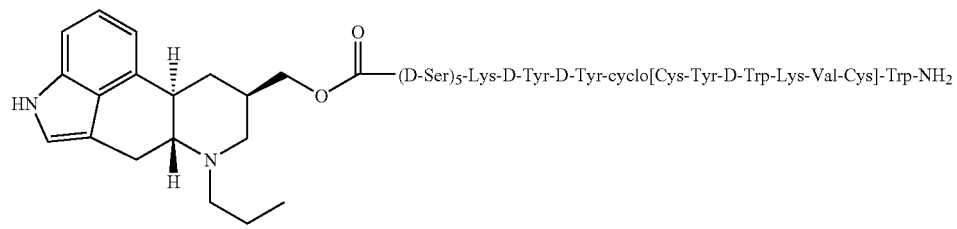
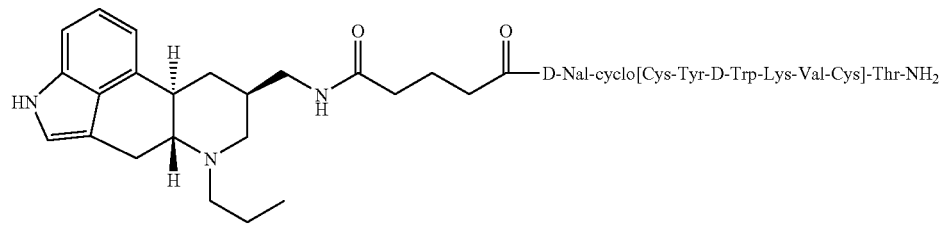
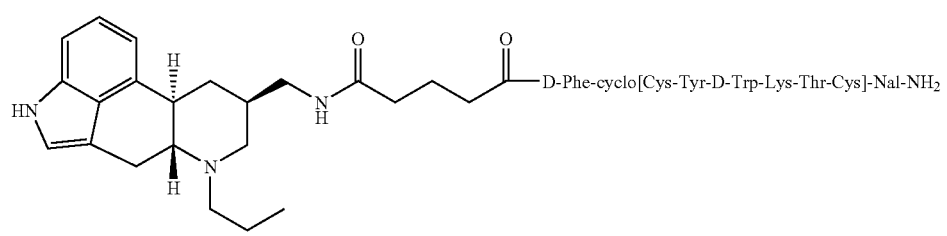
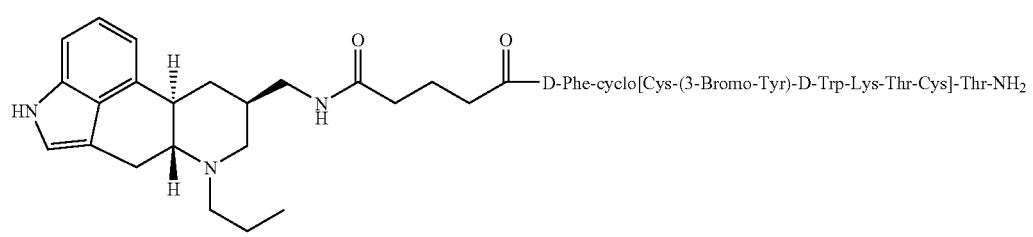

-continued

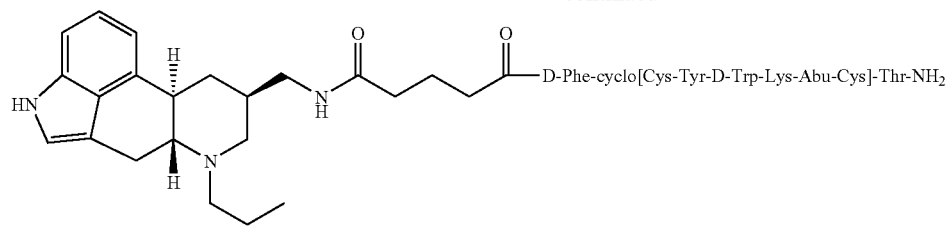
D-Phe-cyclo[Cys-Tyr-D-Trp-Lys-Abu-Cys]-Thr-NH$_2$

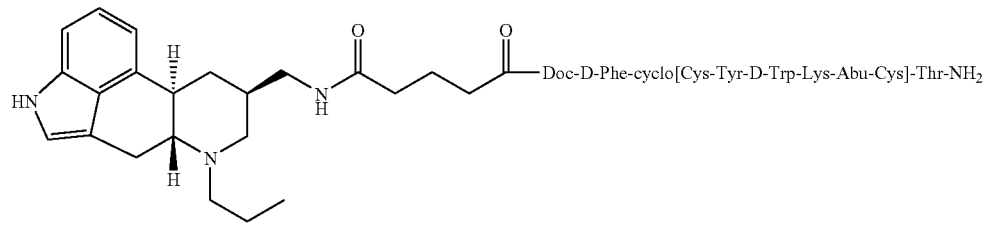
Doc-D-Phe-cyclo[Cys-Tyr-D-Trp-Lys-Abu-Cys]-Thr-NH$_2$

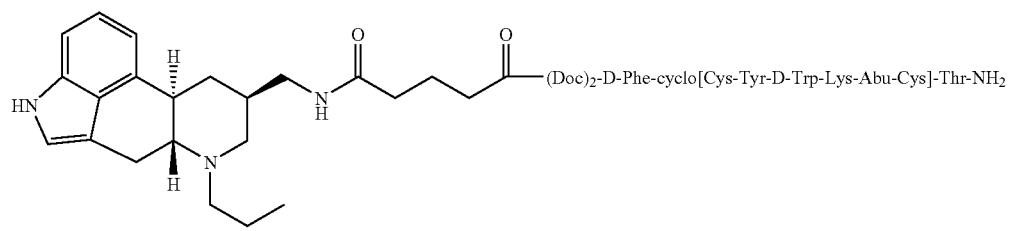
(Doc)$_2$-D-Phe-cyclo[Cys-Tyr-D-Trp-Lys-Abu-Cys]-Thr-NH$_2$

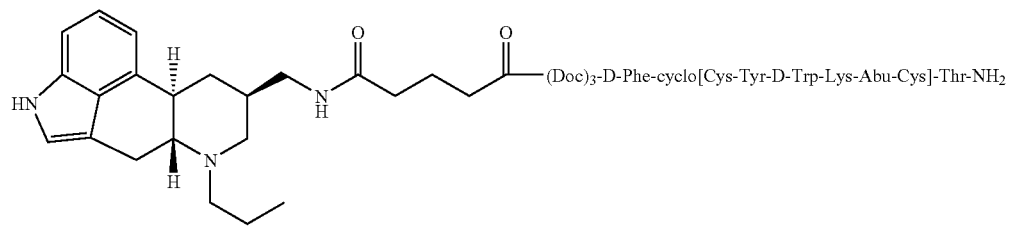
(Doc)$_3$-D-Phe-cyclo[Cys-Tyr-D-Trp-Lys-Abu-Cys]-Thr-NH$_2$

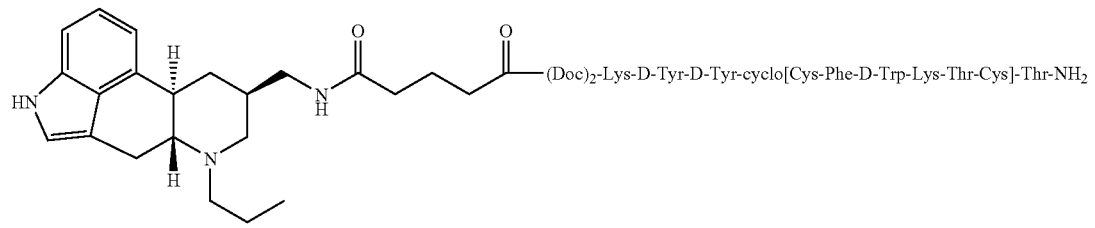
(Doc)$_2$-Lys-D-Tyr-D-Tyr-cyclo[Cys-Phe-D-Trp-Lys-Thr-Cys]-Thr-NH$_2$

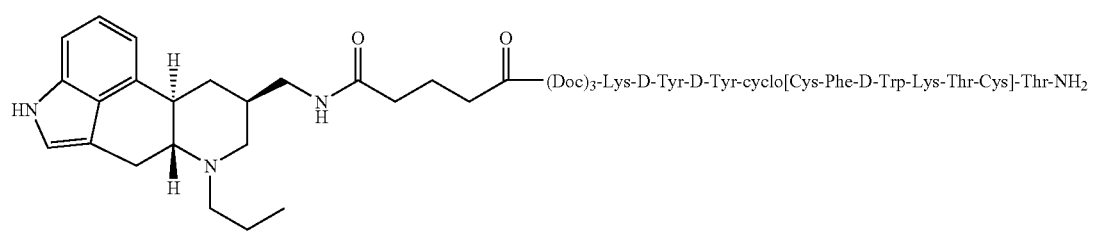
(Doc)$_3$-Lys-D-Tyr-D-Tyr-cyclo[Cys-Phe-D-Trp-Lys-Thr-Cys]-Thr-NH$_2$

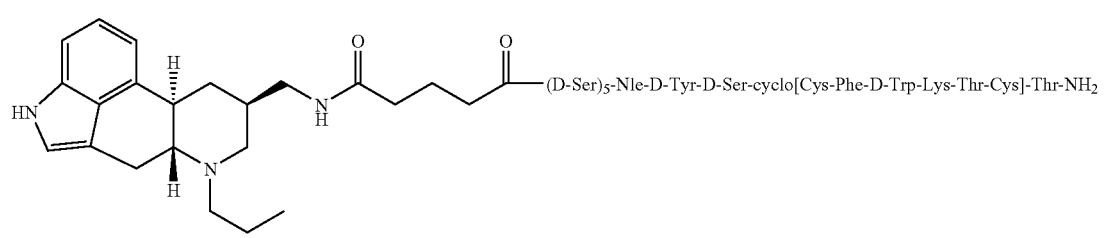
(D-Ser)$_5$-Nle-D-Tyr-D-Ser-cyclo[Cys-Phe-D-Trp-Lys-Thr-Cys]-Thr-NH$_2$ -continued
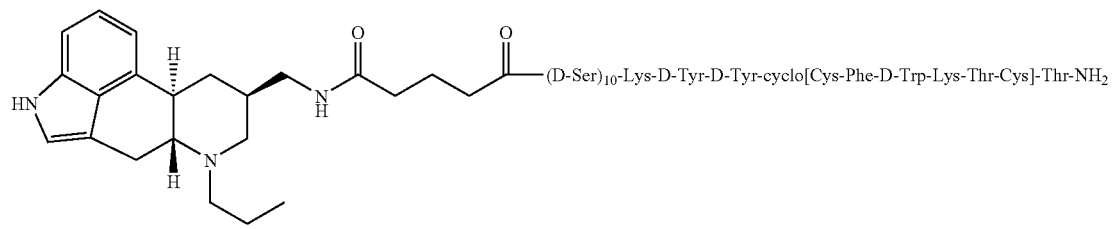
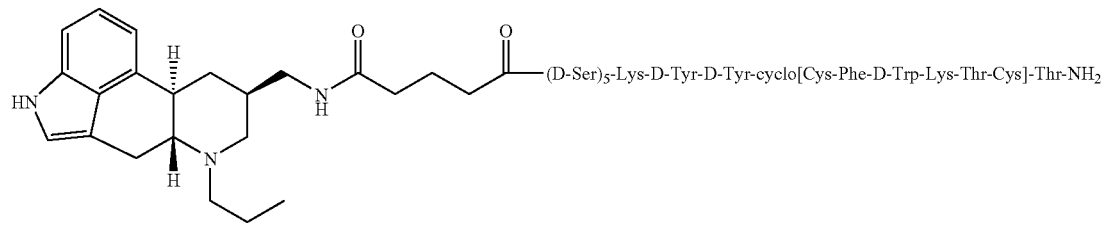
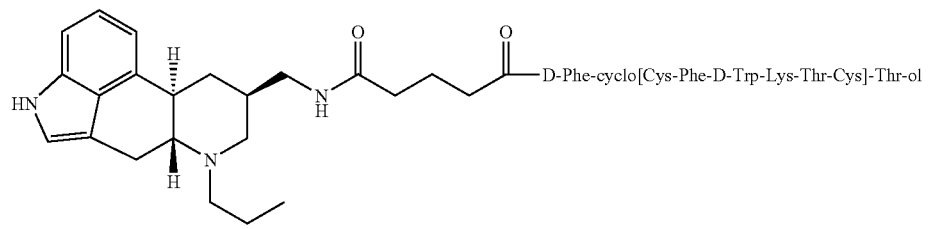
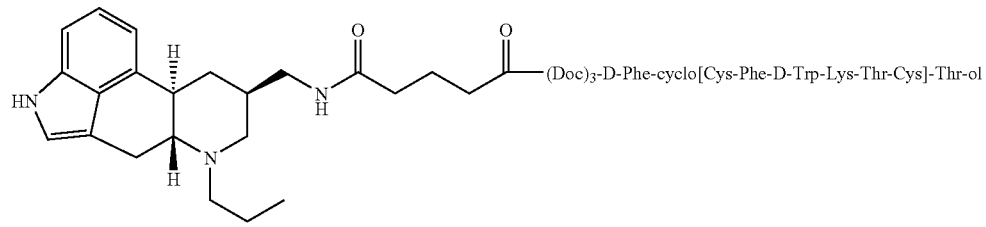
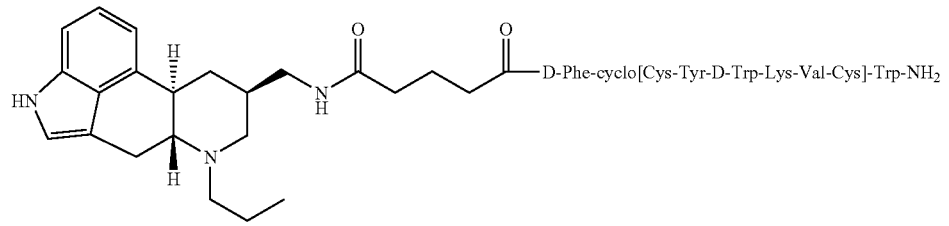
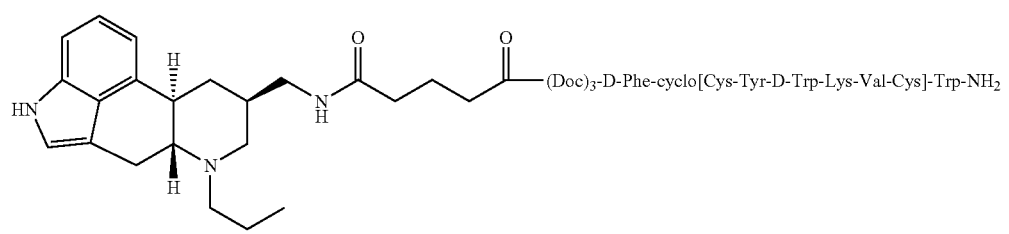
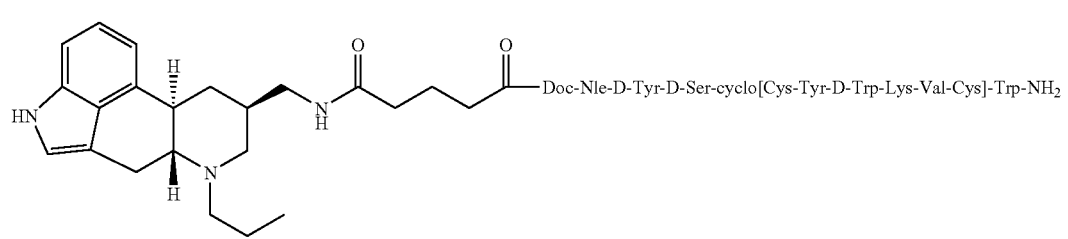

-continued
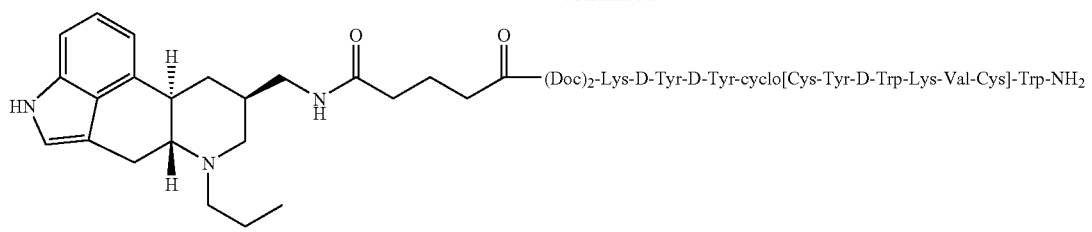
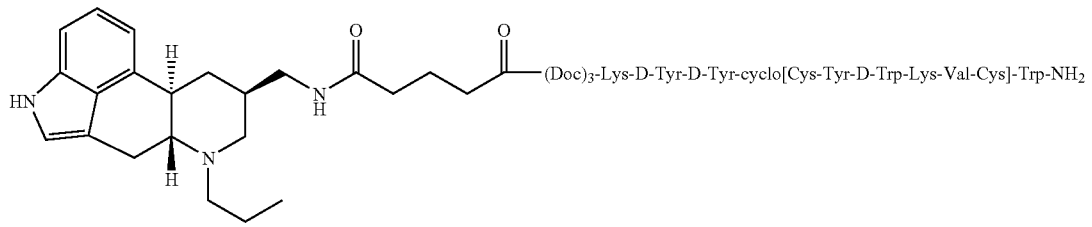
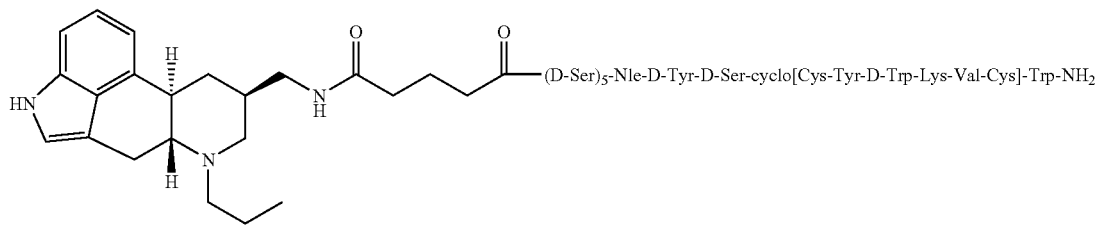
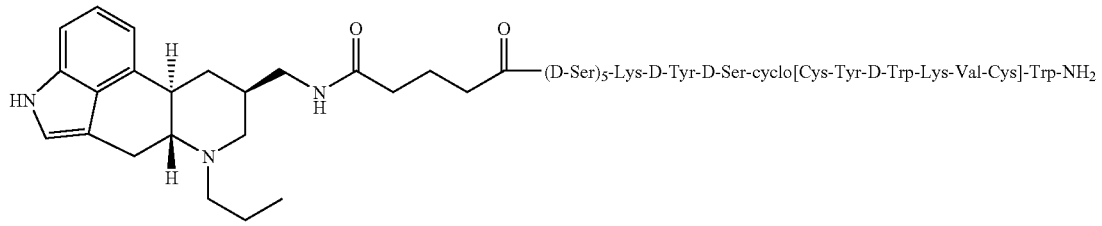
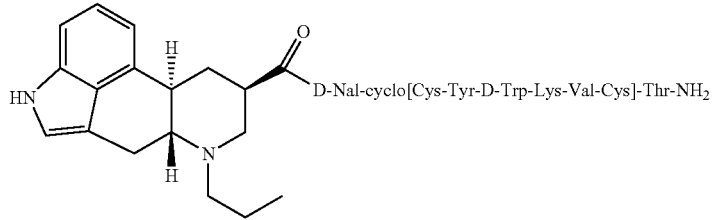
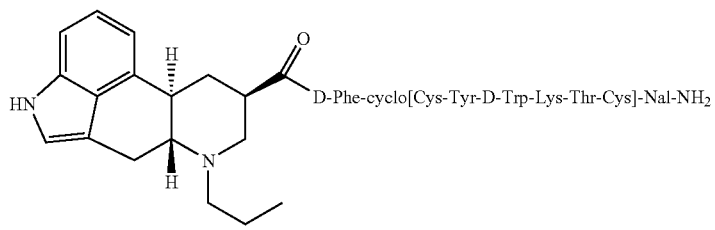
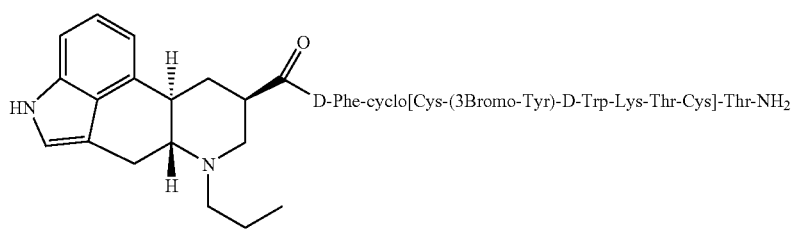

-continued
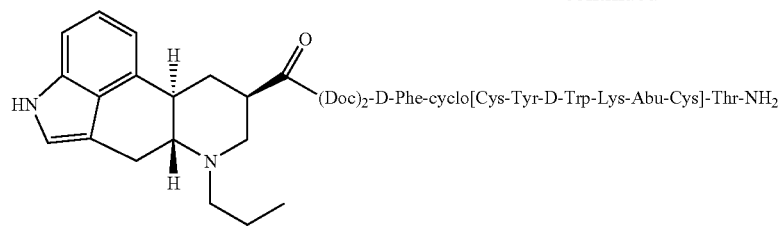
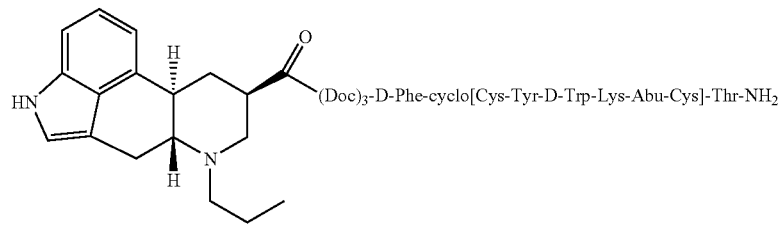
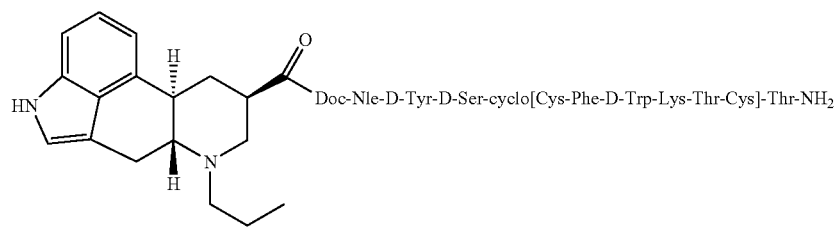
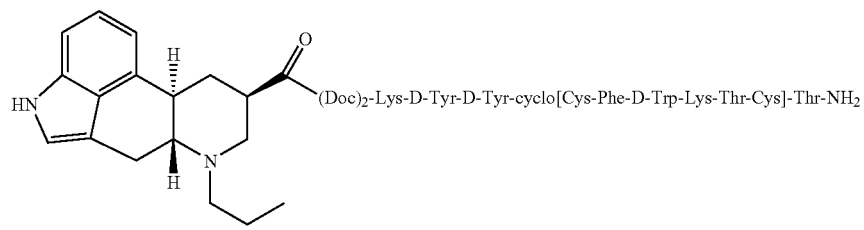
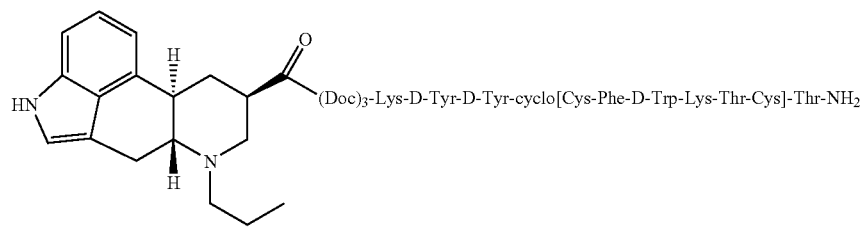
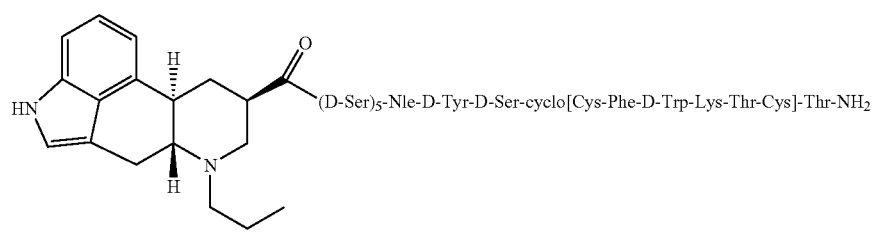
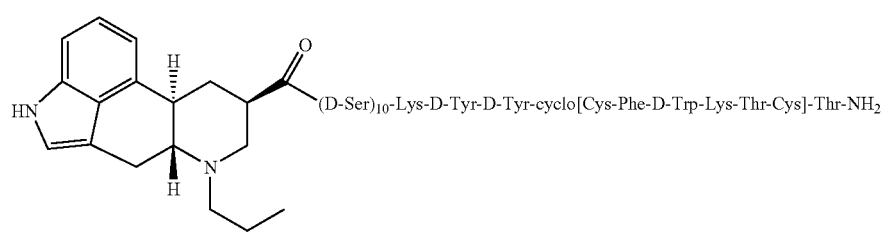

-continued
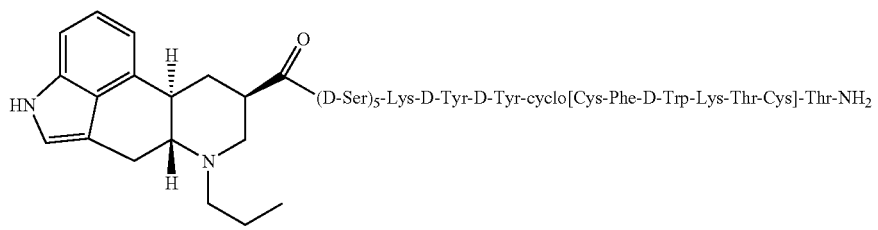
(D-Ser)₅-Lys-D-Tyr-D-Tyr-cyclo[Cys-Phe-D-Trp-Lys-Thr-Cys]-Thr-NH₂
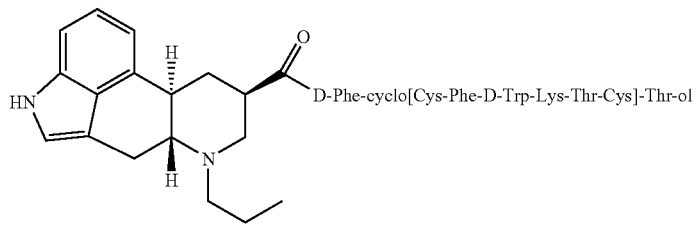
D-Phe-cyclo[Cys-Phe-D-Trp-Lys-Thr-Cys]-Thr-ol
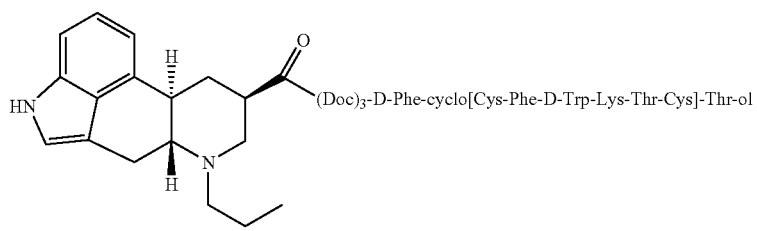
(Doc)₃-D-Phe-cyclo[Cys-Phe-D-Trp-Lys-Thr-Cys]-Thr-ol
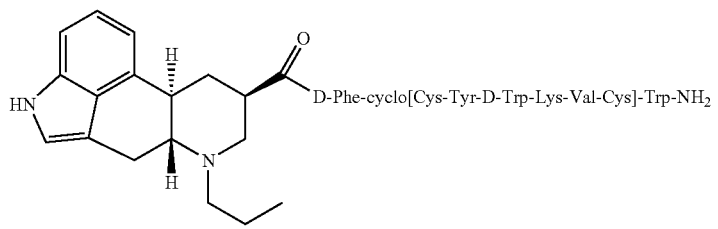
D-Phe-cyclo[Cys-Tyr-D-Trp-Lys-Val-Cys]-Trp-NH₂
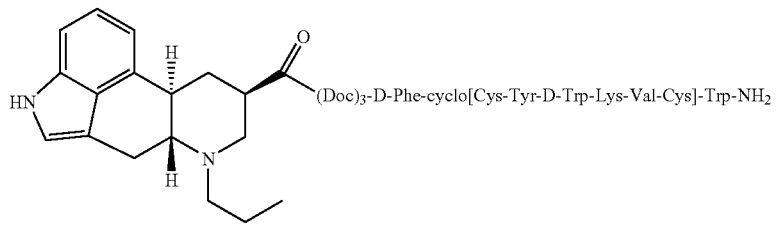
(Doc)₃-D-Phe-cyclo[Cys-Tyr-D-Trp-Lys-Val-Cys]-Trp-NH₂
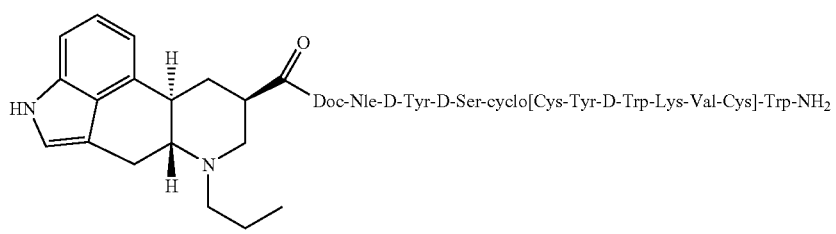
Doc-Nle-D-Tyr-D-Ser-cyclo[Cys-Tyr-D-Trp-Lys-Val-Cys]-Trp-NH₂
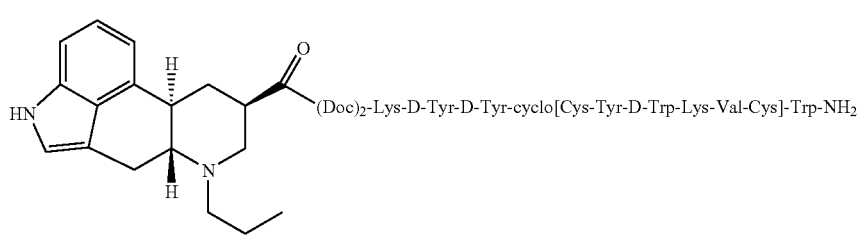
(Doc)₂-Lys-D-Tyr-D-Tyr-cyclo[Cys-Tyr-D-Trp-Lys-Val-Cys]-Trp-NH₂

-continued
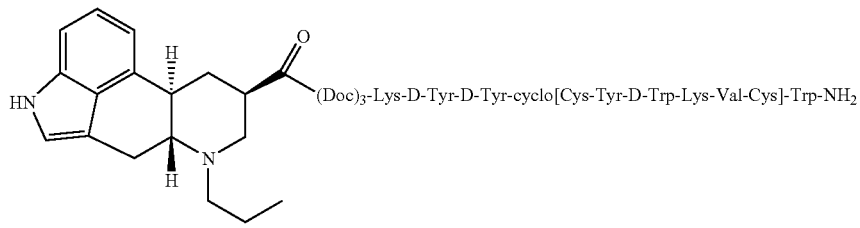
(Doc)₃-Lys-D-Tyr-D-Tyr-cyclo[Cys-Tyr-D-Trp-Lys-Val-Cys]-Trp-NH₂
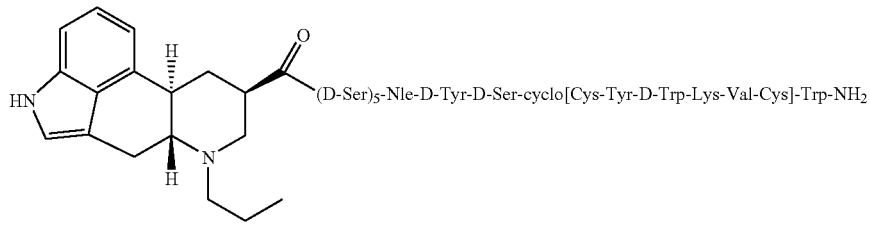
(D-Ser)₅-Nle-D-Tyr-D-Ser-cyclo[Cys-Tyr-D-Trp-Lys-Val-Cys]-Trp-NH₂
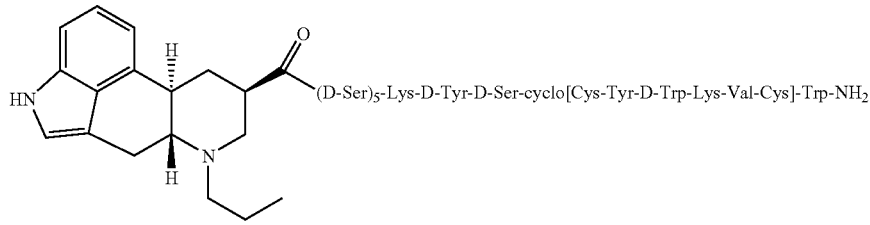
(D-Ser)₅-Lys-D-Tyr-D-Ser-cyclo[Cys-Tyr-D-Trp-Lys-Val-Cys]-Trp-NH₂
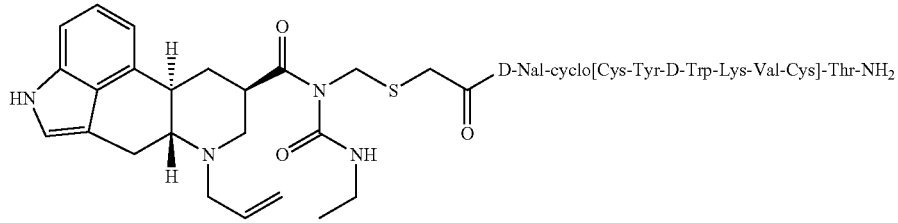
D-Nal-cyclo[Cys-Tyr-D-Trp-Lys-Val-Cys]-Thr-NH₂
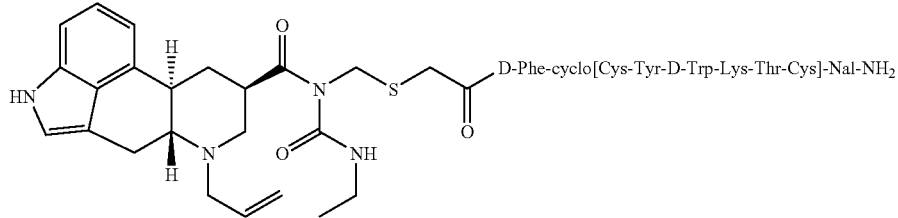
D-Phe-cyclo[Cys-Tyr-D-Trp-Lys-Thr-Cys]-Nal-NH₂
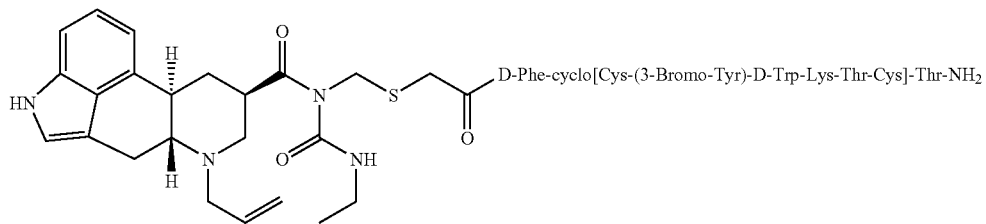
D-Phe-cyclo[Cys-(3-Bromo-Tyr)-D-Trp-Lys-Thr-Cys]-Thr-NH₂
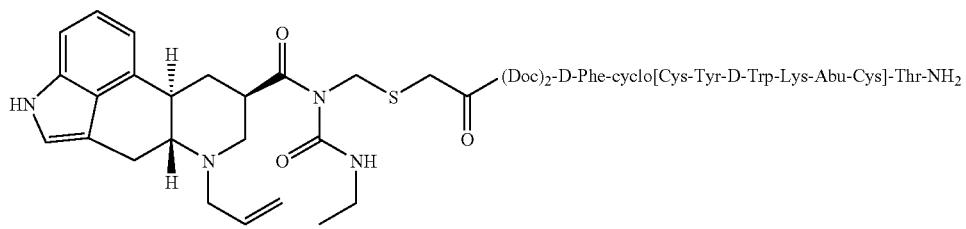
(Doc)₂-D-Phe-cyclo[Cys-Tyr-D-Trp-Lys-Abu-Cys]-Thr-NH₂

-continued

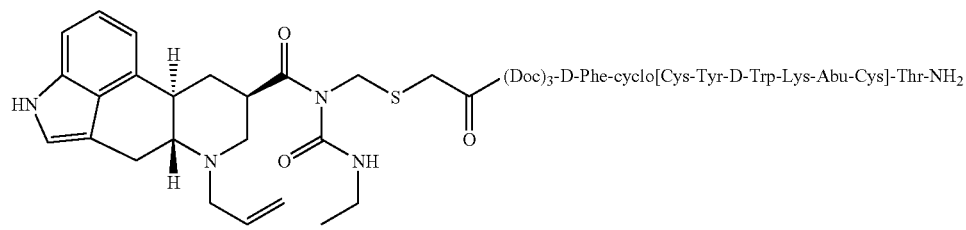 (Doc)₃-D-Phe-cyclo[Cys-Tyr-D-Trp-Lys-Abu-Cys]-Thr-NH₂

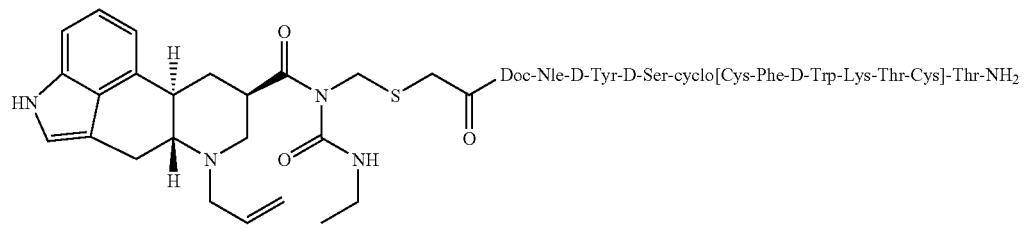 Doc-Nle-D-Tyr-D-Ser-cyclo[Cys-Phe-D-Trp-Lys-Thr-Cys]-Thr-NH₂

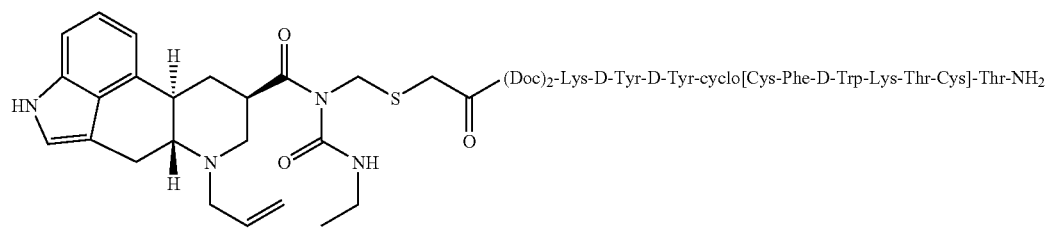 (Doc)₂-Lys-D-Tyr-D-Tyr-cyclo[Cys-Phe-D-Trp-Lys-Thr-Cys]-Thr-NH₂

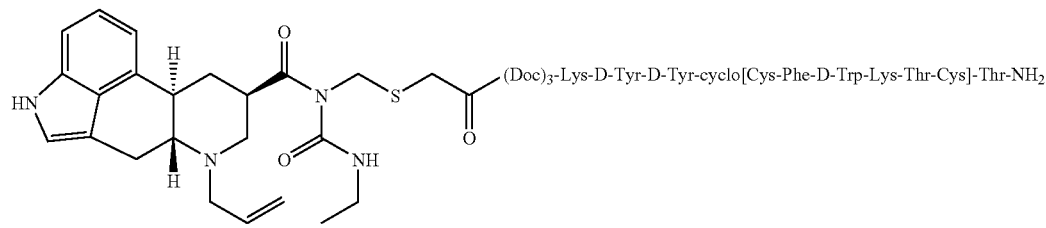 (Doc)₃-Lys-D-Tyr-D-Tyr-cyclo[Cys-Phe-D-Trp-Lys-Thr-Cys]-Thr-NH₂

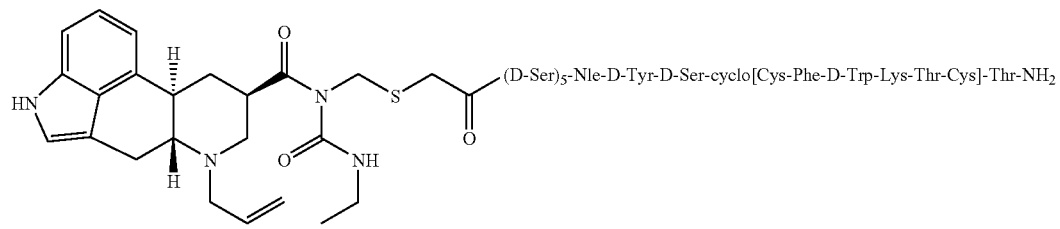 (D-Ser)₅-Nle-D-Tyr-D-Ser-cyclo[Cys-Phe-D-Trp-Lys-Thr-Cys]-Thr-NH₂

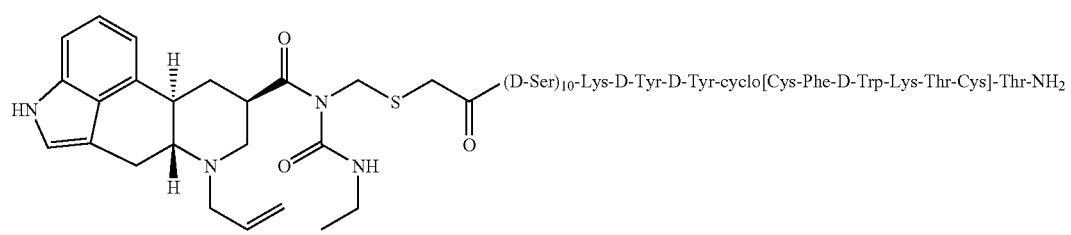 (D-Ser)₁₀-Lys-D-Tyr-D-Tyr-cyclo[Cys-Phe-D-Trp-Lys-Thr-Cys]-Thr-NH₂

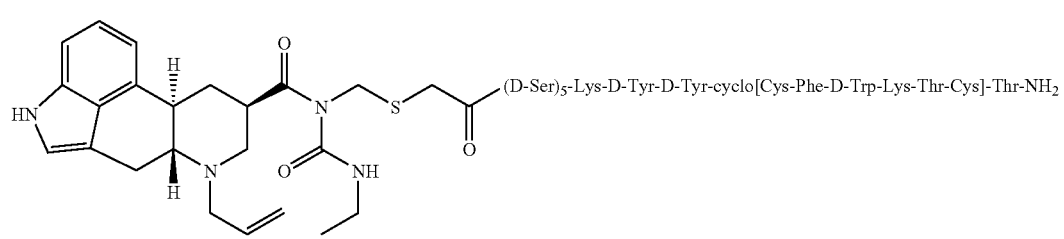 (D-Ser)₅-Lys-D-Tyr-D-Tyr-cyclo[Cys-Phe-D-Trp-Lys-Thr-Cys]-Thr-NH₂

-continued
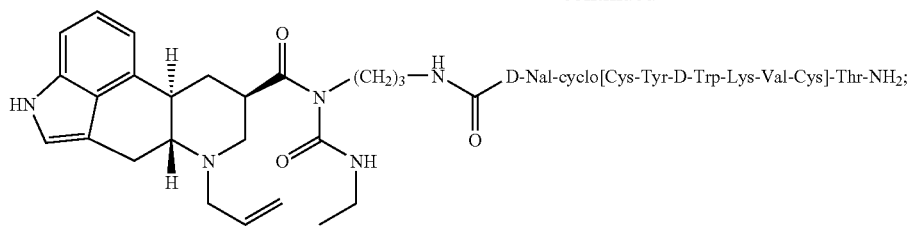 D-Nal-cyclo[Cys-Tyr-D-Trp-Lys-Val-Cys]-Thr-NH$_2$;
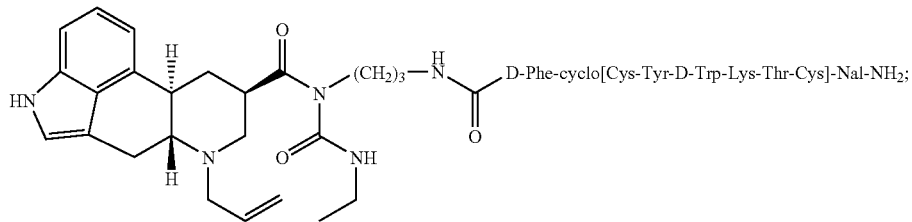 D-Phe-cyclo[Cys-Tyr-D-Trp-Lys-Thr-Cys]-Nal-NH$_2$;
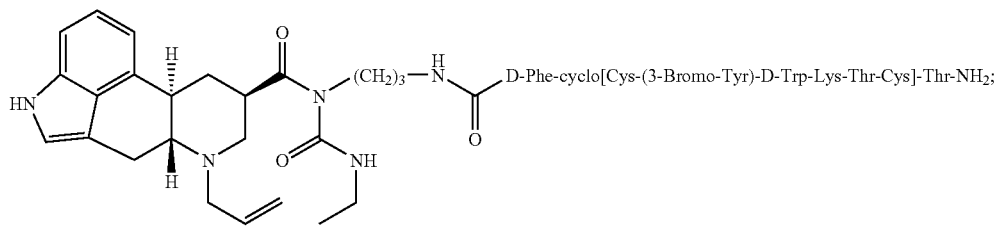 D-Phe-cyclo[Cys-(3-Bromo-Tyr)-D-Trp-Lys-Thr-Cys]-Thr-NH$_2$;
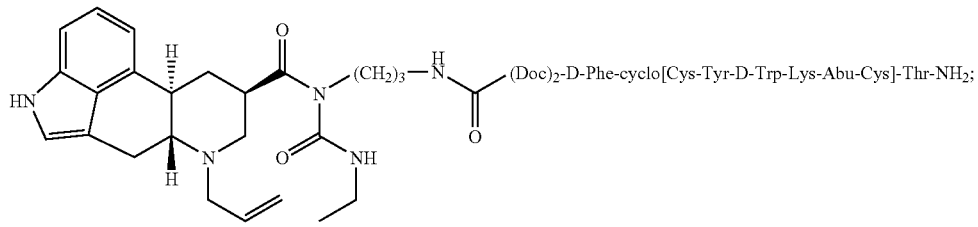 (Doc)$_2$-D-Phe-cyclo[Cys-Tyr-D-Trp-Lys-Abu-Cys]-Thr-NH$_2$
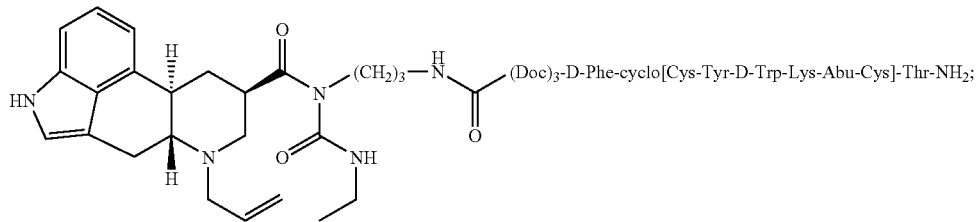 (Doc)$_3$-D-Phe-cyclo[Cys-Tyr-D-Trp-Lys-Abu-Cys]-Thr-NH$_2$;
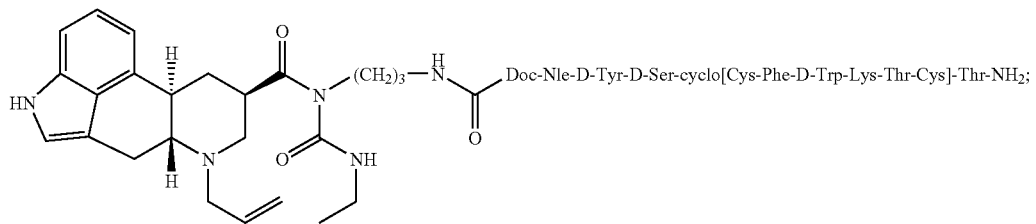 Doc-Nle-D-Tyr-D-Ser-cyclo[Cys-Phe-D-Trp-Lys-Thr-Cys]-Thr-NH$_2$;
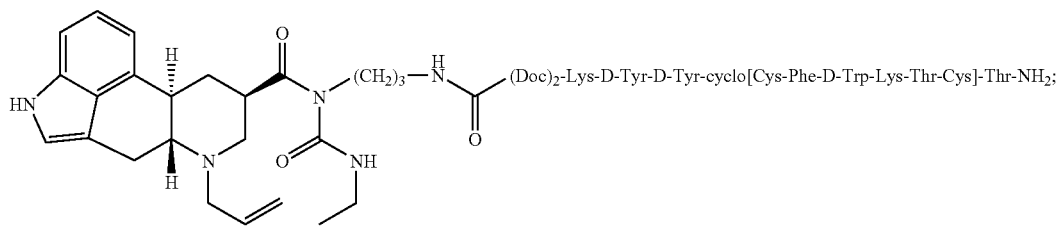 (Doc)$_2$-Lys-D-Tyr-D-Tyr-cyclo[Cys-Phe-D-Trp-Lys-Thr-Cys]-Thr-NH$_2$;

-continued

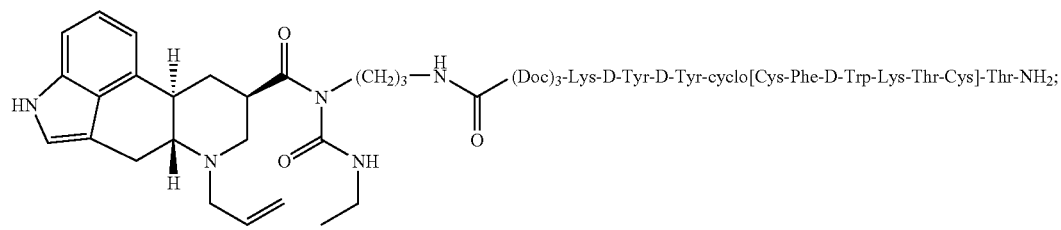 (Doc)₃-Lys-D-Tyr-D-Tyr-cyclo[Cys-Phe-D-Trp-Lys-Thr-Cys]-Thr-NH₂;

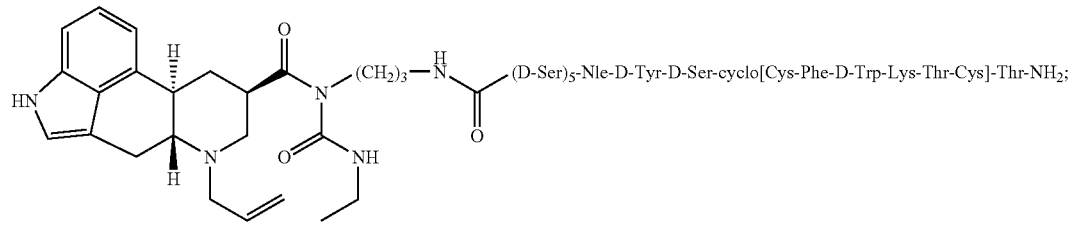 (D-Ser)₅-Nle-D-Tyr-D-Ser-cyclo[Cys-Phe-D-Trp-Lys-Thr-Cys]-Thr-NH₂;

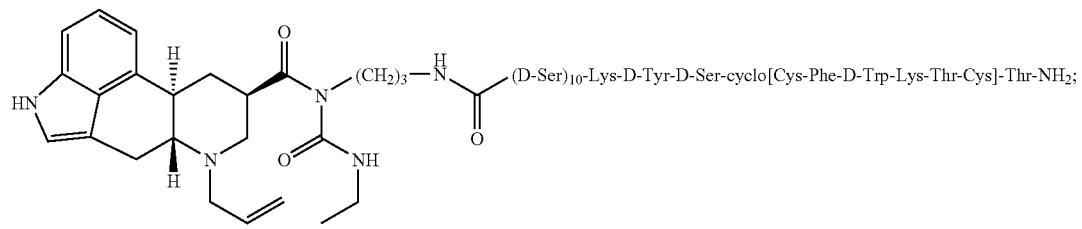 (D-Ser)₁₀-Lys-D-Tyr-D-Ser-cyclo[Cys-Phe-D-Trp-Lys-Thr-Cys]-Thr-NH₂;

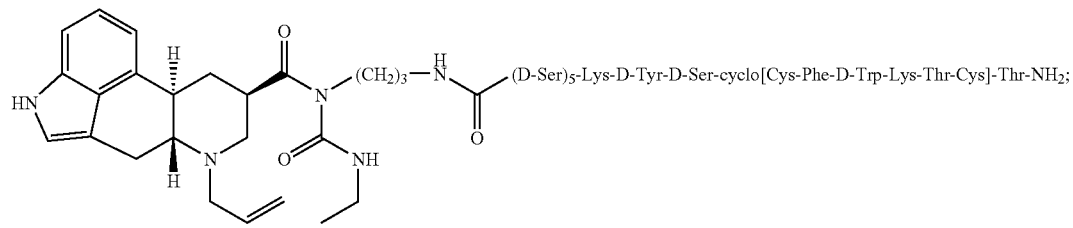 (D-Ser)₅-Lys-D-Tyr-D-Ser-cyclo[Cys-Phe-D-Trp-Lys-Thr-Cys]-Thr-NH₂;

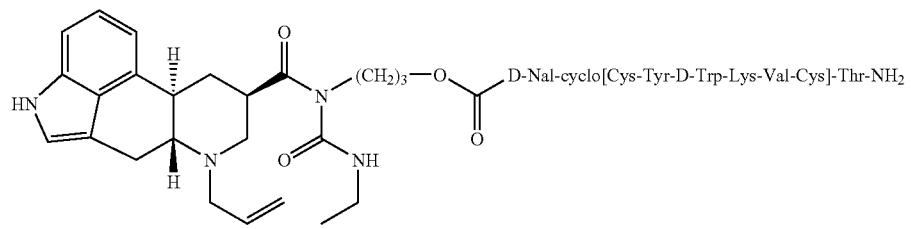 D-Nal-cyclo[Cys-Tyr-D-Trp-Lys-Val-Cys]-Thr-NH₂

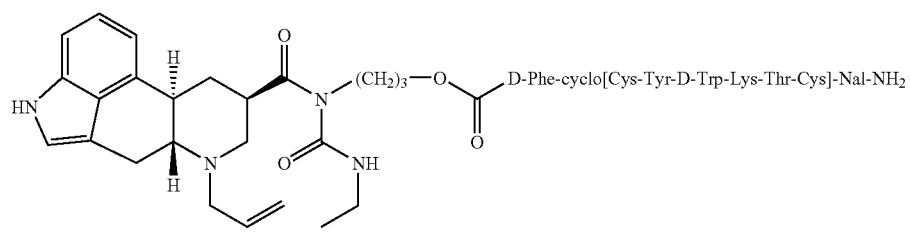 D-Phe-cyclo[Cys-Tyr-D-Trp-Lys-Thr-Cys]-Nal-NH₂

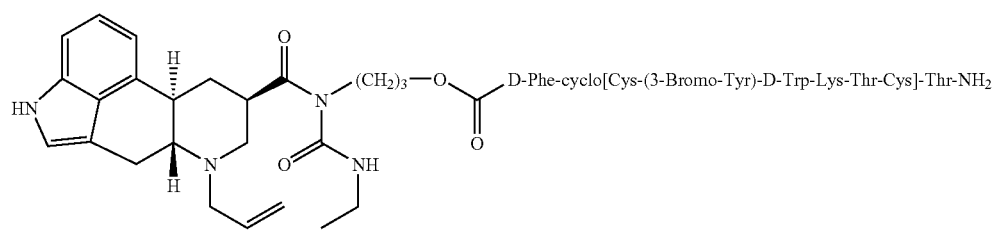 D-Phe-cyclo[Cys-(3-Bromo-Tyr)-D-Trp-Lys-Thr-Cys]-Thr-NH₂

-continued

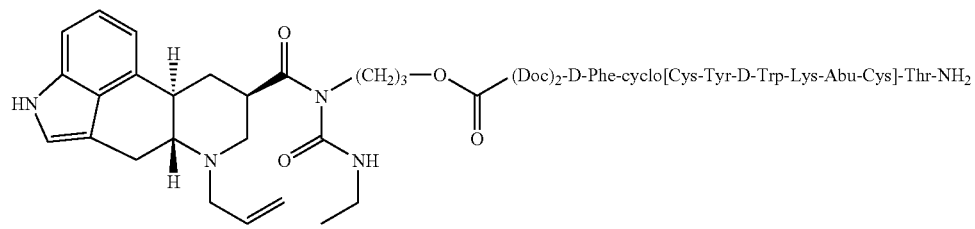
(Doc)₂-D-Phe-cyclo[Cys-Tyr-D-Trp-Lys-Abu-Cys]-Thr-NH₂

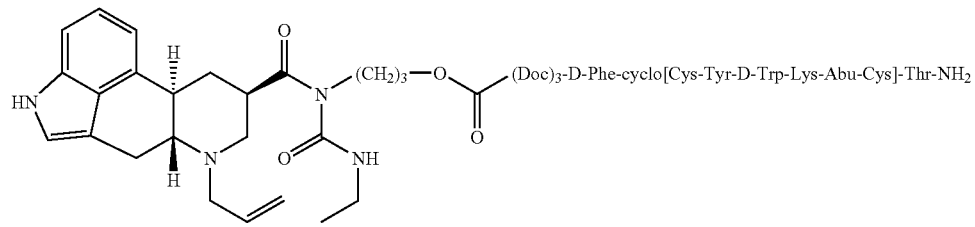
(Doc)₃-D-Phe-cyclo[Cys-Tyr-D-Trp-Lys-Abu-Cys]-Thr-NH₂

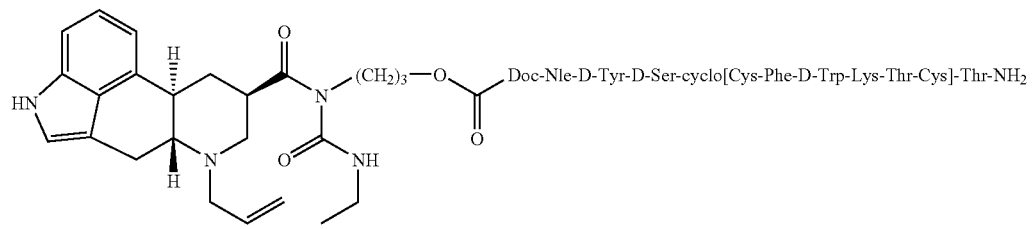
Doc-Nle-D-Tyr-D-Ser-cyclo[Cys-Phe-D-Trp-Lys-Thr-Cys]-Thr-NH₂

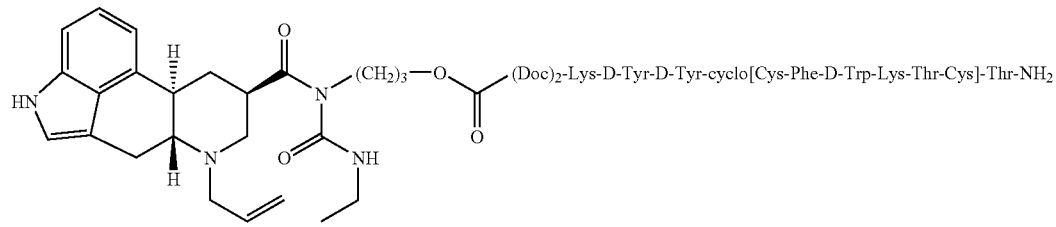
(Doc)₂-Lys-D-Tyr-D-Tyr-cyclo[Cys-Phe-D-Trp-Lys-Thr-Cys]-Thr-NH₂

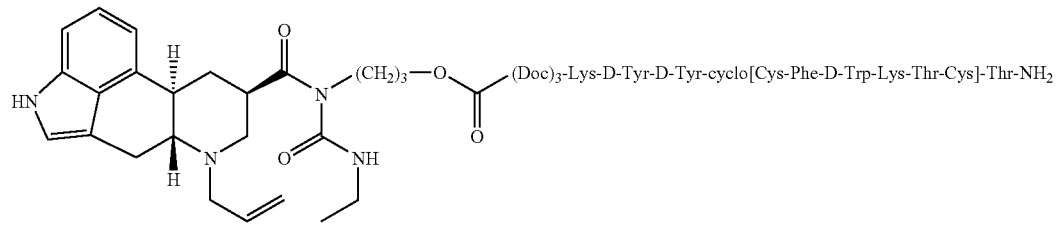
(Doc)₃-Lys-D-Tyr-D-Tyr-cyclo[Cys-Phe-D-Trp-Lys-Thr-Cys]-Thr-NH₂

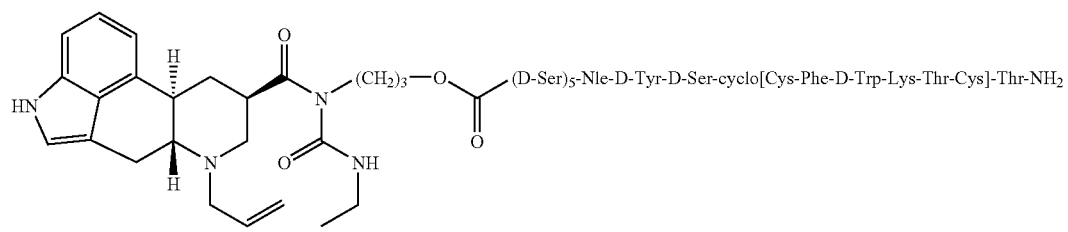
(D-Ser)₅-Nle-D-Tyr-D-Ser-cyclo[Cys-Phe-D-Trp-Lys-Thr-Cys]-Thr-NH₂

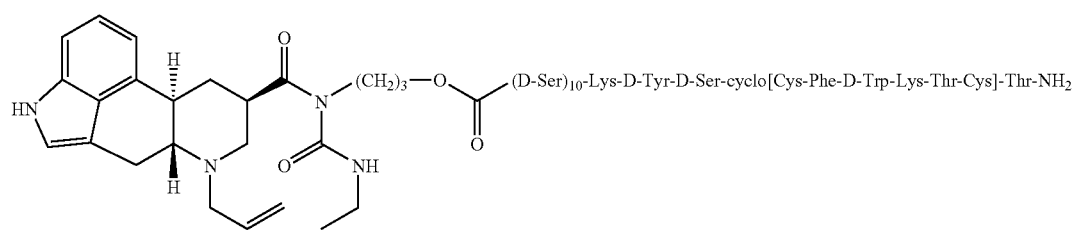
(D-Ser)₁₀-Lys-D-Tyr-D-Ser-cyclo[Cys-Phe-D-Trp-Lys-Thr-Cys]-Thr-NH₂

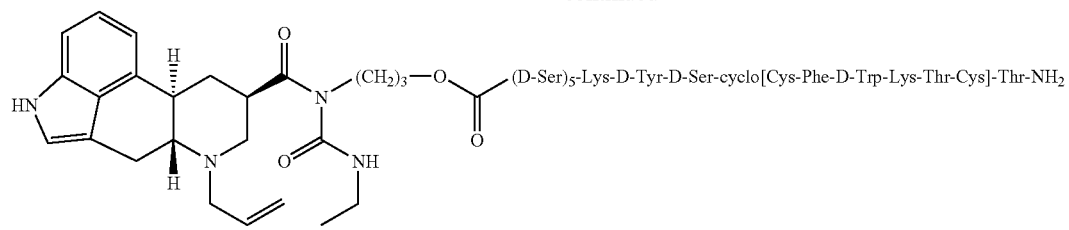
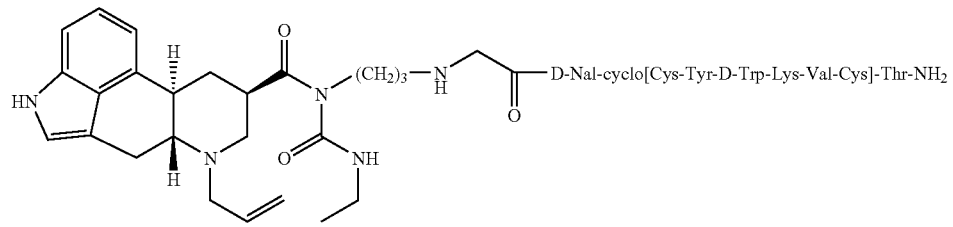
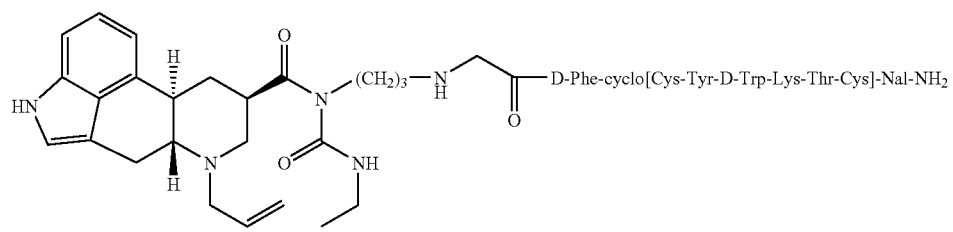
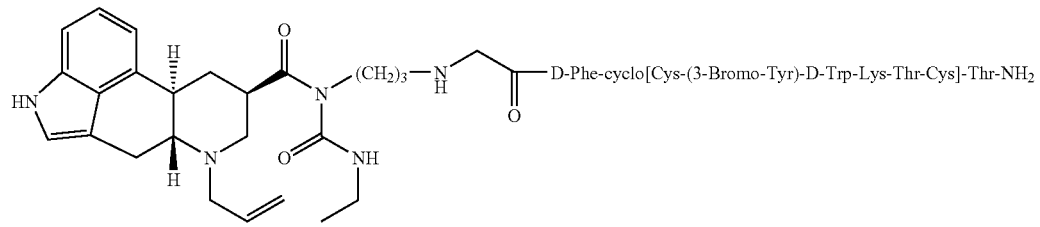
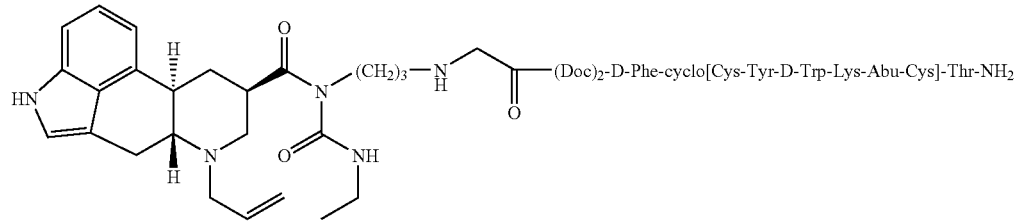
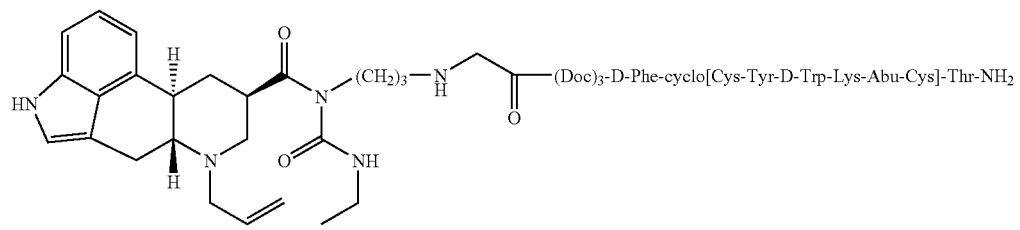
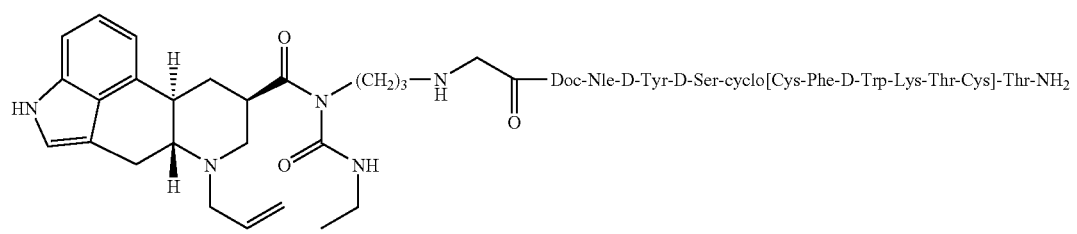

-continued

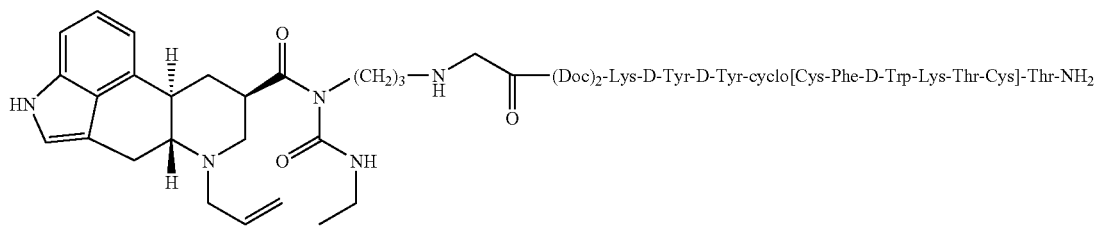(Doc)$_2$-Lys-D-Tyr-D-Tyr-cyclo[Cys-Phe-D-Trp-Lys-Thr-Cys]-Thr-NH$_2$

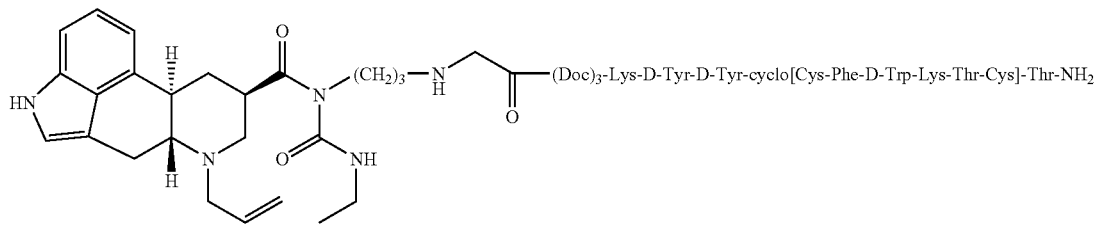(Doc)$_3$-Lys-D-Tyr-D-Tyr-cyclo[Cys-Phe-D-Trp-Lys-Thr-Cys]-Thr-NH$_2$

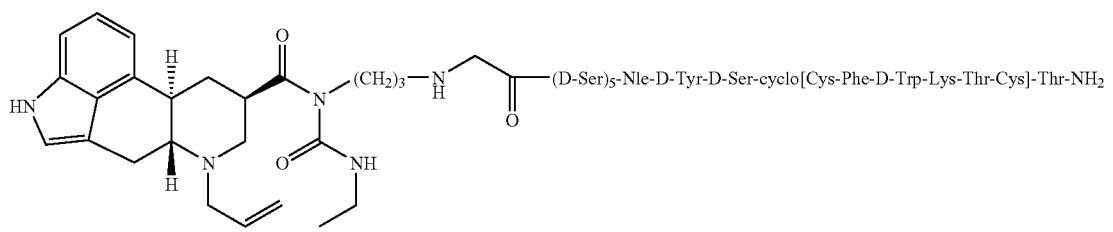(D-Ser)$_5$-Nle-D-Tyr-D-Ser-cyclo[Cys-Phe-D-Trp-Lys-Thr-Cys]-Thr-NH$_2$

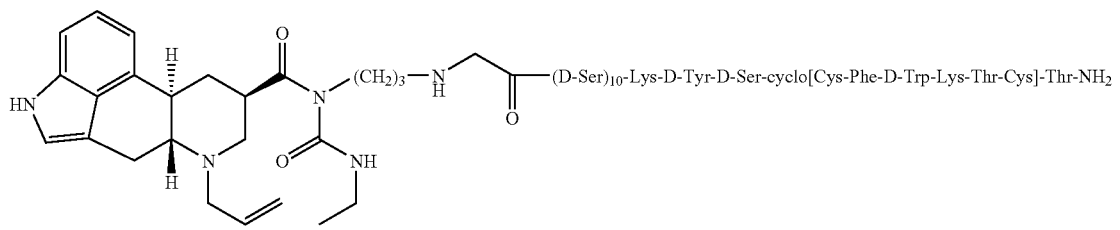(D-Ser)$_{10}$-Lys-D-Tyr-D-Ser-cyclo[Cys-Phe-D-Trp-Lys-Thr-Cys]-Thr-NH$_2$

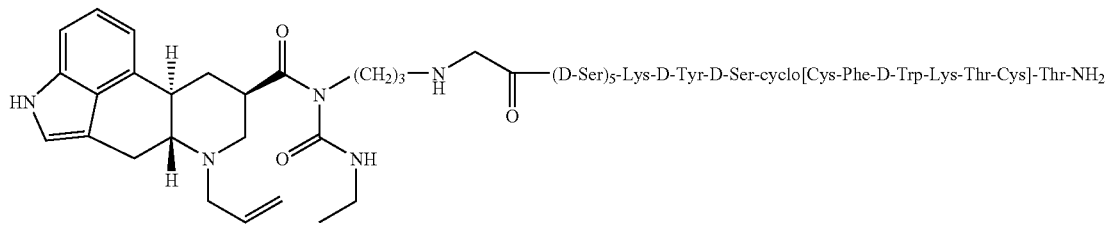(D-Ser)$_5$-Lys-D-Tyr-D-Ser-cyclo[Cys-Phe-D-Trp-Lys-Thr-Cys]-Thr-NH$_2$

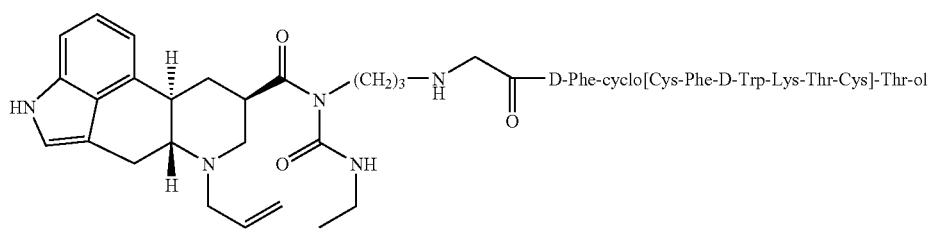D-Phe-cyclo[Cys-Phe-D-Trp-Lys-Thr-Cys]-Thr-ol

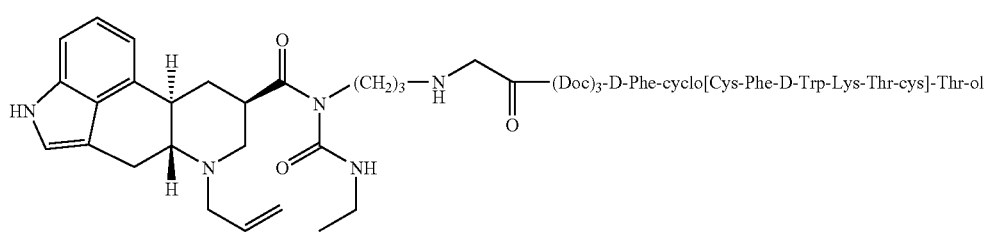(Doc)$_3$-D-Phe-cyclo[Cys-Phe-D-Trp-Lys-Thr-cys]-Thr-ol

-continued
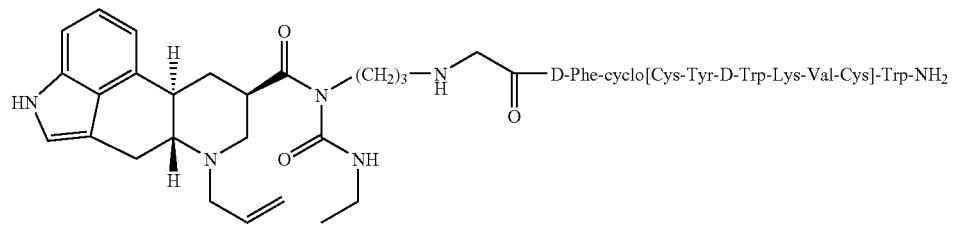
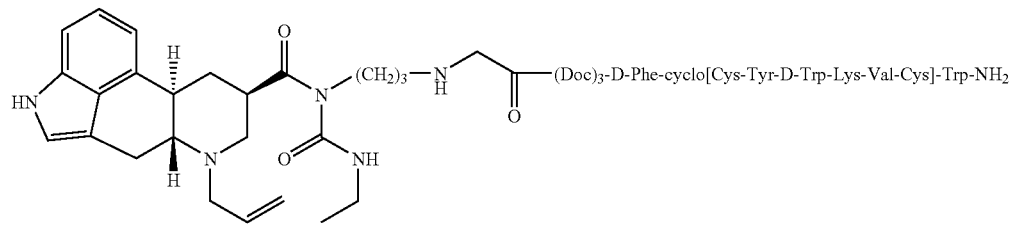
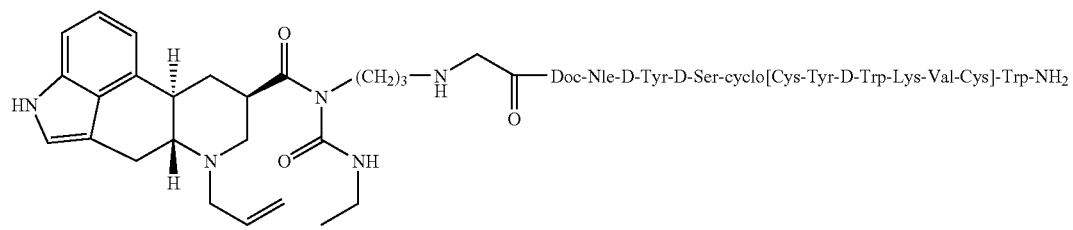
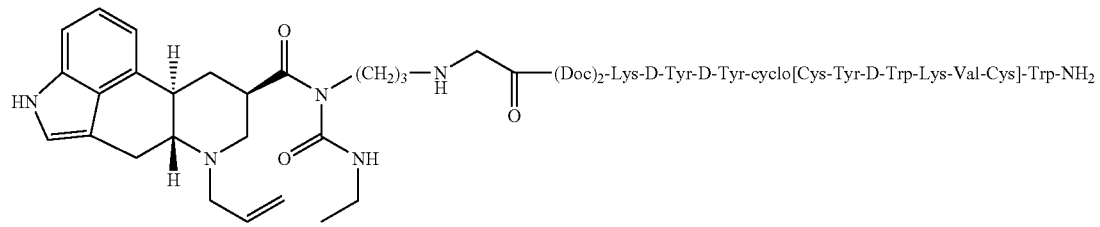
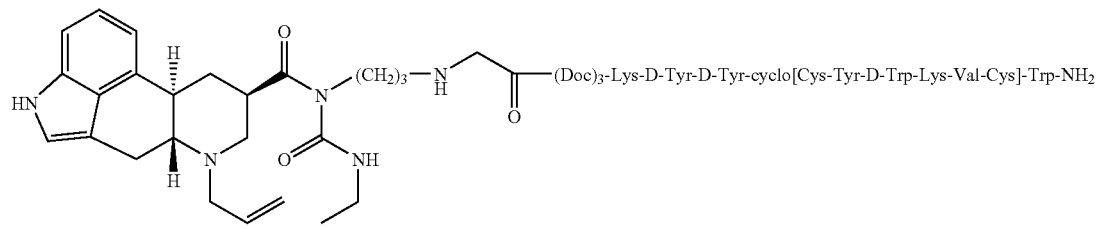
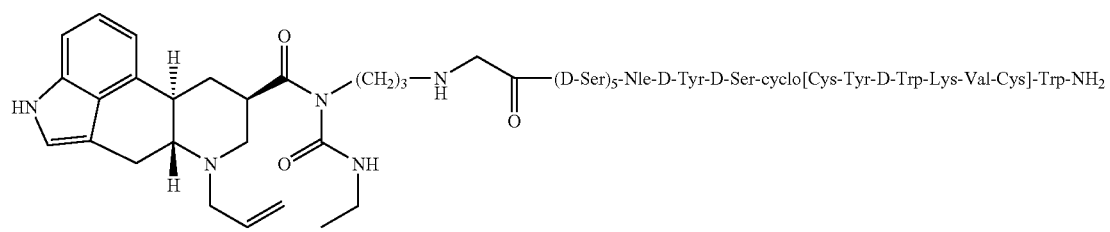
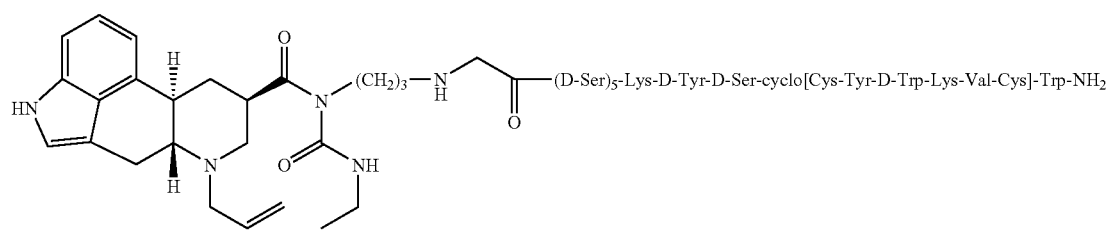

-continued
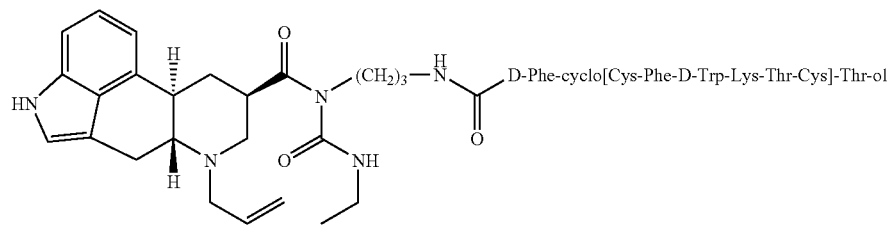 D-Phe-cyclo[Cys-Phe-D-Trp-Lys-Thr-Cys]-Thr-ol
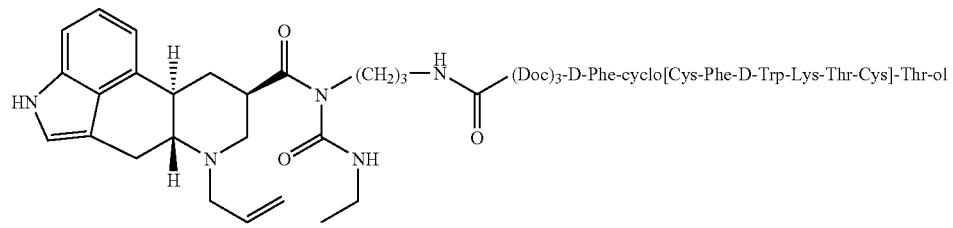 (Doc)₃-D-Phe-cyclo[Cys-Phe-D-Trp-Lys-Thr-Cys]-Thr-ol
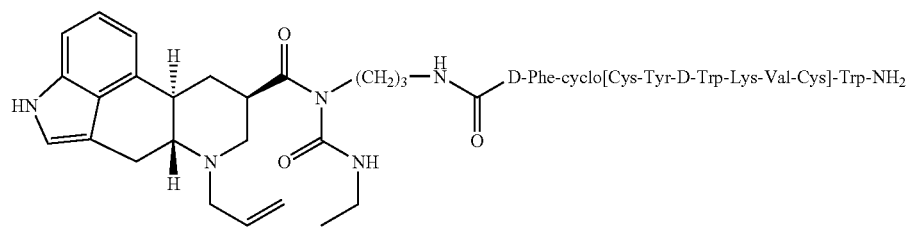 D-Phe-cyclo[Cys-Tyr-D-Trp-Lys-Val-Cys]-Trp-NH₂
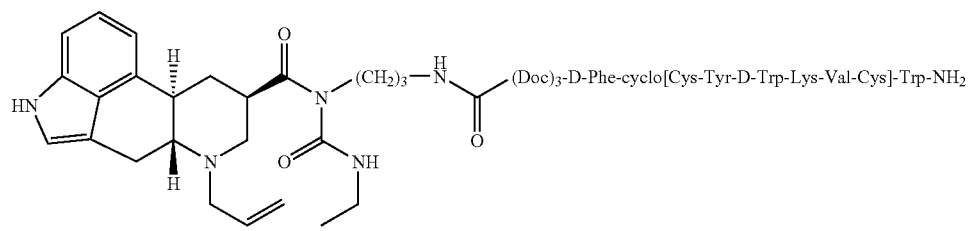 (Doc)₃-D-Phe-cyclo[Cys-Tyr-D-Trp-Lys-Val-Cys]-Trp-NH₂
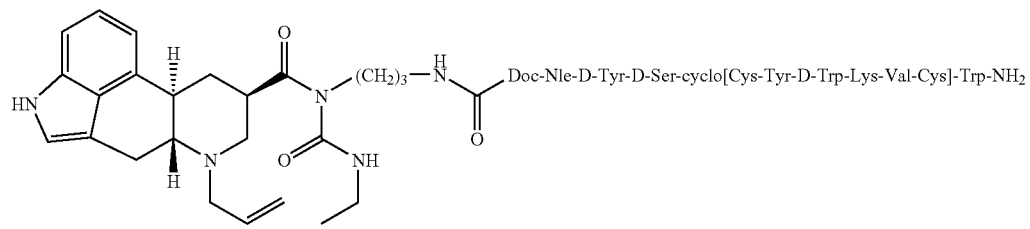 Doc-Nle-D-Tyr-D-Ser-cyclo[Cys-Tyr-D-Trp-Lys-Val-Cys]-Trp-NH₂
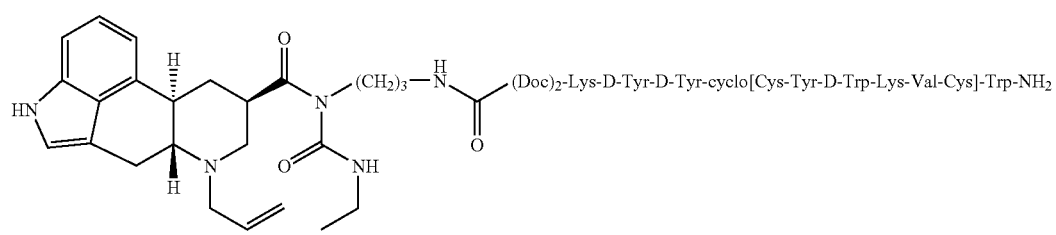 (Doc)₂-Lys-D-Tyr-D-Tyr-cyclo[Cys-Tyr-D-Trp-Lys-Val-Cys]-Trp-NH₂
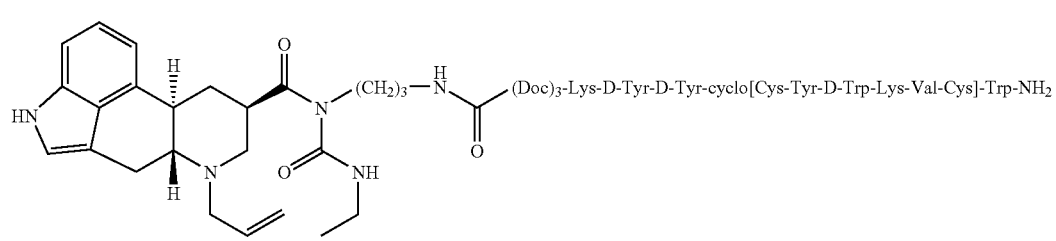 (Doc)₃-Lys-D-Tyr-D-Tyr-cyclo[Cys-Tyr-D-Trp-Lys-Val-Cys]-Trp-NH₂

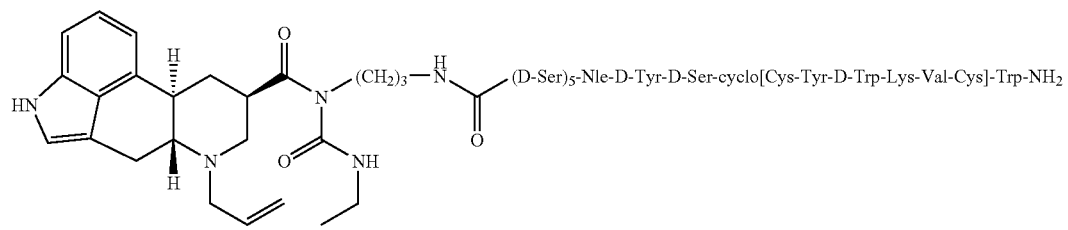
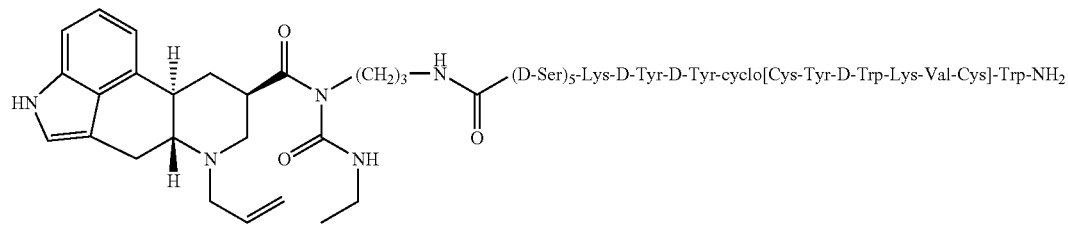
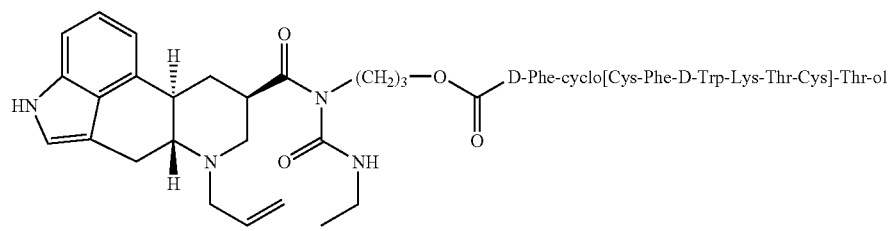
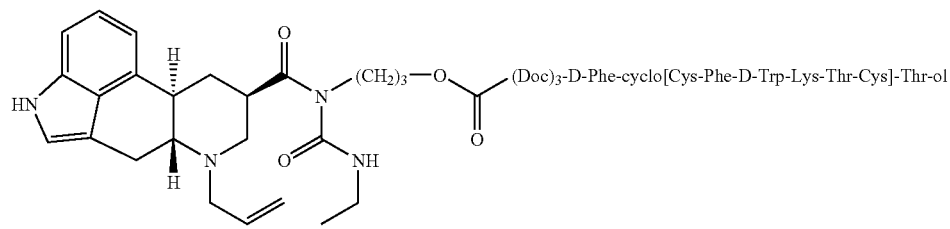
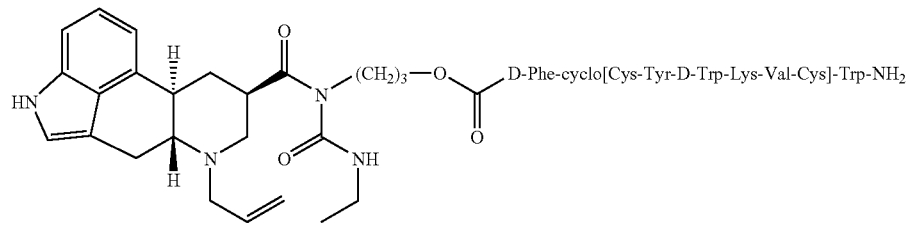
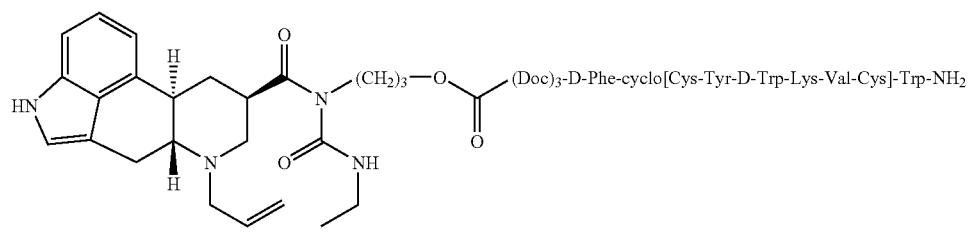
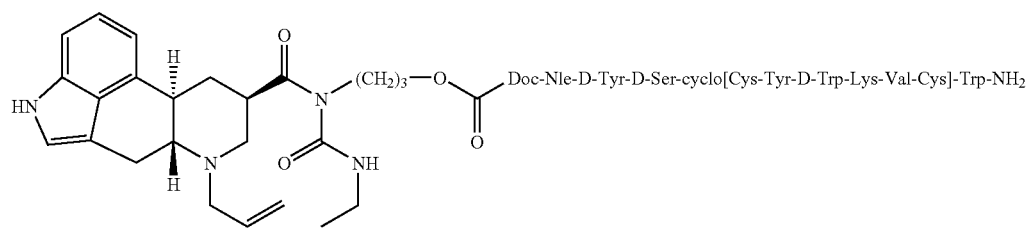

-continued
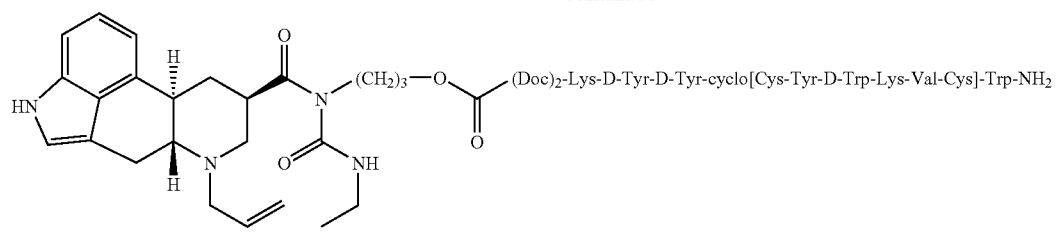
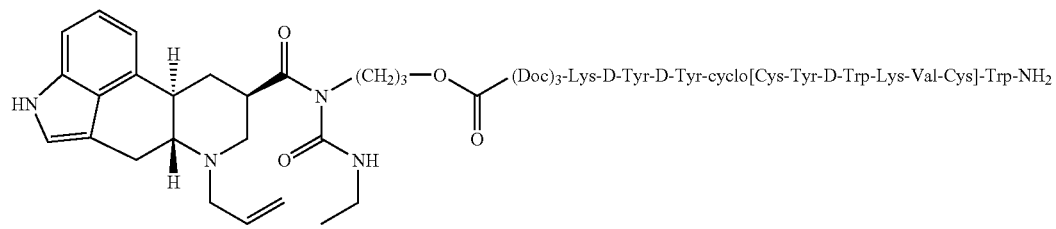
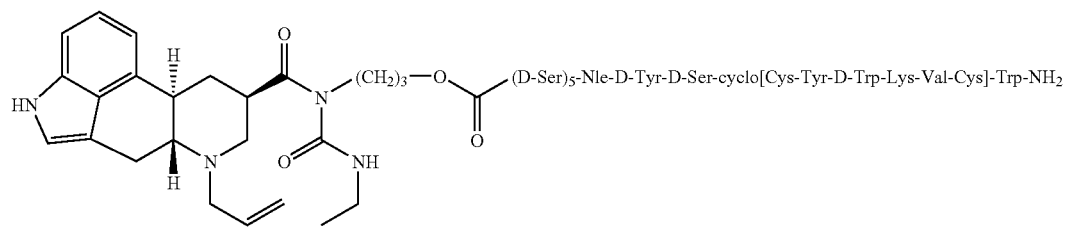
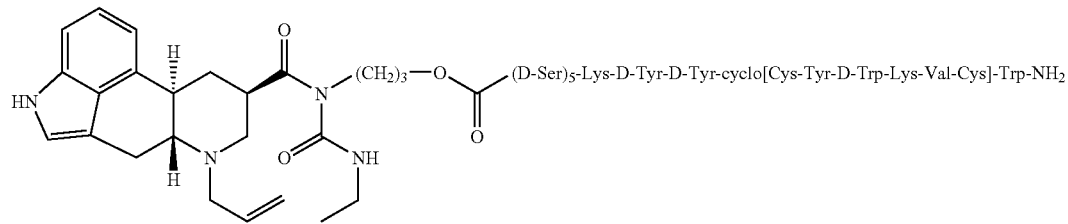
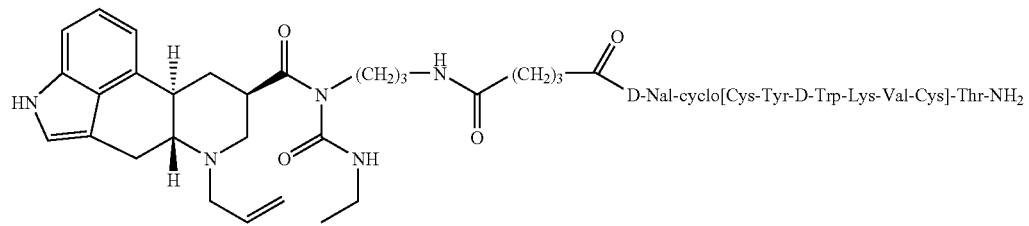
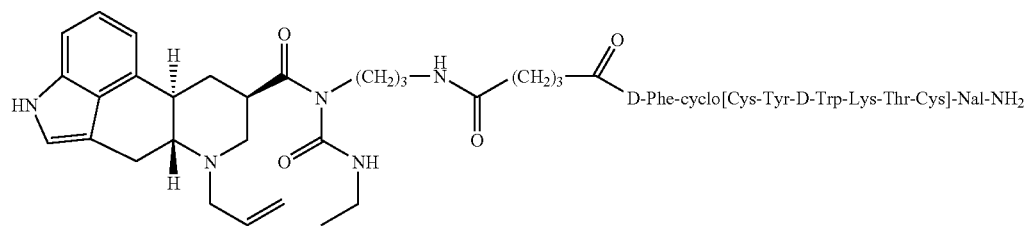
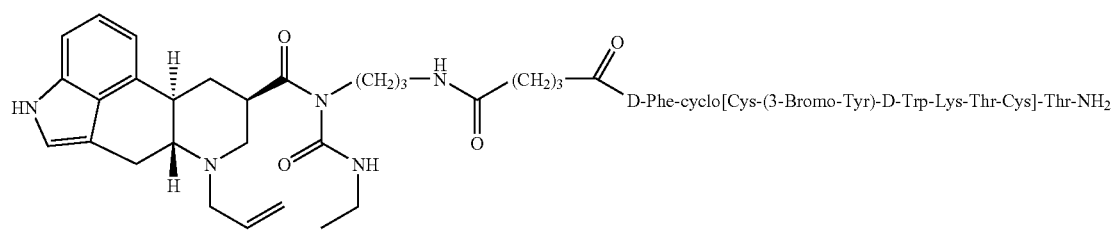

-continued

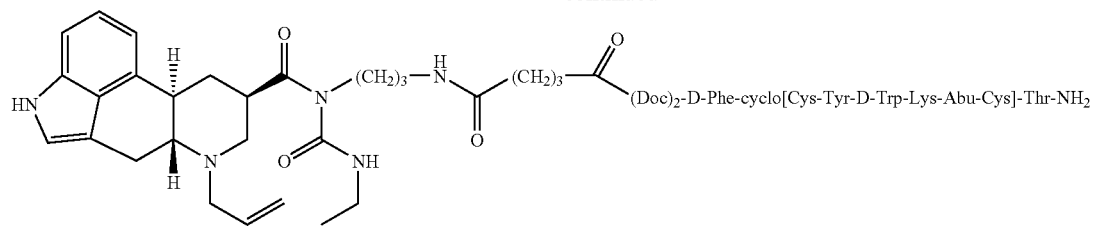
(Doc)₂-D-Phe-cyclo[Cys-Tyr-D-Trp-Lys-Abu-Cys]-Thr-NH₂

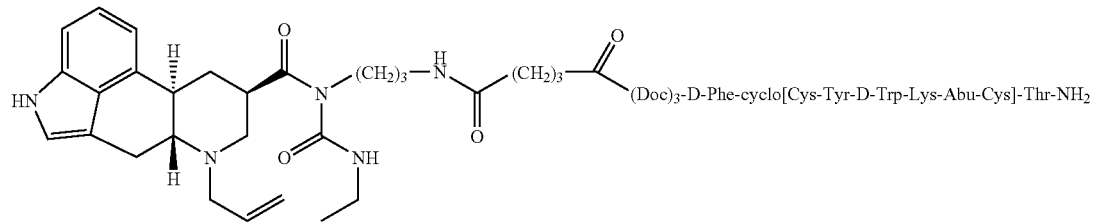
(Doc)₃-D-Phe-cyclo[Cys-Tyr-D-Trp-Lys-Abu-Cys]-Thr-NH₂

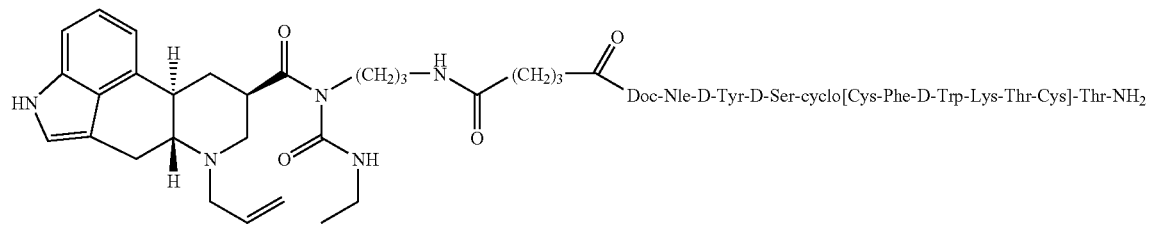
Doc-Nle-D-Tyr-D-Ser-cyclo[Cys-Phe-D-Trp-Lys-Thr-Cys]-Thr-NH₂

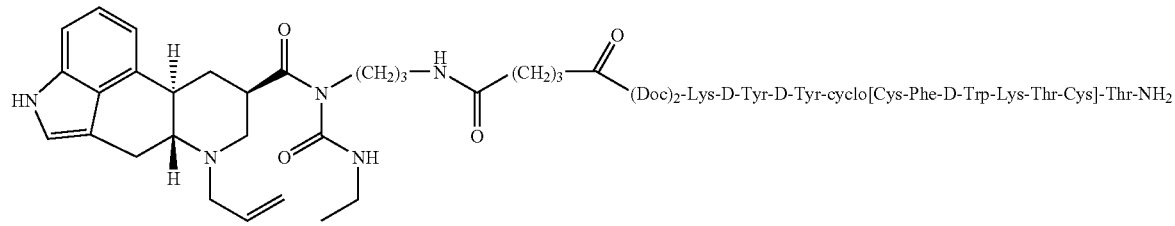
(Doc)₂-Lys-D-Tyr-D-Tyr-cyclo[Cys-Phe-D-Trp-Lys-Thr-Cys]-Thr-NH₂

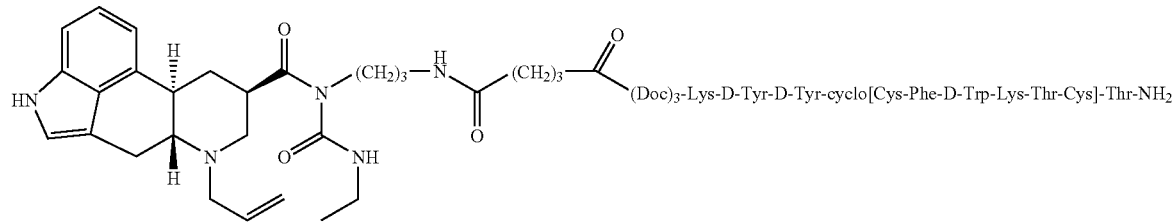
(Doc)₃-Lys-D-Tyr-D-Tyr-cyclo[Cys-Phe-D-Trp-Lys-Thr-Cys]-Thr-NH₂

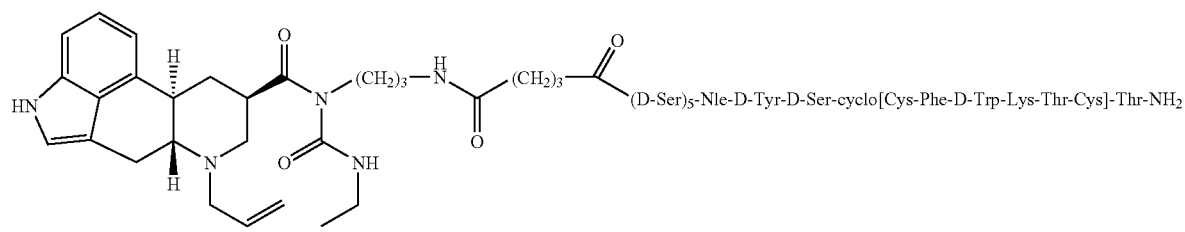
(D-Ser)₅-Nle-D-Tyr-D-Ser-cyclo[Cys-Phe-D-Trp-Lys-Thr-Cys]-Thr-NH₂

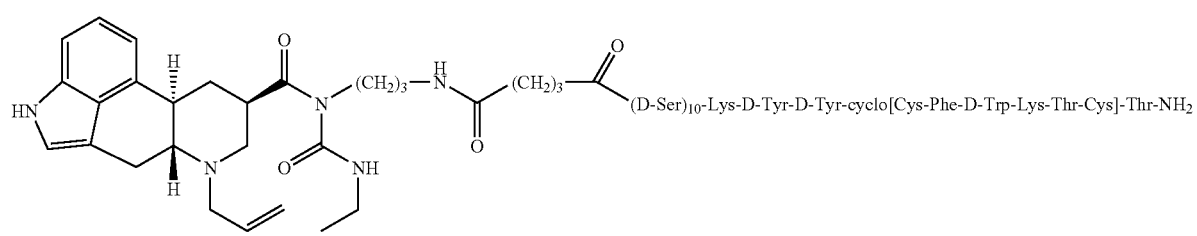
(D-Ser)₁₀-Lys-D-Tyr-D-Tyr-cyclo[Cys-Phe-D-Trp-Lys-Thr-Cys]-Thr-NH₂

-continued
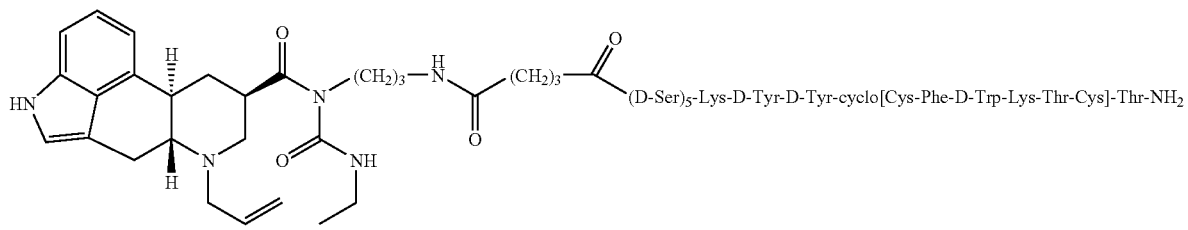
(D-Ser)$_5$-Lys-D-Tyr-D-Tyr-cyclo[Cys-Phe-D-Trp-Lys-Thr-Cys]-Thr-NH$_2$
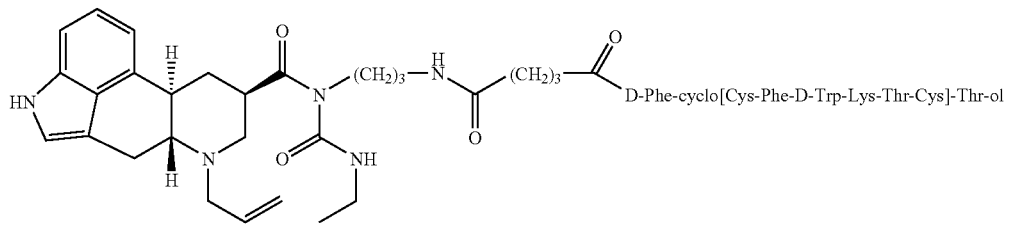
D-Phe-cyclo[Cys-Phe-D-Trp-Lys-Thr-Cys]-Thr-ol
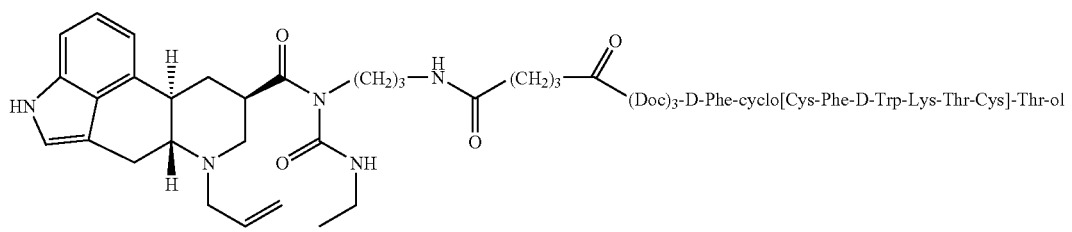
(Doc)$_3$-D-Phe-cyclo[Cys-Phe-D-Trp-Lys-Thr-Cys]-Thr-ol
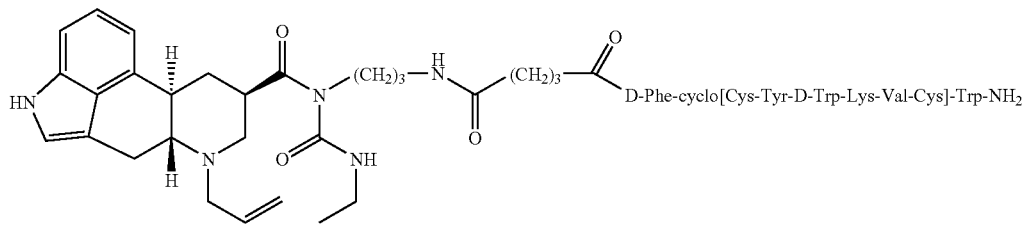
D-Phe-cyclo[Cys-Tyr-D-Trp-Lys-Val-Cys]-Trp-NH$_2$
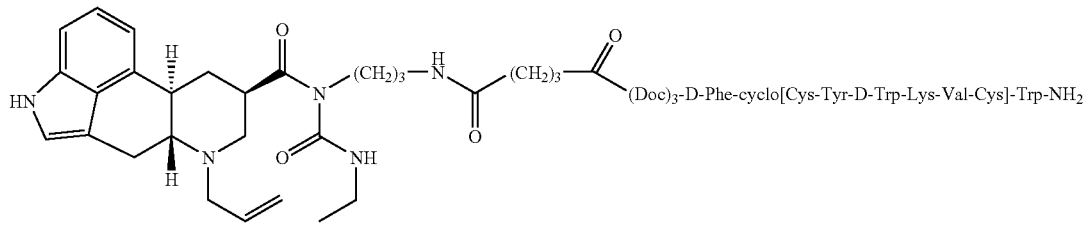
(Doc)$_3$-D-Phe-cyclo[Cys-Tyr-D-Trp-Lys-Val-Cys]-Trp-NH$_2$
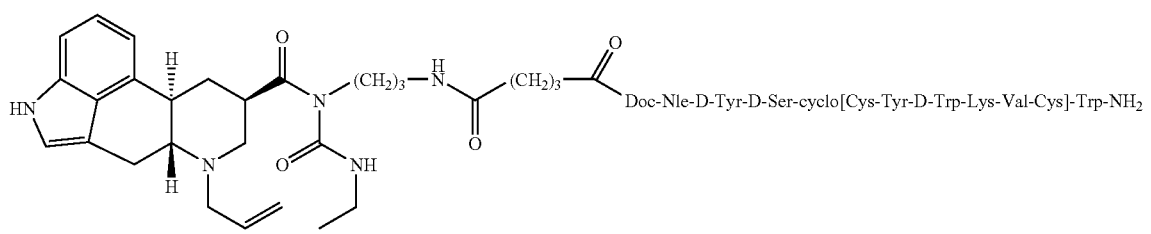
Doc-Nle-D-Tyr-D-Ser-cyclo[Cys-Tyr-D-Trp-Lys-Val-Cys]-Trp-NH$_2$
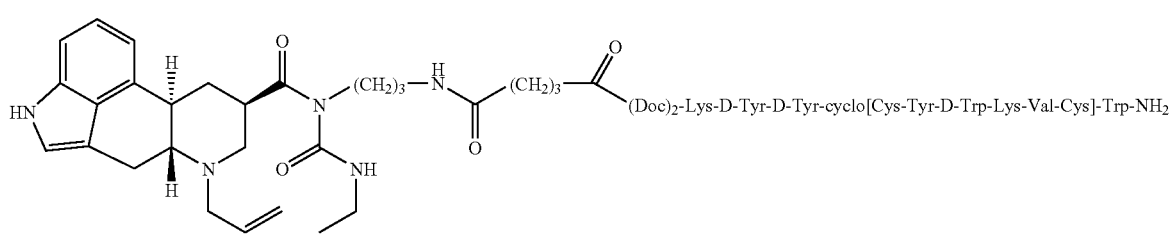
(Doc)$_2$-Lys-D-Tyr-D-Tyr-cyclo[Cys-Tyr-D-Trp-Lys-Val-Cys]-Trp-NH$_2$ -continued
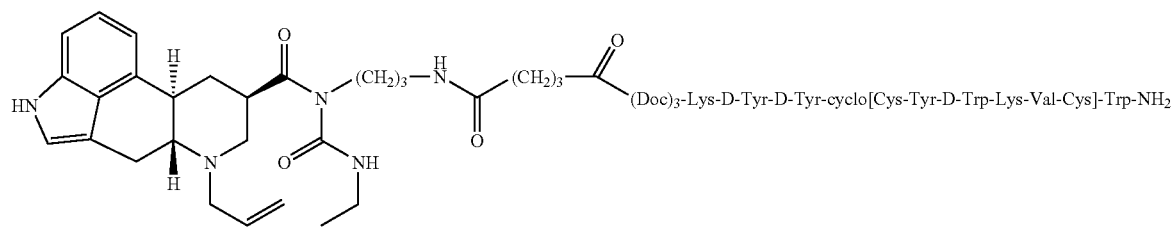
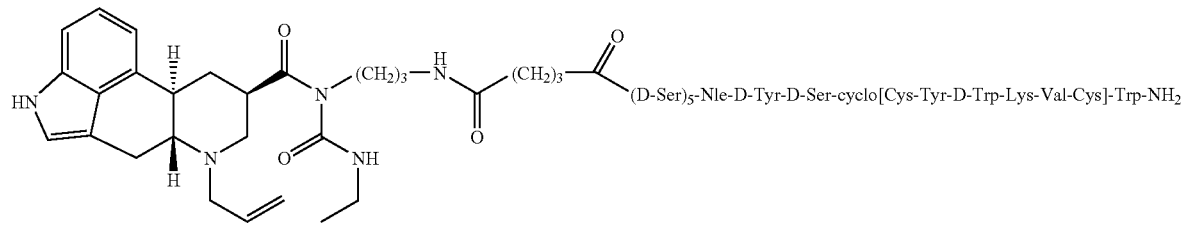
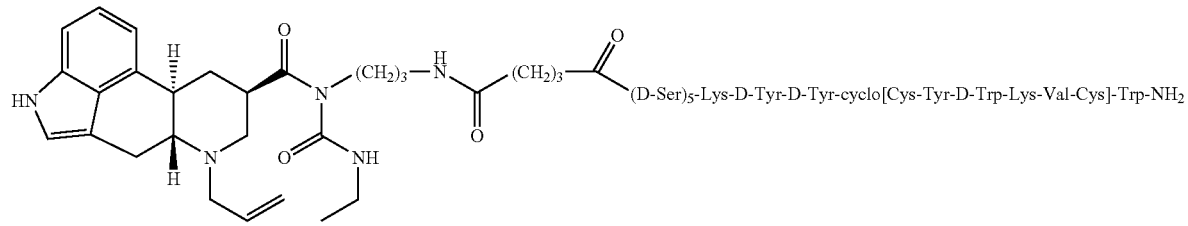
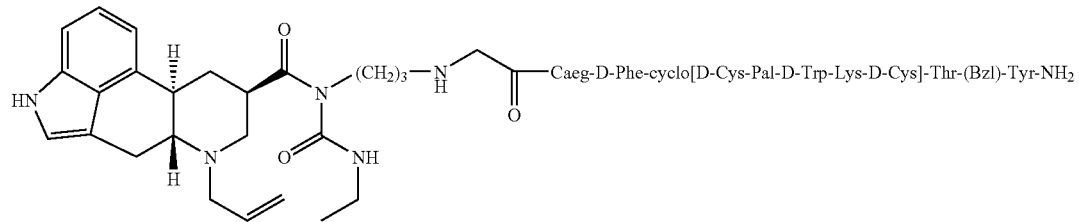
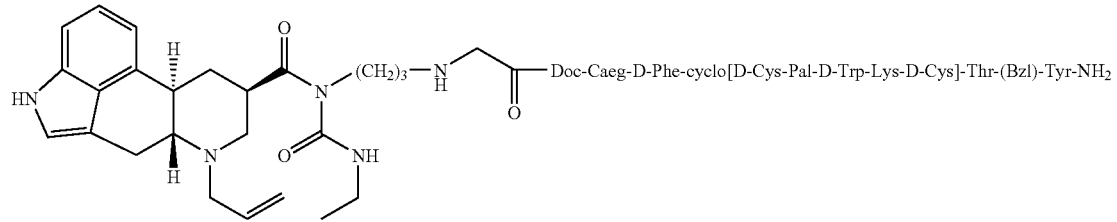
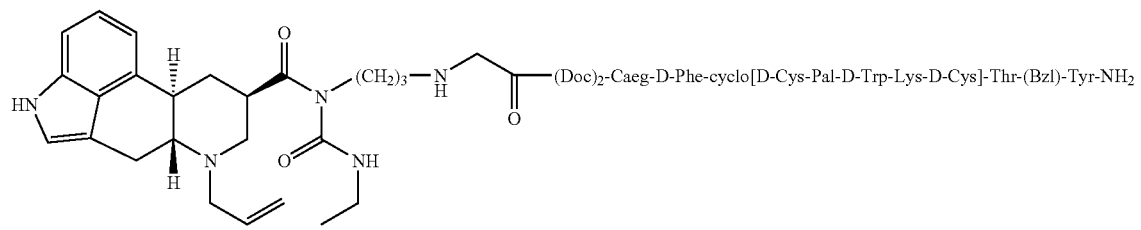
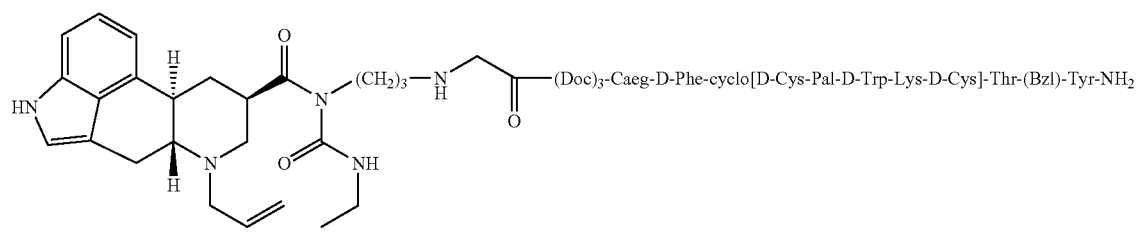

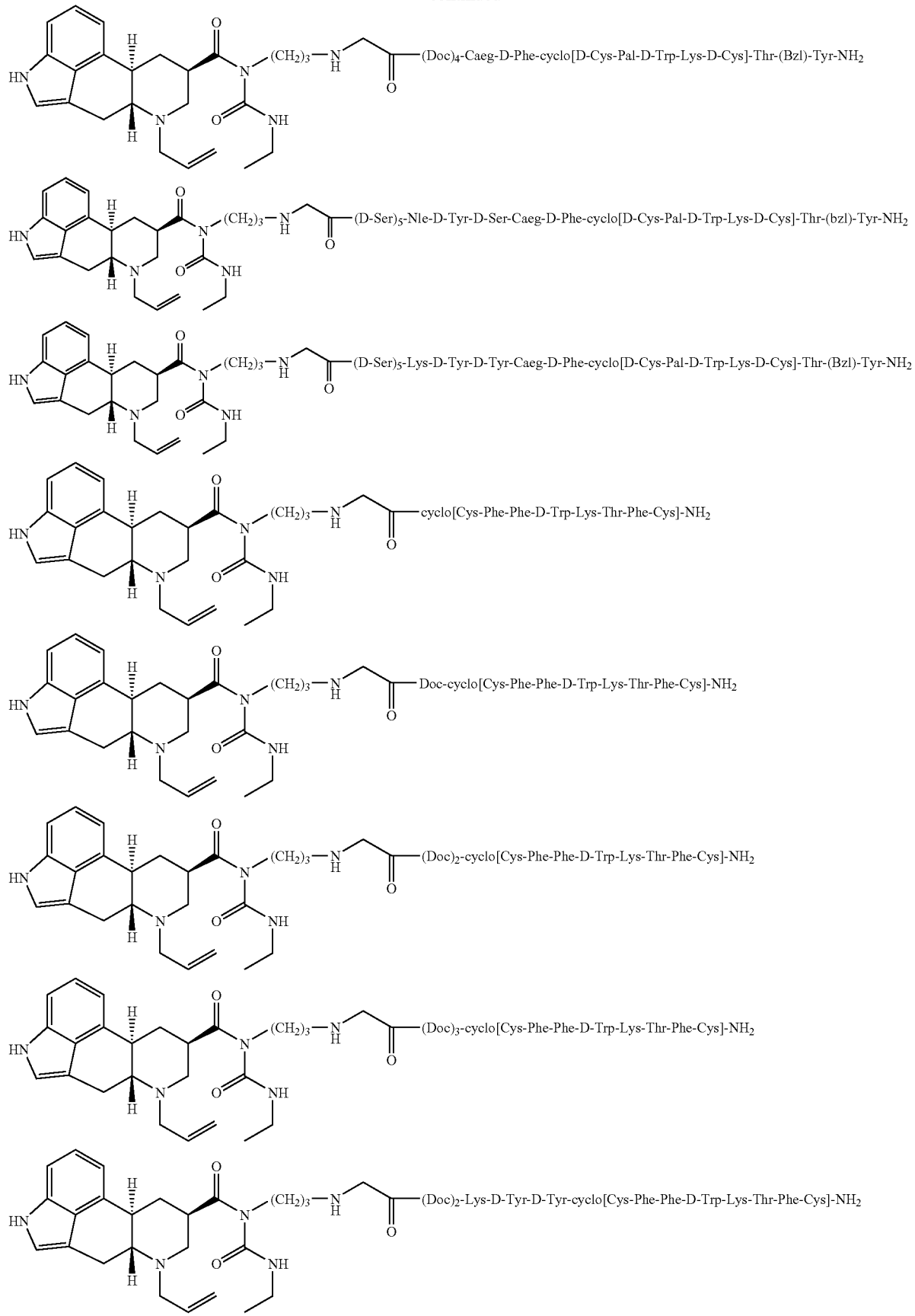

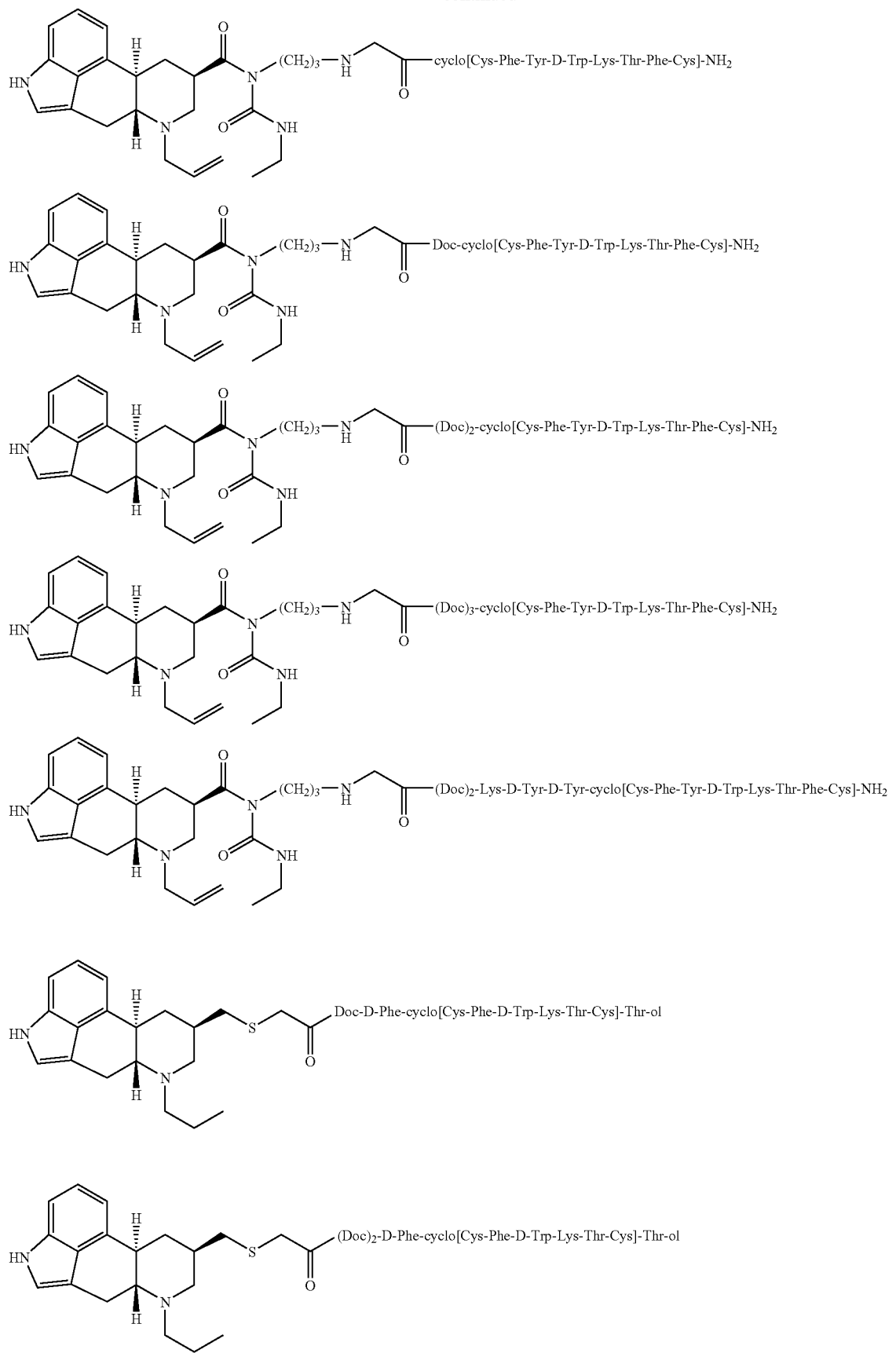

-continued
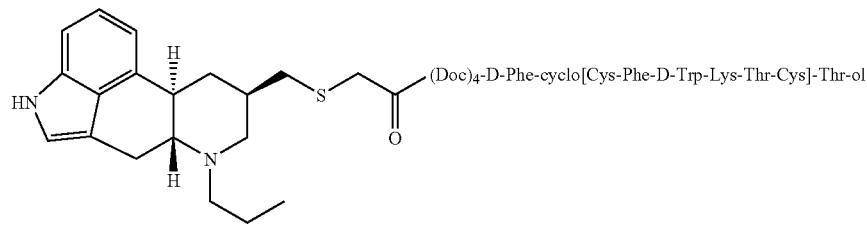
(Doc)₄-D-Phe-cyclo[Cys-Phe-D-Trp-Lys-Thr-Cys]-Thr-ol
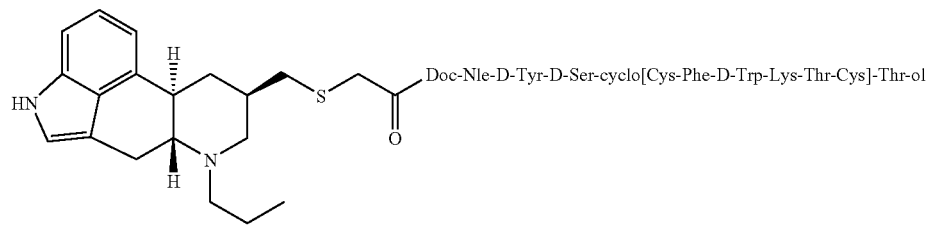
Doc-Nle-D-Tyr-D-Ser-cyclo[Cys-Phe-D-Trp-Lys-Thr-Cys]-Thr-ol
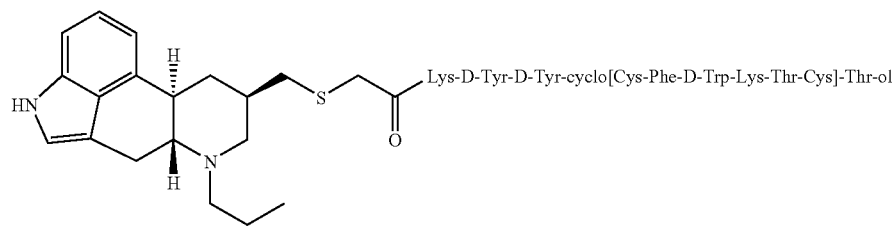
Lys-D-Tyr-D-Tyr-cyclo[Cys-Phe-D-Trp-Lys-Thr-Cys]-Thr-ol
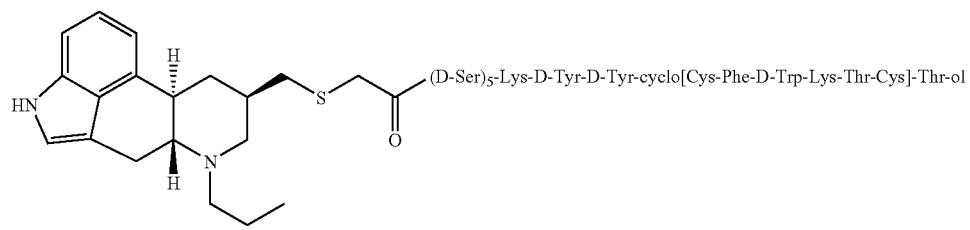
(D-Ser)₅-Lys-D-Tyr-D-Tyr-cyclo[Cys-Phe-D-Trp-Lys-Thr-Cys]-Thr-ol
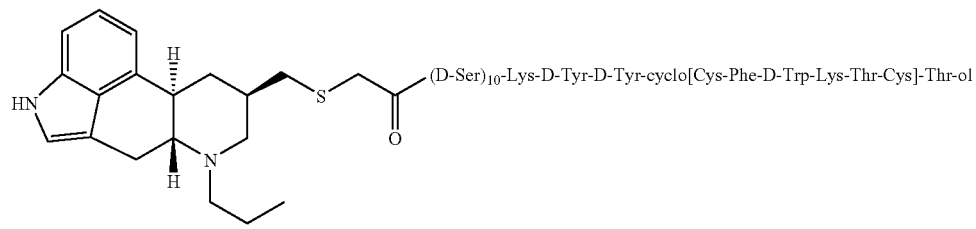
(D-Ser)₁₀-Lys-D-Tyr-D-Tyr-cyclo[Cys-Phe-D-Trp-Lys-Thr-Cys]-Thr-ol
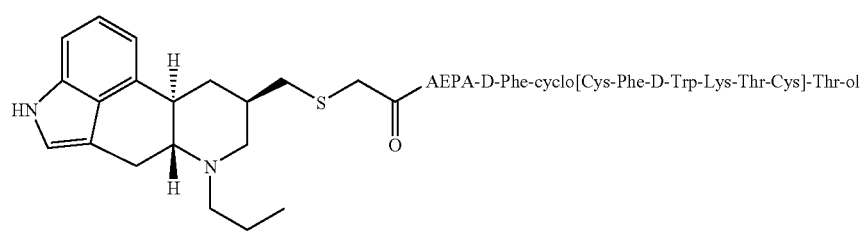
AEPA-D-Phe-cyclo[Cys-Phe-D-Trp-Lys-Thr-Cys]-Thr-ol
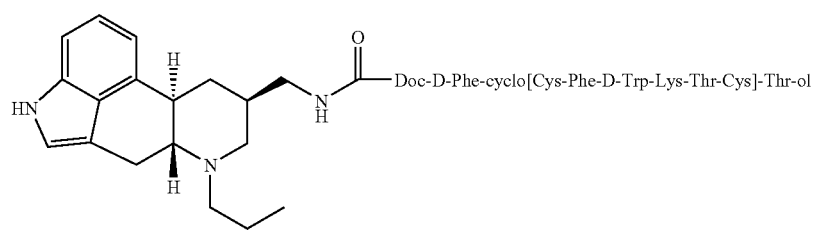
Doc-D-Phe-cyclo[Cys-Phe-D-Trp-Lys-Thr-Cys]-Thr-ol -continued
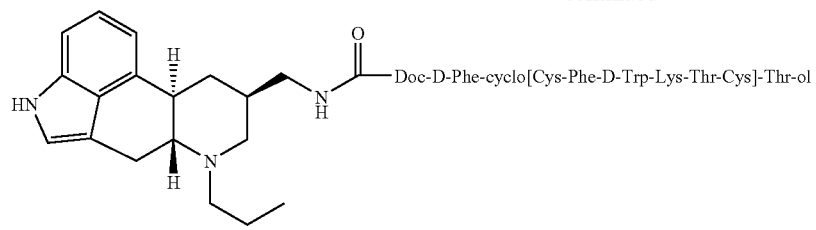
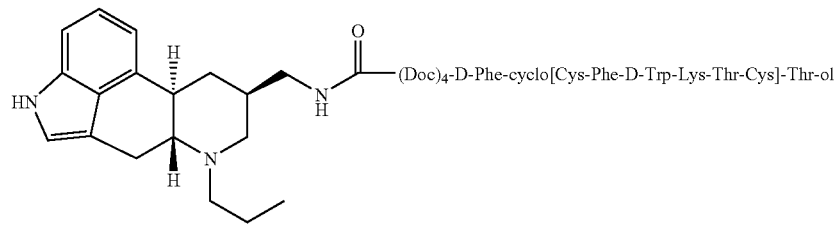
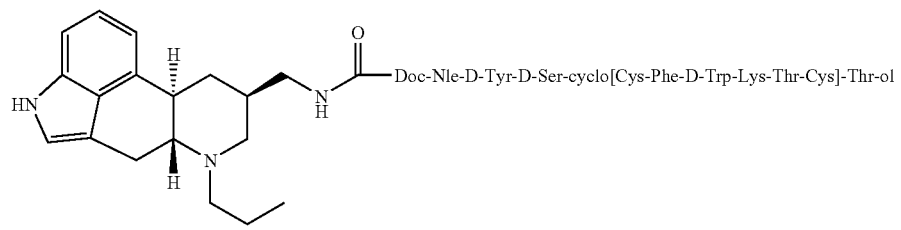
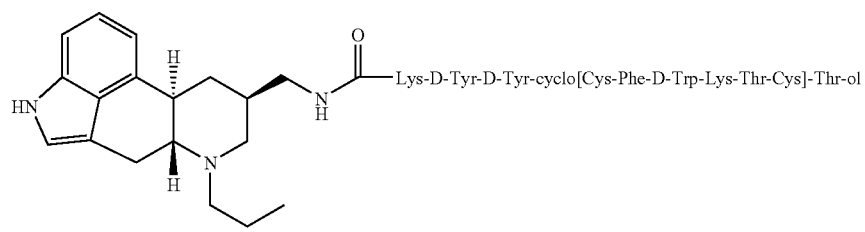
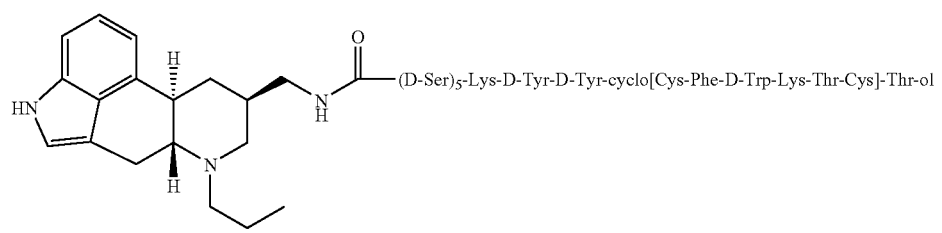
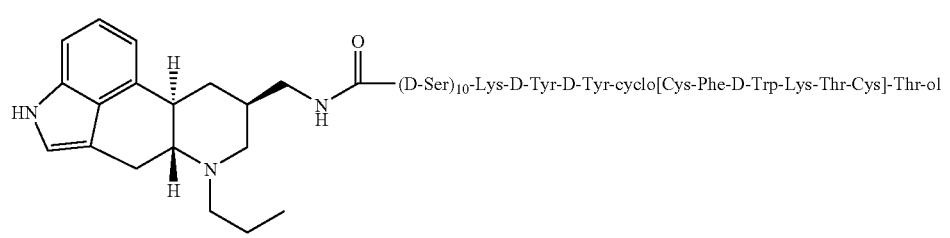
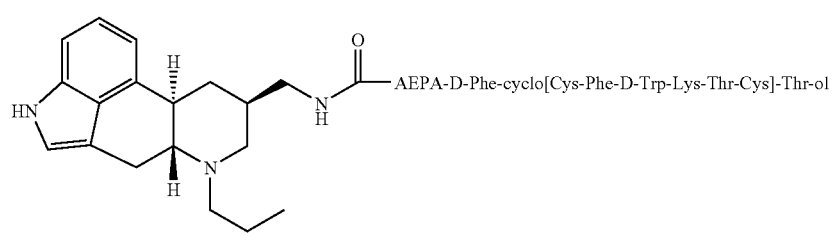

-continued
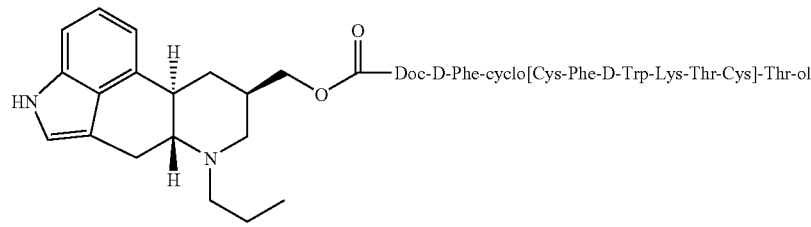
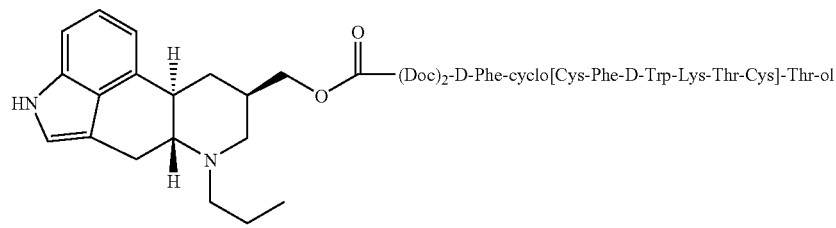
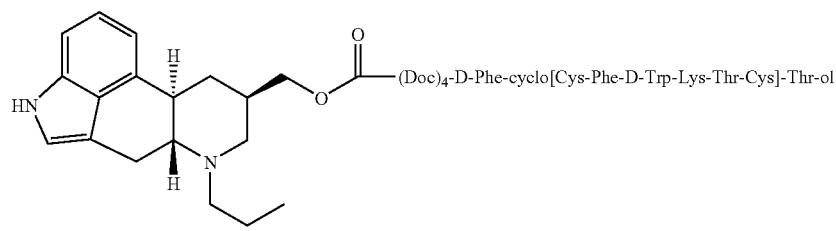
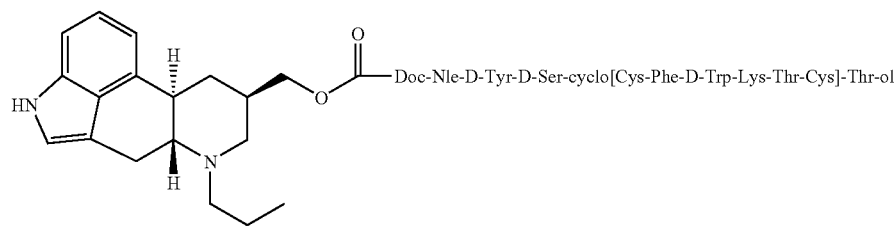
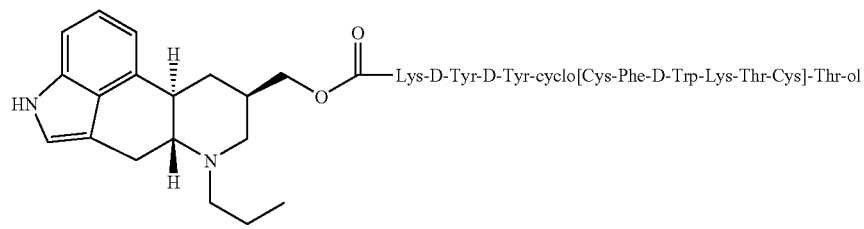
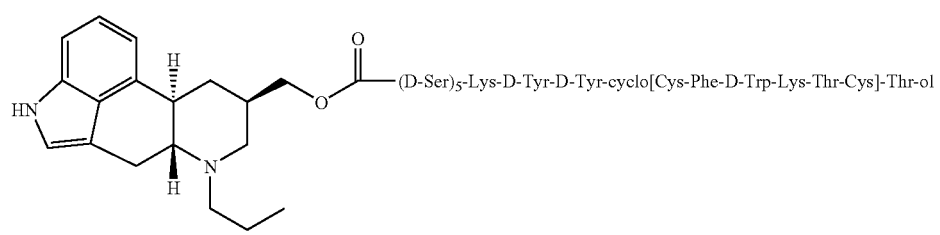
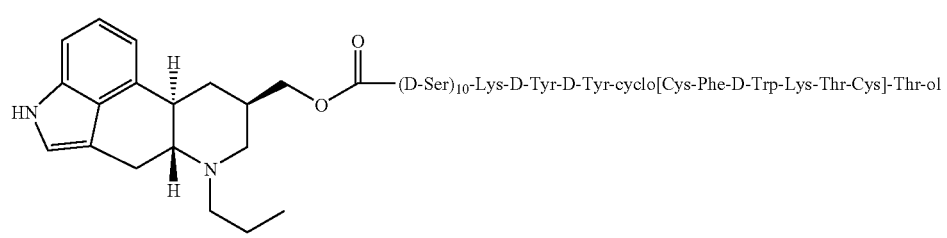

-continued
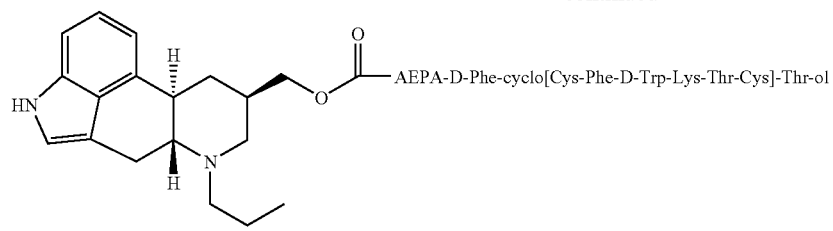
AEPA-D-Phe-cyclo[Cys-Phe-D-Trp-Lys-Thr-Cys]-Thr-ol
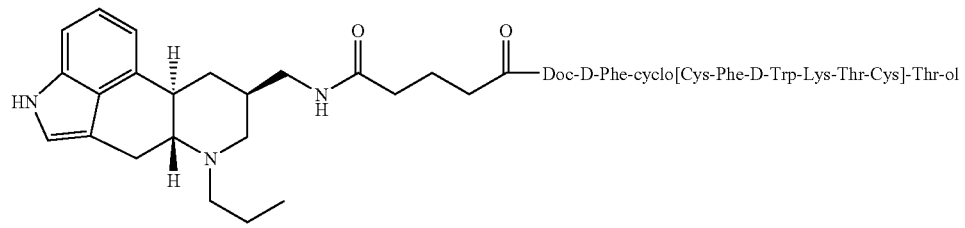
Doc-D-Phe-cyclo[Cys-Phe-D-Trp-Lys-Thr-Cys]-Thr-ol
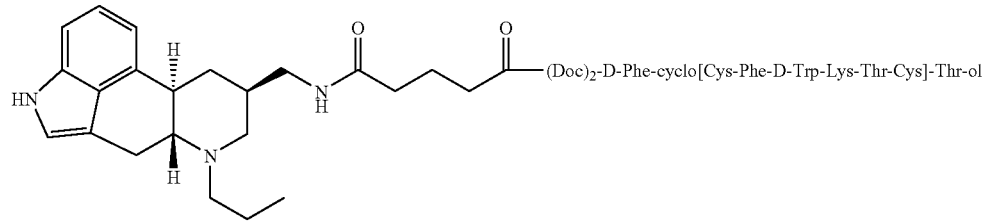
(Doc)$_2$-D-Phe-cyclo[Cys-Phe-D-Trp-Lys-Thr-Cys]-Thr-ol
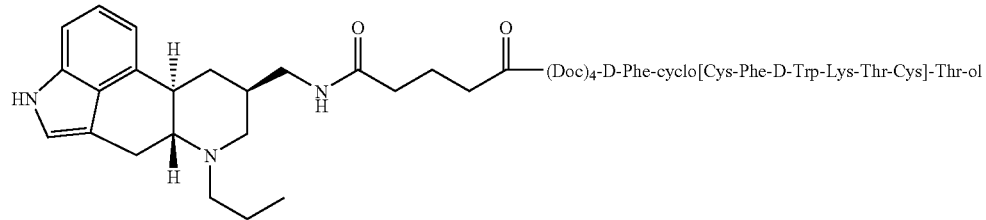
(Doc)$_4$-D-Phe-cyclo[Cys-Phe-D-Trp-Lys-Thr-Cys]-Thr-ol
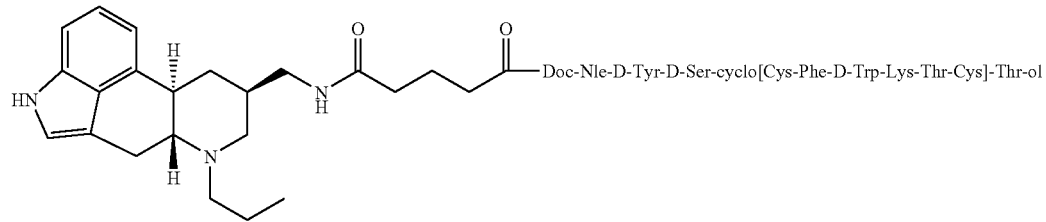
Doc-Nle-D-Tyr-D-Ser-cyclo[Cys-Phe-D-Trp-Lys-Thr-Cys]-Thr-ol
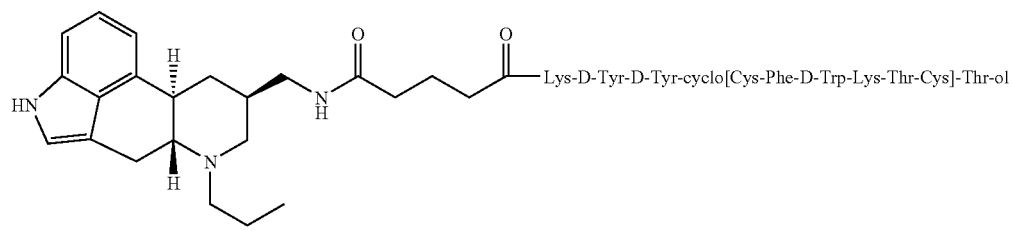
Lys-D-Tyr-D-Tyr-cyclo[Cys-Phe-D-Trp-Lys-Thr-Cys]-Thr-ol
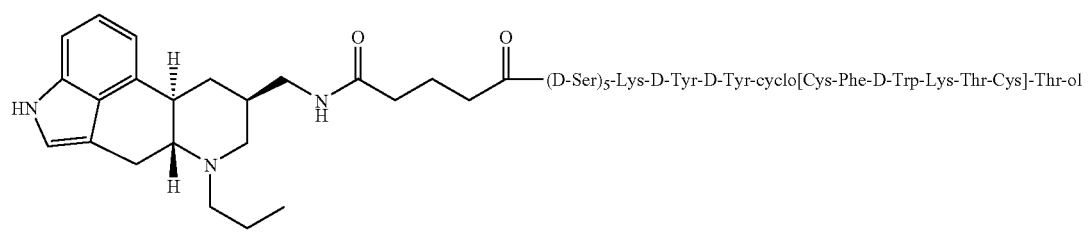
(D-Ser)$_5$-Lys-D-Tyr-D-Tyr-cyclo[Cys-Phe-D-Trp-Lys-Thr-Cys]-Thr-ol

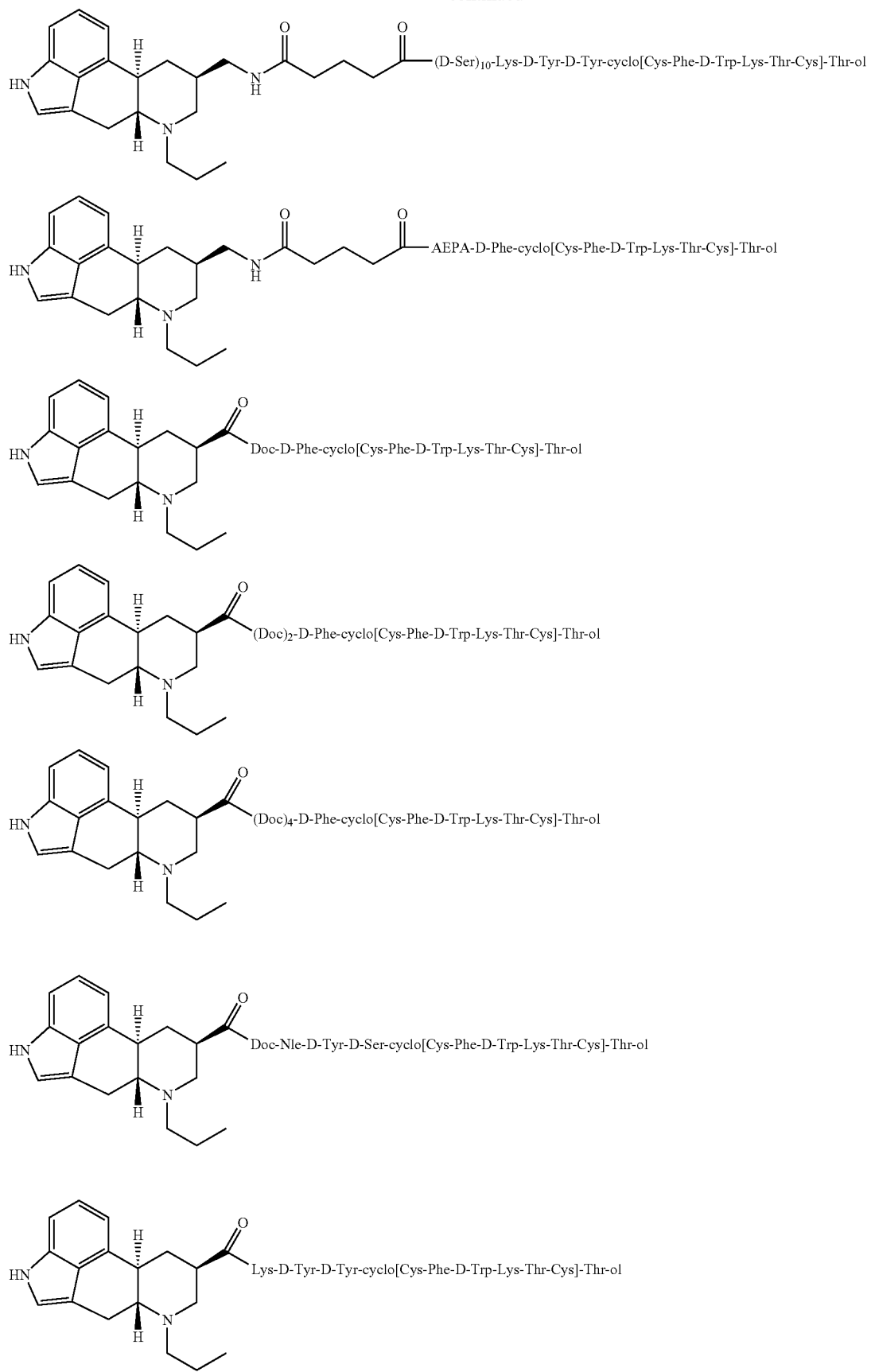

-continued
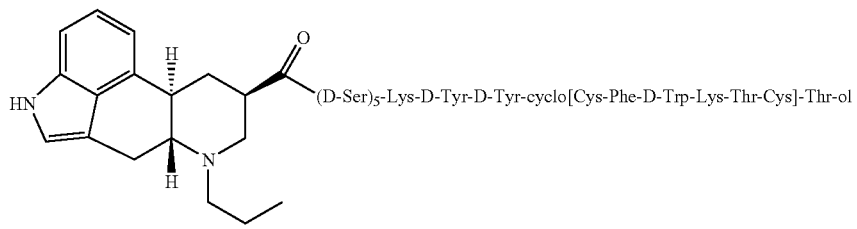
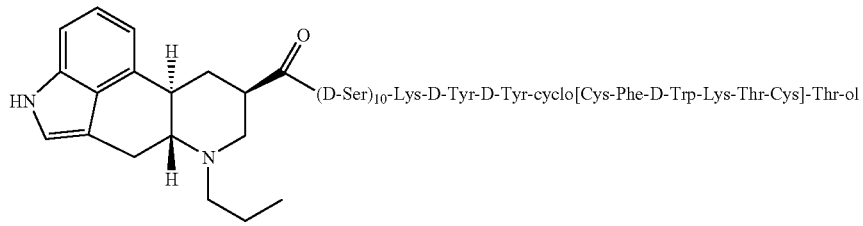
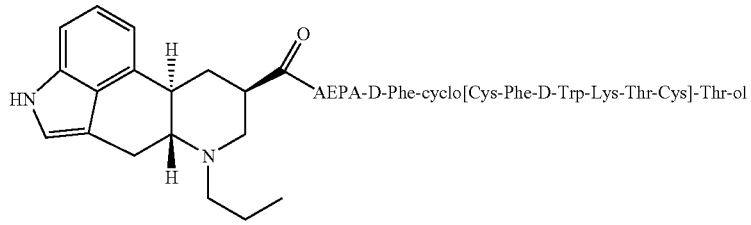
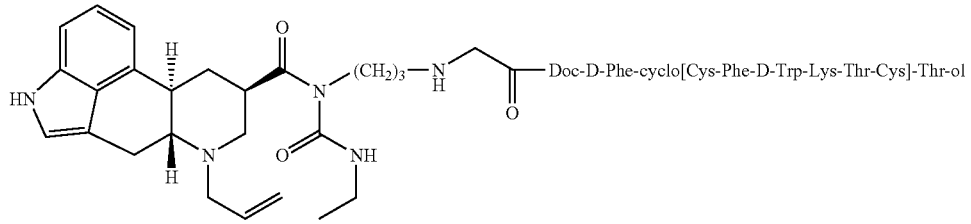
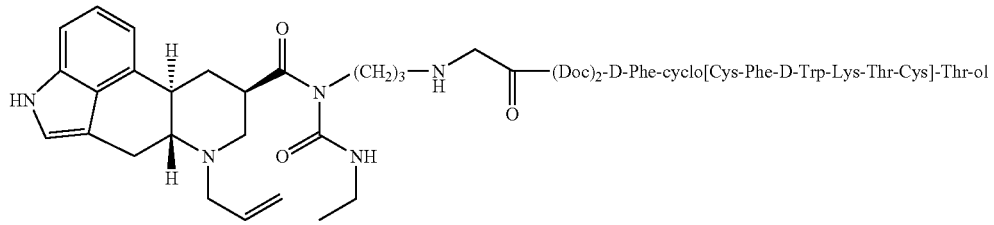
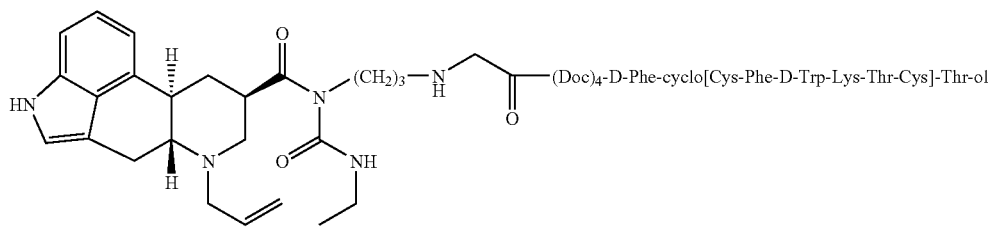
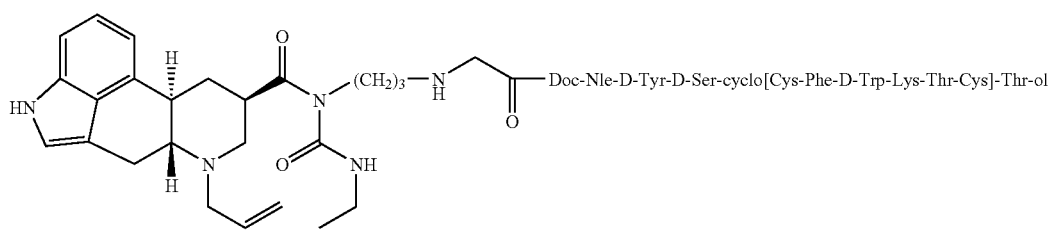

-continued
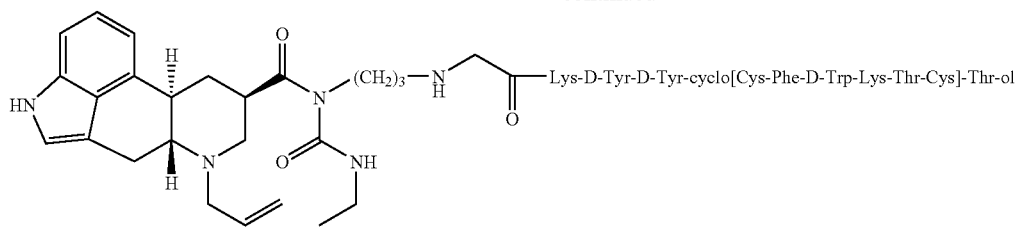
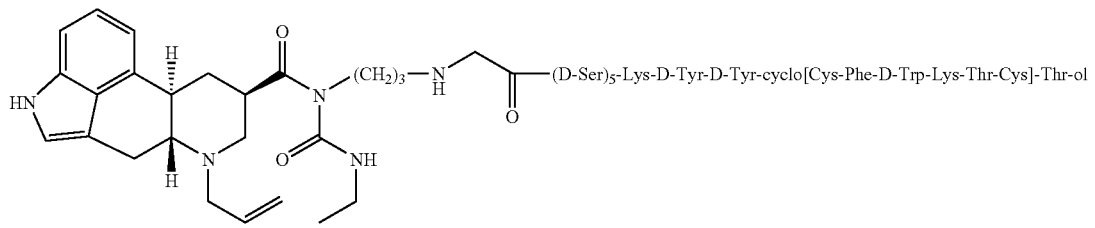
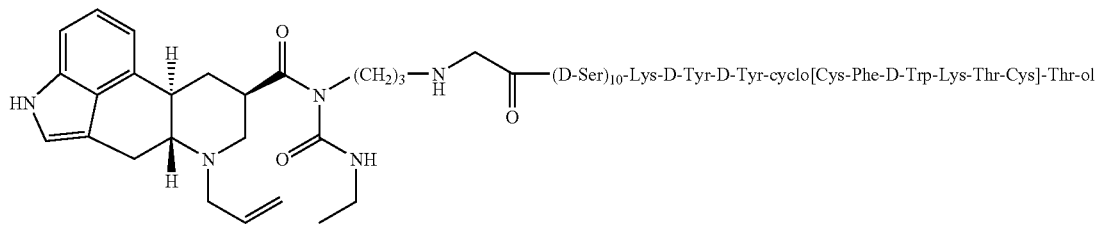
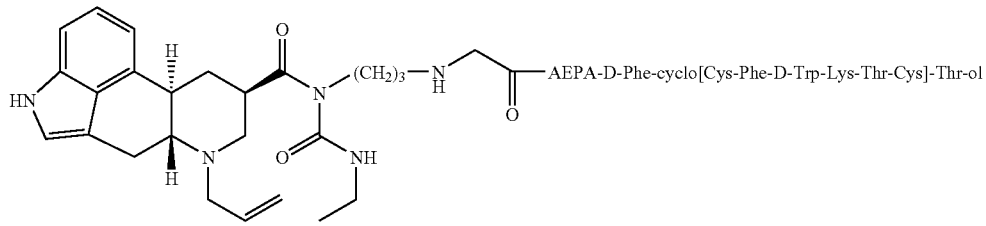
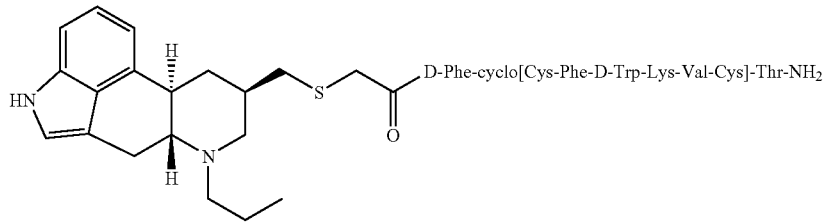
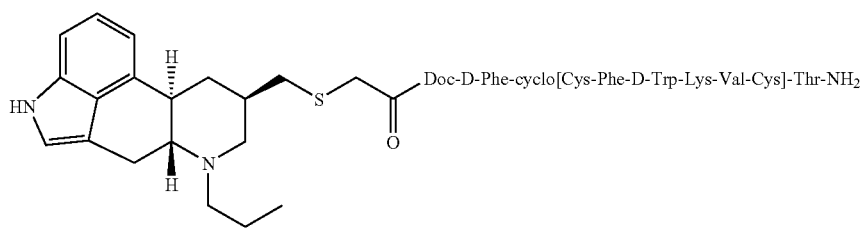
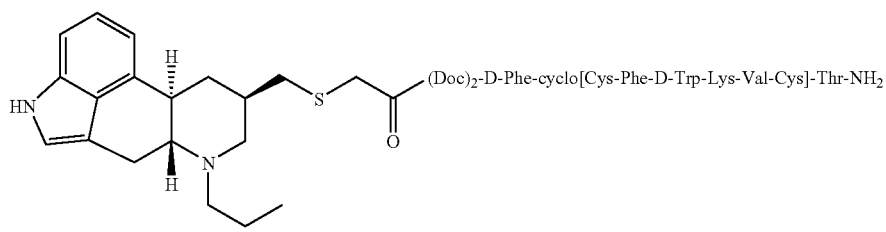

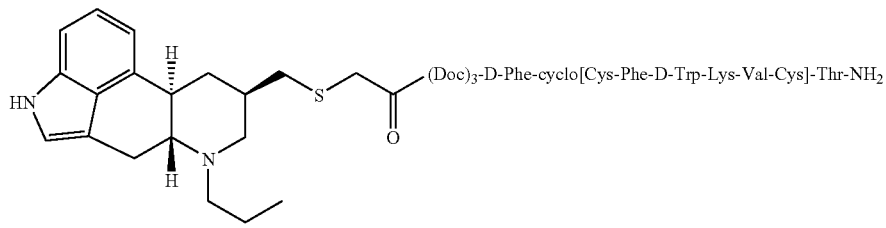
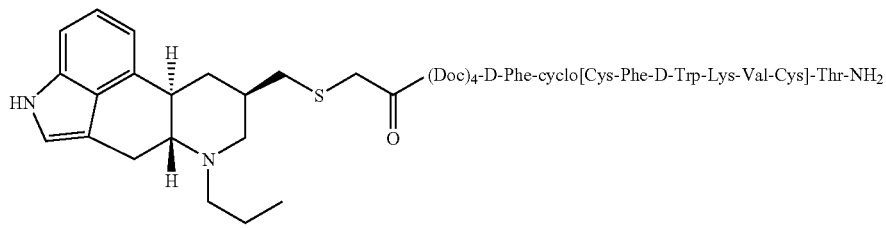
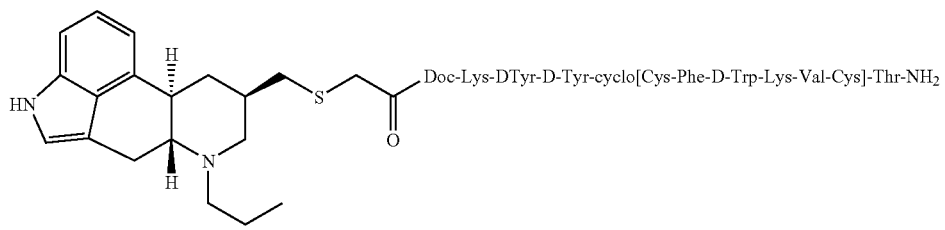
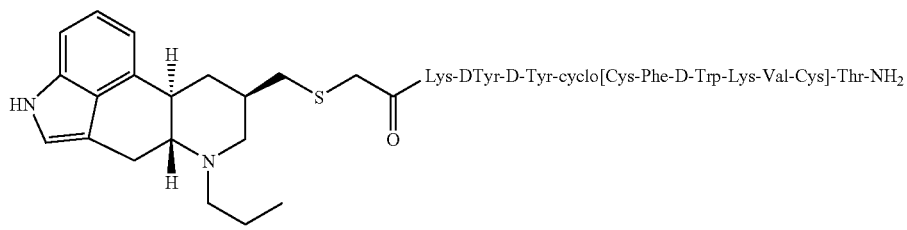
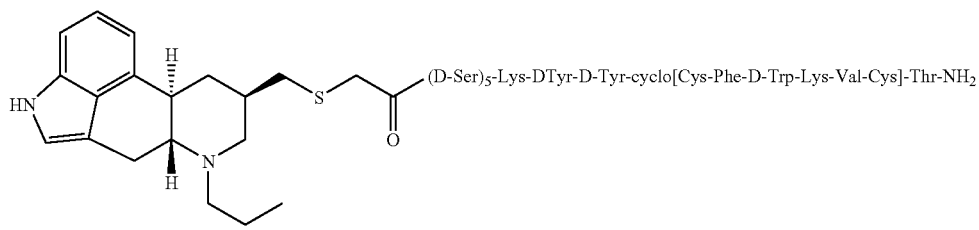
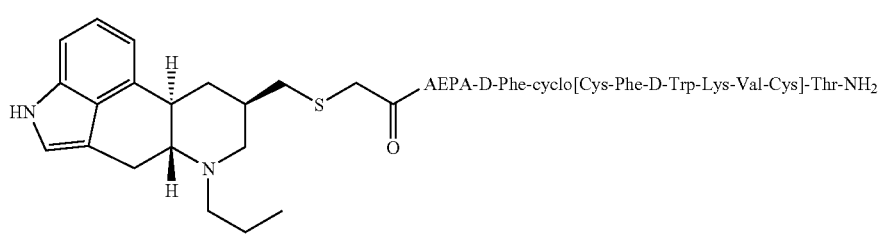
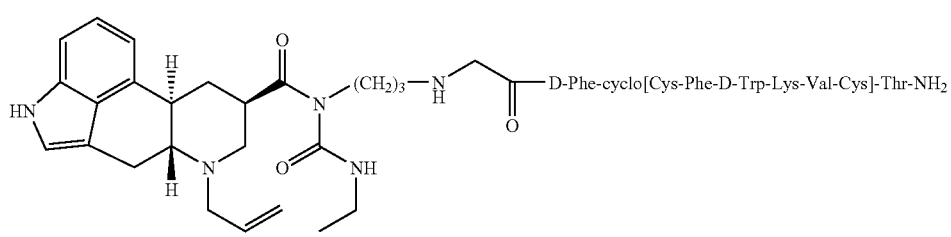

-continued
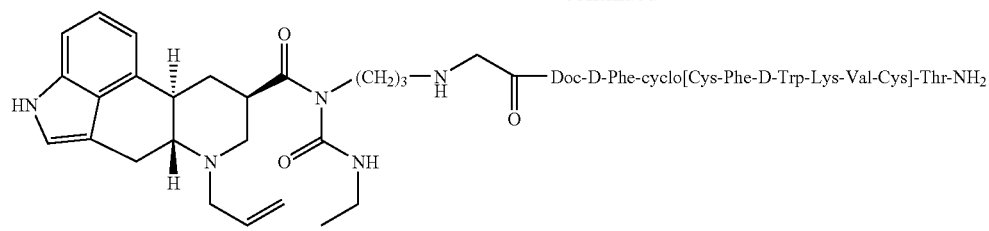
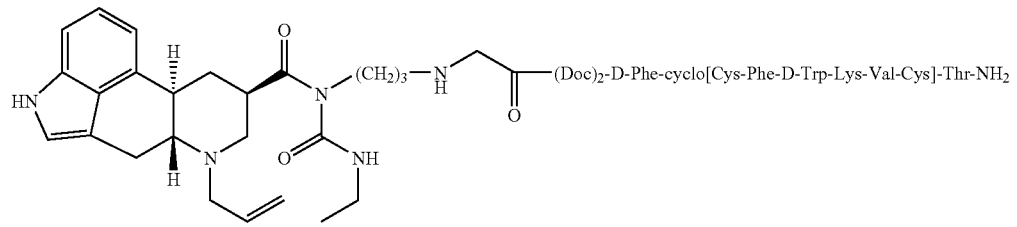
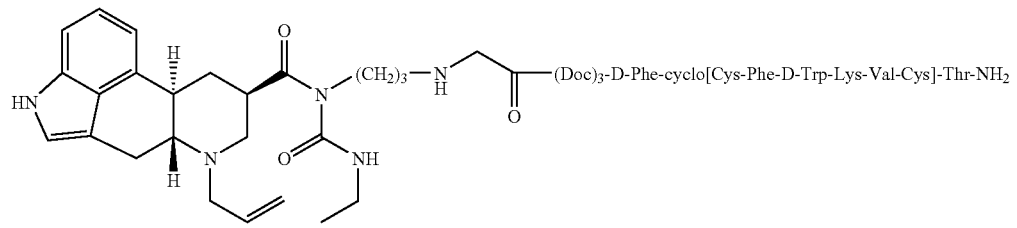
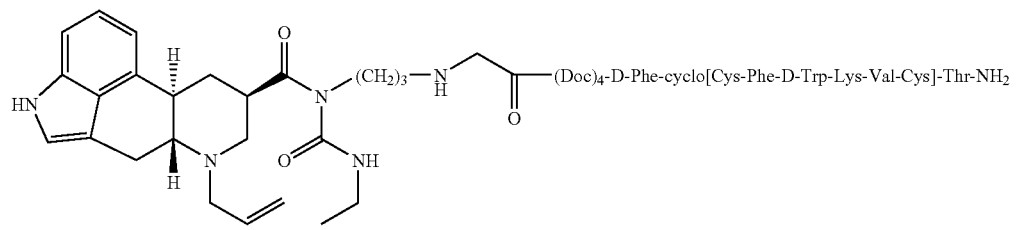
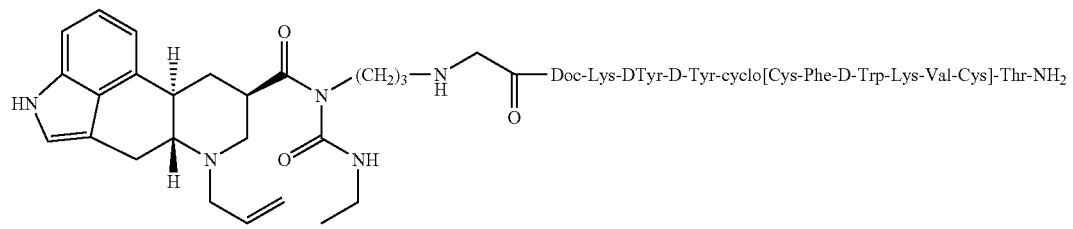
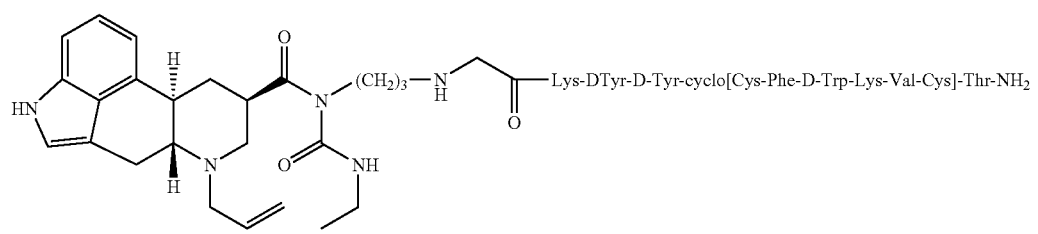
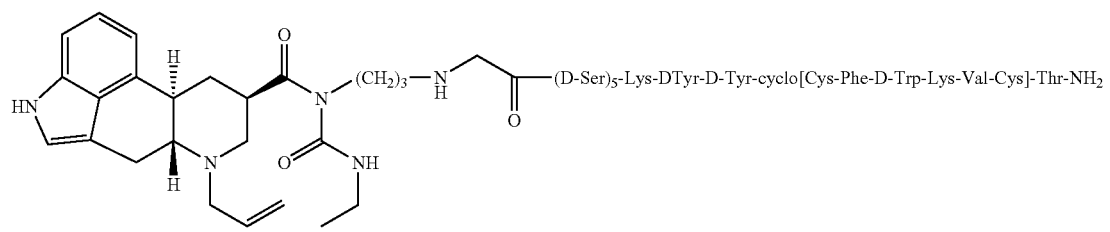

-continued
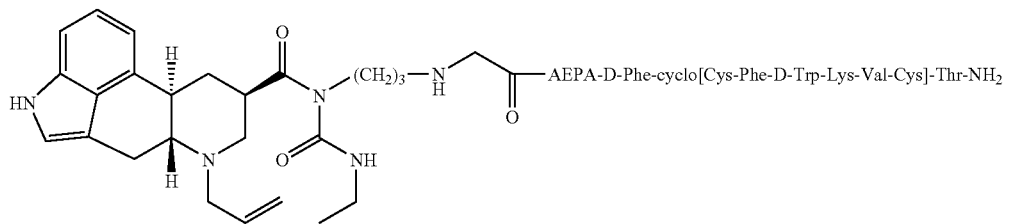
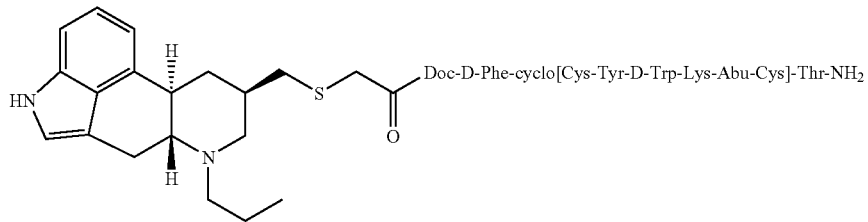
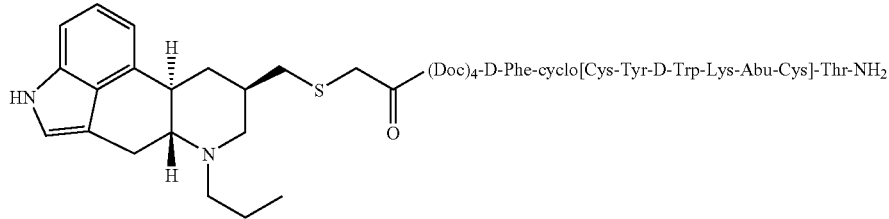
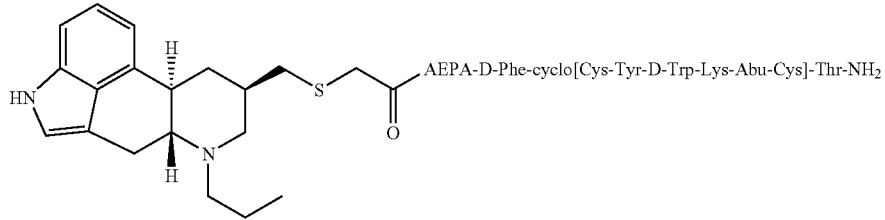
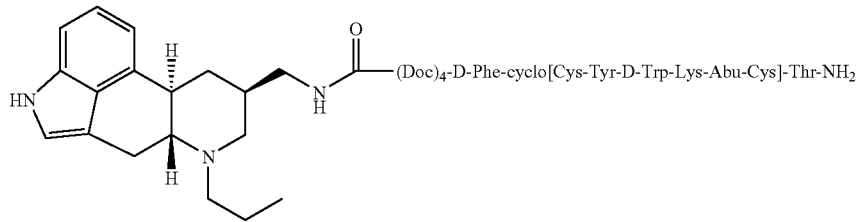
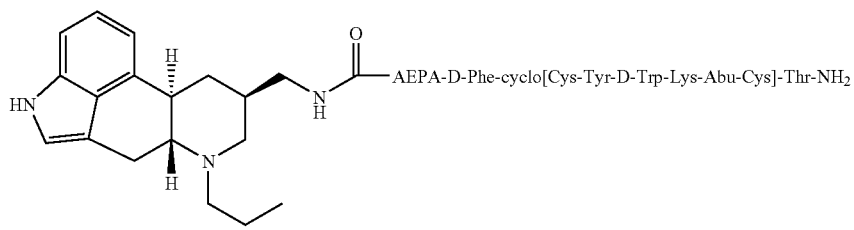
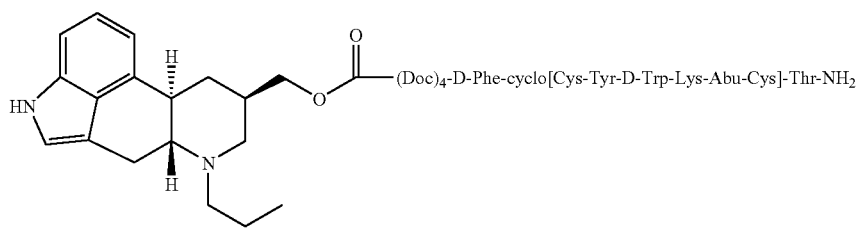

-continued
Compound C
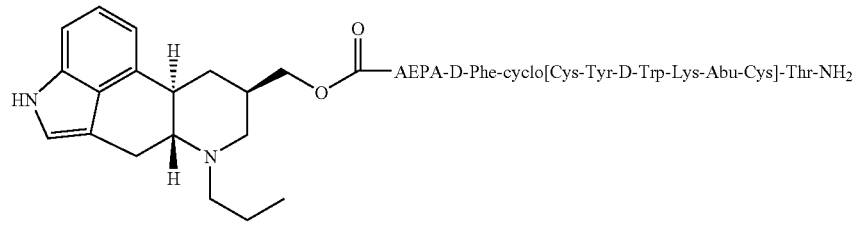
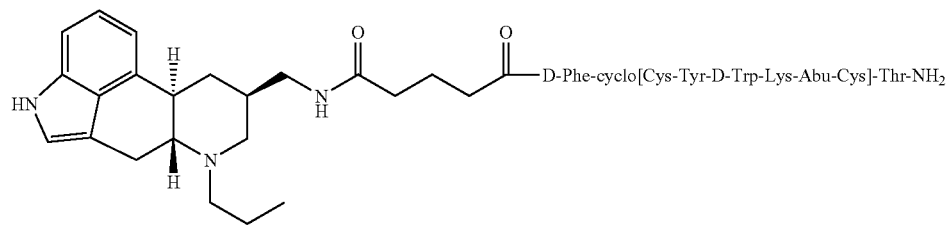
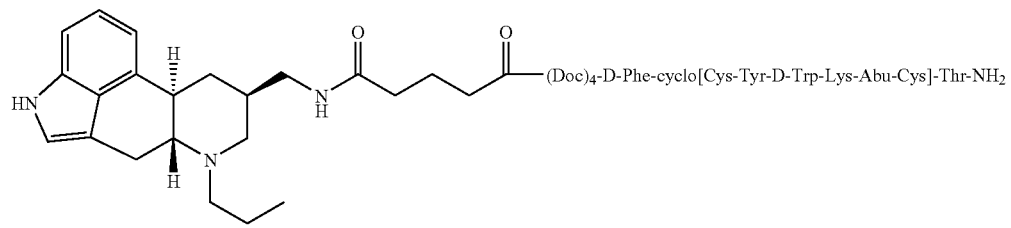
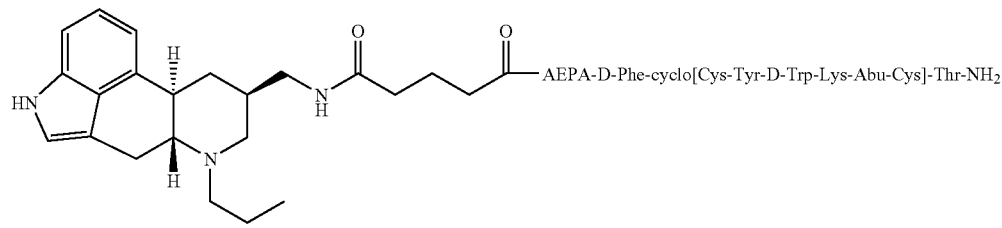
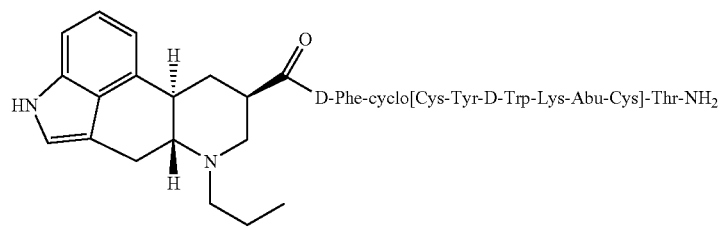
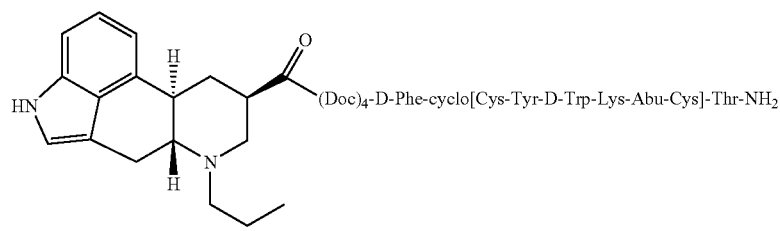
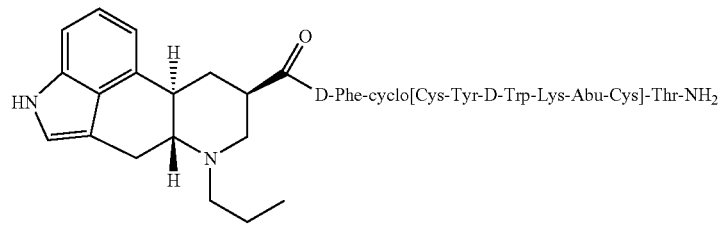

-continued
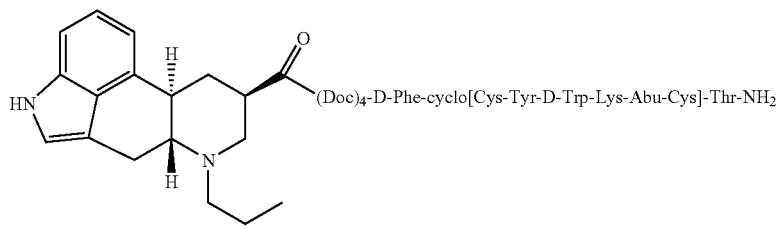
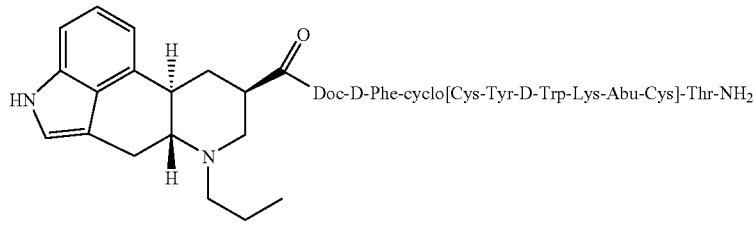
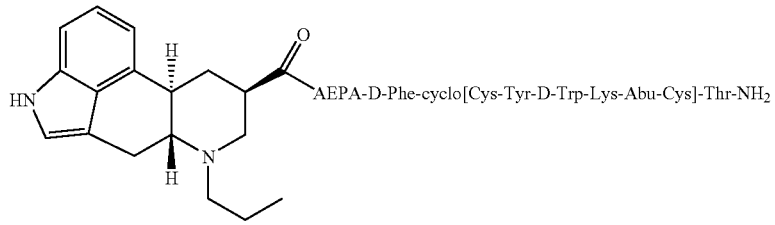
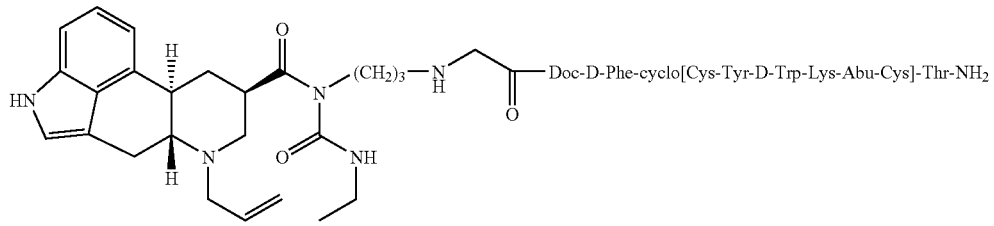
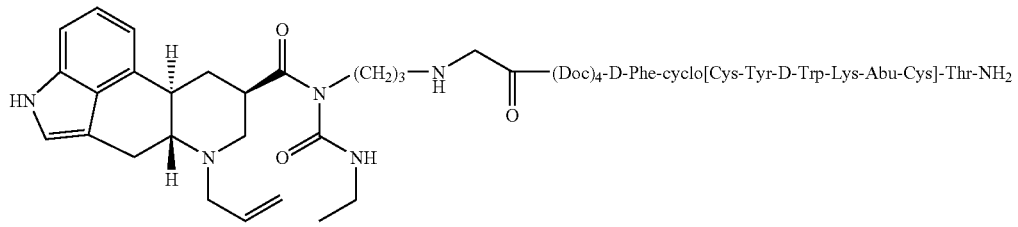
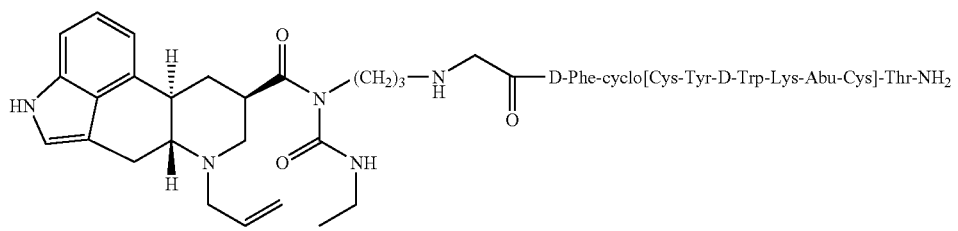
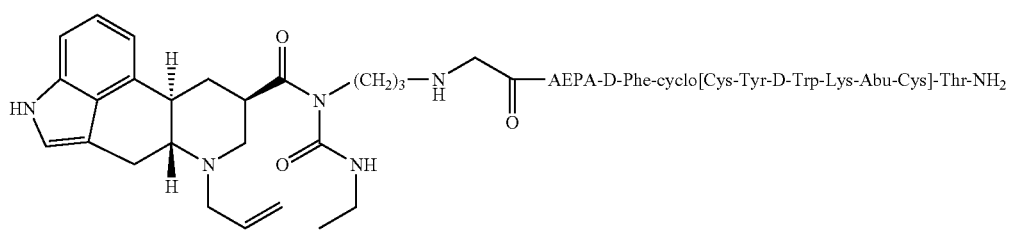

-continued

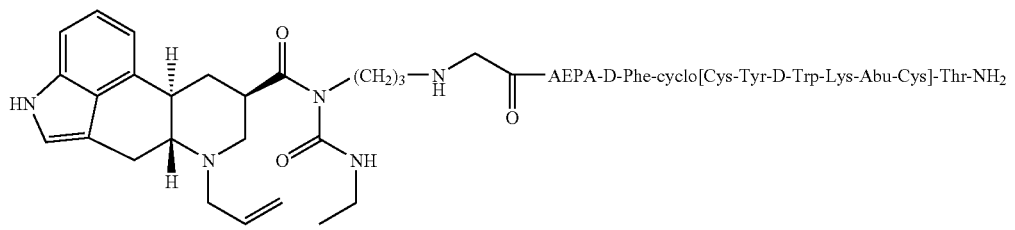
AEPA-D-Phe-cyclo[Cys-Tyr-D-Trp-Lys-Abu-Cys]-Thr-NH$_2$

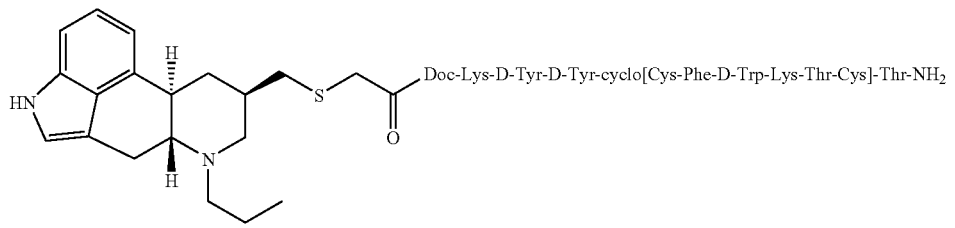
Doc-Lys-D-Tyr-D-Tyr-cyclo[Cys-Phe-D-Trp-Lys-Thr-Cys]-Thr-NH$_2$

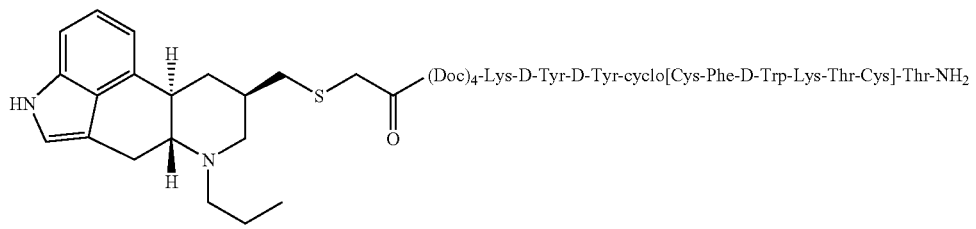
(Doc)$_4$-Lys-D-Tyr-D-Tyr-cyclo[Cys-Phe-D-Trp-Lys-Thr-Cys]-Thr-NH$_2$

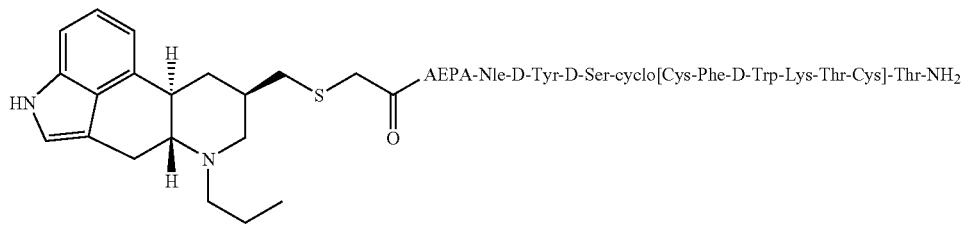
AEPA-Nle-D-Tyr-D-Ser-cyclo[Cys-Phe-D-Trp-Lys-Thr-Cys]-Thr-NH$_2$

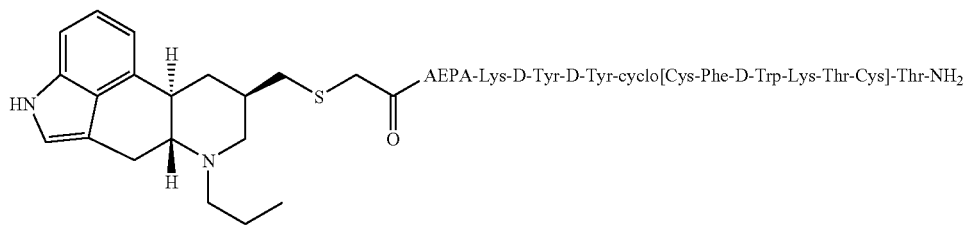
AEPA-Lys-D-Tyr-D-Tyr-cyclo[Cys-Phe-D-Trp-Lys-Thr-Cys]-Thr-NH$_2$

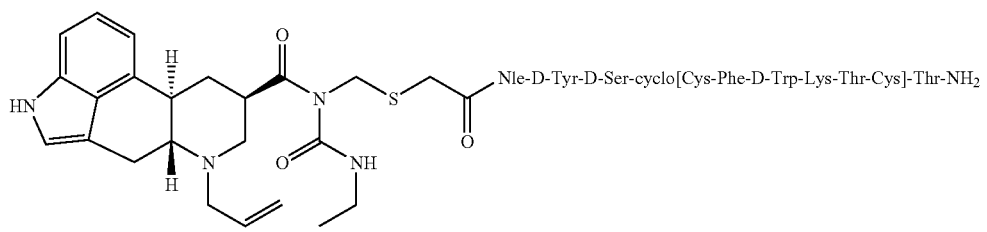
Nle-D-Tyr-D-Ser-cyclo[Cys-Phe-D-Trp-Lys-Thr-Cys]-Thr-NH$_2$

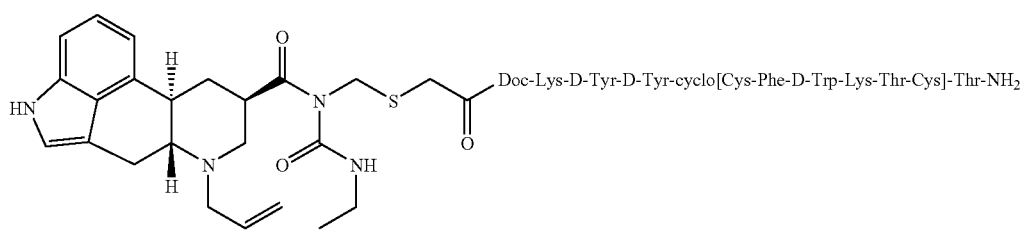
Doc-Lys-D-Tyr-D-Tyr-cyclo[Cys-Phe-D-Trp-Lys-Thr-Cys]-Thr-NH$_2$

-continued

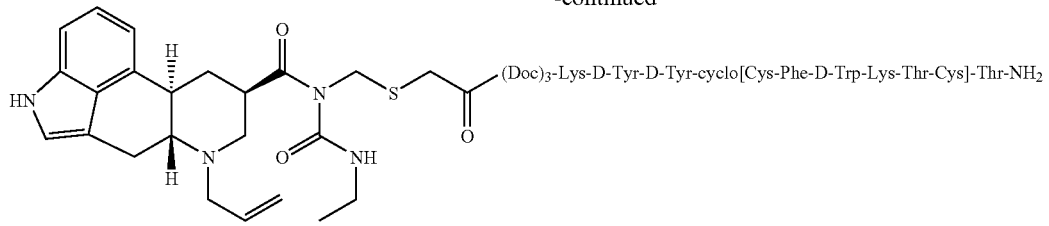
(Doc)₃-Lys-D-Tyr-D-Tyr-cyclo[Cys-Phe-D-Trp-Lys-Thr-Cys]-Thr-NH₂

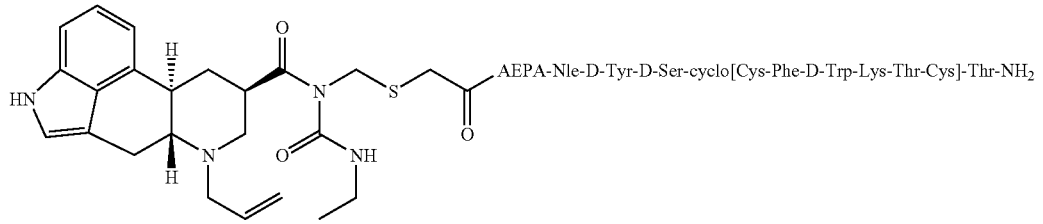
AEPA-Nle-D-Tyr-D-Ser-cyclo[Cys-Phe-D-Trp-Lys-Thr-Cys]-Thr-NH₂ or

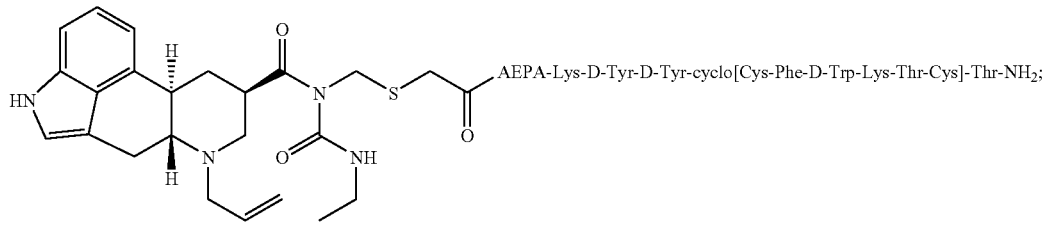
AEPA-Lys-D-Tyr-D-Tyr-cyclo[Cys-Phe-D-Trp-Lys-Thr-Cys]-Thr-NH₂;

or a pharmaceutically acceptable salt thereof; or
d) a compound according to formulae:

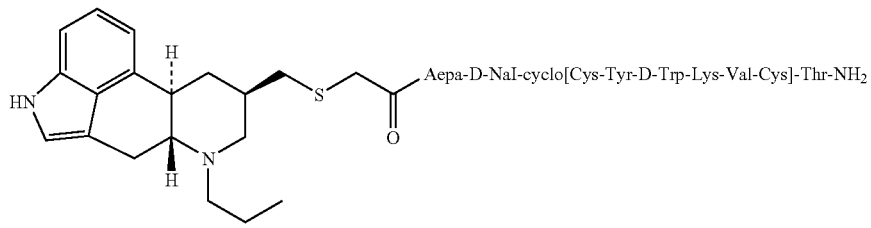
Aepa-D-Nal-cyclo[Cys-Tyr-D-Trp-Lys-Val-Cys]-Thr-NH₂

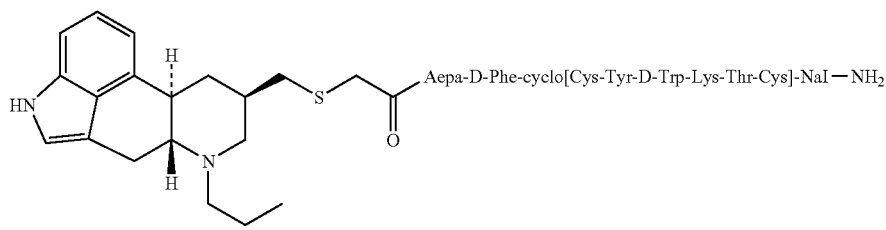
Aepa-D-Phe-cyclo[Cys-Tyr-D-Trp-Lys-Thr-Cys]-Nal—NH₂

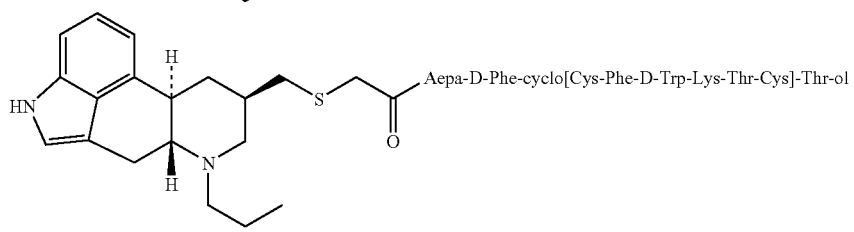
Aepa-D-Phe-cyclo[Cys-Phe-D-Trp-Lys-Thr-Cys]-Thr-ol

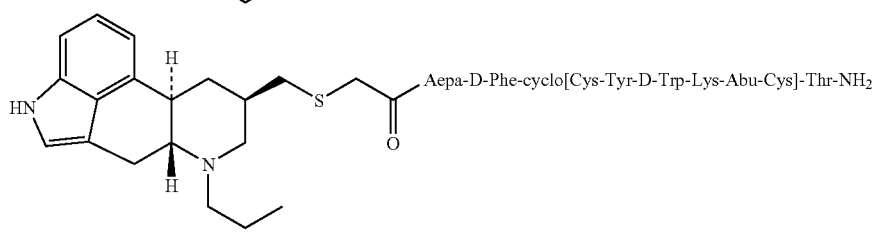
Aepa-D-Phe-cyclo[Cys-Tyr-D-Trp-Lys-Abu-Cys]-Thr-NH₂

-continued

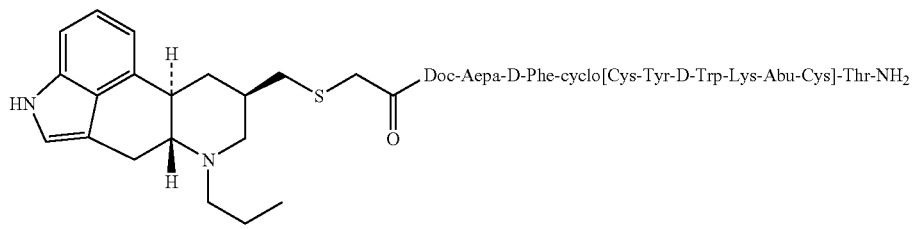
Doc-Aepa-D-Phe-cyclo[Cys-Tyr-D-Trp-Lys-Abu-Cys]-Thr-NH$_2$

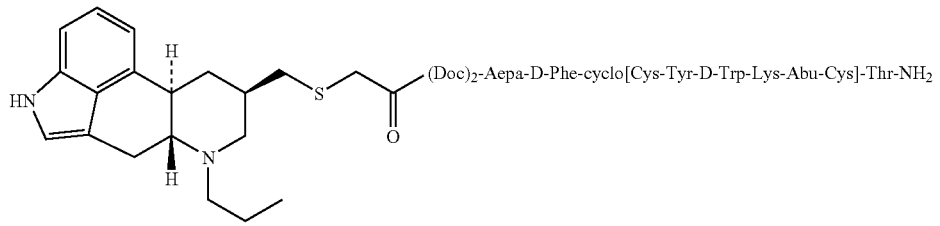
(Doc)$_2$-Aepa-D-Phe-cyclo[Cys-Tyr-D-Trp-Lys-Abu-Cys]-Thr-NH$_2$

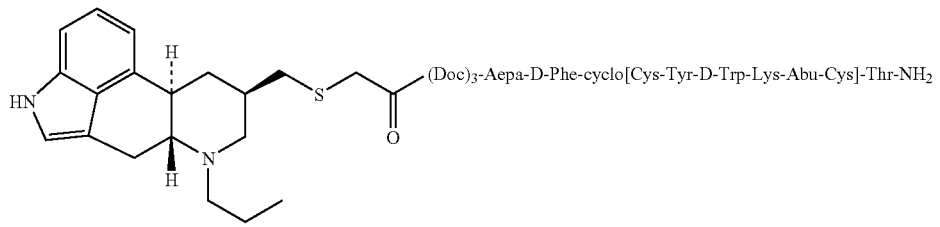
(Doc)$_3$-Aepa-D-Phe-cyclo[Cys-Tyr-D-Trp-Lys-Abu-Cys]-Thr-NH$_2$

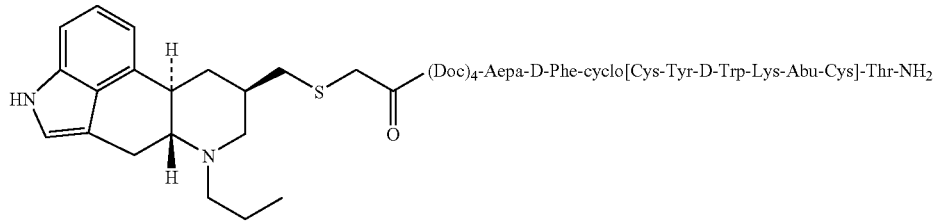
(Doc)$_4$-Aepa-D-Phe-cyclo[Cys-Tyr-D-Trp-Lys-Abu-Cys]-Thr-NH$_2$

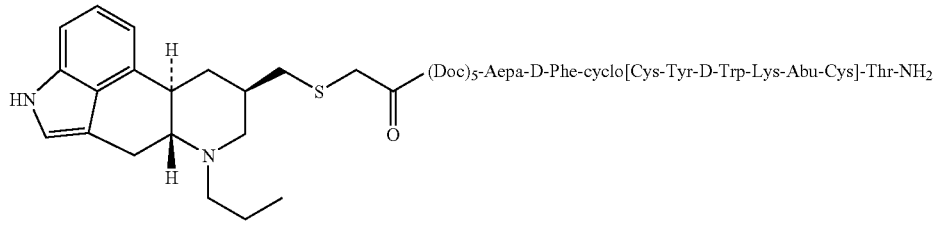
(Doc)$_5$-Aepa-D-Phe-cyclo[Cys-Tyr-D-Trp-Lys-Abu-Cys]-Thr-NH$_2$

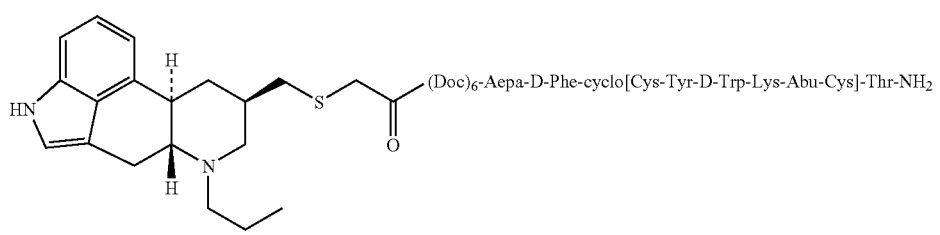
(Doc)$_6$-Aepa-D-Phe-cyclo[Cys-Tyr-D-Trp-Lys-Abu-Cys]-Thr-NH$_2$

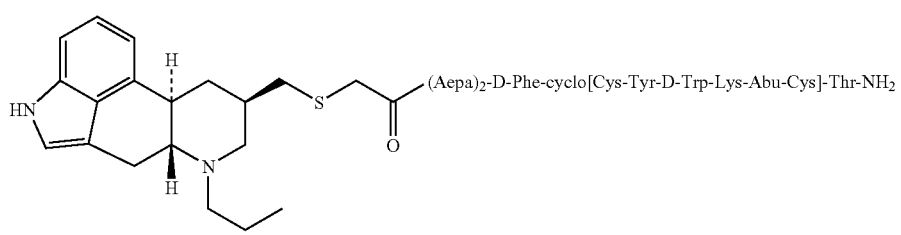
(Aepa)$_2$-D-Phe-cyclo[Cys-Tyr-D-Trp-Lys-Abu-Cys]-Thr-NH$_2$

-continued

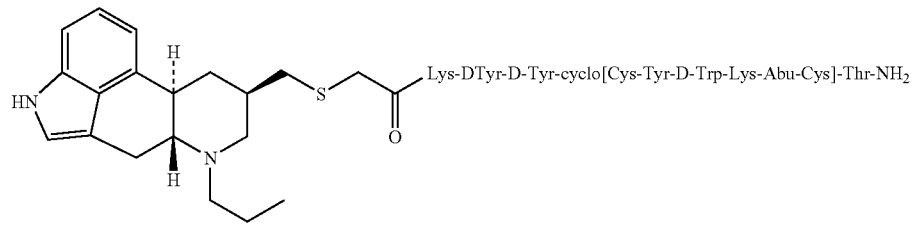
Lys-DTyr-D-Tyr-cyclo[Cys-Tyr-D-Trp-Lys-Abu-Cys]-Thr-NH₂

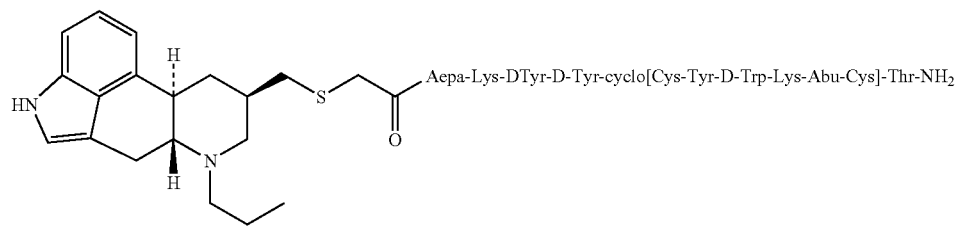
Aepa-Lys-DTyr-D-Tyr-cyclo[Cys-Tyr-D-Trp-Lys-Abu-Cys]-Thr-NH₂

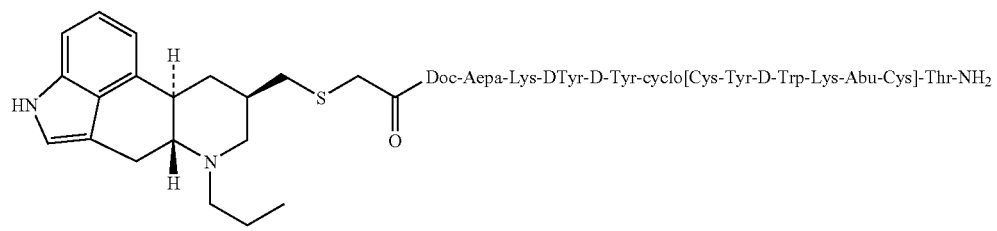
Doc-Aepa-Lys-DTyr-D-Tyr-cyclo[Cys-Tyr-D-Trp-Lys-Abu-Cys]-Thr-NH₂

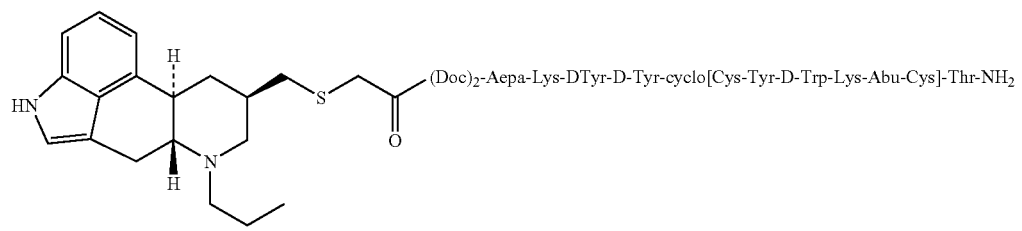
(Doc)₂-Aepa-Lys-DTyr-D-Tyr-cyclo[Cys-Tyr-D-Trp-Lys-Abu-Cys]-Thr-NH₂

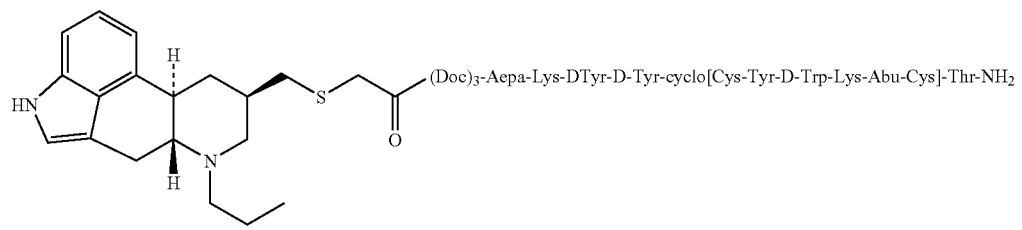
(Doc)₃-Aepa-Lys-DTyr-D-Tyr-cyclo[Cys-Tyr-D-Trp-Lys-Abu-Cys]-Thr-NH₂

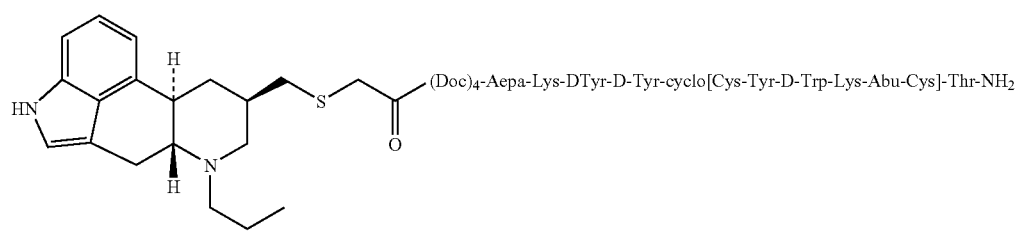
(Doc)₄-Aepa-Lys-DTyr-D-Tyr-cyclo[Cys-Tyr-D-Trp-Lys-Abu-Cys]-Thr-NH₂

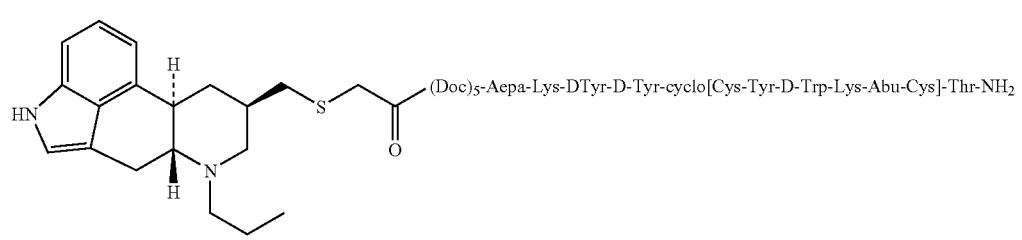
(Doc)₅-Aepa-Lys-DTyr-D-Tyr-cyclo[Cys-Tyr-D-Trp-Lys-Abu-Cys]-Thr-NH₂

-continued

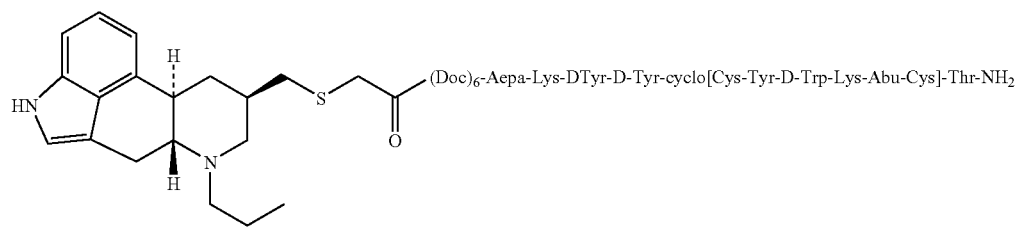(Doc)₆-Aepa-Lys-DTyr-D-Tyr-cyclo[Cys-Tyr-D-Trp-Lys-Abu-Cys]-Thr-NH₂

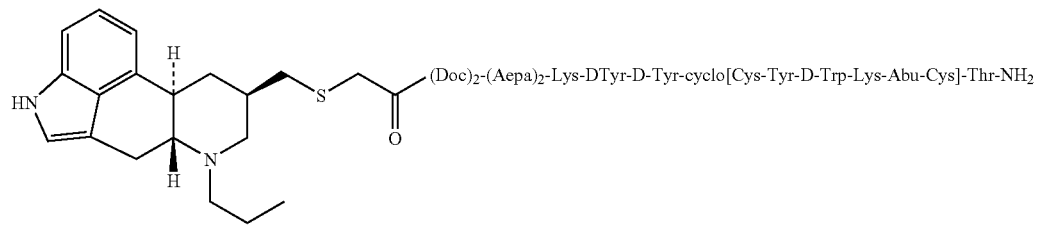(Doc)₂-(Aepa)₂-Lys-DTyr-D-Tyr-cyclo[Cys-Tyr-D-Trp-Lys-Abu-Cys]-Thr-NH₂

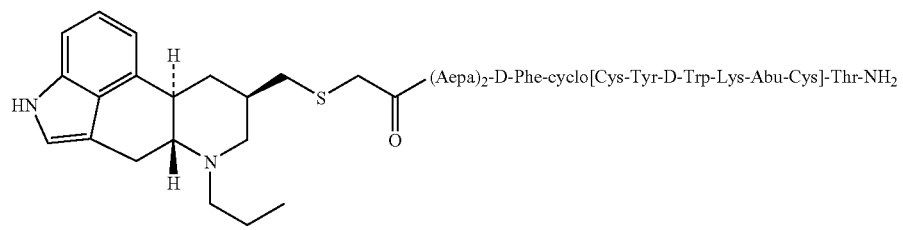(Aepa)₂-D-Phe-cyclo[Cys-Tyr-D-Trp-Lys-Abu-Cys]-Thr-NH₂

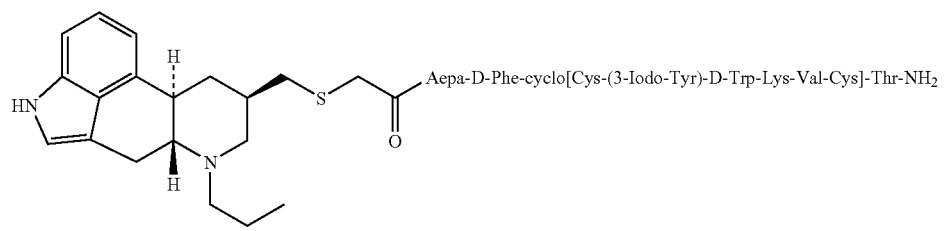Aepa-D-Phe-cyclo[Cys-(3-Iodo-Tyr)-D-Trp-Lys-Val-Cys]-Thr-NH₂

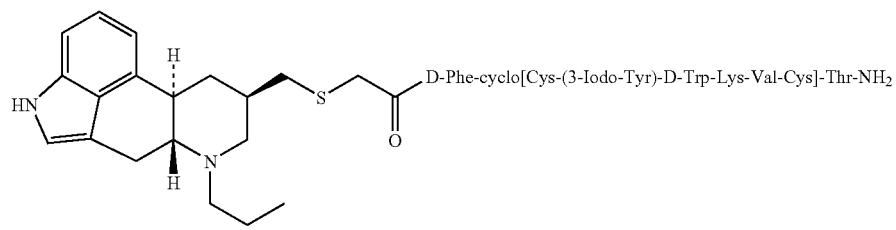D-Phe-cyclo[Cys-(3-Iodo-Tyr)-D-Trp-Lys-Val-Cys]-Thr-NH₂

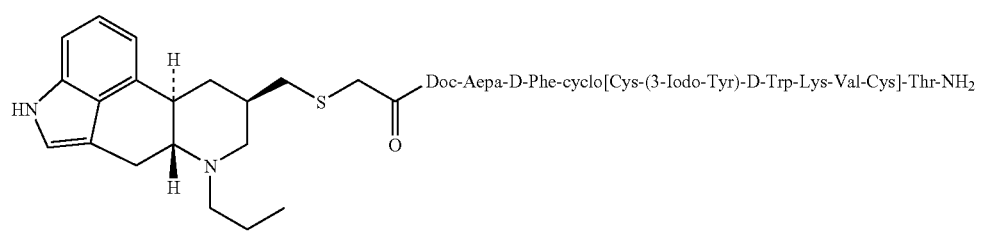Doc-Aepa-D-Phe-cyclo[Cys-(3-Iodo-Tyr)-D-Trp-Lys-Val-Cys]-Thr-NH₂

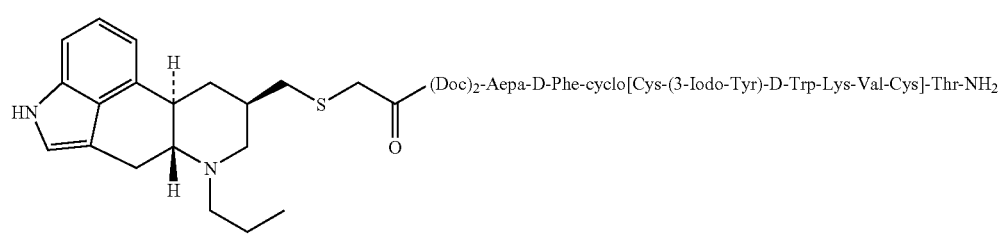(Doc)₂-Aepa-D-Phe-cyclo[Cys-(3-Iodo-Tyr)-D-Trp-Lys-Val-Cys]-Thr-NH₂

-continued
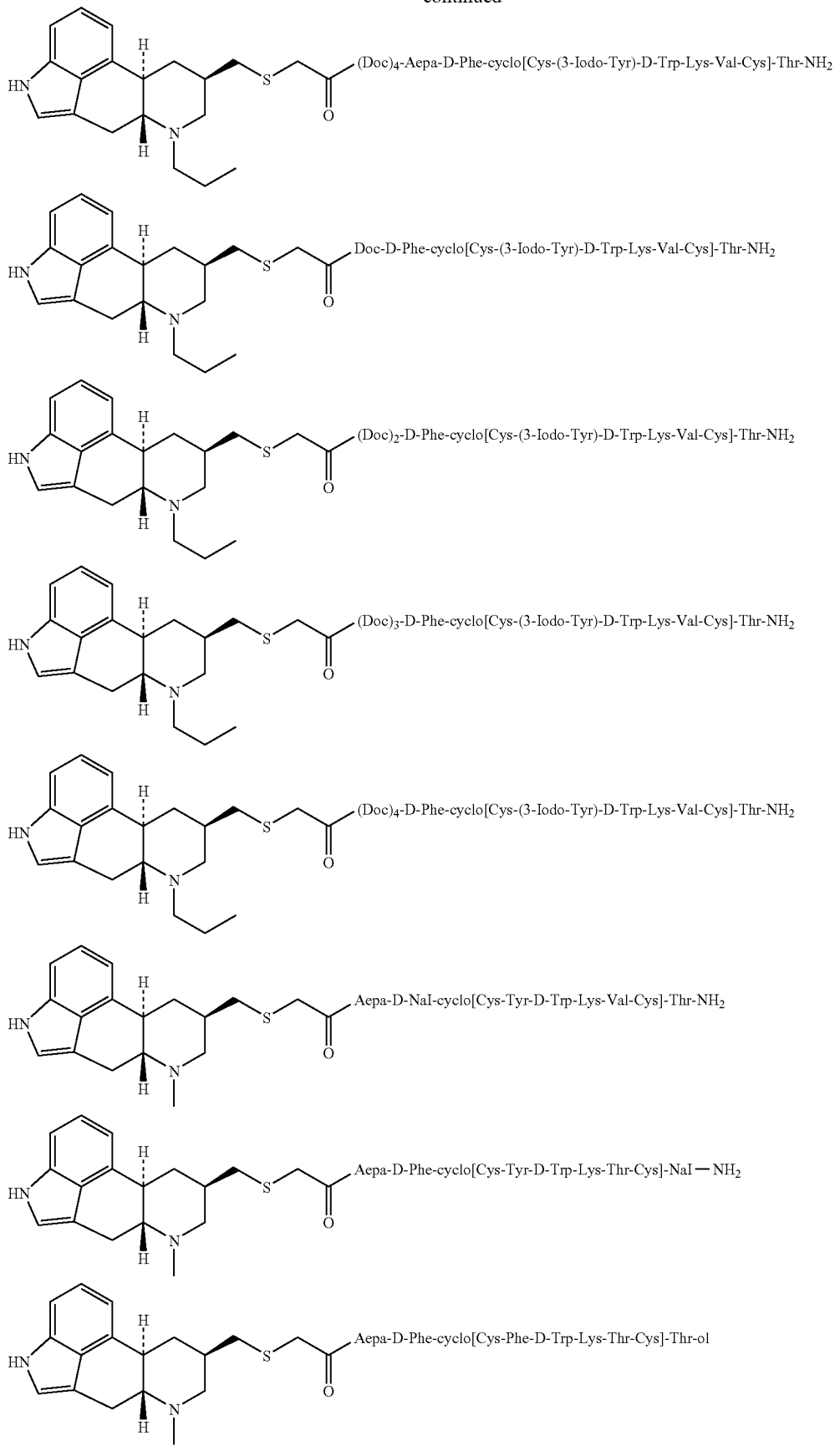

-continued

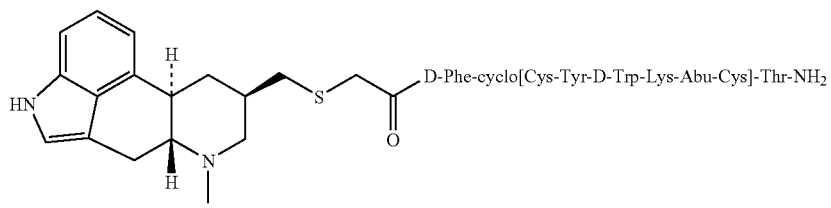
D-Phe-cyclo[Cys-Tyr-D-Trp-Lys-Abu-Cys]-Thr-NH$_2$

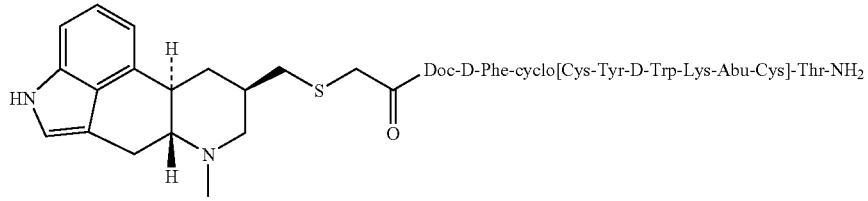
Doc-D-Phe-cyclo[Cys-Tyr-D-Trp-Lys-Abu-Cys]-Thr-NH$_2$

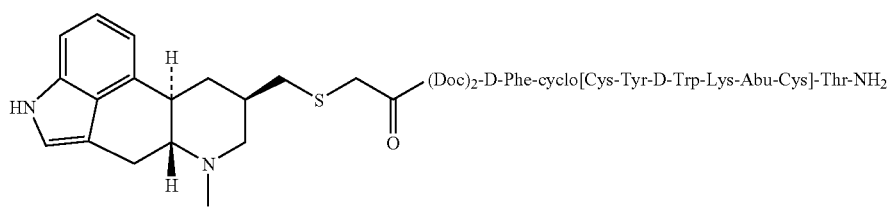
(Doc)$_2$-D-Phe-cyclo[Cys-Tyr-D-Trp-Lys-Abu-Cys]-Thr-NH$_2$

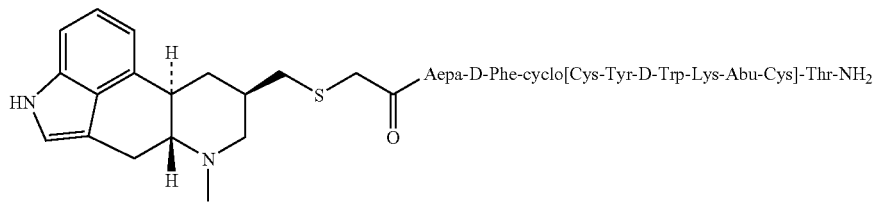
Aepa-D-Phe-cyclo[Cys-Tyr-D-Trp-Lys-Abu-Cys]-Thr-NH$_2$

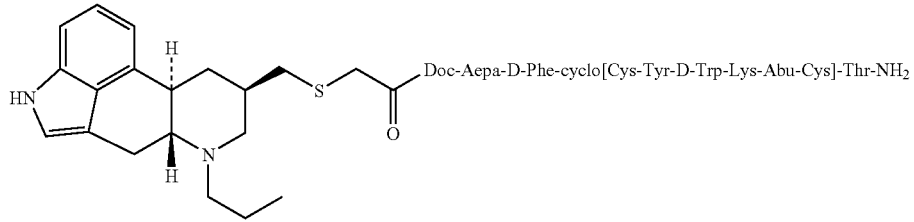
Doc-Aepa-D-Phe-cyclo[Cys-Tyr-D-Trp-Lys-Abu-Cys]-Thr-NH$_2$

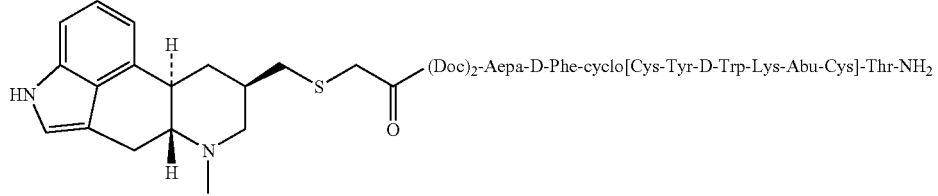
(Doc)$_2$-Aepa-D-Phe-cyclo[Cys-Tyr-D-Trp-Lys-Abu-Cys]-Thr-NH$_2$

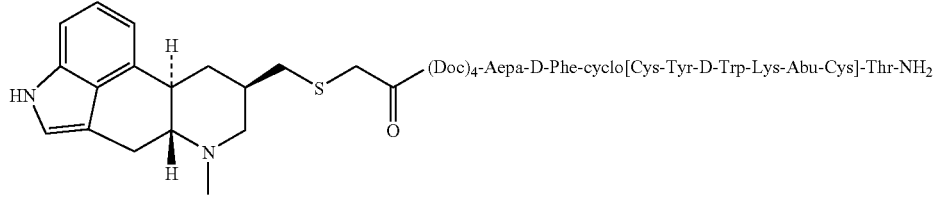
(Doc)$_4$-Aepa-D-Phe-cyclo[Cys-Tyr-D-Trp-Lys-Abu-Cys]-Thr-NH$_2$

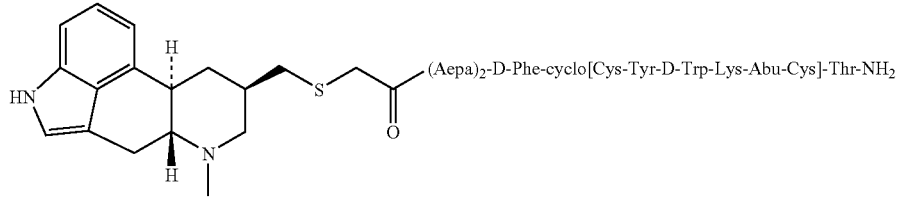
(Aepa)$_2$-D-Phe-cyclo[Cys-Tyr-D-Trp-Lys-Abu-Cys]-Thr-NH$_2$

-continued

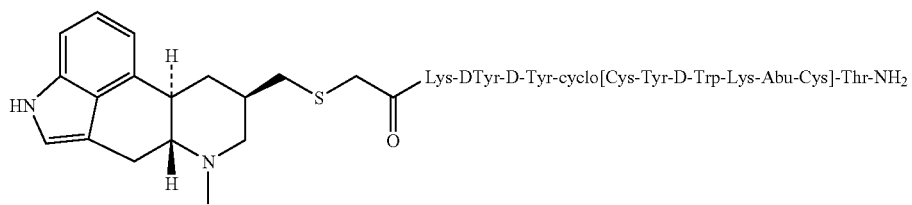
Lys-DTyr-D-Tyr-cyclo[Cys-Tyr-D-Trp-Lys-Abu-Cys]-Thr-NH$_2$

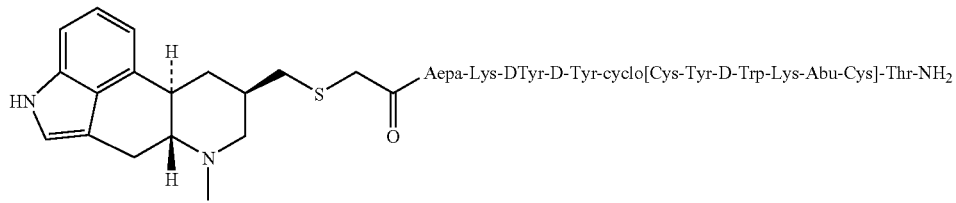
Aepa-Lys-DTyr-D-Tyr-cyclo[Cys-Tyr-D-Trp-Lys-Abu-Cys]-Thr-NH$_2$

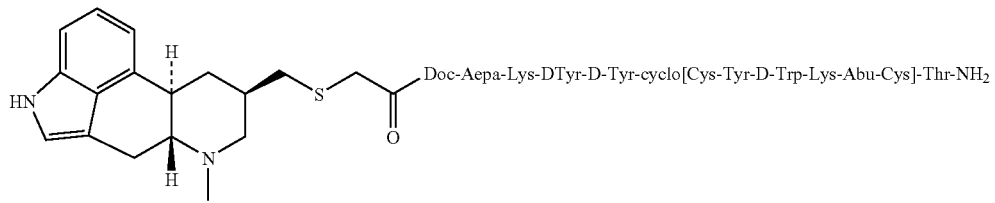
Doc-Aepa-Lys-DTyr-D-Tyr-cyclo[Cys-Tyr-D-Trp-Lys-Abu-Cys]-Thr-NH$_2$

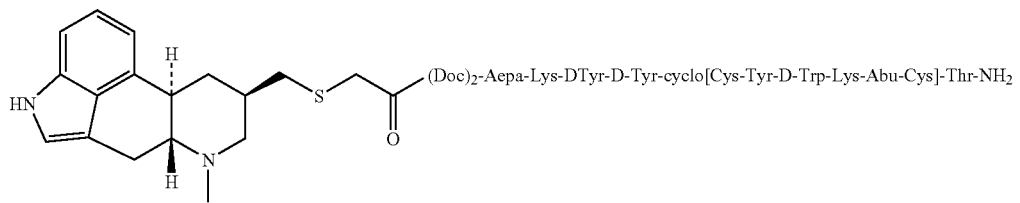
(Doc)$_2$-Aepa-Lys-DTyr-D-Tyr-cyclo[Cys-Tyr-D-Trp-Lys-Abu-Cys]-Thr-NH$_2$

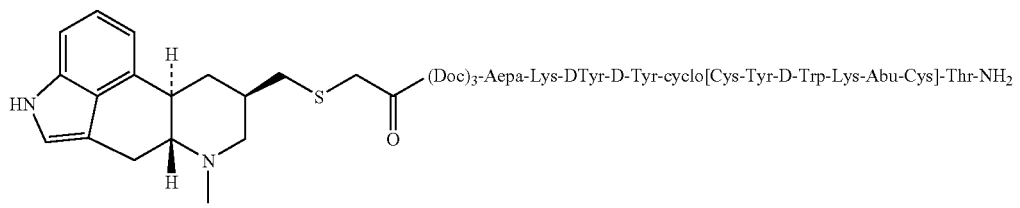
(Doc)$_3$-Aepa-Lys-DTyr-D-Tyr-cyclo[Cys-Tyr-D-Trp-Lys-Abu-Cys]-Thr-NH$_2$

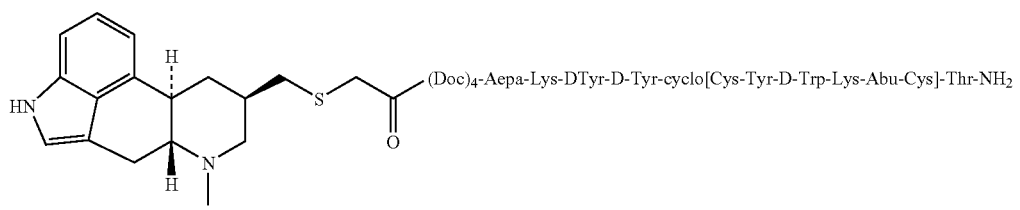
(Doc)$_4$-Aepa-Lys-DTyr-D-Tyr-cyclo[Cys-Tyr-D-Trp-Lys-Abu-Cys]-Thr-NH$_2$

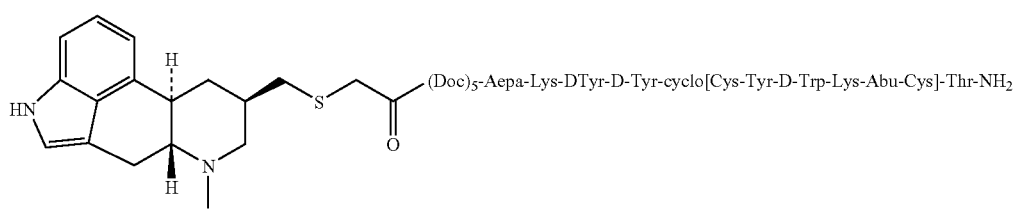
(Doc)$_5$-Aepa-Lys-DTyr-D-Tyr-cyclo[Cys-Tyr-D-Trp-Lys-Abu-Cys]-Thr-NH$_2$

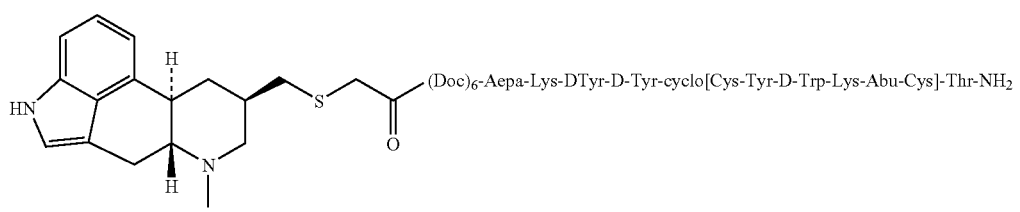
(Doc)$_6$-Aepa-Lys-DTyr-D-Tyr-cyclo[Cys-Tyr-D-Trp-Lys-Abu-Cys]-Thr-NH$_2$ -continued

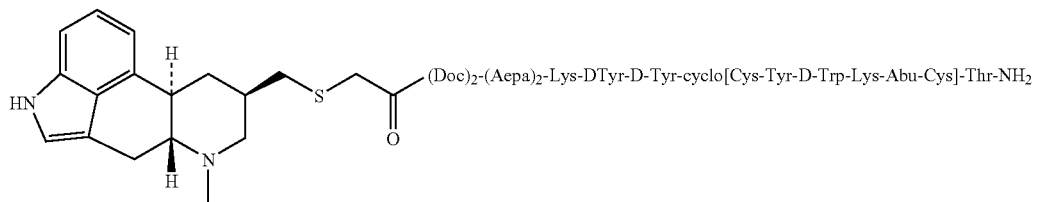
(Doc)₂-(Aepa)₂-Lys-DTyr-D-Tyr-cyclo[Cys-Tyr-D-Trp-Lys-Abu-Cys]-Thr-NH₂

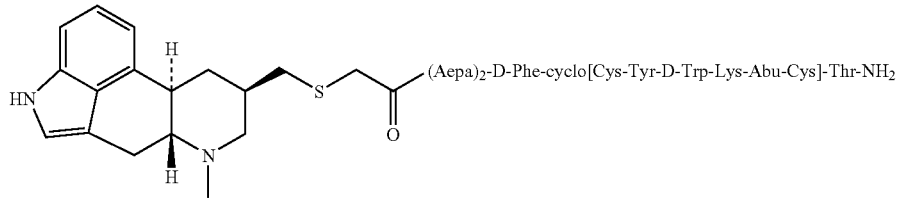
(Aepa)₂-D-Phe-cyclo[Cys-Tyr-D-Trp-Lys-Abu-Cys]-Thr-NH₂

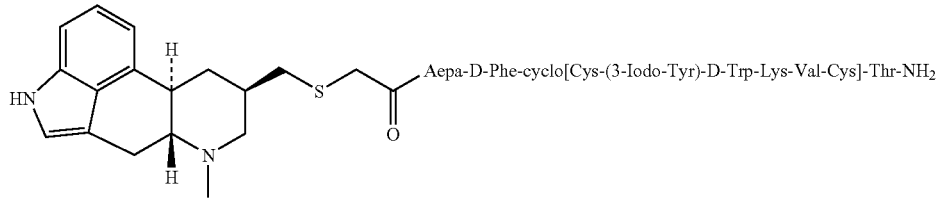
Aepa-D-Phe-cyclo[Cys-(3-Iodo-Tyr)-D-Trp-Lys-Val-Cys]-Thr-NH₂

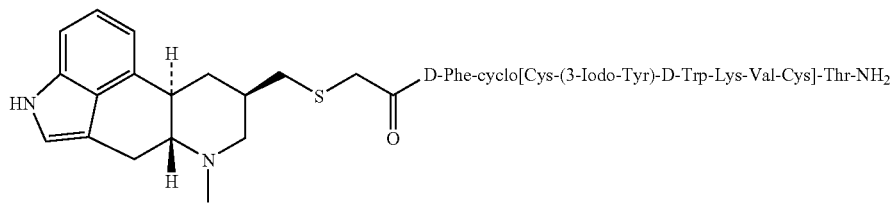
D-Phe-cyclo[Cys-(3-Iodo-Tyr)-D-Trp-Lys-Val-Cys]-Thr-NH₂

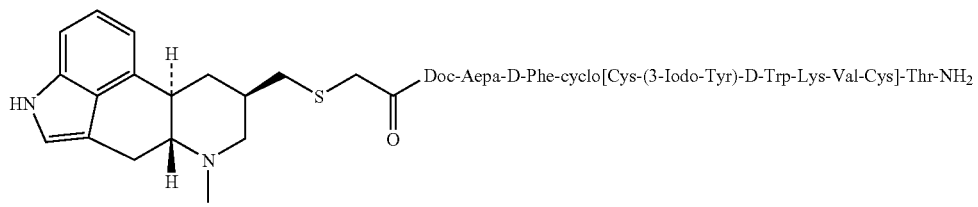
Doc-Aepa-D-Phe-cyclo[Cys-(3-Iodo-Tyr)-D-Trp-Lys-Val-Cys]-Thr-NH₂

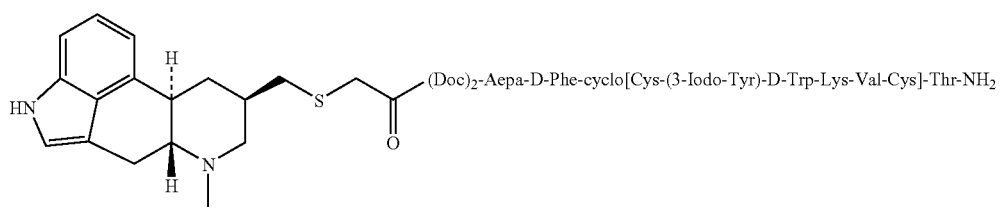
(Doc)₂-Aepa-D-Phe-cyclo[Cys-(3-Iodo-Tyr)-D-Trp-Lys-Val-Cys]-Thr-NH₂

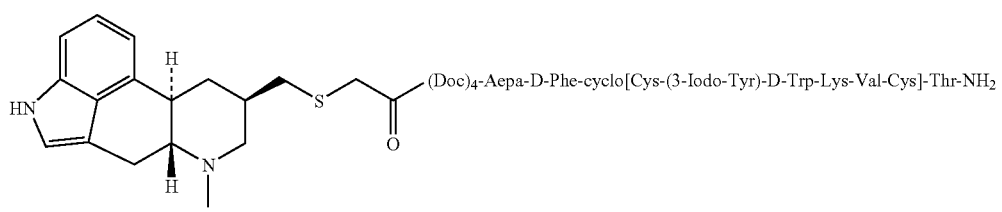
(Doc)₄-Aepa-D-Phe-cyclo[Cys-(3-Iodo-Tyr)-D-Trp-Lys-Val-Cys]-Thr-NH₂

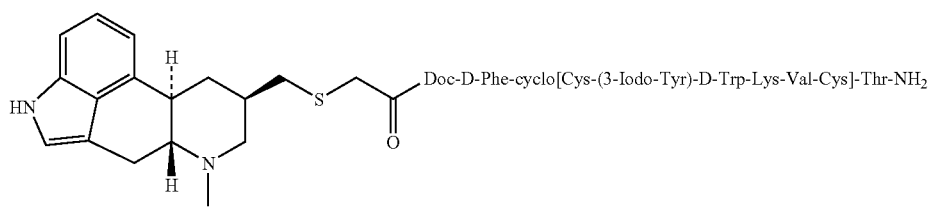
Doc-D-Phe-cyclo[Cys-(3-Iodo-Tyr)-D-Trp-Lys-Val-Cys]-Thr-NH₂

-continued

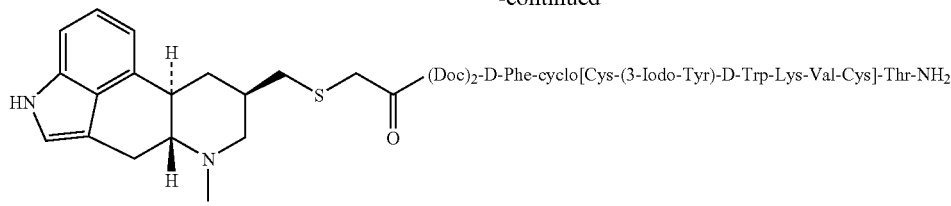 (Doc)₂-D-Phe-cyclo[Cys-(3-Iodo-Tyr)-D-Trp-Lys-Val-Cys]-Thr-NH₂

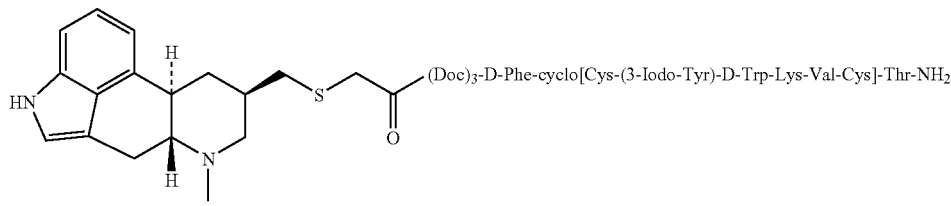 (Doc)₃-D-Phe-cyclo[Cys-(3-Iodo-Tyr)-D-Trp-Lys-Val-Cys]-Thr-NH₂

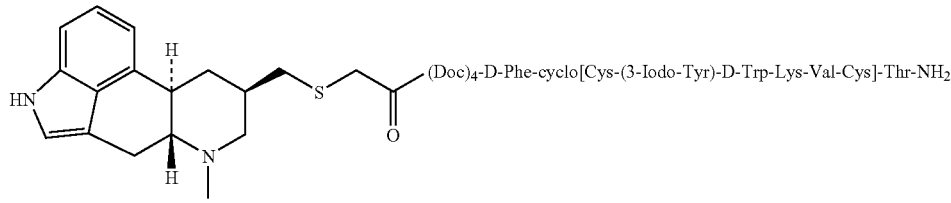 (Doc)₄-D-Phe-cyclo[Cys-(3-Iodo-Tyr)-D-Trp-Lys-Val-Cys]-Thr-NH₂

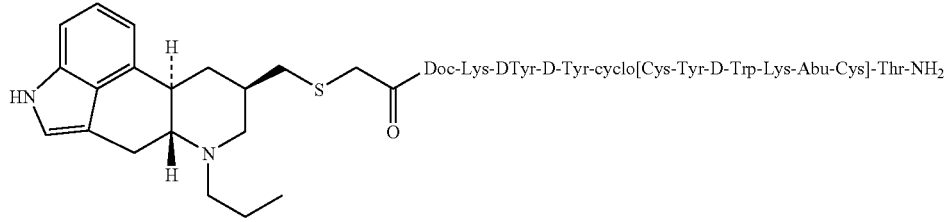 Doc-Lys-DTyr-D-Tyr-cyclo[Cys-Tyr-D-Trp-Lys-Abu-Cys]-Thr-NH₂

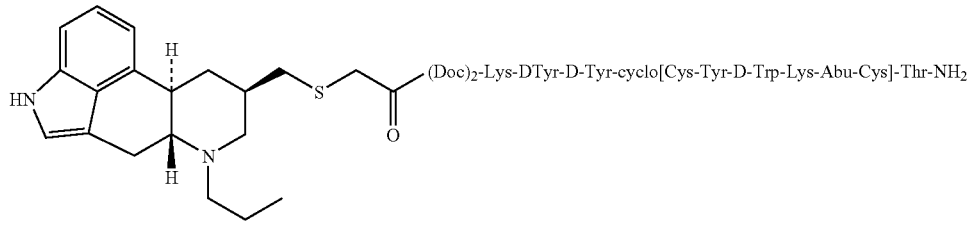 (Doc)₂-Lys-DTyr-D-Tyr-cyclo[Cys-Tyr-D-Trp-Lys-Abu-Cys]-Thr-NH₂

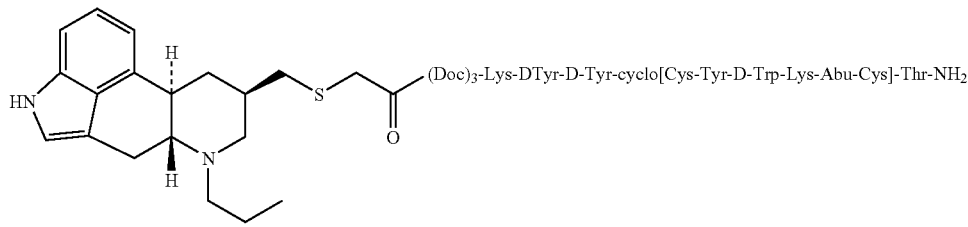 (Doc)₃-Lys-DTyr-D-Tyr-cyclo[Cys-Tyr-D-Trp-Lys-Abu-Cys]-Thr-NH₂

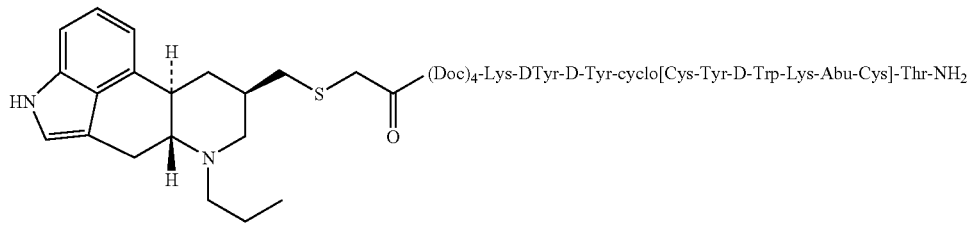 (Doc)₄-Lys-DTyr-D-Tyr-cyclo[Cys-Tyr-D-Trp-Lys-Abu-Cys]-Thr-NH₂

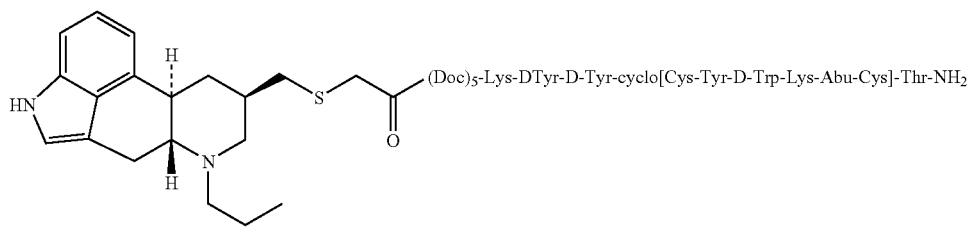 (Doc)₅-Lys-DTyr-D-Tyr-cyclo[Cys-Tyr-D-Trp-Lys-Abu-Cys]-Thr-NH₂

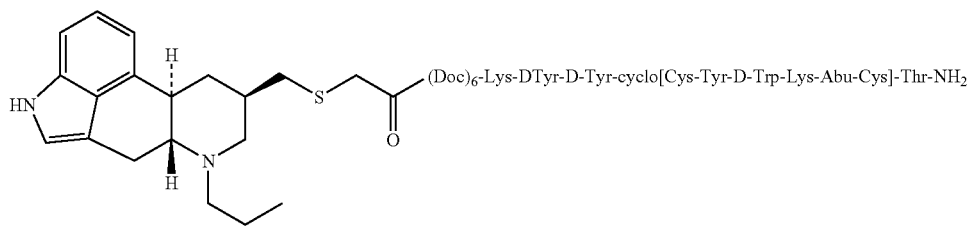(Doc)₆-Lys-DTyr-D-Tyr-cyclo[Cys-Tyr-D-Trp-Lys-Abu-Cys]-Thr-NH₂

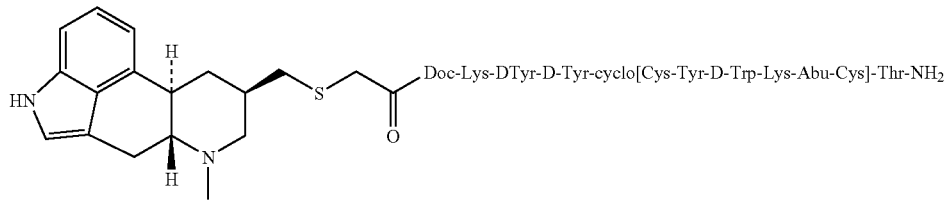Doc-Lys-DTyr-D-Tyr-cyclo[Cys-Tyr-D-Trp-Lys-Abu-Cys]-Thr-NH₂

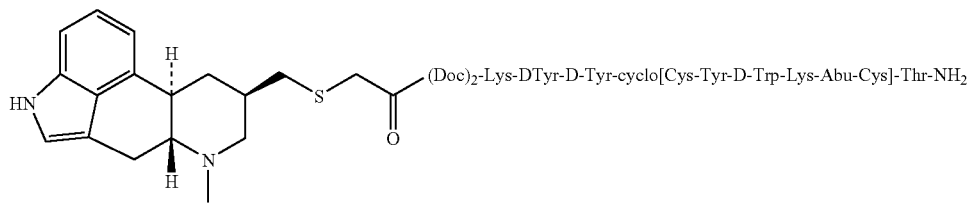(Doc)₂-Lys-DTyr-D-Tyr-cyclo[Cys-Tyr-D-Trp-Lys-Abu-Cys]-Thr-NH₂

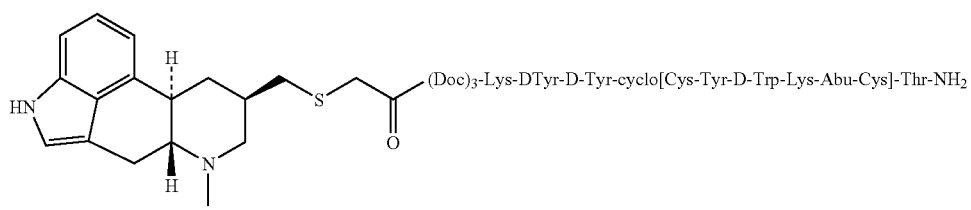(Doc)₃-Lys-DTyr-D-Tyr-cyclo[Cys-Tyr-D-Trp-Lys-Abu-Cys]-Thr-NH₂

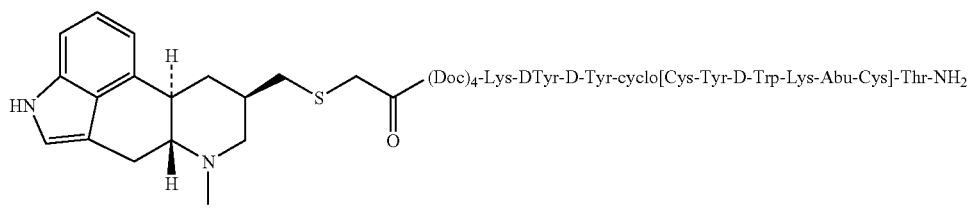(Doc)₄-Lys-DTyr-D-Tyr-cyclo[Cys-Tyr-D-Trp-Lys-Abu-Cys]-Thr-NH₂

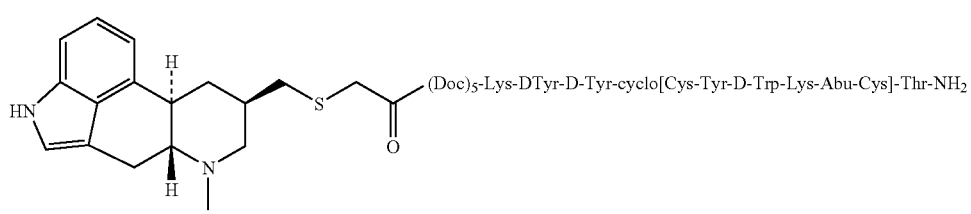(Doc)₅-Lys-DTyr-D-Tyr-cyclo[Cys-Tyr-D-Trp-Lys-Abu-Cys]-Thr-NH₂

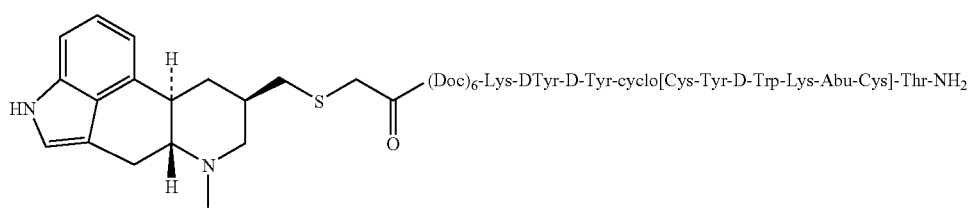(Doc)₆-Lys-DTyr-D-Tyr-cyclo[Cys-Tyr-D-Trp-Lys-Abu-Cys]-Thr-NH₂

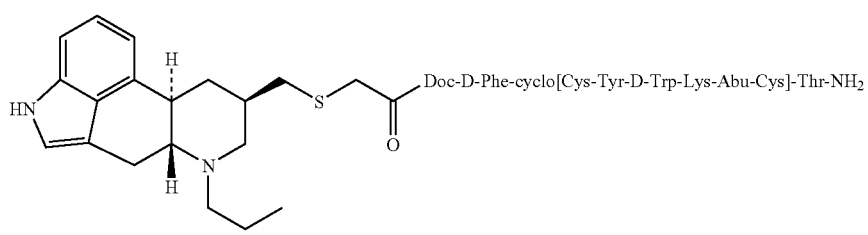Doc-D-Phe-cyclo[Cys-Tyr-D-Trp-Lys-Abu-Cys]-Thr-NH₂

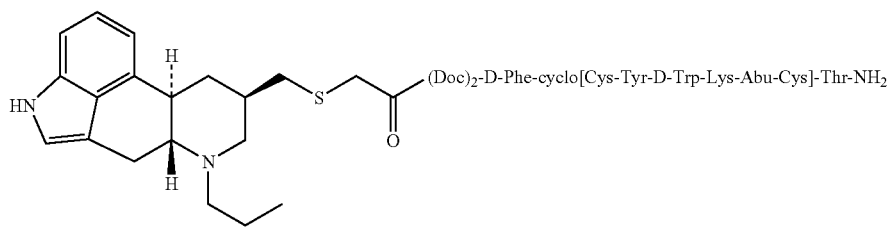
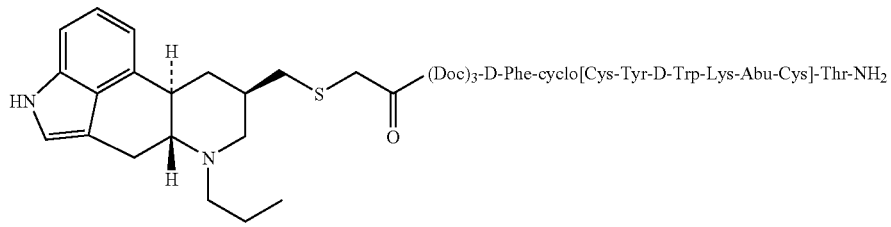
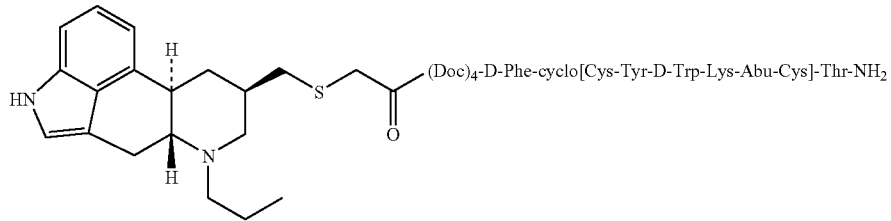
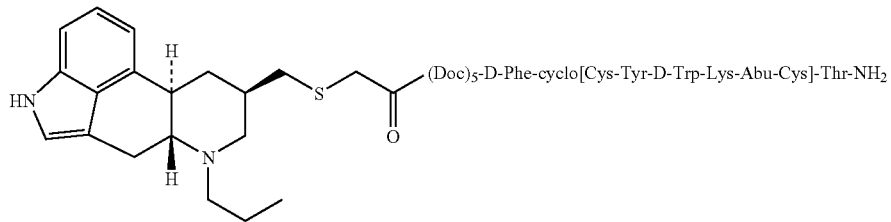
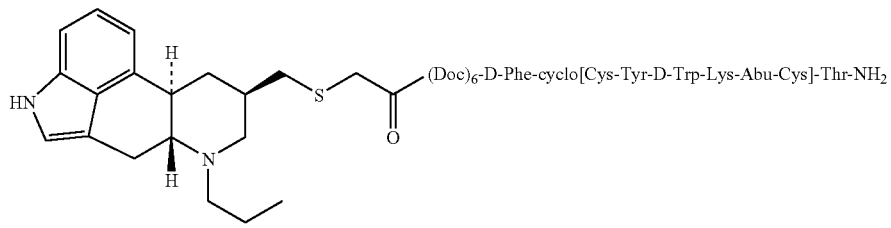
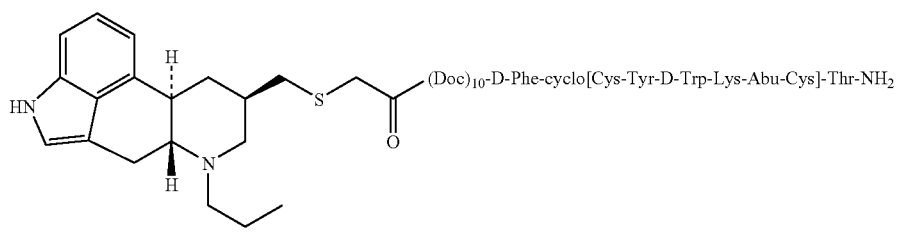
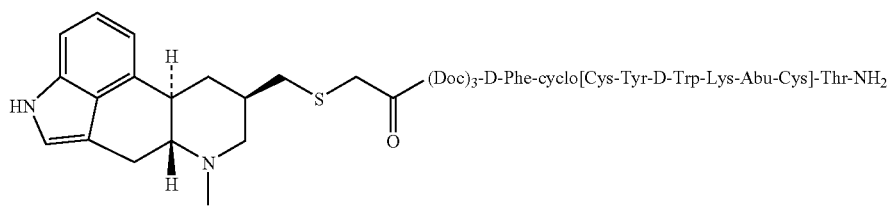

-continued
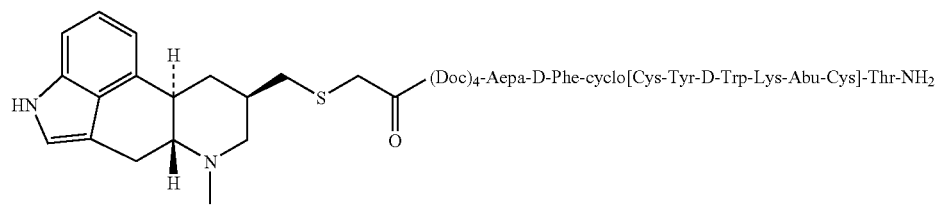
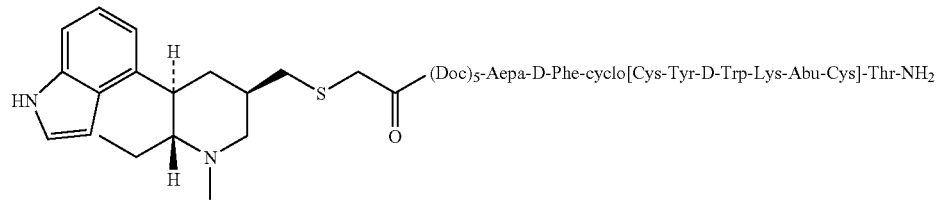
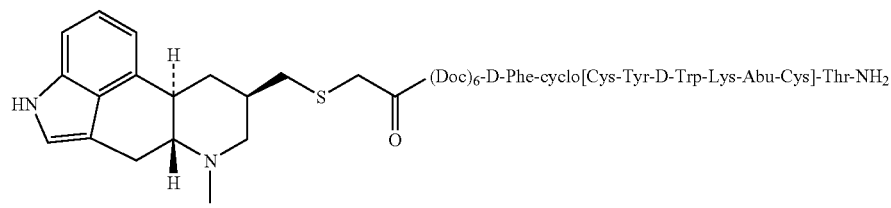
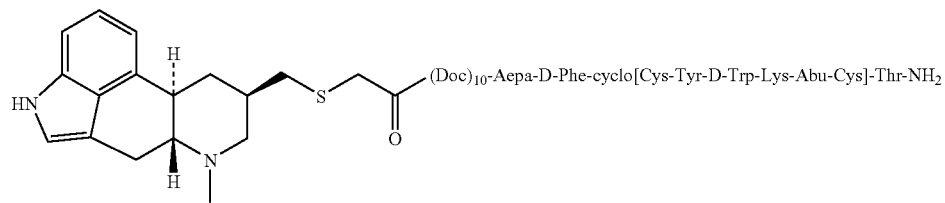
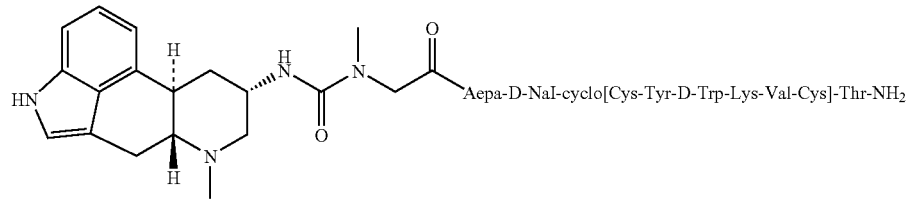
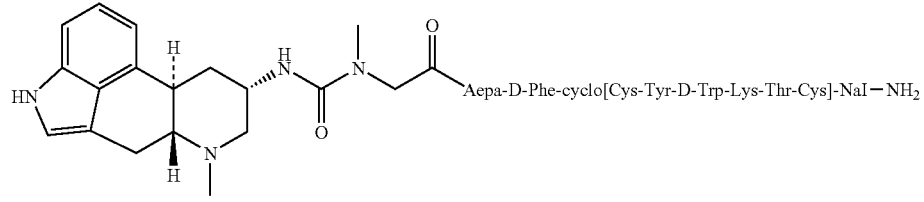
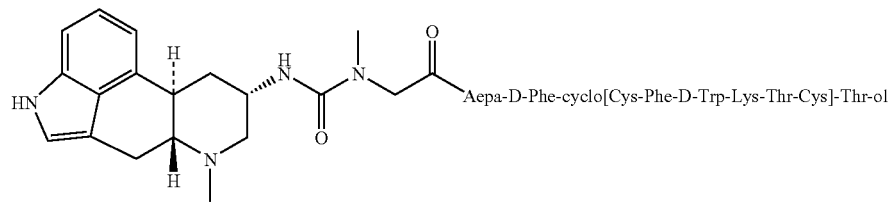
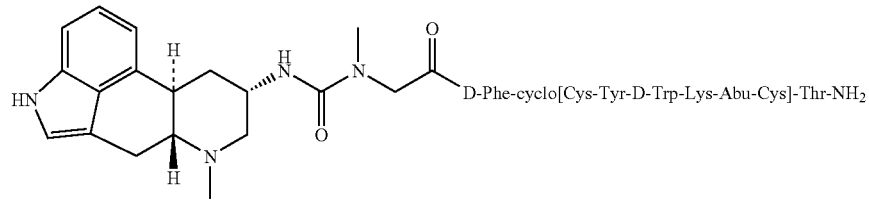

-continued

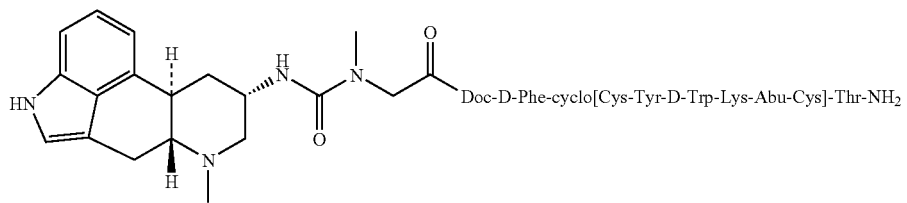
Doc-D-Phe-cyclo[Cys-Tyr-D-Trp-Lys-Abu-Cys]-Thr-NH$_2$

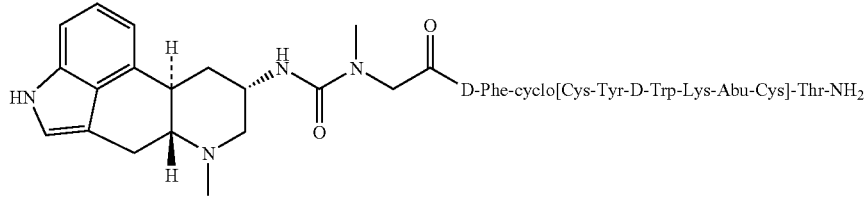
D-Phe-cyclo[Cys-Tyr-D-Trp-Lys-Abu-Cys]-Thr-NH$_2$

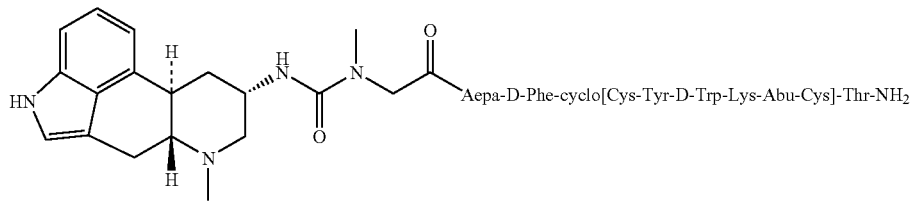
Aepa-D-Phe-cyclo[Cys-Tyr-D-Trp-Lys-Abu-Cys]-Thr-NH$_2$

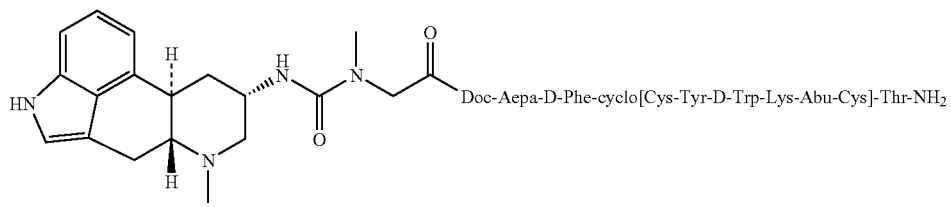
Doc-Aepa-D-Phe-cyclo[Cys-Tyr-D-Trp-Lys-Abu-Cys]-Thr-NH$_2$

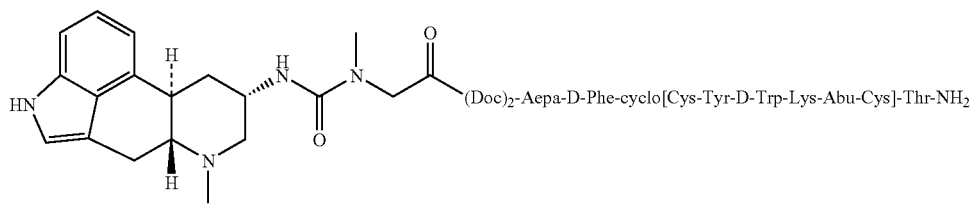
(Doc)$_2$-Aepa-D-Phe-cyclo[Cys-Tyr-D-Trp-Lys-Abu-Cys]-Thr-NH$_2$

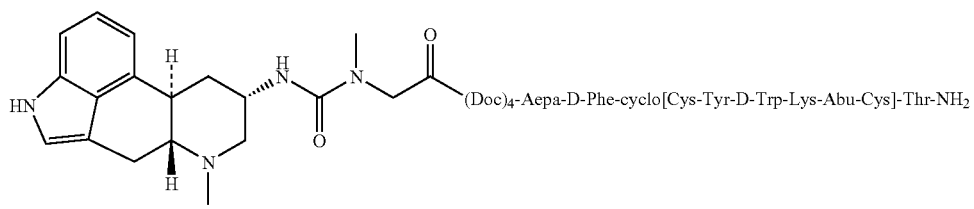
(Doc)$_4$-Aepa-D-Phe-cyclo[Cys-Tyr-D-Trp-Lys-Abu-Cys]-Thr-NH$_2$

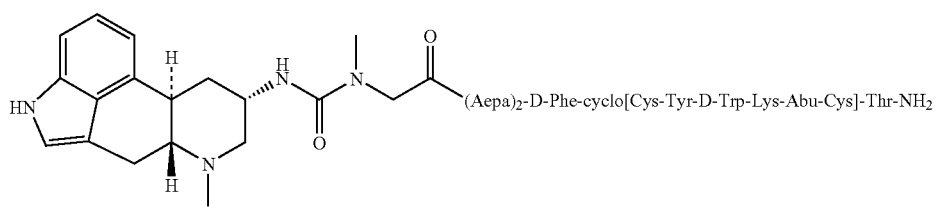
(Aepa)$_2$-D-Phe-cyclo[Cys-Tyr-D-Trp-Lys-Abu-Cys]-Thr-NH$_2$

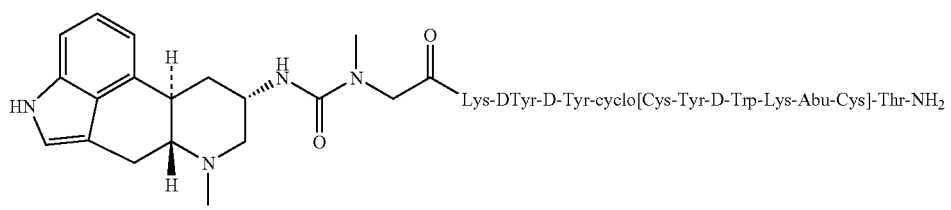
Lys-DTyr-D-Tyr-cyclo[Cys-Tyr-D-Trp-Lys-Abu-Cys]-Thr-NH$_2$

-continued

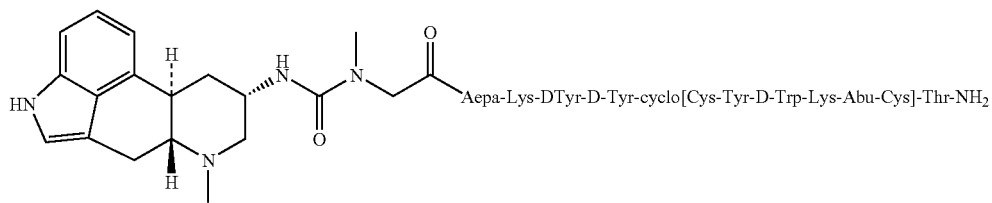Aepa-Lys-DTyr-D-Tyr-cyclo[Cys-Tyr-D-Trp-Lys-Abu-Cys]-Thr-NH$_2$

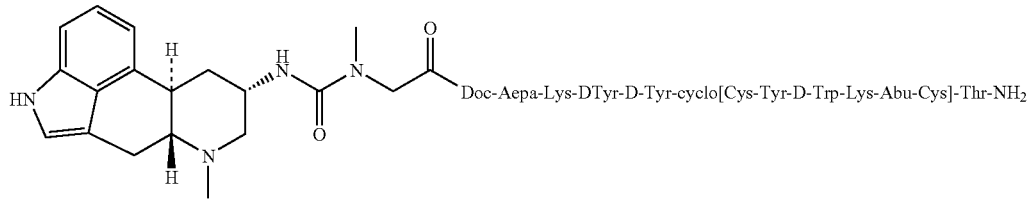Doc-Aepa-Lys-DTyr-D-Tyr-cyclo[Cys-Tyr-D-Trp-Lys-Abu-Cys]-Thr-NH$_2$

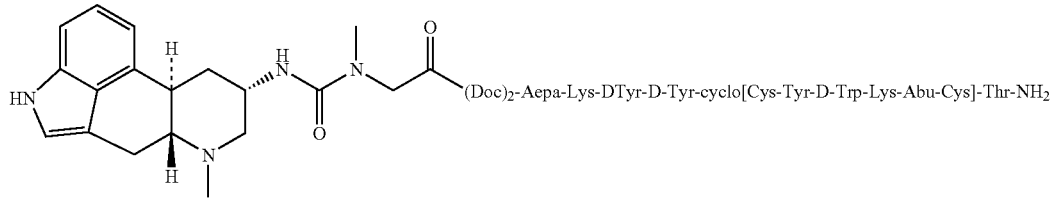(Doc)$_2$-Aepa-Lys-DTyr-D-Tyr-cyclo[Cys-Tyr-D-Trp-Lys-Abu-Cys]-Thr-NH$_2$

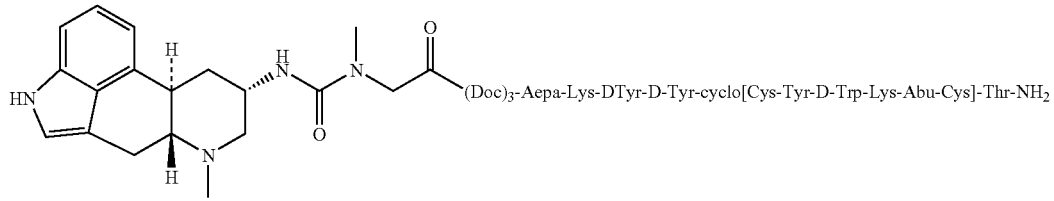(Doc)$_3$-Aepa-Lys-DTyr-D-Tyr-cyclo[Cys-Tyr-D-Trp-Lys-Abu-Cys]-Thr-NH$_2$

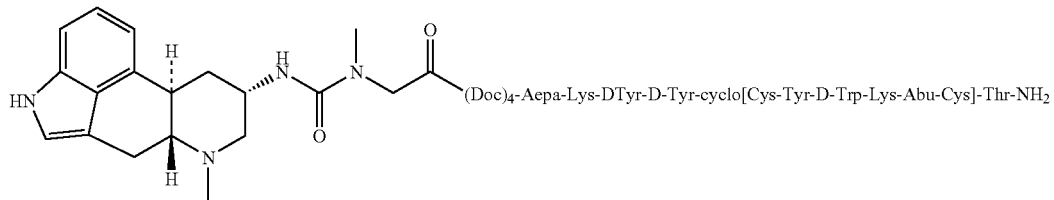(Doc)$_4$-Aepa-Lys-DTyr-D-Tyr-cyclo[Cys-Tyr-D-Trp-Lys-Abu-Cys]-Thr-NH$_2$

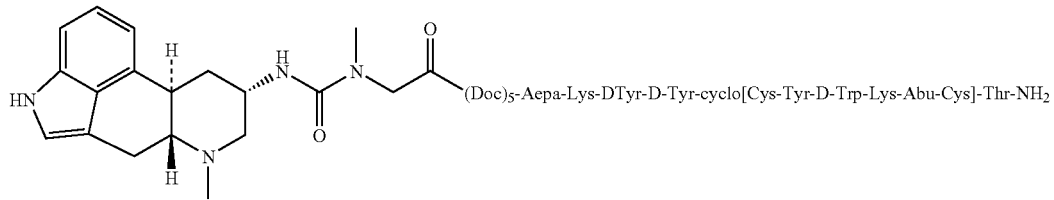(Doc)$_5$-Aepa-Lys-DTyr-D-Tyr-cyclo[Cys-Tyr-D-Trp-Lys-Abu-Cys]-Thr-NH$_2$

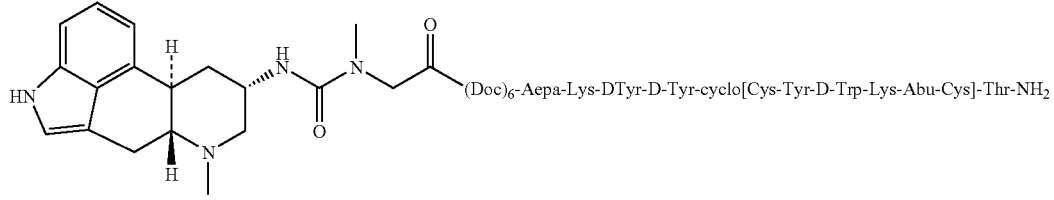(Doc)$_6$-Aepa-Lys-DTyr-D-Tyr-cyclo[Cys-Tyr-D-Trp-Lys-Abu-Cys]-Thr-NH$_2$

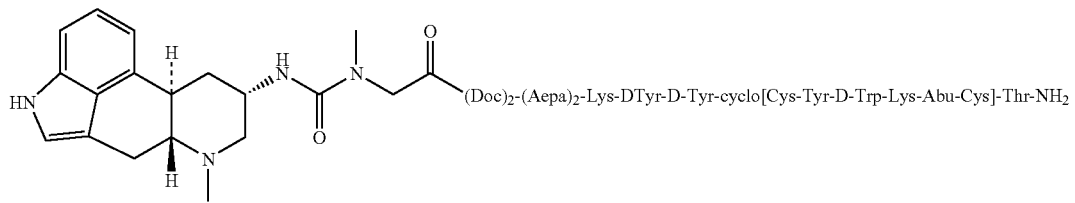(Doc)$_2$-(Aepa)$_2$-Lys-DTyr-D-Tyr-cyclo[Cys-Tyr-D-Trp-Lys-Abu-Cys]-Thr-NH$_2$ -continued
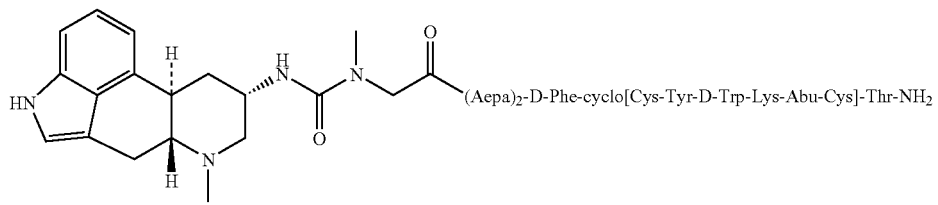
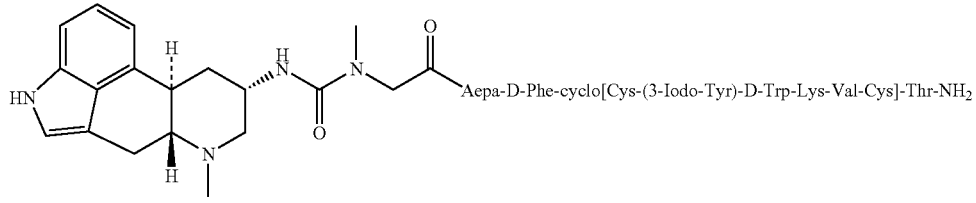
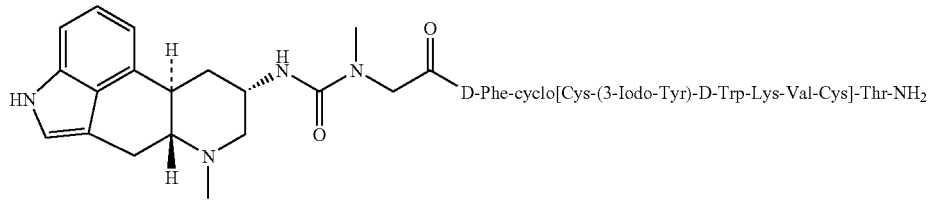
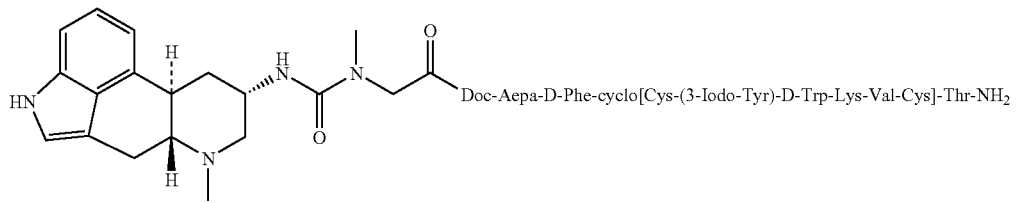
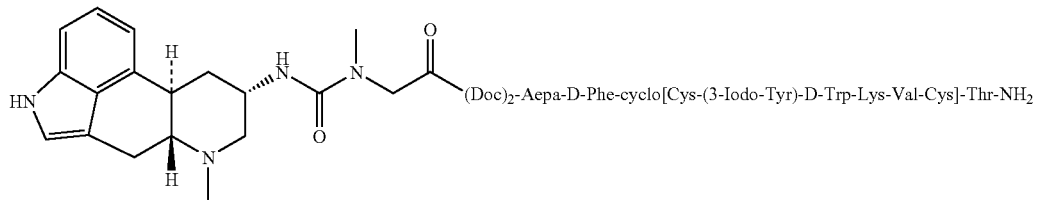
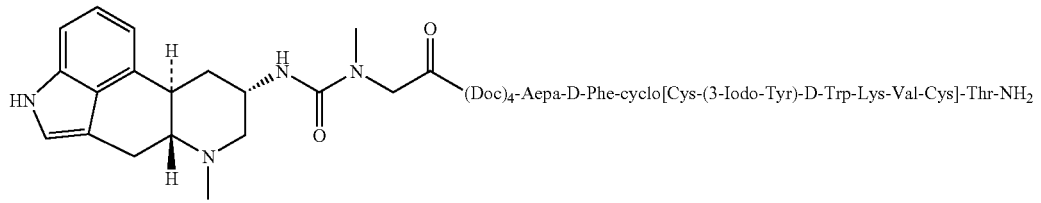
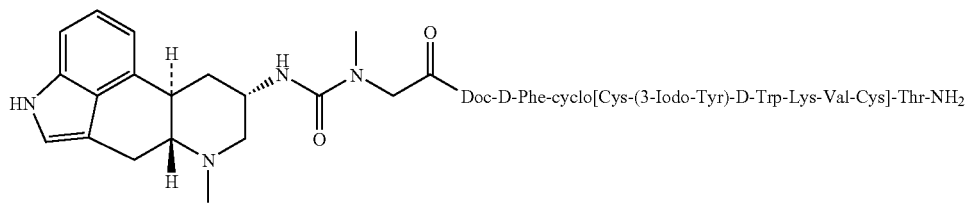
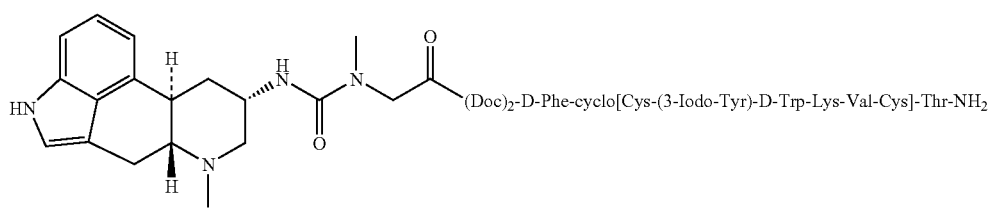

-continued

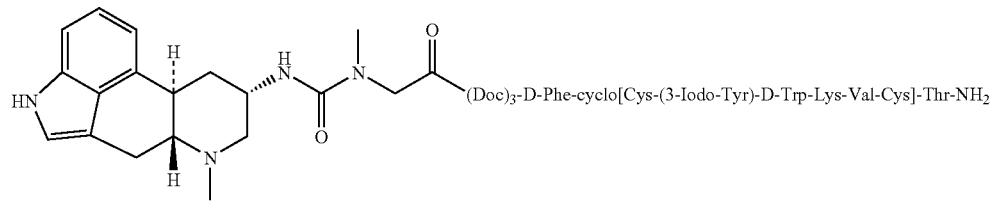
(Doc)₃-D-Phe-cyclo[Cys-(3-Iodo-Tyr)-D-Trp-Lys-Val-Cys]-Thr-NH₂

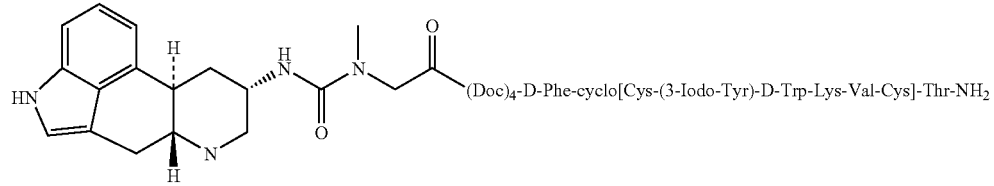
(Doc)₄-D-Phe-cyclo[Cys-(3-Iodo-Tyr)-D-Trp-Lys-Val-Cys]-Thr-NH₂

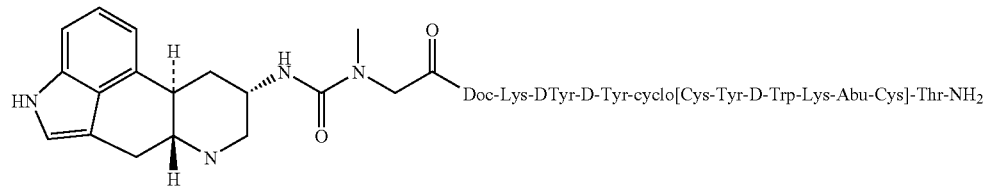
Doc-Lys-DTyr-D-Tyr-cyclo[Cys-Tyr-D-Trp-Lys-Abu-Cys]-Thr-NH₂

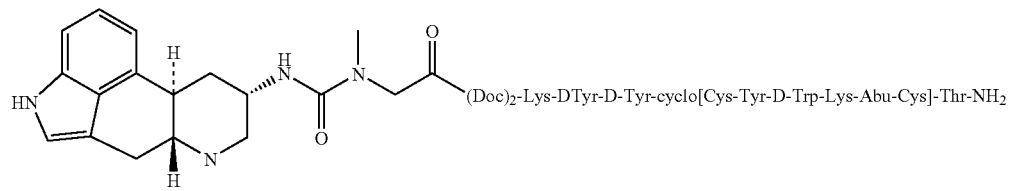
(Doc)₂-Lys-DTyr-D-Tyr-cyclo[Cys-Tyr-D-Trp-Lys-Abu-Cys]-Thr-NH₂

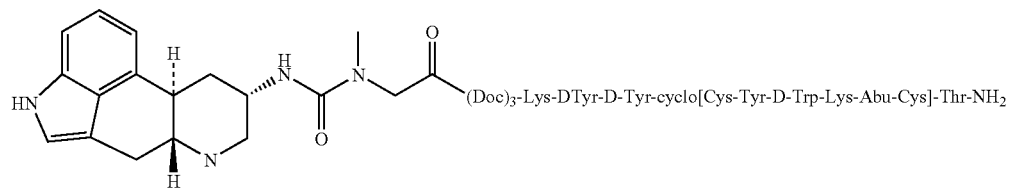
(Doc)₃-Lys-DTyr-D-Tyr-cyclo[Cys-Tyr-D-Trp-Lys-Abu-Cys]-Thr-NH₂

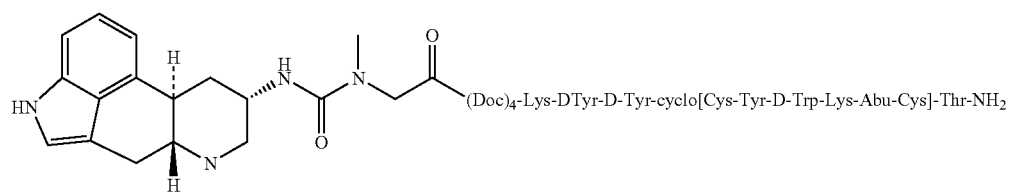
(Doc)₄-Lys-DTyr-D-Tyr-cyclo[Cys-Tyr-D-Trp-Lys-Abu-Cys]-Thr-NH₂

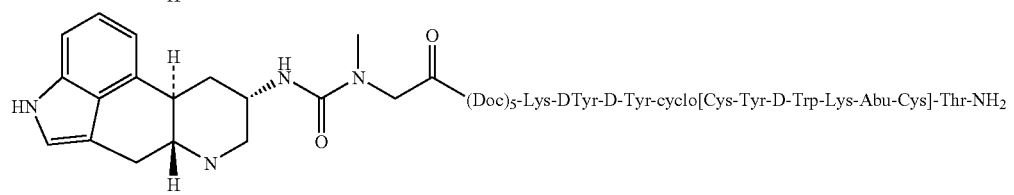
(Doc)₅-Lys-DTyr-D-Tyr-cyclo[Cys-Tyr-D-Trp-Lys-Abu-Cys]-Thr-NH₂

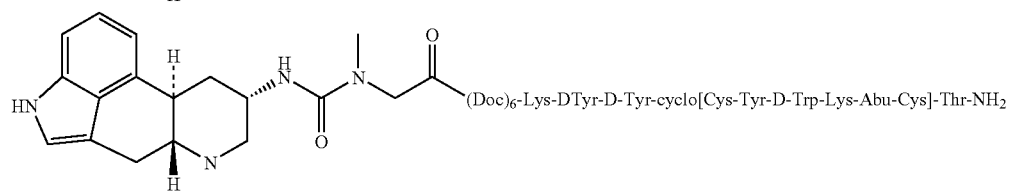
(Doc)₆-Lys-DTyr-D-Tyr-cyclo[Cys-Tyr-D-Trp-Lys-Abu-Cys]-Thr-NH₂

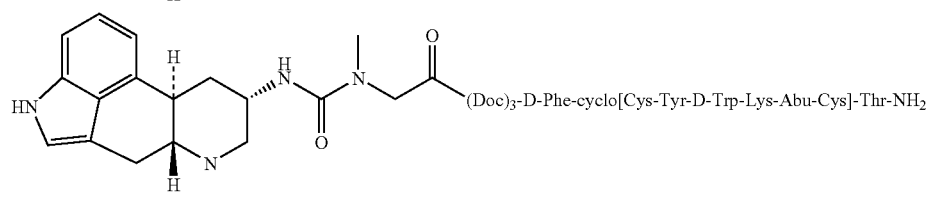
(Doc)₃-D-Phe-cyclo[Cys-Tyr-D-Trp-Lys-Abu-Cys]-Thr-NH₂

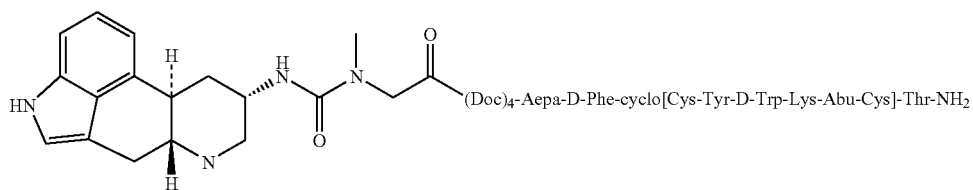
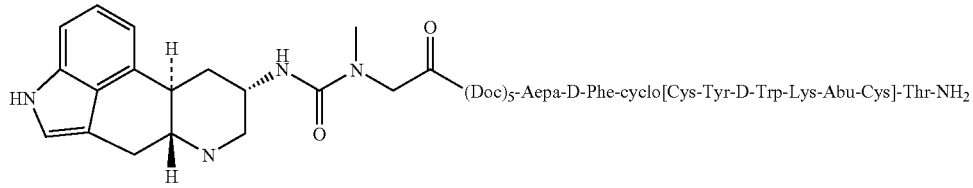
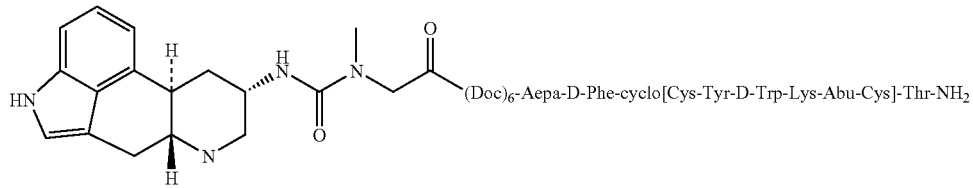
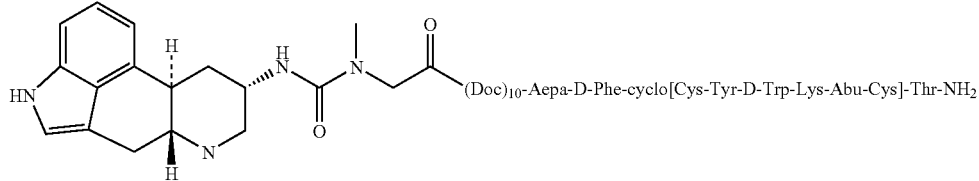
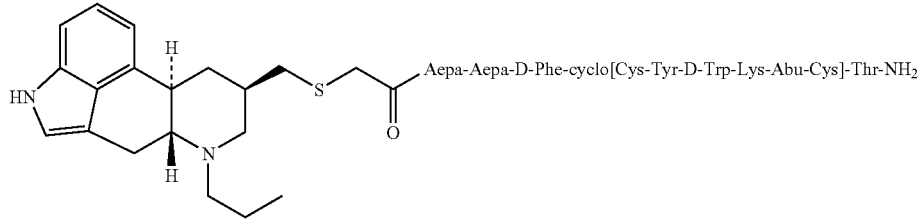
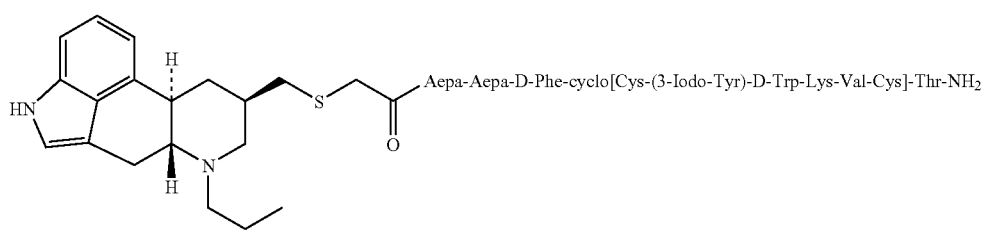
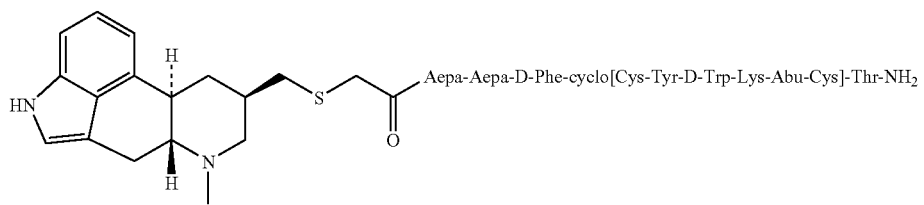
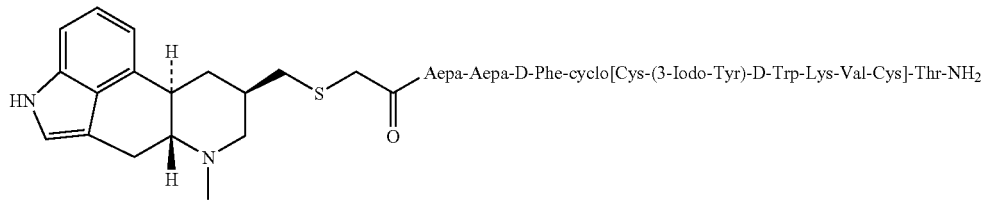

-continued

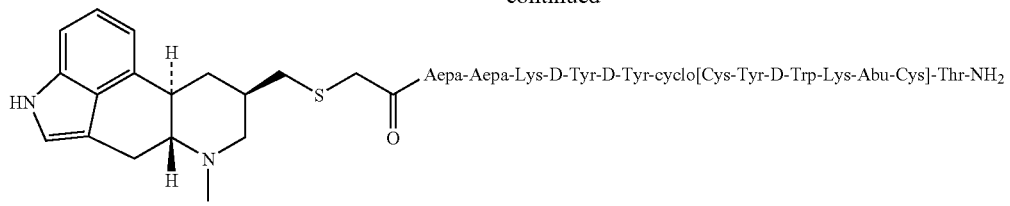
Aepa-Aepa-Lys-D-Tyr-D-Tyr-cyclo[Cys-Tyr-D-Trp-Lys-Abu-Cys]-Thr-NH$_2$

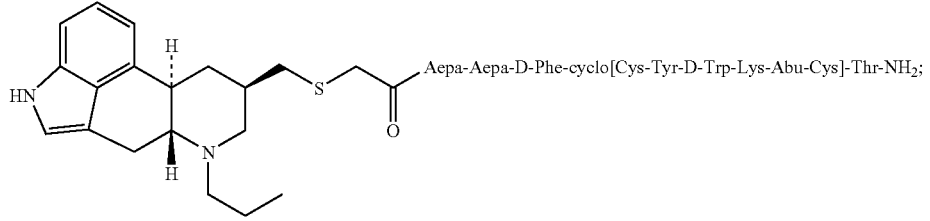
Aepa-Aepa-D-Phe-cyclo[Cys-Tyr-D-Trp-Lys-Abu-Cys]-Thr-NH$_2$;

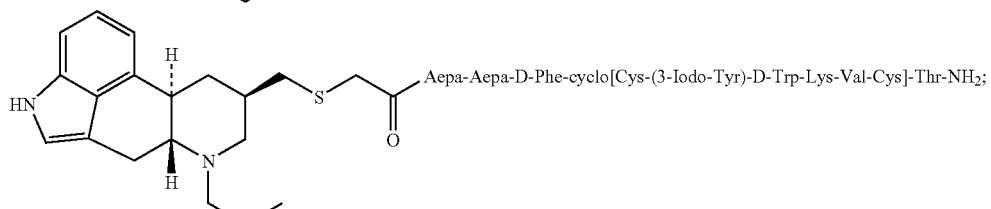
Aepa-Aepa-D-Phe-cyclo[Cys-(3-Iodo-Tyr)-D-Trp-Lys-Val-Cys]-Thr-NH$_2$;

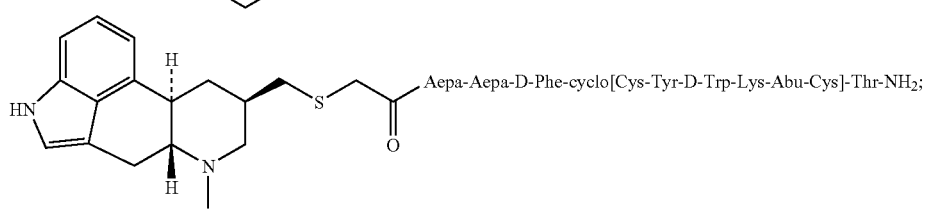
Aepa-Aepa-D-Phe-cyclo[Cys-Tyr-D-Trp-Lys-Abu-Cys]-Thr-NH$_2$;

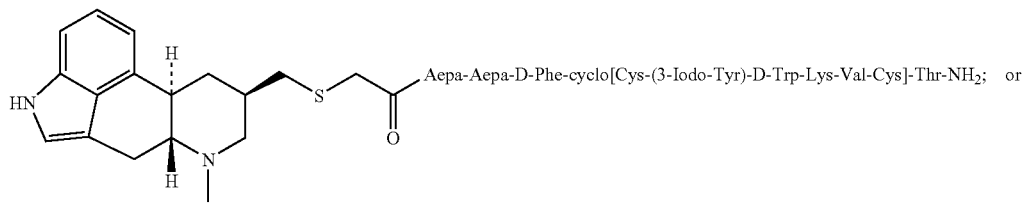
Aepa-Aepa-D-Phe-cyclo[Cys-(3-Iodo-Tyr)-D-Trp-Lys-Val-Cys]-Thr-NH$_2$;   or

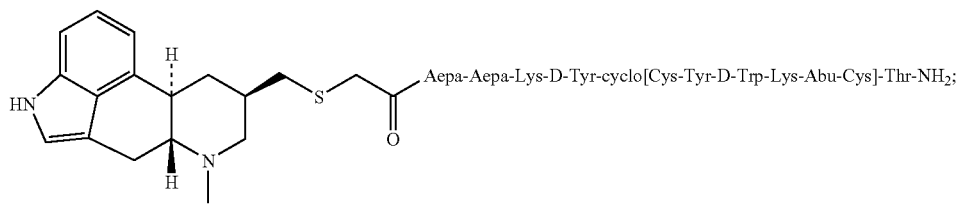
Aepa-Aepa-Lys-D-Tyr-cyclo[Cys-Tyr-D-Trp-Lys-Abu-Cys]-Thr-NH$_2$;

or a pharmaceutically acceptable salt thereof; or
e) a compound according to formulae:

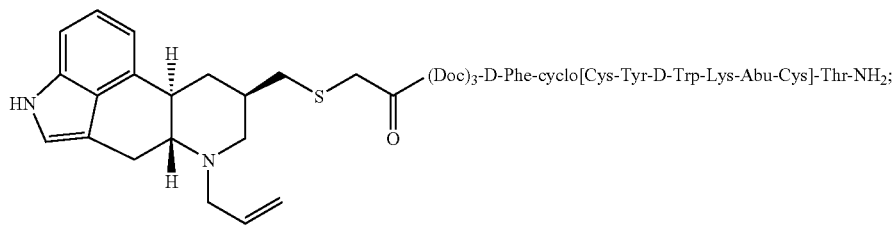
(Doc)$_3$-D-Phe-cyclo[Cys-Tyr-D-Trp-Lys-Abu-Cys]-Thr-NH$_2$;

-continued
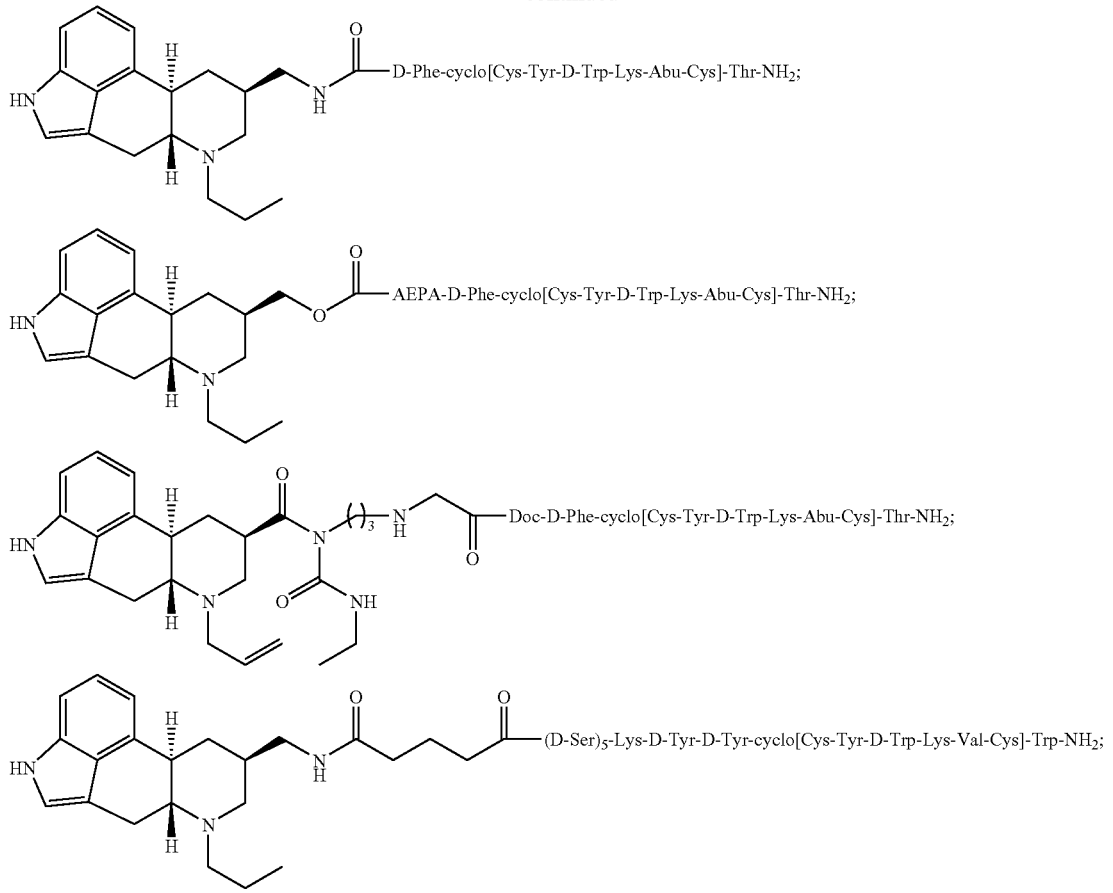
Ethyl-[6-methyl-8β-ergolinylmethyl]thioacetate;
6-Methyl-8β-ergolinylmethylthioacetyl-D-Phe-c(Cys-Tyr-D-Trp-Lys-Abu-Cys)-Thr-NH$_2$;
Ethyl-(6-n-propyl-8β-ergolinyl)methylthioacetate;
6-n-propyl-8β-ergolinylmethylthioacetyl-D-Phe-c(Cys-Tyr-D-Trp-Lys-Abu-Cys)-Thr-NH$_2$;
6-D-Methyl-8β-ergolinylmethylthlaminosuccinoyl-D-Phe-c(Cys-Tyr-D-Trp-Lys-Abu-Cys)-Thr-NH$_2$;
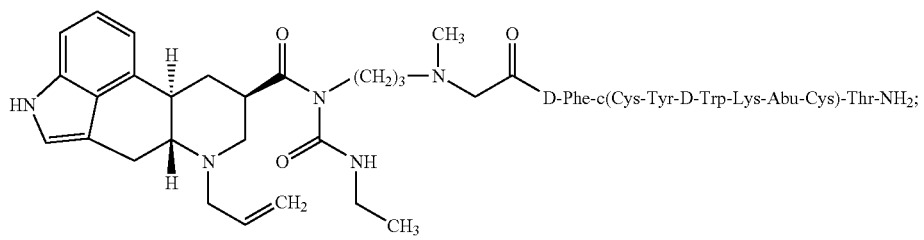
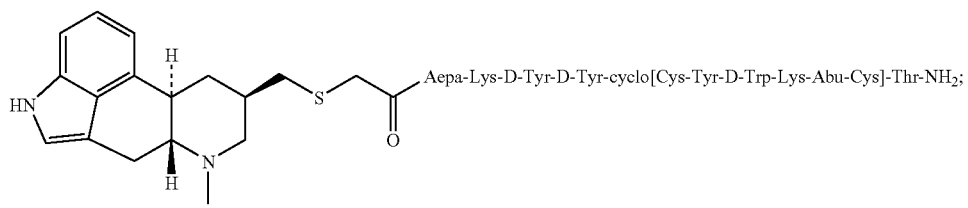

-continued

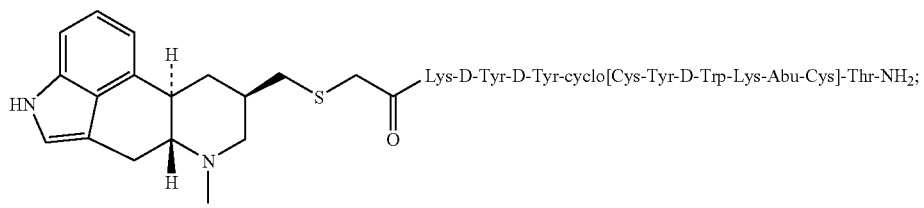
Lys-D-Tyr-D-Tyr-cyclo[Cys-Tyr-D-Trp-Lys-Abu-Cys]-Thr-NH$_2$;

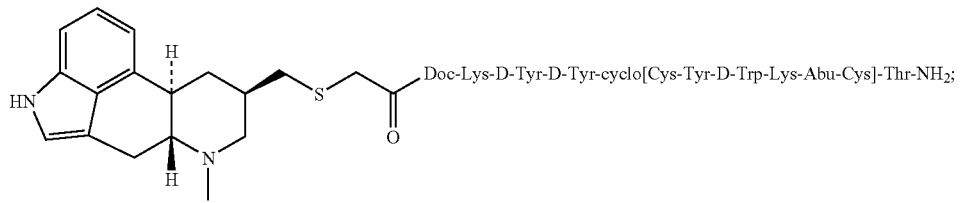
Doc-Lys-D-Tyr-D-Tyr-cyclo[Cys-Tyr-D-Trp-Lys-Abu-Cys]-Thr-NH$_2$;

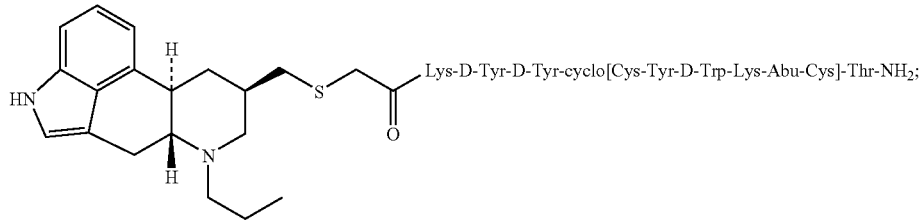
Lys-D-Tyr-D-Tyr-cyclo[Cys-Tyr-D-Trp-Lys-Abu-Cys]-Thr-NH$_2$;

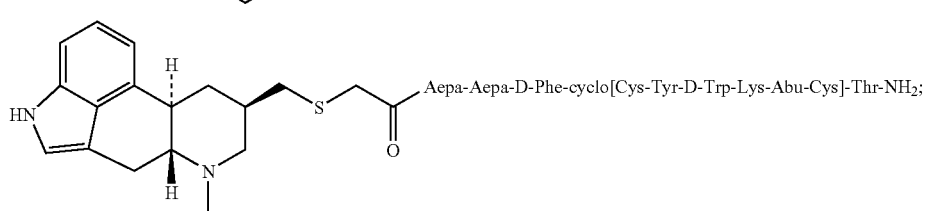
Aepa-Aepa-D-Phe-cyclo[Cys-Tyr-D-Trp-Lys-Abu-Cys]-Thr-NH$_2$;

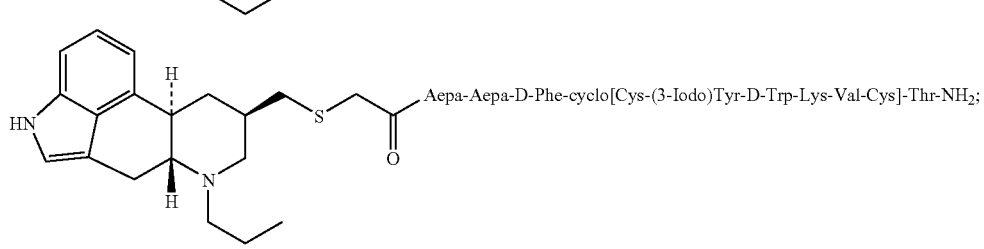
Aepa-Aepa-D-Phe-cyclo[Cys-(3-Iodo)Tyr-D-Trp-Lys-Val-Cys]-Thr-NH$_2$;

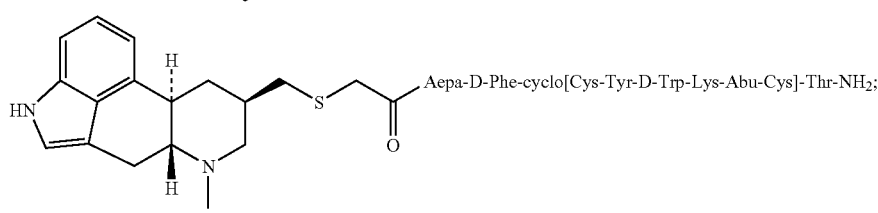
Aepa-D-Phe-cyclo[Cys-Tyr-D-Trp-Lys-Abu-Cys]-Thr-NH$_2$;

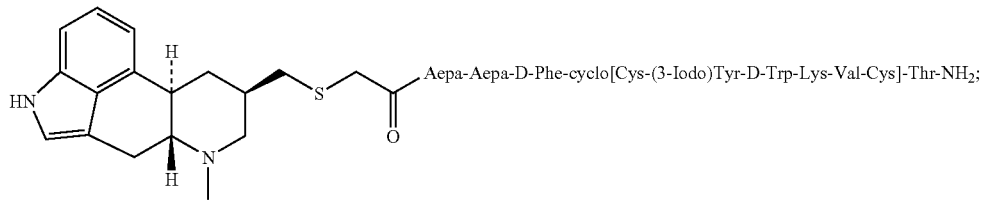
Aepa-Aepa-D-Phe-cyclo[Cys-(3-Iodo)Tyr-D-Trp-Lys-Val-Cys]-Thr-NH$_2$;

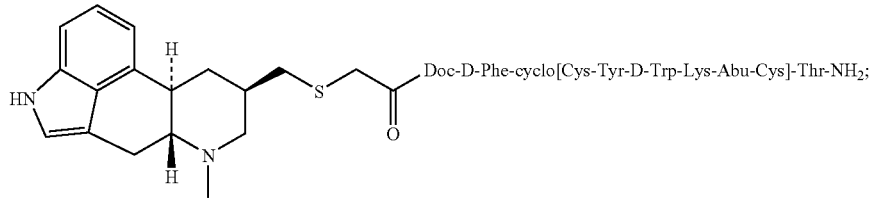
Doc-D-Phe-cyclo[Cys-Tyr-D-Trp-Lys-Abu-Cys]-Thr-NH$_2$;

-continued

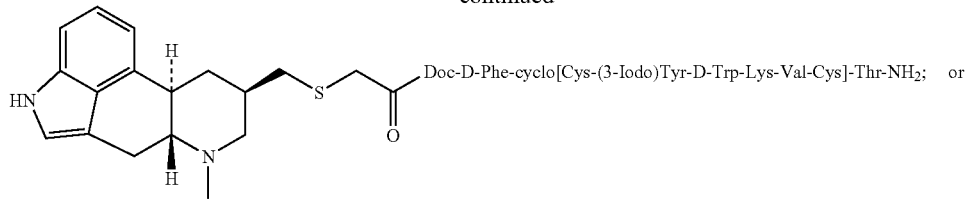
Doc-D-Phe-cyclo[Cys-(3-Iodo)Tyr-D-Trp-Lys-Val-Cys]-Thr-NH₂;   or

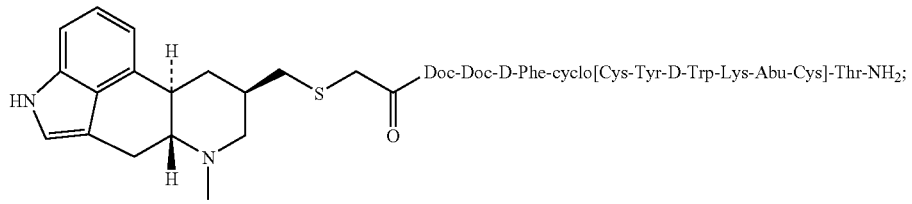
Doc-Doc-D-Phe-cyclo[Cys-Tyr-D-Trp-Lys-Abu-Cys]-Thr-NH₂;

or a pharmaceutically acceptable salt thereof; or
f) a compound according to formulae:

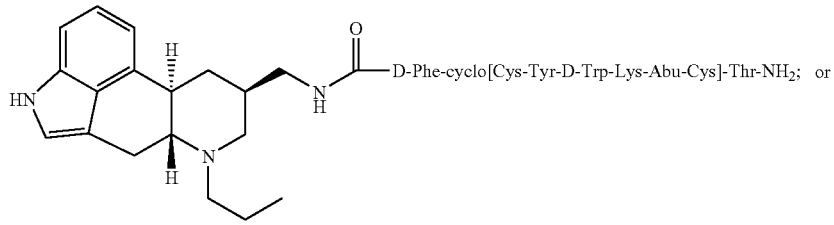
D-Phe-cyclo[Cys-Tyr-D-Trp-Lys-Abu-Cys]-Thr-NH₂;   or

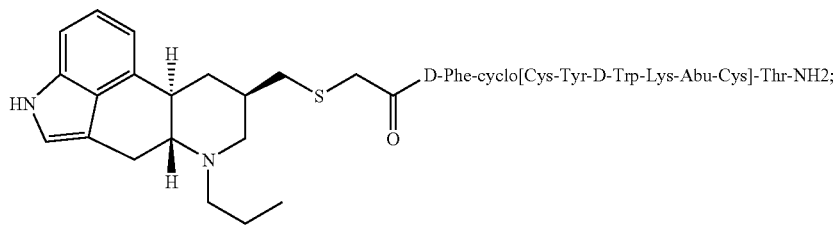
D-Phe-cyclo[Cys-Tyr-D-Trp-Lys-Abu-Cys]-Thr-NH2;

or a pharmaceutically acceptable salt thereof,
wherein said therapeutically effective amount of said compound or pharmaceutically acceptable salt thereof treats acromegaly, GH secreting adenomas, or prolactin secreting adenomas in said subject in need thereof.

2. A method according to claim 1, wherein said disease is acromegaly.

3. A method according to claim 1, wherein said disease is a GH secreting adenoma.

4. A method according to claim 1, wherein said disease is a prolactin secreting adenoma.

5. A method of treating, acromegaly, GH secreting adenomas, or prolactin secreting adenomas in a subject, said method comprising administering to said subject a therapeutically effective amount of

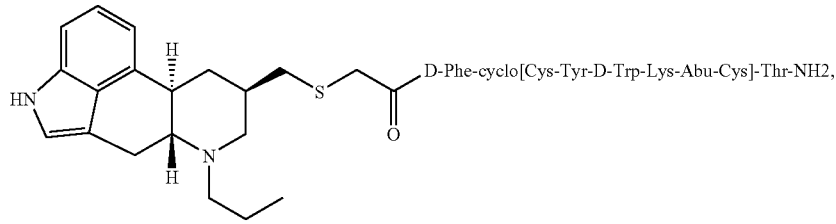

or a pharmaceutically acceptable salt thereof;
wherein said therapeutically effective amount of said compound or pharmaceutically acceptable salt thereof treats, acromegaly, GH secreting adenomas, or prolactin secreting adenomas in said subject in need thereof.

6. A method according to claim 5, wherein said disease is selected from the group consisting of acromegaly, GH secreting adenomas and prolactin secreting adenomas.

7. A method according to claim 6, wherein said disease is acromegaly.

8. A method according to claim 6, wherein said disease is a GH secreting adenoma.

9. A method according to claim 6, wherein said disease is a prolactin secreting adenoma.

10. A method of treating acromegaly, GH secreting adenomas, or prolactin secreting adenomas in a subject, said method comprising administering to said subject a therapeutically effective amount of

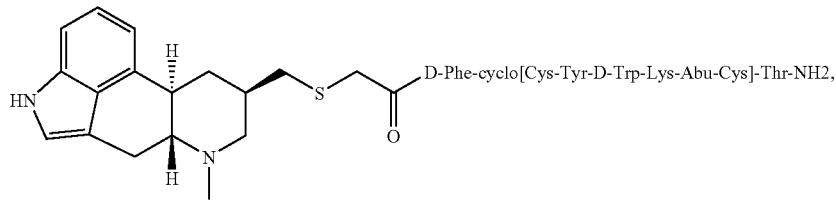

or a pharmaceutically acceptable salt thereof;
wherein said therapeutically effective amount of said compound or pharmaceutically acceptable salt thereof treats acromegaly, GH secreting adenomas, or prolactin secreting adenomas in said subject in need thereof.

11. A method according to claim 10, wherein said disease is selected from the group consisting of acromegaly, GH secreting adenomas and prolactin secreting adenomas.

12. A method according to claim 11, wherein said disease is acromegaly.

13. A method according to claim 11, wherein said disease is a GH secreting adenoma.

14. A method according to claim 11, wherein said disease is a prolactin secreting adenoma.

* * * * *